US012533233B2

(12) United States Patent
Srinimukesh et al.

(10) Patent No.: US 12,533,233 B2
(45) Date of Patent: Jan. 27, 2026

(54) SYSTEM AND METHOD FOR CRIMPING AND LOADING A PROSTHETIC HEART VALVE

(71) Applicant: EDWARDS LIFESCIENCES CORPORATION, Irvine, CA (US)

(72) Inventors: Harish Manickam Srinimukesh, Costa Mesa, CA (US); Kevin M. Stewart, Powell, TN (US); Matthew Michael Becerra, Lake Forest, CA (US); Richard D. White, Costa Mesa, CA (US); David Robert Landon, Huntington Beach, CA (US); Jonathan Yeh, Brea, CA (US); Hieu Minh Luong, Westminster, CA (US); Deena Jamal Malaeb, San Ramon, CA (US); Parth Himanshu Parikh, Newport Beach, CA (US); Christopher Aguayo, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 19/077,896

(22) Filed: Mar. 12, 2025

(65) Prior Publication Data

US 2025/0213359 A1 Jul. 3, 2025

Related U.S. Application Data

(63) Continuation of application No. 18/626,109, filed on Apr. 3, 2024, which is a continuation of application No. PCT/US2022/047316, filed on Oct. 20, 2022.

(Continued)

(51) Int. Cl.
*A61F 2/24* (2006.01)

(52) U.S. Cl.
CPC .................................. *A61F 2/243* (2013.01)

(58) Field of Classification Search
CPC .......... A61F 2/24; A61F 2/243; A61F 2/2436; A61F 2/2427; A61F 2250/0062; A61F 2/9522; A61F 2/9524
See application file for complete search history.

(56) References Cited

U.S. PATENT DOCUMENTS 3,409,013 A 11/1968 Berry
3,472,230 A 10/1969 Fogarty
(Continued)

FOREIGN PATENT DOCUMENTS

CA 2304325 A1 10/2000
DE 2246526 A1 3/1973
(Continued)

OTHER PUBLICATIONS

Neale, Todd, "Flushing TAVI Valves With Carbon Dioxide May Protect Against Brain Injury", News > Conference News, EuroPCR 2023, TCTMD, May 16, 2023, Paris France.
(Continued)

*Primary Examiner* — Alvin J Stewart
(74) *Attorney, Agent, or Firm* — Thomas C. Richardson

(57) ABSTRACT

A loading assembly, can include a support tube configured to be disposed over a shaft of a delivery apparatus, a funnel member disposed over a first end portion of the support tube and configured to be disposed over at least a portion of a medical device, a first clamp member disposed over a portion of the funnel member, and a second clamp member disposed over a second end portion of the support tube. The funnel member can be axially advanced over a medical device, or the medical device can be retracted inside the funnel member to radially compresses the medical device.

25 Claims, 93 Drawing Sheets

Related U.S. Application Data

(60) Provisional application No. 63/272,577, filed on Oct. 27, 2021.

(56) References Cited

U.S. PATENT DOCUMENTS 3,548,417 A 12/1970 Kisher
3,587,115 A 6/1971 Shiley
3,657,744 A 4/1972 Ersek
3,671,979 A 6/1972 Moulopoulos
3,714,671 A 2/1973 Edwards et al.
3,739,402 A 6/1973 Cooley et al.
3,755,823 A 9/1973 Hancock
4,011,947 A 3/1977 Sawyer
4,035,849 A 7/1977 Angell et al.
4,056,854 A 11/1977 Boretos et al.
4,079,468 A 3/1978 Liotta et al.
4,106,129 A 8/1978 Carpentier et al.
4,204,283 A 5/1980 Bellhouse et al.
4,222,126 A 9/1980 Boretos et al.
4,265,694 A 5/1981 Boretos et al.
4,297,749 A 11/1981 Davis et al.
4,339,831 A 7/1982 Johnson
4,340,977 A 7/1982 Brownlee et al.
4,343,048 A 8/1982 Ross et al.
4,345,340 A 8/1982 Rosen
4,373,216 A 2/1983 Klawitter
4,406,022 A 9/1983 Roy
4,470,157 A 9/1984 Love
4,477,930 A 10/1984 Totten et al.
4,490,859 A 1/1985 Black et al.
4,535,483 A 8/1985 Klawitter et al.
4,553,545 A 11/1985 Maass et al.
4,574,803 A 3/1986 Storz
4,592,340 A 6/1986 Boyles
4,605,407 A 8/1986 Black et al.
4,612,011 A 9/1986 Kautzky
4,643,732 A 2/1987 Pietsch et al.
4,655,771 A 4/1987 Wallsten
4,692,164 A 9/1987 Dzemeshkevich et al.
4,733,665 A 3/1988 Palmaz
4,759,758 A 7/1988 Gabbay
4,762,128 A 8/1988 Rosenbluth
4,777,951 A 10/1988 Cribier et al.
4,787,899 A 11/1988 Lazarus
4,787,901 A 11/1988 Baykut
4,796,629 A 1/1989 Grayzel
4,829,990 A 5/1989 Thuroff et al.
4,851,001 A 7/1989 Taheri
4,856,516 A 8/1989 Hillstead
4,865,600 A 9/1989 Carpentier et al.
4,878,495 A 11/1989 Grayzel
4,878,906 A 11/1989 Lindemann et al.
4,883,458 A 11/1989 Shiber
4,922,905 A 5/1990 Strecker
4,966,604 A 10/1990 Reiss
4,979,939 A 12/1990 Shiber
4,986,830 A 1/1991 Owens et al.
4,994,077 A 2/1991 Dobben
5,007,896 A 4/1991 Shiber
5,026,366 A 6/1991 Leckrone
5,032,128 A 7/1991 Alonso
5,037,434 A 8/1991 Lane
5,047,041 A 9/1991 Samuels
5,059,177 A 10/1991 Towne et al.
5,080,668 A 1/1992 Bolz et al.
5,085,635 A 2/1992 Cragg
5,089,015 A 2/1992 Ross
5,108,370 A 4/1992 Walinsky
5,152,771 A 10/1992 Sabbaghian et al.
5,163,953 A 11/1992 Vince
5,167,628 A 12/1992 Boyles
5,192,297 A 3/1993 Hull
5,232,446 A 8/1993 Arney
5,266,073 A 11/1993 Wall
5,282,847 A 2/1994 Trescony et al.
5,295,958 A 3/1994 Shturman
5,326,371 A 7/1994 Love et al.
5,332,402 A 7/1994 Teitelbaum
5,360,444 A 11/1994 Kusuhara
5,370,685 A 12/1994 Stevens
5,397,351 A 3/1995 Pavcnik et al.
5,411,055 A 5/1995 Kane
5,411,522 A 5/1995 Trott
5,411,552 A 5/1995 Andersen et al.
5,415,667 A 5/1995 Frater
5,443,446 A 8/1995 Shturman
5,480,424 A 1/1996 Cox
5,500,014 A 3/1996 Quijano et al.
5,545,209 A 8/1996 Roberts et al.
5,545,214 A 8/1996 Stevens
5,549,665 A 8/1996 Vesely et al.
5,554,185 A 9/1996 Block et al.
5,571,175 A 11/1996 Vanney et al.
5,591,185 A 1/1997 Kilmer et al.
5,599,305 A 2/1997 Hermann et al.
5,607,464 A 3/1997 Trescony et al.
5,609,626 A 3/1997 Quijano et al.
5,639,274 A 6/1997 Fischell et al.
5,665,115 A 9/1997 Cragg
5,697,382 A 12/1997 Love et al.
5,716,417 A 2/1998 Girard et al.
5,728,068 A 3/1998 Leone et al.
5,749,890 A 5/1998 Shaknovich
5,756,476 A 5/1998 Epstein et al.
5,769,812 A 6/1998 Stevens et al.
5,800,508 A 9/1998 Goicoechea et al.
5,840,081 A 11/1998 Andersen et al.
5,855,597 A 1/1999 Jayaraman
5,855,601 A 1/1999 Bessler et al.
5,855,602 A 1/1999 Angell
5,906,619 A 5/1999 Olson et al.
5,925,063 A 7/1999 Khosravi
5,957,949 A 9/1999 Leonhardt et al.
5,968,068 A 10/1999 Dehdashtian et al.
5,992,000 A * 11/1999 Humphrey .............. A61F 2/958 29/516
6,027,525 A 2/2000 Suh et al.
6,042,607 A 3/2000 Williamson, IV et al.
6,063,092 A * 5/2000 Shin ........................ A61F 2/958 606/108
6,068,635 A * 5/2000 Gianotti ................ A61F 2/9526 606/198
6,086,612 A 7/2000 Jansen
6,113,631 A 9/2000 Jansen
6,132,473 A 10/2000 Williams et al.
6,168,614 B1 1/2001 Andersen et al.
6,171,335 B1 1/2001 Wheatley et al.
6,174,327 B1 1/2001 Mertens et al.
6,210,408 B1 4/2001 Chandrasekaran et al.
6,217,585 B1 4/2001 Houser et al.
6,221,091 B1 4/2001 Khosravi
6,231,602 B1 5/2001 Carpentier et al.
6,245,040 B1 6/2001 Inderbitzen et al.
6,245,102 B1 6/2001 Jayaraman
6,251,093 B1 6/2001 Valley et al.
6,287,339 B1 9/2001 Vazquez et al.
6,299,637 B1 10/2001 Shaolian et al.
6,302,906 B1 10/2001 Goicoechea et al.
6,306,141 B1 10/2001 Jervis
6,312,465 B1 11/2001 Griffin et al.
6,338,740 B1 1/2002 Carpentier
6,350,277 B1 2/2002 Kocur
6,358,277 B1 3/2002 Duran
6,379,372 B1 4/2002 Dehdashtian et al.
6,425,916 B1 7/2002 Garrison et al.
6,440,164 B1 8/2002 Di Matteo et al.
6,454,799 B1 9/2002 Schreck
6,458,153 B1 10/2002 Bailey et al.
6,461,382 B1 10/2002 Cao
6,468,660 B2 10/2002 Ogle et al.
6,482,228 B1 11/2002 Norred
6,488,704 B1 12/2002 Connelly et al.
6,527,800 B1 3/2003 McGuckin, Jr. et al.
6,527,979 B2 3/2003 Constantz et al.

(56) References Cited

U.S. PATENT DOCUMENTS 6,540,782 B1 4/2003 Snyders
6,569,196 B1 5/2003 Vesely
6,575,959 B1 6/2003 Sarge et al.
6,582,462 B1 6/2003 Andersen et al.
6,605,112 B1 8/2003 Moll et al.
6,610,088 B1 8/2003 Gabbay
6,629,534 B1 10/2003 St. Goar et al.
6,676,698 B2 1/2004 McGuckin, Jr. et al.
6,695,878 B2 2/2004 McGuckin, Jr. et al.
6,712,836 B1 3/2004 Berg et al.
6,716,207 B2 4/2004 Farnholtz
6,729,356 B1 5/2004 Baker et al.
6,730,118 B2 5/2004 Spenser et al.
6,733,525 B2 5/2004 Yang et al.
6,746,422 B1 6/2004 Noriega et al.
6,749,560 B1 6/2004 Konstorum et al.
6,767,362 B2 7/2004 Schreck
6,780,200 B2 8/2004 Jansen
6,790,229 B1 9/2004 Berreklouw
6,790,230 B2 9/2004 Beyersdorf et al.
6,830,584 B1 12/2004 Seguin
6,875,231 B2 4/2005 Anduiza et al.
6,893,460 B2 5/2005 Spenser et al.
6,908,481 B2 6/2005 Cribier
6,974,476 B2 12/2005 McGuckin, Jr. et al.
7,018,406 B2 3/2006 Seguin et al.
7,186,265 B2 3/2007 Sharkawy et al.
7,192,440 B2 3/2007 Andreas et al.
7,198,646 B2 4/2007 Figulla et al.
7,201,772 B2 4/2007 Schwammenthal et al.
7,276,078 B2 10/2007 Spenser et al.
7,276,084 B2 10/2007 Yang et al.
7,318,278 B2 1/2008 Zhang et al.
7,374,571 B2 5/2008 Pease et al.
7,381,210 B2 6/2008 Zarbatany et al.
7,381,219 B2 6/2008 Salahieh et al.
7,393,360 B2 7/2008 Spenser et al.
7,429,269 B2 9/2008 Schwammenthal et al.
7,442,204 B2 10/2008 Schwammenthal et al.
7,445,631 B2 11/2008 Salahieh et al.
7,462,191 B2 12/2008 Spenser et al.
7,510,575 B2 3/2009 Spenser et al.
7,524,330 B2 4/2009 Berreklouw
7,530,253 B2 5/2009 Spenser et al.
7,553,324 B2 6/2009 Andreas et al.
7,579,381 B2 8/2009 Dove
7,585,321 B2 9/2009 Cribier
7,618,446 B2 11/2009 Andersen et al.
7,621,948 B2 11/2009 Herrmann et al.
7,704,222 B2 4/2010 Wilk et al.
7,736,327 B2 6/2010 Wilk et al.
7,748,389 B2 7/2010 Salahieh et al.
7,753,949 B2 7/2010 Lamphere et al.
7,806,919 B2 10/2010 Bloom et al.
7,824,443 B2 11/2010 Salahieh et al.
7,837,727 B2 11/2010 Goetz et al.
7,892,281 B2 2/2011 Seguin et al.
7,914,569 B2 3/2011 Nguyen et al.
7,914,575 B2 3/2011 Guyenot et al.
7,959,672 B2 6/2011 Salahieh et al.
7,972,378 B2 7/2011 Tabor et al.
7,981,151 B2 7/2011 Rowe
7,993,392 B2 8/2011 Righini et al.
7,993,394 B2 8/2011 Hariton et al.
8,007,992 B2 8/2011 Tian et al.
8,016,877 B2 9/2011 Seguin et al.
8,029,556 B2 10/2011 Rowe
8,052,750 B2 11/2011 Tuval et al.
8,070,800 B2 12/2011 Lock et al.
8,070,802 B2 12/2011 Lamphere et al.
8,075,615 B2 12/2011 Eberhardt et al.
8,080,054 B2 12/2011 Rowe
8,092,520 B2 1/2012 Quadri
8,092,521 B2 1/2012 Figulla et al.
8,109,996 B2 2/2012 Stacchino et al.
8,118,866 B2 2/2012 Herrmann et al.
8,136,218 B2 3/2012 Millwee et al.
8,137,398 B2 3/2012 Tuval et al.
8,157,852 B2 4/2012 Bloom et al.
8,167,932 B2 5/2012 Bourang et al.
8,167,934 B2 5/2012 Styrc et al.
8,182,530 B2 5/2012 Huber
8,206,437 B2 6/2012 Bonhoeffer et al.
8,216,174 B2 7/2012 Wilk et al.
8,216,301 B2 7/2012 Bonhoeffer et al.
8,219,229 B2 7/2012 Cao et al.
8,220,121 B2 * 7/2012 Hendriksen ........... A61F 2/0105
254/134.3 FT
8,236,045 B2 8/2012 Benichou et al.
8,246,675 B2 8/2012 Zegdi
8,246,678 B2 8/2012 Salahieh et al.
8,252,051 B2 8/2012 Chau et al.
8,252,052 B2 8/2012 Salahieh et al.
8,287,584 B2 10/2012 Salahieh et al.
8,313,525 B2 11/2012 Tuval et al.
8,317,858 B2 11/2012 Straubinger et al.
8,323,335 B2 12/2012 Rowe et al.
8,337,541 B2 12/2012 Quadri et al.
8,353,953 B2 1/2013 Giannetti et al.
8,398,704 B2 3/2013 Straubinger et al.
8,403,983 B2 3/2013 Quadri et al.
8,414,644 B2 4/2013 Quadri et al.
8,414,645 B2 4/2013 Dwork et al.
8,416,643 B2 4/2013 Magee
8,444,689 B2 5/2013 Zhang
8,449,599 B2 5/2013 Chau et al.
8,454,685 B2 6/2013 Hariton et al.
8,460,368 B2 6/2013 Taylor et al.
8,460,370 B2 6/2013 Zakay et al.
8,470,023 B2 6/2013 Eidenschink et al.
8,470,028 B2 6/2013 Thornton et al.
8,475,521 B2 7/2013 Suri et al.
8,475,523 B2 7/2013 Duffy
8,479,380 B2 7/2013 Malewicz et al.
8,491,650 B2 7/2013 Wiemeyer et al.
8,500,733 B2 8/2013 Watson
8,500,798 B2 8/2013 Rowe et al.
8,511,244 B2 8/2013 Holecek et al.
8,512,401 B2 8/2013 Murray, III et al.
8,518,096 B2 8/2013 Nelson
8,518,106 B2 8/2013 Duffy et al.
8,562,663 B2 * 10/2013 Mearns ................. A61F 2/2412
623/2.11
8,579,963 B2 11/2013 Tabor
8,579,964 B2 11/2013 Lane et al.
8,591,570 B2 11/2013 Revuelta et al.
8,617,236 B2 12/2013 Paul et al.
8,640,521 B2 2/2014 Righini et al.
8,647,381 B2 2/2014 Essinger et al.
8,652,145 B2 * 2/2014 Maimon ................ B21D 41/00
606/198
8,652,201 B2 2/2014 Oberti et al.
8,652,202 B2 * 2/2014 Alon ..................... A61F 2/2439
623/2.11
8,652,203 B2 2/2014 Quadri et al.
8,668,733 B2 3/2014 Haug et al.
8,679,174 B2 3/2014 Ottma et al.
8,679,404 B2 3/2014 Liburd et al.
8,685,086 B2 4/2014 Navia et al.
8,721,708 B2 5/2014 Seguin et al.
8,721,714 B2 5/2014 Kelley
8,728,154 B2 5/2014 Alkhatib
8,728,155 B2 5/2014 Montorfano et al.
8,740,974 B2 6/2014 Lambrecht et al.
8,740,976 B2 6/2014 Tran et al.
8,747,458 B2 * 6/2014 Tuval .................... A61F 2/2427
623/2.11
8,747,459 B2 6/2014 Nguyen et al.
8,758,432 B2 6/2014 Solem
8,764,818 B2 7/2014 Gregg
8,771,344 B2 7/2014 Tran et al.
8,778,020 B2 7/2014 Gregg et al.
8,784,337 B2 7/2014 Voeller et al.
8,784,478 B2 7/2014 Tuval et al.

(56) References Cited

U.S. PATENT DOCUMENTS

| | | | | |
|---|---|---|---|---|
| 8,784,481 | B2 | 7/2014 | Alkhatib et al. | |
| 8,790,387 | B2 | 7/2014 | Nguyen et al. | |
| 8,795,357 | B2 | 8/2014 | Yohanan et al. | |
| 8,808,356 | B2 | 8/2014 | Braido et al. | |
| 8,828,078 | B2 | 9/2014 | Salahieh et al. | |
| 8,828,079 | B2 | 9/2014 | Thielen et al. | |
| 8,834,564 | B2 * | 9/2014 | Tuval | A61F 2/24 623/2.38 |
| 8,858,620 | B2 | 10/2014 | Salahieh et al. | |
| 8,870,948 | B1 | 10/2014 | Erzberger et al. | |
| 8,870,950 | B2 | 10/2014 | Hacohen | |
| 8,876,893 | B2 | 11/2014 | Dwork et al. | |
| 8,911,455 | B2 | 12/2014 | Quadri et al. | |
| 8,926,693 | B2 | 1/2015 | Duffy et al. | |
| 8,926,694 | B2 | 1/2015 | Costello | |
| 8,939,960 | B2 | 1/2015 | Rosenman et al. | |
| 8,945,209 | B2 | 2/2015 | Bonyuet et al. | |
| 8,961,593 | B2 | 2/2015 | Bonhoeffer et al. | |
| 8,961,595 | B2 | 2/2015 | Alkhatib | |
| 8,974,524 | B2 | 3/2015 | Yeung et al. | |
| 8,979,922 | B2 | 3/2015 | Jayasinghe et al. | |
| 8,986,375 | B2 | 3/2015 | Garde et al. | |
| 8,998,980 | B2 | 4/2015 | Shipley et al. | |
| 9,005,273 | B2 | 4/2015 | Salahieh et al. | |
| 9,011,521 | B2 | 4/2015 | Haug et al. | |
| 9,011,523 | B2 | 4/2015 | Seguin | |
| 9,011,524 | B2 | 4/2015 | Eberhardt | |
| 9,028,545 | B2 | 5/2015 | Taylor | |
| 9,034,032 | B2 | 5/2015 | McLean et al. | |
| 9,055,937 | B2 | 6/2015 | Rowe et al. | |
| 9,066,801 | B2 | 6/2015 | Kovalsky et al. | |
| 9,078,749 | B2 | 7/2015 | Lutter et al. | |
| 9,078,751 | B2 | 7/2015 | Naor | |
| 9,125,738 | B2 | 9/2015 | Figulla et al. | |
| 9,173,737 | B2 | 11/2015 | Hill et al. | |
| 9,180,004 | B2 | 11/2015 | Alkhatib | |
| 9,186,249 | B2 | 11/2015 | Rolando et al. | |
| 9,277,990 | B2 | 3/2016 | Klima et al. | |
| 9,277,993 | B2 | 3/2016 | Gamarra et al. | |
| 9,289,291 | B2 | 3/2016 | Gorman, III et al. | |
| 9,295,551 | B2 | 3/2016 | Straubinger et al. | |
| 9,445,897 | B2 | 9/2016 | Bishop et al. | |
| 9,456,877 | B2 | 10/2016 | Weitzner et al. | |
| 9,681,968 | B2 | 6/2017 | Goetz et al. | |
| 9,687,345 | B2 | 6/2017 | Rabito et al. | |
| 9,700,329 | B2 | 7/2017 | Metzger et al. | |
| 9,700,411 | B2 | 7/2017 | Klima et al. | |
| 9,724,083 | B2 | 8/2017 | Quadri et al. | |
| 9,730,790 | B2 | 8/2017 | Quadri et al. | |
| 9,730,791 | B2 | 8/2017 | Ratz et al. | |
| 9,795,479 | B2 | 10/2017 | Lim et al. | |
| 9,833,313 | B2 | 12/2017 | Board et al. | |
| 9,861,473 | B2 | 1/2018 | Lafontaine | |
| 9,861,476 | B2 | 1/2018 | Salahieh et al. | |
| 9,861,477 | B2 | 1/2018 | Backus et al. | |
| 9,867,698 | B2 | 1/2018 | Kovalsky et al. | |
| 9,877,830 | B2 | 1/2018 | Lim et al. | |
| 9,889,029 | B2 * | 2/2018 | Li | A61F 2/82 |
| 9,895,225 | B2 | 2/2018 | Rolando et al. | |
| 9,925,045 | B2 | 3/2018 | Creaven et al. | |
| 10,004,599 | B2 | 6/2018 | Rabito et al. | |
| 10,016,275 | B2 * | 7/2018 | Nyuli | A61F 2/2436 |
| 10,022,211 | B2 * | 7/2018 | Braido | A61F 2/2418 |
| 10,039,642 | B2 * | 8/2018 | Hillukka | A61F 2/2418 |
| 10,117,744 | B2 | 11/2018 | Ratz et al. | |
| 10,123,892 | B2 * | 11/2018 | Hacker | A61F 2/2415 |
| 10,149,760 | B2 * | 12/2018 | Johnson | B23P 11/025 |
| 10,179,044 | B2 | 1/2019 | Ratz et al. | |
| 10,219,897 | B2 | 3/2019 | Essinger et al. | |
| 10,350,065 | B2 | 7/2019 | Quadri | |
| 10,350,066 | B2 | 7/2019 | Cooper et al. | |
| 10,376,363 | B2 | 8/2019 | Quadri et al. | |
| 10,555,809 | B2 | 2/2020 | Hastings et al. | |
| 10,575,951 | B2 | 3/2020 | Johnson et al. | |
| 10,583,000 | B2 | 3/2020 | Ratz et al. | |
| 10,639,146 | B2 | 5/2020 | Quadri et al. | |
| 10,695,177 | B2 | 6/2020 | Hariton et al. | |
| 10,722,357 | B2 * | 7/2020 | High | A61F 2/2418 |
| 10,758,344 | B2 | 9/2020 | Hariton et al. | |
| 11,109,968 | B2 * | 9/2021 | Gale | A61F 2/2436 |
| 11,344,409 | B2 * | 5/2022 | Landon | B21D 39/04 |
| 11,406,499 | B2 | 8/2022 | Zhang et al. | |
| 11,452,598 | B2 | 9/2022 | Essinger et al. | |
| 11,672,658 | B2 | 6/2023 | Hariton et al. | |
| 11,684,474 | B2 * | 6/2023 | Srinimukesh | A61F 2/2436 623/2.11 |
| 11,701,225 | B2 | 7/2023 | Hammer et al. | |
| 11,903,829 | B1 | 2/2024 | Ma et al. | |
| 2001/0021872 | A1 | 9/2001 | Bailey et al. | |
| 2002/0032481 | A1 | 3/2002 | Gabbay | |
| 2002/0045929 | A1 | 4/2002 | Diaz | |
| 2002/0052644 | A1 | 5/2002 | Shaolian et al. | |
| 2002/0107565 | A1 | 8/2002 | Greenhalgh | |
| 2002/0123802 | A1 | 9/2002 | Snyders | |
| 2002/0173842 | A1 | 11/2002 | Buchanan | |
| 2003/0050694 | A1 | 3/2003 | Yang et al. | |
| 2003/0100939 | A1 | 5/2003 | Yodfat et al. | |
| 2003/0105517 | A1 | 6/2003 | White et al. | |
| 2003/0114913 | A1 | 6/2003 | Spenser et al. | |
| 2003/0120333 | A1 | 6/2003 | Ouriel et al. | |
| 2003/0130729 | A1 | 7/2003 | Paniagua et al. | |
| 2003/0149477 | A1 | 8/2003 | Gabbay | |
| 2003/0149478 | A1 | 8/2003 | Figulla et al. | |
| 2003/0158597 | A1 | 8/2003 | Quiachon et al. | |
| 2003/0176914 | A1 | 9/2003 | Rabkin et al. | |
| 2003/0199971 | A1 | 10/2003 | Tower et al. | |
| 2003/0212454 | A1 | 11/2003 | Scott et al. | |
| 2003/0220683 | A1 | 11/2003 | Minasian et al. | |
| 2004/0039436 | A1 | 2/2004 | Spenser et al. | |
| 2004/0092858 | A1 | 5/2004 | Wilson et al. | |
| 2004/0093075 | A1 | 5/2004 | Kuehne | |
| 2004/0117009 | A1 | 6/2004 | Cali et al. | |
| 2004/0133263 | A1 | 7/2004 | Dusbabek et al. | |
| 2004/0133273 | A1 | 7/2004 | Cox | |
| 2004/0186563 | A1 | 9/2004 | Lobbi | |
| 2004/0186565 | A1 | 9/2004 | Schreck | |
| 2004/0210307 | A1 | 10/2004 | Khairkhahan | |
| 2004/0215325 | A1 | 10/2004 | Penn et al. | |
| 2004/0225353 | A1 | 11/2004 | McGuckin et al. | |
| 2004/0236411 | A1 | 11/2004 | Sarac et al. | |
| 2004/0260389 | A1 | 12/2004 | Case et al. | |
| 2005/0033398 | A1 | 2/2005 | Seguin | |
| 2005/0075727 | A1 | 4/2005 | Wheatley | |
| 2005/0090887 | A1 | 4/2005 | Pryor | |
| 2005/0096738 | A1 | 5/2005 | Cali et al. | |
| 2005/0107872 | A1 | 5/2005 | Mensah et al. | |
| 2005/0137682 | A1 | 6/2005 | Justino | |
| 2005/0137686 | A1 | 6/2005 | Salahieh et al. | |
| 2005/0137687 | A1 | 6/2005 | Salahieh et al. | |
| 2005/0137688 | A1 | 6/2005 | Salahieh et al. | |
| 2005/0137691 | A1 | 6/2005 | Salahieh et al. | |
| 2005/0137698 | A1 | 6/2005 | Salahieh et al. | |
| 2005/0159811 | A1 | 7/2005 | Lane | |
| 2005/0182486 | A1 | 8/2005 | Gabbay | |
| 2005/0203614 | A1 | 9/2005 | Forster et al. | |
| 2005/0203617 | A1 | 9/2005 | Forster et al. | |
| 2005/0216079 | A1 | 9/2005 | MaCoviak | |
| 2005/0234546 | A1 | 10/2005 | Nugent et al. | |
| 2005/0288766 | A1 | 12/2005 | Plain et al. | |
| 2006/0020327 | A1 | 1/2006 | Lashinski et al. | |
| 2006/0025857 | A1 | 2/2006 | Bergheim et al. | |
| 2006/0058872 | A1 | 3/2006 | Salahieh et al. | |
| 2006/0095115 | A1 | 5/2006 | Bladillah et al. | |
| 2006/0142837 | A1 | 6/2006 | Haverkost et al. | |
| 2006/0149350 | A1 | 7/2006 | Patel et al. | |
| 2006/0161249 | A1 | 7/2006 | Realyvasquez et al. | |
| 2006/0173537 | A1 | 8/2006 | Yang et al. | |
| 2006/0195134 | A1 | 8/2006 | Crittenden | |
| 2006/0195183 | A1 | 8/2006 | Navia et al. | |
| 2006/0212110 | A1 | 9/2006 | Osborne et al. | |
| 2006/0229719 | A1 | 10/2006 | Marquez et al. | |
| 2006/0241745 | A1 | 10/2006 | Solem | |
| 2006/0259135 | A1 | 11/2006 | Navia et al. | |
| 2006/0259137 | A1 | 11/2006 | Artof et al. | |

(56) References Cited

U.S. PATENT DOCUMENTS

2006/0276874 A1 12/2006 Wilson et al.
2006/0293745 A1 12/2006 Carpentier et al.
2007/0005131 A1 1/2007 Taylor
2007/0010877 A1 1/2007 Salahieh et al.
2007/0027534 A1 2/2007 Bergheim et al.
2007/0043435 A1 2/2007 Seguin et al.
2007/0050021 A1 3/2007 Johnson
2007/0066863 A1 3/2007 Rafiee et al.
2007/0088431 A1 4/2007 Bourang et al.
2007/0100432 A1 5/2007 Case et al.
2007/0100439 A1 5/2007 Cangialosi et al.
2007/0112422 A1 5/2007 Dehdashtian
2007/0129794 A1 6/2007 Realyvasquez
2007/0142906 A1 6/2007 Figulla et al.
2007/0156224 A1 7/2007 Cioanta et al.
2007/0203503 A1 8/2007 Salahieh et al.
2007/0203575 A1 8/2007 Forster et al.
2007/0213813 A1 9/2007 Von Segesser et al.
2007/0239271 A1* 10/2007 Nguyen ................ A61F 2/9525 623/2.11
2007/0255394 A1 11/2007 Ryan
2007/0270943 A1 11/2007 Solem et al.
2008/0021546 A1 1/2008 Patz et al.
2008/0065011 A1 3/2008 Marchand et al.
2008/0071361 A1 3/2008 Tuval et al.
2008/0071362 A1 3/2008 Tuval et al.
2008/0071363 A1 3/2008 Tuval et al.
2008/0071366 A1 3/2008 Tuval et al.
2008/0071368 A1 3/2008 Tuval et al.
2008/0071369 A1 3/2008 Tuval et al.
2008/0082164 A1 4/2008 Friedman
2008/0082165 A1 4/2008 Wilson et al.
2008/0082166 A1 4/2008 Styrc et al.
2008/0097581 A1 4/2008 Shanley
2008/0114442 A1 5/2008 Mitchell et al.
2008/0125853 A1 5/2008 Bailey et al.
2008/0147179 A1 6/2008 Cai et al.
2008/0147183 A1 6/2008 Styrc
2008/0154355 A1 6/2008 Benichou et al.
2008/0161910 A1 7/2008 Revuelta et al.
2008/0177381 A1 7/2008 Navia et al.
2008/0183273 A1 7/2008 Mesana et al.
2008/0208328 A1 8/2008 Antocci et al.
2008/0208332 A1 8/2008 Lamphere et al.
2008/0221672 A1 9/2008 Lamphere et al.
2008/0228254 A1 9/2008 Ryan
2008/0255660 A1 10/2008 Guyenot et al.
2008/0255661 A1 10/2008 Straubinger et al.
2008/0281411 A1 11/2008 Berreklouw
2009/0005863 A1 1/2009 Goetz et al.
2009/0054968 A1 2/2009 Bonhoeffer et al.
2009/0054974 A1 2/2009 McGuckin, Jr. et al.
2009/0076598 A1 3/2009 Salahieh et al.
2009/0093876 A1* 4/2009 Nitzan .................. A61F 2/2427 623/2.11
2009/0112309 A1 4/2009 Jaramillo et al.
2009/0138079 A1 5/2009 Tuval et al.
2009/0157175 A1 6/2009 Benichou
2009/0164005 A1 6/2009 Dove et al.
2009/0171432 A1 7/2009 Von Segesser et al.
2009/0171447 A1 7/2009 Von Segesser et al.
2009/0171456 A1 7/2009 Kveen et al.
2009/0182413 A1 7/2009 Burkart et al.
2009/0188964 A1 7/2009 Orlov
2009/0216310 A1 8/2009 Straubinger et al.
2009/0216313 A1 8/2009 Straubinger et al.
2009/0216322 A1 8/2009 Le et al.
2009/0222076 A1 9/2009 Figulla et al.
2009/0234443 A1 9/2009 Ottma et al.
2009/0240320 A1 9/2009 Tuval et al.
2009/0270972 A1 10/2009 Lane
2009/0276027 A1 11/2009 Glynn
2009/0276040 A1 11/2009 Rowe et al.
2009/0281618 A1 11/2009 Hill et al.
2009/0281619 A1 11/2009 Le et al.
2009/0287296 A1 11/2009 Manasse
2009/0287299 A1 11/2009 Tabor et al.
2009/0292350 A1 11/2009 Eberhardt et al.
2009/0306768 A1 12/2009 Quadri
2009/0319037 A1 12/2009 Rowe et al.
2010/0016958 A1 1/2010 St. Goar et al.
2010/0024818 A1 2/2010 Stenzler et al.
2010/0049313 A1* 2/2010 Alon ..................... A61F 2/2439 623/2.11
2010/0069852 A1 3/2010 Kelley
2010/0114305 A1 5/2010 Kang et al.
2010/0131054 A1 5/2010 Tuval et al.
2010/0137979 A1 6/2010 Tuval et al.
2010/0145438 A1 6/2010 Barone
2010/0174362 A1 7/2010 Straubinger et al.
2010/0191326 A1 7/2010 Alkhatib
2010/0204781 A1 8/2010 Alkhatib
2010/0217382 A1 8/2010 Chau et al.
2010/0249894 A1 9/2010 Oba et al.
2010/0249911 A1 9/2010 Alkhatib
2010/0256723 A1 10/2010 Murray
2010/0262231 A1 10/2010 Tuval et al.
2010/0292780 A1* 11/2010 Straubinger .............. A61F 2/95 623/1.23
2010/0305685 A1 12/2010 Millwee et al.
2010/0312333 A1 12/2010 Navia et al.
2011/0015616 A1 1/2011 Straubinger et al.
2011/0015729 A1 1/2011 Jimenez et al.
2011/0029072 A1 2/2011 Gabbay
2011/0137397 A1 6/2011 Chau et al.
2011/0178597 A9 7/2011 Navia et al.
2011/0208290 A1 8/2011 Straubinger et al.
2011/0208296 A1* 8/2011 Duffy .................... A61F 2/2436 623/2.11
2011/0208297 A1 8/2011 Tuval et al.
2011/0208298 A1 8/2011 Tuval et al.
2011/0224785 A1 9/2011 Hacohen
2011/0238159 A1 9/2011 Guyenot et al.
2011/0264196 A1 10/2011 Savage et al.
2011/0264198 A1 10/2011 Murray, III et al.
2011/0288634 A1 11/2011 Tuval et al.
2011/0313515 A1 12/2011 Quadri et al.
2011/0319989 A1 12/2011 Lane et al.
2012/0022639 A1 1/2012 Hacohen et al.
2012/0035722 A1 2/2012 Tuval
2012/0041550 A1 2/2012 Salahieh et al.
2012/0046741 A1 2/2012 Tuval et al.
2012/0046742 A1 2/2012 Tuval et al.
2012/0073126 A1 3/2012 Adams et al.
2012/0078360 A1 3/2012 Rafiee
2012/0101570 A1 4/2012 Tuval et al.
2012/0101571 A1 4/2012 Thambar et al.
2012/0101572 A1 4/2012 Kovalsky et al.
2012/0123529 A1 5/2012 Levi et al.
2012/0185039 A1 7/2012 Tuval et al.
2012/0197386 A1 8/2012 Von Segesser et al.
2012/0209374 A1 8/2012 Bonhoeffer et al.
2012/0215303 A1 8/2012 Quadri et al.
2012/0271398 A1 10/2012 Essinger et al.
2012/0283823 A1 11/2012 Bonhoeffer et al.
2012/0290062 A1 11/2012 McNamara et al.
2012/0296418 A1 11/2012 Bonyuet et al.
2012/0310328 A1 12/2012 Olson et al.
2012/0310336 A1 12/2012 Figulla et al.
2013/0006294 A1 1/2013 Kashkarov et al.
2013/0035759 A1 2/2013 Gross et al.
2013/0073035 A1 3/2013 Tuval et al.
2013/0079869 A1 3/2013 Straubinger et al.
2013/0172992 A1 7/2013 Gross et al.
2013/0190861 A1 7/2013 Chau et al.
2013/0190862 A1 7/2013 Pintor et al.
2013/0197622 A1 8/2013 Mitra et al.
2013/0211508 A1 8/2013 Lane et al.
2013/0253635 A1 9/2013 Straubinger et al.
2013/0253642 A1 9/2013 Brecker
2013/0310928 A1 11/2013 Morriss et al.
2013/0331929 A1 12/2013 Mitra et al.
2013/0338766 A1 12/2013 Hastings et al.
2013/0345786 A1 12/2013 Behan

(56) References Cited

U.S. PATENT DOCUMENTS

2014/0018912 A1 1/2014 Delaloye et al.
2014/0025163 A1 1/2014 Padala et al.
2014/0039611 A1 2/2014 Lane et al.
2014/0052237 A1 2/2014 Lane et al.
2014/0100651 A1 4/2014 Kheradvar et al.
2014/0163668 A1 6/2014 Rafiee
2014/0172077 A1 6/2014 Bruchman et al.
2014/0172083 A1 6/2014 Bruchman et al.
2014/0194981 A1 7/2014 Menk et al.
2014/0207231 A1 7/2014 Hacohen et al.
2014/0214157 A1 7/2014 Bortlein et al.
2014/0222136 A1 8/2014 Geist et al.
2014/0222139 A1 8/2014 Nguyen et al.
2014/0222142 A1 8/2014 Kovalsky et al.
2014/0222144 A1 8/2014 Eberhardt et al.
2014/0243966 A1 8/2014 Garde et al.
2014/0257467 A1 9/2014 Lane et al.
2014/0277390 A1 9/2014 Ratz et al.
2014/0277403 A1 9/2014 Peter
2014/0277412 A1 9/2014 Bortlein et al.
2014/0277422 A1 9/2014 Ratz et al.
2014/0277426 A1 9/2014 Dakin et al.
2014/0277427 A1 9/2014 Ratz et al.
2014/0296973 A1 10/2014 Bergheim et al.
2014/0296975 A1 10/2014 Tegels et al.
2014/0303719 A1 10/2014 Cox et al.
2014/0309728 A1 10/2014 Dehdashtian et al.
2014/0324160 A1 10/2014 Benichou et al.
2014/0324164 A1 10/2014 Gross et al.
2014/0330368 A1 11/2014 Gloss et al.
2014/0330371 A1 11/2014 Gloss et al.
2014/0330372 A1 11/2014 Weston et al.
2014/0336754 A1 11/2014 Gurskis et al.
2014/0343669 A1 11/2014 Lane et al.
2014/0343670 A1 11/2014 Bakis et al.
2014/0350666 A1 11/2014 Righini
2014/0350668 A1 11/2014 Delaloye et al.
2014/0358223 A1 12/2014 Rafiee et al.
2014/0364939 A1 12/2014 Deshmukh et al.
2014/0364943 A1 12/2014 Conklin
2014/0371842 A1 12/2014 Marquez et al.
2014/0371844 A1 12/2014 Dale et al.
2014/0371847 A1 12/2014 Madrid et al.
2014/0371848 A1 12/2014 Murray, III et al.
2015/0005863 A1 1/2015 Para
2015/0018944 A1 1/2015 O'Connell et al.
2015/0039083 A1 2/2015 Rafiee
2015/0142100 A1 5/2015 Morriss et al.
2015/0142103 A1 5/2015 Vidlund
2015/0148731 A1 5/2015 Mcnamara et al.
2015/0173897 A1 6/2015 Raanani et al.
2015/0196390 A1 7/2015 Ma et al.
2015/0209141 A1 7/2015 Braido et al.
2015/0272737 A1 10/2015 Dale et al.
2015/0297346 A1 10/2015 Duffy et al.
2015/0297381 A1* 10/2015 Essinger ............... A61F 2/2427
623/1.26
2015/0335429 A1 11/2015 Morriss et al.
2015/0351903 A1 12/2015 Morriss et al.
2015/0359629 A1 12/2015 Ganesan et al.
2016/0000591 A1 1/2016 Lei et al.
2016/0030169 A1 2/2016 Shahriari
2016/0030170 A1 2/2016 Alkhatib et al.
2016/0030171 A1 2/2016 Quijano et al.
2016/0038280 A1 2/2016 Morriss et al.
2016/0038281 A1 2/2016 Delaloye et al.
2016/0074160 A1 3/2016 Christianson et al.
2016/0106537 A1 4/2016 Christianson et al.
2016/0113765 A1 4/2016 Ganesan et al.
2016/0113768 A1 4/2016 Ganesan et al.
2016/0128819 A1* 5/2016 Giordano .............. A61F 2/2427
623/2.11
2016/0143732 A1 5/2016 Glimsdale
2016/0158010 A1 6/2016 Lim et al.
2016/0166383 A1 6/2016 Lim et al.
2016/0184097 A1 6/2016 Lim et al.
2016/0199206 A1 7/2016 Lim et al.
2016/0213473 A1 7/2016 Hacohen et al.
2016/0235529 A1 8/2016 Ma et al.
2016/0278923 A1 9/2016 Krans et al.
2016/0279386 A1 9/2016 Dale et al.
2016/0310267 A1 10/2016 Zeng et al.
2017/0042678 A1 2/2017 Ganesan et al.
2017/0079785 A1 3/2017 Li
2017/0128209 A1 5/2017 Morriss et al.
2017/0216023 A1 8/2017 Lane et al.
2017/0216575 A1 8/2017 Asleson et al.
2017/0257902 A1 9/2017 Xing et al.
2017/0258614 A1 9/2017 Griffin
2017/0325945 A1 11/2017 Dale et al.
2017/0325954 A1 11/2017 Perszyk
2017/0333186 A1 11/2017 Spargias
2017/0348096 A1 12/2017 Anderson
2017/0367821 A1* 12/2017 Landon ................. A61F 2/2412
2017/0367823 A1 12/2017 Hariton et al.
2018/0014931 A1 1/2018 Morriss et al.
2018/0021129 A1 1/2018 Peterson et al.
2018/0028314 A1 2/2018 Ekvall et al.
2018/0055629 A1 3/2018 Oba et al.
2018/0055636 A1 3/2018 Valencia et al.
2018/0085218 A1 3/2018 Eidenschink
2018/0110534 A1 4/2018 Gavala et al.
2018/0110622 A1 4/2018 Gregg et al.
2018/0116790 A1 5/2018 Ratz et al.
2018/0126119 A1 5/2018 McNiven et al.
2018/0206983 A1 7/2018 Noe et al.
2018/0214664 A1 8/2018 Kim et al.
2018/0296341 A1 10/2018 Noe et al.
2018/0344457 A1 12/2018 Gross et al.
2018/0344490 A1 12/2018 Fox et al.
2019/0008639 A1 1/2019 Landon et al.
2019/0008640 A1 1/2019 Cooper et al.
2019/0060072 A1 2/2019 Zeng
2019/0262129 A1 8/2019 Cooper et al.
2020/0000579 A1 1/2020 Manash et al.
2020/0108225 A1 4/2020 Jamal et al.
2020/0138572 A1 5/2020 Zhao et al.
2020/0323668 A1 10/2020 Diedering et al.
2020/0345494 A1 11/2020 Srinimukesh et al.
2020/0352718 A1 11/2020 Rowe et al.
2021/0015615 A1 1/2021 Groothuis et al.
2021/0145576 A1 5/2021 Becerra et al.
2021/0186692 A1* 6/2021 Frisby ................... A61F 2/9525
2021/0228354 A1 7/2021 Rafiee et al.
2021/0259835 A1 8/2021 Tyler, II et al.
2021/0307900 A1 10/2021 Hacohen
2021/0378817 A1 12/2021 Nia et al.
2021/0386544 A1 12/2021 Cooper et al.
2022/0142777 A1 5/2022 Scheinblum et al.
2022/0287833 A1* 9/2022 Landon .................. B21D 39/04
2022/0287836 A1 9/2022 Landon et al.
2022/0346991 A1* 11/2022 Higgins ................ A61F 2/9522
2022/0346993 A1 11/2022 Srinimukesh et al.
2022/0401243 A1 12/2022 Diedering et al.
2023/0000624 A1 1/2023 Okabe et al.
2023/0109958 A1* 4/2023 Duffy ........................ A61F 2/95
29/446
2023/0111435 A1* 4/2023 O'Connor ............. A61F 2/0095
623/1.12
2023/0200980 A1 6/2023 Peterson et al.
2023/0218391 A1 7/2023 Dass et al.
2023/0380963 A1 11/2023 Kaufman et al.
2023/0390052 A1 12/2023 Okafor et al.
2023/0404753 A1 12/2023 Luong et al.
2024/0008978 A1 1/2024 Nawalakhe et al.
2024/0091000 A1 3/2024 King et al.
2024/0225830 A1* 7/2024 Frisby ................... A61F 2/9525
2024/0366372 A1* 11/2024 Becerra ................... A61F 2/243

FOREIGN PATENT DOCUMENTS

DE 19532846 A1 3/1997
DE 19546692 A1 6/1997
DE 19857887 A1 7/2000

(56) References Cited

FOREIGN PATENT DOCUMENTS

DE 19907646 A1 8/2000
DE 10010074 A1 10/2001
DE 10049812 A1 4/2002
DE 10049813 C1 4/2002
DE 10049814 A1 4/2002
DE 10049815 A1 4/2002
DE 102006052564 B3 12/2007
EP 0103546 A1 3/1984
EP 0144167 A2 6/1985
EP 0592410 A1 4/1994
EP 0597967 A1 5/1994
EP 0850607 A1 7/1998
EP 1057460 A1 12/2000
EP 1088529 A2 4/2001
EP 1171059 A1 1/2002
EP 1239901 A1 9/2002
EP 1255510 A1 11/2002
EP 1259194 A1 11/2002
EP 1369098 A1 12/2003
EP 1469797 A1 10/2004
EP 1472996 A1 11/2004
EP 1570809 A1 9/2005
EP 1653888 A2 5/2006
EP 1849440 A1 10/2007
EP 1935377 A1 6/2008
EP 2124826 A1 12/2009
EP 2168536 A1 3/2010
EP 2413842 A1 2/2012
EP 2446915 A1 5/2012
EP 2745805 A1 6/2014
EP 2749254 A1 7/2014
EP 2750630 A1 7/2014
EP 2777616 A1 9/2014
EP 2777617 A1 9/2014
EP 2918249 A2 9/2015
EP 2948103 A2 12/2015
EP 2967858 A2 1/2016
EP 2168536 B1 4/2016
EP 3037064 A1 6/2016
EP 3046511 A2 7/2016
EP 3057541 A1 8/2016
EP 3075354 A2 10/2016
EP 3139864 A1 3/2017
EP 3142603 A1 3/2017
EP 3184083 A1 6/2017
EP 2413842 B1 8/2017
EP 2446915 B1 1/2018
EP 3294220 A1 3/2018
EP 3417813 A1 12/2018
EP 3570779 A1 11/2019
EP 2918249 B1 4/2020
EP 2777616 B1 8/2020
EP 2777617 B1 9/2022
FR 2788217 A1 7/2000
GB 1264471 A 2/1972
GB 1315844 A 5/1973
GB 2056023 A 3/1981
GB 2398245 A 8/2004
SU 1271508 A1 11/1986
WO 9116041 A1 10/1991
WO 9117720 A1 11/1991
WO 9217118 A1 10/1992
WO 9301768 A1 2/1993
WO 9724080 A1 7/1997
WO 9829057 A1 7/1998
WO 9933414 A1 7/1999
WO 9940964 A1 8/1999
WO 9947075 A1 9/1999
WO WO-2000018333 A1 4/2000
WO 0041652 A1 7/2000
WO 0047139 A1 8/2000
WO 0061034 A1 10/2000
WO WO-2001028459 A1 4/2001
WO WO-2001035878 A2 5/2001
WO WO-2001049213 A2 7/2001
WO WO-2001054624 A1 8/2001
WO WO-2001054625 A1 8/2001
WO WO-2001064137 A1 9/2001
WO WO-2001076510 A2 10/2001
WO 0236048 A1 5/2002
WO WO-2002041789 A2 5/2002
WO 03047468 A1 6/2003
WO 03092554 A1 11/2003
WO 2004030569 A2 4/2004
WO 2005011534 A1 2/2005
WO 2005034812 A1 4/2005
WO WO-2005062980 A2 7/2005
WO 2005087140 A1 9/2005
WO 2005102015 A2 11/2005
WO 2006014233 A2 2/2006
WO 2006034008 A2 3/2006
WO 2006085225 A1 8/2006
WO 2006108090 A2 10/2006
WO 2006111391 A1 10/2006
WO 2006138173 A2 12/2006
WO 2007025028 A1 3/2007
WO 2008005405 A2 1/2008
WO 2008035337 A2 3/2008
WO 2008125153 A1 10/2008
WO 2008147964 A1 12/2008
WO 2008150529 A1 12/2008
WO 2009024859 A2 2/2009
WO 2009026563 A2 2/2009
WO 2009042196 A2 4/2009
WO 2009091509 A1 7/2009
WO 2009094500 A1 7/2009
WO 2010005524 A2 1/2010
WO 2010008549 A1 1/2010
WO 2010121076 A2 10/2010
WO 2011002996 A2 1/2011
WO 2011081997 A1 7/2011
WO 2012008459 A1 1/2012
WO 2012032187 A1 3/2012
WO 2012095455 A2 7/2012
WO 2013005878 A1 1/2013
WO 2013028387 A2 2/2013
WO 2013106585 A1 7/2013
WO 2014009213 A1 1/2014
WO 2014018432 A2 1/2014
WO 2014079291 A1 5/2014
WO 2014145338 A1 9/2014
WO 2014149865 A1 9/2014
WO 2014163706 A1 10/2014
WO 2014194178 A1 12/2014
WO 2015004624 A1 1/2015
WO 2015004625 A1 1/2015
WO 2015057407 A1 4/2015
WO 2015077274 A1 5/2015
WO 2016002189 A1 1/2016
WO 2016004137 A1 1/2016
WO 2016016899 A1 2/2016
WO 2017006510 A1 1/2017
WO 2017035487 A1 3/2017
WO WO-2017195125 A1 * 11/2017 ........... A61F 2/0095
WO 2018000333 A1 1/2018
WO 2018213209 A1 11/2018
WO WO-2019179221 A1 * 9/2019 ........... A61F 2/9525
WO 2022002054 A1 1/2022
WO WO-2022266003 A1 * 12/2022 ........... A61F 2/9525
WO 2023006048 A1 2/2023
WO 2023081236 A1 5/2023
WO 2023091769 A1 5/2023
WO WO-2023076103 A1 * 5/2023 ............. A61F 2/243
WO 2023096804 A1 6/2023
WO 2023154250 A1 8/2023
WO WO-2023156307 A1 * 8/2023 ............... A61F 2/95
WO 2023196150 A1 10/2023
WO WO-2023213544 A1 * 11/2023 ........... A61F 2/9525
WO 2023244454 A1 12/2023
WO 2023244767 A1 12/2023
WO 2023250114 A1 12/2023
WO 2024001789 A1 1/2024
WO 2024003620 A1 1/2024
WO 2024007575 A1 1/2024

(56) References Cited

FOREIGN PATENT DOCUMENTS

| | | | | |
|---|---|---|---|---|
| WO | 2024009540 A1 | | 1/2024 | |
| WO | 2024010739 A1 | | 1/2024 | |
| WO | 2024030520 A1 | | 2/2024 | |
| WO | WO-2024044597 A1 | * | 2/2024 | A61F 2/9525 |

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.
Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.
Dotter, M.D., Charles T., "Transluminal Treatment of Arteriosclerotic Obstruction," University of Oregon's. Minthorn Memorial Laboratory for Cardiovascular Research through Radiology, Circulation, vol. XXX, Nov. 1964, pp. 654-670.
Inoue, M.D., Kanji, et al., "Clinical Application of Transvenous Mitral Commissurotomy by a New Balloon Catheter," The Journal of Thoracic and Cardiovascular Surgery 87:394-402, 1984.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Rösch, M.D., Josef, "The Birth, Early Years and Future of Interventional Radiology," J Vasc Interv Radiol 2003; 14:841-853.
Ross, F.R.C.S., D.N., "Aortic Valve Surgery," Guy's Hospital, London, pp. 192-197, approximately 1968.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Wheatley, M.D., David J., "Valve Prostheses," Rob & Smith's Operative Surgery, Fourth Edition, pp. 415-424, Butterworths 1986.
Bavaria, Joseph E. M.D et al.: "Transcatheter Mitral Valve Implantation: The Future Gold Standard for MR?," Applicant requests the Examiner to consider this reference to be prior art as of Dec. 2010.
Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. 2014.
Bavaria, Joseph E. M.D.: "CardiAQ Valve Technologies: Transcatheter Mitral Valve Implantation," Sep. 21, 2009.
Berreklouw, Eric, PhD, et al., "Sutureless Mitral Valve Replacement With Bioprostheses and Nitinol Attachment Rings: Feasibility In Acute Pig Experiments," The Journal of Thoracic and Cardiovascular Surgery, vol. 142, No. 2, Aug. 2011 in 7 pages, Applicant believes this may have been available online as early as Feb. 7, 2011.
Boudjemline, Younes, et al., "Steps Toward the Percutaneous Replacement of Atrioventricular Valves," JACC, vol. 46, No. 2, Jul. 19, 2005:360-5.
CardiAQ Valve Technologies, "Innovations in Heart Valve Therapy," In3 San Francisco, Jun. 18, 2008, PowerPoint presentation in 19 slides.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31, Applicant believes this may have been available as early as Dec. 2006.
Feldman, Ted, MD. "Prospects for Percutaneous Valve Therapies," Circulation 2007;116:2866-2877. Applicant believes that this may be available as early as Dec. 11, 2007.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Fornell, Dave, ""Transcatheter Mitral Valve replacement Devices in Development,"" Diagnostic and Interventional Cardiology, Dec. 30, 2014, p. 3, <http://www.dicardiology.com/article/transcatheter-mitral-valve-replacement-devices-development>.
Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Karimi, Houshang, et al., "Percutaneous Valve Therapies," SIS 2007 Yearbook, Chapter 11, pp. 1-11.
Kronemyer, Bob, ""CardiAQ Valve Technologies: Percutaneous Mitral Valve Replacement,"" Start Up—Windhover Review of Emerging Medical Ventures, vol. 14, Issue No. 6, Jun. 2009, pp. 48-49.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "Double-Crowned Valved Stents For Off-Pump Mitral Valve Replacement," European Journal of Cardio-thoracic Surgery 28 (2005) 194-199, Applicant believes this may have been available as early as Aug. 2005.
Mack, Michael, M.D., "Antegrade Transcatheter Mitral valve Implantation: A Short-term Experience in Swine Model," Applicant believes this may have been presented on May of 2011 at TVT.
Mack, Michael, M.D., "Antegrade Transcatheter Mitral valve Implantation: On-Going Experience in Swine Model," Applicant believes this may have been presented on Nov. 2011 at TCT.
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
Quadri, Arshad M.D., "Transcatheter Mitral Valve Implantation (TMVI) (An Acute In Vivo Study)," Applicant believes this may have been presented on Sep. 22, 2010 at TCT.
Ratz, J. Brent, "LSI EMT Spotlight," May 15, 2009.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ratz, J. Brent, "In3 Company Overview," Jun. 24, 2009.
Ruiz, Carlos E., "Overview of Novel Transcatheter Valve Technologies," Applicant believes this may have been presented on May 27, 2010 at EuroPCR.
Spillner, J et al., "New Sutureless 'Atrial- Mitral-Valve Prosthesis' For Minimally Invasive Mitral Valve Therapy," Textile Research Journal, 2010, in 7 pages, Applicant believes this may have been available as early as Aug. 9, 2010.
Sondergaard, Lars, et al., "Transcatheter Mitral Valve Implantation: CardiAQ™," Applicant believes this may have been presented at TCT 2013.
Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.

(56) References Cited

OTHER PUBLICATIONS

Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Webb, John G., et al., "Transcatheter Aortic Valve Implantation: The Evolution Of Prostheses, Delivery Systems And Approaches," Archives of Cardiovascular Disease (2012) 105, 153-159. Applicant believes this may have been available as early as Mar. 16, 2012.
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
"Company Overview," at TVT on Jun. 25, 2009.
Biospace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
Biospace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
Neovasc corporate presentation, Oct. 2009, available at http://www.neovasc.com/investors/documents/Neovasc-Corporate-Presentation-October-2009.pdf.
Medtronic, "Transcatheter Aortic Valve Delivery Catheter System Compression Loading System", Core Valve Sytem, 2014, Medtronic Inc., Santa Ana, CA.
Herrmann, Howard C. MD, "Advances in Transseptal Transcatheter Mitral Valve Replacement", tct 2018, Cardiovascular Research Foundation.
Rashkind et al., "Historical Aspects of Interventional Cardiology: Past, Present, and Future", Texas Heart Institute Journal, Interventional Cardiology, vol. 13, No. 4, Dec. 1986, pp. 363-367, Houston, Texas.

* cited by examiner

SYSTEM AND METHOD FOR CRIMPING AND LOADING A PROSTHETIC HEART VALVE

CROSS-REFERENCE TO RELATED APPLICATIONS

The present application is a continuation of U.S. application Ser. No. 18/626,109 filed Apr. 3, 2024, which is a continuation of International Application No. PCT/US2022/047316, filed Oct. 20, 2022, which claims the benefit of U.S. Provisional Application No. 63/272,577, filed Oct. 27, 2021, each of which is incorporated herein by reference in its entirety.

FIELD

The present disclosure relates to systems and methods for crimping implantable prosthetic devices, such as prosthetic heart valves, for delivery into a patient's body.

BACKGROUND

The human heart can suffer from various valvular diseases. These valvular diseases can result in significant malfunctioning of the heart and ultimately require replacement of the native valve with an artificial valve. There are a number of known repair devices (e.g., stents) and artificial valves, as well as a number of known methods of implanting these devices and valves in humans. Percutaneous and minimally invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery apparatus and advanced through the patient's vasculature (e.g., through a femoral artery and the aorta) until the prosthetic heart valve reaches the implantation site in the heart. The prosthetic heart valve is then expanded to its functional size, for example, by inflating a balloon on which the prosthetic valve is mounted, actuating a mechanical actuator that applies an expansion force to the prosthetic heart valve, or by deploying the prosthetic heart valve from a sheath of the delivery apparatus so that the prosthetic heart valve can self-expand to its functional size.

A prosthetic valve for use in such a procedure can include a radially collapsible and expandable frame to which leaflets of the prosthetic valve can be coupled. The leaflets typically are made of biological materials such as pericardium valves or harvested valves. For improved function after deployment, it is often desirable to package and store such valves in the open (i.e., expanded) diameter inside a preserving solution up until the time the valve is mounted on a delivery device for implantation. Accordingly, it may be necessary to crimp the valve in the operating room a few minutes before implantation, therefore precluding pre-crimping by the manufacturer. Thus, many loading devices and/or crimping devices are now shipped as a disposable accessory along with the valve and delivery system, thus increasing the importance of portability and case of use of such devices.

Generally, conventional loading and crimping devices operate by one of two methods. In one method, a stent is driven through a cone-like surface, which compresses the stent to a smaller diameter. For example, a static conical tube can be passed over a stent, thereby reducing its diameter. This method typically is used for crimping prosthetic valves having self-expanding metal frames (e.g., frames made of Nitinol), which are easily deformable. Self-expandable prosthetic valves typically are pushed from the conical tube of the loading/crimping device into a sheath of a delivery apparatus, which retains the prosthetic valve in a radially compressed state. The second crimping method uses crimping jaws to create a cylinder-like surface that can change diameter. This method typically is used for crimping prosthetic valves having plastically expandable frames (e.g., frames made of stainless steel or cobalt chromium alloys).

Self-expandable prosthetic valves typically have multiple connection features extending from the frame that form a releasable connection with the distal end of the delivery apparatus. Once the prosthetic valve has been deployed from the sheath inside the patient's body, the physician can release the connection between the delivery apparatus and the connection features of the prosthetic valve. A challenge in crimping self-expandable prosthetic valves involves the ability of the physician to easily and quickly crimp and load a prosthetic valve into a sheath of a delivery apparatus while aligning and connecting the connection features of the prosthetic valve with mating connection features of the delivery apparatus. There thus remains a need for improved loading and crimping devices that address these and other disadvantages in the prior art.

SUMMARY

Described herein are various exemplary devices and methods for crimping a prosthetic heart valve and loading such a valve into a delivery apparatus.

A crimping device can comprise a housing sized to receive a radially expandable and compressible prosthetic heart valve in a radially expanded state, the housing comprising a funnel segment extending at least partially along an axial length of the housing, an actuator, and a pusher member coupled to the actuator, the pusher member configured to abut the prosthetic valve within the housing and cause the prosthetic valve to move axially through the funnel segment.

In addition to these components, a crimping device can further comprise one or more of the components disclosed herein.

In some examples, a crimping device can comprise an extender portion extending from an inlet portion of the housing and comprising a threaded inner surface, and a correspondingly threaded outer surface on a cylindrical extension member of the housing.

In some examples, the threaded inner surface of the housing and the threaded outer surface of the actuator are configured to convert rotation of the actuator into axial advancement of the pusher member into the funnel segment of the housing.

In some examples, the housing comprises first and second side portions and the first and second side portions are releasably coupled to one another using one or more engagement elements.

In some examples, the one or more engagement members include flanges extending laterally from an outer surface of the first side portion, and hooked members extending laterally from an outer surface of the second side portion and configured to receive the flanges.

In a representative example, a crimping device can comprise a housing sized to receive a radially expandable and compressible prosthetic heart valve in a radially expanded state. The housing can comprise a funnel segment extending at least partially along an axial length of the housing, an outlet in communication with the funnel segment, and an extender portion extending from an inlet portion of the housing and comprising a threaded inner surface. The crimping device can further comprise an actuator comprising a base and a cylindrical extension member having a correspondingly threaded outer surface configured to engage with the threaded inner surface of the extender portion, and a pusher member coupled to the base of the actuator and configured to abut the prosthetic valve within the housing. The inner surface of the housing and the threaded outer surface of the actuator can be configured to convert rotation of the actuator into axial advancement of the pusher member into the funnel segment of the housing causing the prosthetic valve to move axially through the funnel segment.

In another representative example, a crimping device can comprise a housing sized to receive a radially expandable and compressible prosthetic heart valve in a radially expanded state. The housing can comprise a funnel segment extending at least partially along an axial length of the housing, an outlet in communication with the funnel segment, and an extender portion extending from an inlet portion of the housing and comprising a threaded inner surface. The crimping device can further comprise an actuator comprising a base and a cylindrical extension member having a correspondingly threaded outer surface configured to engage with the threaded inner surface of the extender portion, and a pusher member coupled to the base of the actuator and configured to abut the prosthetic valve within the housing, the pusher member having an outer diameter less than an inner diameter of the housing such that the pusher member can advance into the housing, the pusher member comprising a plurality of arms extending from a first end portion, each arm comprising a seat configured to engage an adjacent end portion of a prosthetic valve. The inner surface of the housing and the threaded outer surface of the actuator are configured to convert rotation of the actuator into axial advancement of the pusher member into the funnel segment of the housing causing the prosthetic valve to move axially through the funnel segment.

In yet another representative example, a crimping device can comprise a housing sized to receive a radially expandable and compressible prosthetic heart valve in a radially expanded state. The housing can comprise a funnel segment extending at least partially along an axial length of the housing, and an outlet in communication with the funnel segment, the housing comprising first and second side portions releasably coupled together via first and second pairs of engagement elements that restrain the first and second portions against lateral movement relative to one another. The crimping device can further comprise an actuator comprising a base, and a pusher member coupled to the base of the actuator and configured to abut the prosthetic valve within the housing. The first pair of engagement elements can comprise first and second engagement elements disposed diametrically opposite one another adjacent an inlet end of the housing and the second pair of engagement elements comprises third and fourth elements disposed diametrically opposite one another adjacent the outlet. The first and second engagement elements allow axial movement of the first and second portions relative to one another in a first direction but restrain the first and second portions against axial movement relative to one another in a second direction past a selected position.

In a representative example, an assembly can comprise a delivery apparatus comprising a first shaft and a second shaft disposed over the first shaft, and a crimping device. The crimping device comprising a housing disposed over the first shaft and configured to receive a radially expandable and compressible prosthetic valve in a radially expanded state, the housing comprising a funnel segment extending at least partially along an axial length of the housing and an outlet in communication with the funnel segment, a pusher member having an outer diameter less than an inner diameter of the housing such that the pusher member can advance into the housing, and an actuator releasably coupled to the pusher member, wherein axial advancement of the actuator relative to the housing causes the prosthetic valve to move axially through the funnel segment such that at least a portion of the prosthetic valve compresses radially by engagement with the funnel segment and exits the crimping device via the outlet. The assembly further comprising a loading assembly, comprising a support tube disposed over the second shaft and comprising first and second side portions, and a funnel member disposed over a first end portion of the support tube, the funnel member comprising first and second side portions.

In a representative example, a method can comprise disposing a support tube of a loading assembly over a capsule of the delivery apparatus, the support tube comprising first and second side portions, and disposing a housing of a crimping device over a shaft of the delivery apparatus such that an outlet end portion of the crimping device is adjacent an inlet end portion of the loading assembly, the housing defining a funnel segment extending at least partially along an axial length of the housing and an outlet in communication with the funnel segment. The method can further comprise inserting a prosthetic valve in a radially expanded state into an inlet end portion of the housing, advancing the prosthetic valve axially through the funnel segment of the housing and at least partially through the outlet, and disposing a funnel member of the loading assembly over at least a portion of the prosthetic valve, the funnel member comprising first and second side portions. The method can further comprise advancing the loading assembly axially over the prosthetic valve, thereby radially crimping the prosthetic valve and advancing the prosthetic valve into the capsule of the delivery apparatus.

In a representative example, a crimping device can comprise a housing configured to receive a radially expandable and compressible prosthetic valve in a radially expanded state. The housing can comprise a funnel segment extending at least partially along an axial length of the housing and a plurality of ribs spaced about the circumference of the housing, the ribs extending inwardly toward a longitudinal axis of the housing, and an outlet in communication with the funnel segment. The crimping device can further comprise a pusher member configured to abut a prosthetic valve within the housing when a prosthetic valve is received in the housing, the pusher member comprising a plurality of arms extending from the first end portion, each arm comprising a seat configured to engage an adjacent end portion of a prosthetic valve, and an actuator coupled to the pusher member. Wherein the housing is configured to receive the actuator in a selected angular orientation, and the actuator is configured to be slidably advanced into the housing at the selected angular orientation to move a prosthetic valve axially through the funnel segment such that at least a portion of the prosthetic valve compresses radially by engagement with the funnel segment and exits the crimping device via the outlet.

In a representative example, a loading apparatus can comprise a support tube configured to be disposed over a shaft of a delivery apparatus, the support tube comprising first and second side portions; a first clamp member removably coupled to a first end portion of the support tube to retain the first and second side portions together; and a funnel member disposed over a second end portion of the support tube and configured to be disposed over at least a portion of a prosthetic valve, the funnel member comprising first and second side portions. The loading assembly can further comprise a second clamp member removably coupled to a first end portion of the funnel member to retain the first and second side portions together. The loading assembly can be configured such that axial advancement of the funnel member over a prosthetic valve or retraction of the prosthetic valve inside the funnel member radially compresses the prosthetic valve by engagement with the funnel member.

In another representative example, a crimping device can comprise a housing configured to receive a radially expandable and compressible prosthetic valve in a radially expanded state, a pusher member, and an actuator. The housing can comprise a funnel segment extending at least partially along an axial length of the housing and an outlet in communication with the funnel segment. The pusher member can be configured to abut the prosthetic valve within the housing, the pusher member having an outer diameter less than an inner diameter of the housing such that the pusher member can advance into the housing. The actuator can be releasably coupled to the pusher member, the actuator comprising a base member and one or more elongated guide members extending from the base member, each elongated guide member comprising a slot extending at least partially along the length of the guide member and a slidable member slidably disposed within the slot and releasably coupled to the housing. Axial advancement of the housing relative to the base member can cause the slidable members to slide within their respective slots such that the pusher member is inserted into the housing causing the prosthetic valve to move axially through the funnel segment such that at least a portion of the prosthetic valve compresses radially by engagement with the funnel segment and exits the crimping device via the outlet.

In another representative example, a crimping device can comprise a housing configured to receive a radially expandable and compressible prosthetic valve in a radially expanded state, an outer shell in which the housing is disposed, an actuator, and a pusher member. The housing can comprise a funnel segment extending at least partially along an axial length of the housing and an outlet in communication with the funnel segment. The outer shell can have a cylindrical shape and can comprise a threaded inner surface. The actuator can comprise a base and a cylindrical extension member having a correspondingly threaded outer surface configured to engage with the threaded inner surface of the outer shell. The pusher member can be coupled to the base of the actuator, the pusher member having a plurality of radially extending arms configured to engage the prosthetic valve within the housing. The threaded portions can be configured to convert rotation of the actuator into axial advancement of the pusher member into the funnel segment of the housing causing the prosthetic valve to move axially through the funnel segment such that at least a portion of the prosthetic valve compresses radially by engagement with the funnel segment and exits the crimping device via the outlet.

In still another representative example, a crimping device can comprise a housing configured to receive a radially expandable and compressible prosthetic valve in a radially expanded state, an actuator, and a pusher member. The housing comprising a funnel segment extending at least partially along an axial length of the housing and an outlet in communication with the funnel segment. The actuator comprising a base having an aperture extending through a thickness of the base, the aperture comprising a threaded inner surface, a threaded member having a threaded outer surface engaged with the threaded inner surface of the aperture, and one or more extension members coupling the actuator to the housing. The pusher member can be coupled to the threaded member such that the threaded member can rotate relative to the pusher member and axially advance the pusher member, the pusher member configured to abut the prosthetic valve within the housing. Rotation of the threaded member axially advances the pusher member into the funnel segment of the housing causing the prosthetic valve to move axially through the funnel segment such that at least a portion of the prosthetic valve compresses radially by engagement with the funnel segment.

In still another representative example, a crimping device can comprise a housing configured to receive a radially expandable and compressible prosthetic valve in a radially expanded state, an actuator, and a pusher member. The housing can comprise a funnel segment extending at least partially along an axial length of the housing and an outlet in communication with the funnel segment. The actuator can comprise a handle including a lever member configured to advance an actuator member when actuated, and a holder portion extending from the handle and configured to receive the housing, the holder portion having a first end portion including a retaining member configured to releasably couple the housing. The pusher member can be coupled to the actuator member and configured to abut a prosthetic valve when a prosthetic valve is placed within the housing. Actuation of the lever member axially advances the actuator member, and thereby the pusher member, such that the pusher member advances into the funnel segment of the housing causing the prosthetic valve to move axially through the funnel segment such that at least a portion of the prosthetic valve compresses radially by engagement with the funnel segment.

In another representative example, a loading assembly for a prosthetic valve can comprise a support tube positionable around a delivery capsule of a delivery apparatus, the support tube comprising a proximal end portion and a distal end portion, and a funnel member releasably couplable to the distal end portion of the support tube and configured to radially compress and guide a prosthetic valve into the delivery capsule as the loading assembly is advanced over the prosthetic valve or as the prosthetic valve is retracted inside the loading assembly.

The foregoing and other objects, features, and advantages of the disclosure will become more apparent from the following detailed description, which proceeds with reference to the accompanying figures.

DETAILED DESCRIPTION

General Considerations

For purposes of this description, certain aspects, advantages, and novel features of the examples of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present or problems be solved.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

Figure 26:
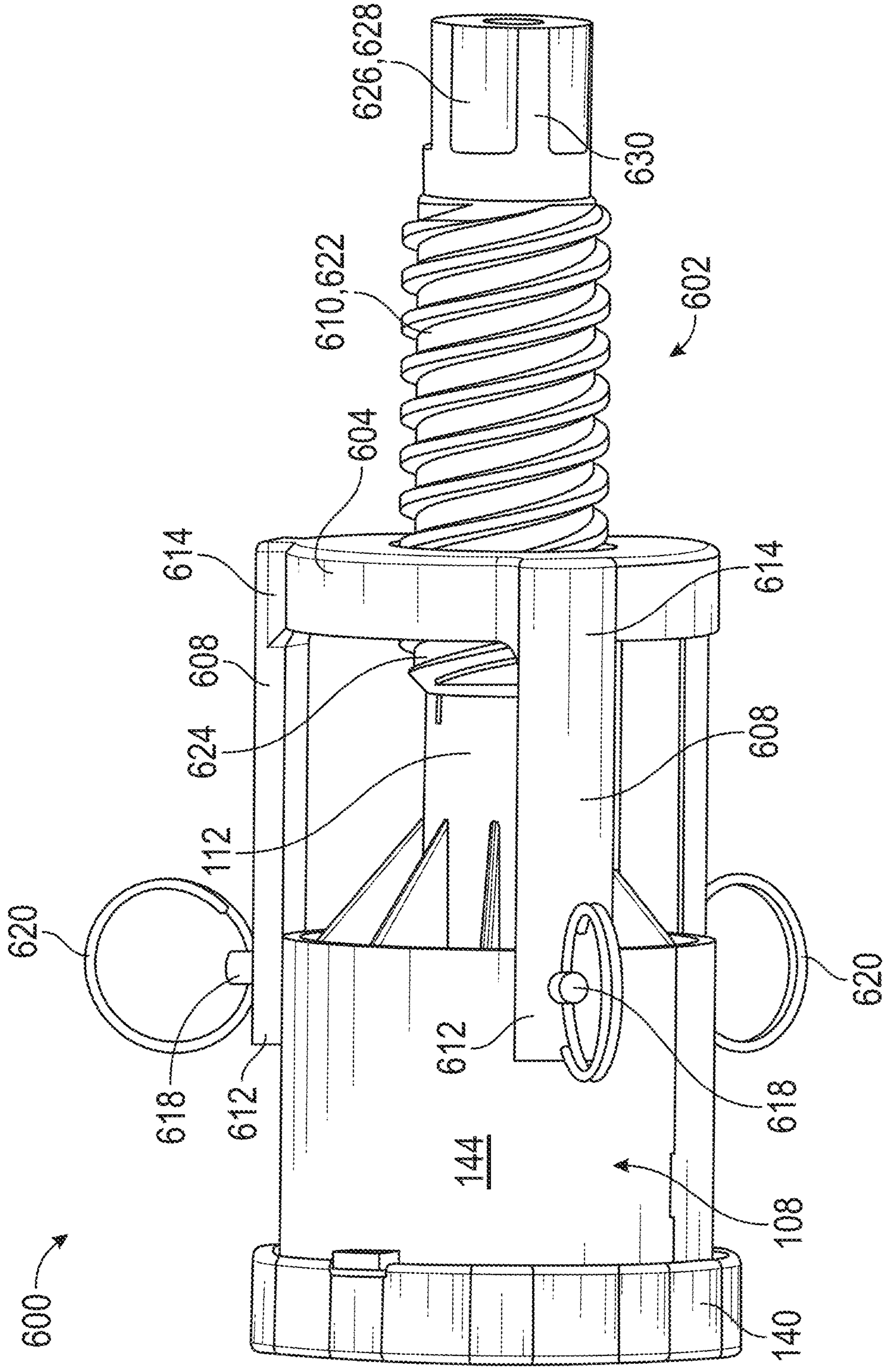
FIG. 26 is a perspective view of another example of a crimping device.
Figure 27:
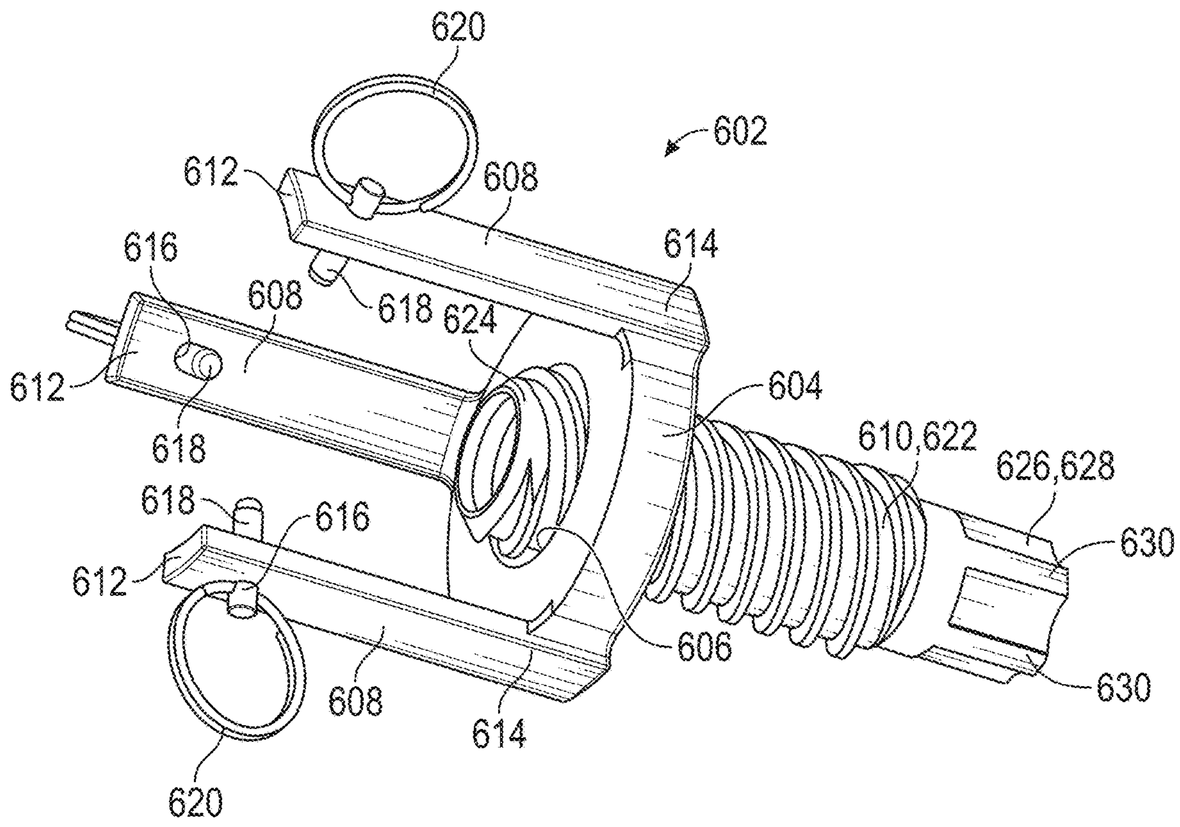
FIG. 27 is a perspective view of the actuator of the crimping device of FIG. 26.
Figure 32:
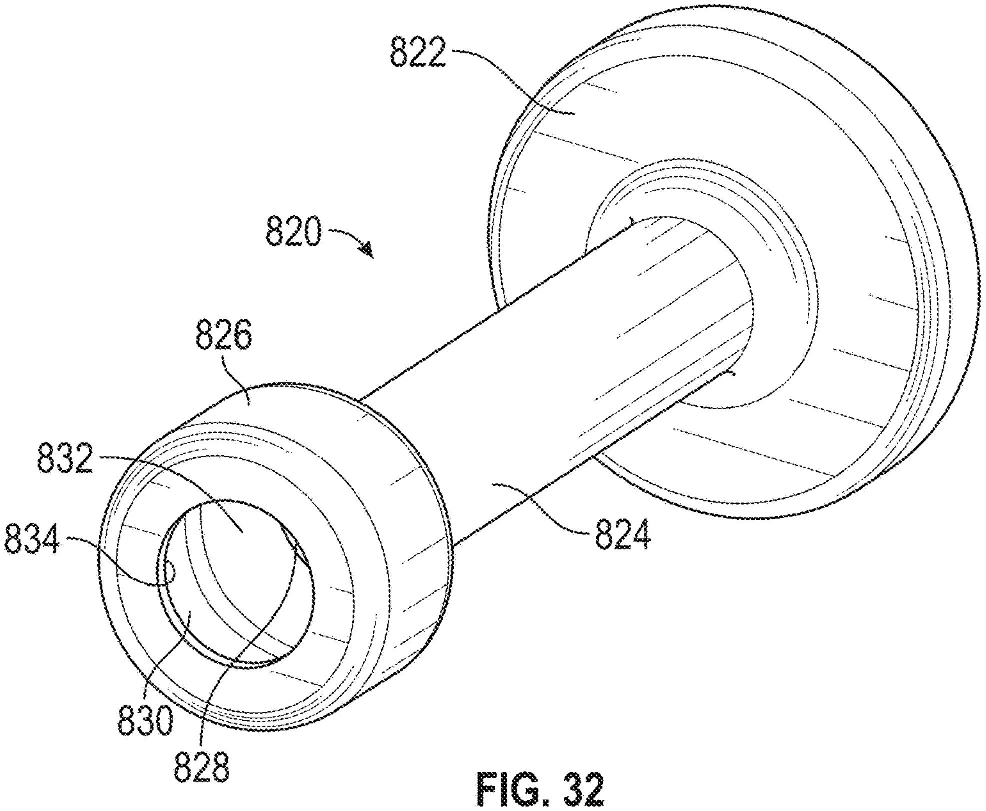
FIG. 32 is a perspective view of the extender of the crimping device of FIG. 31.
Figure 33:
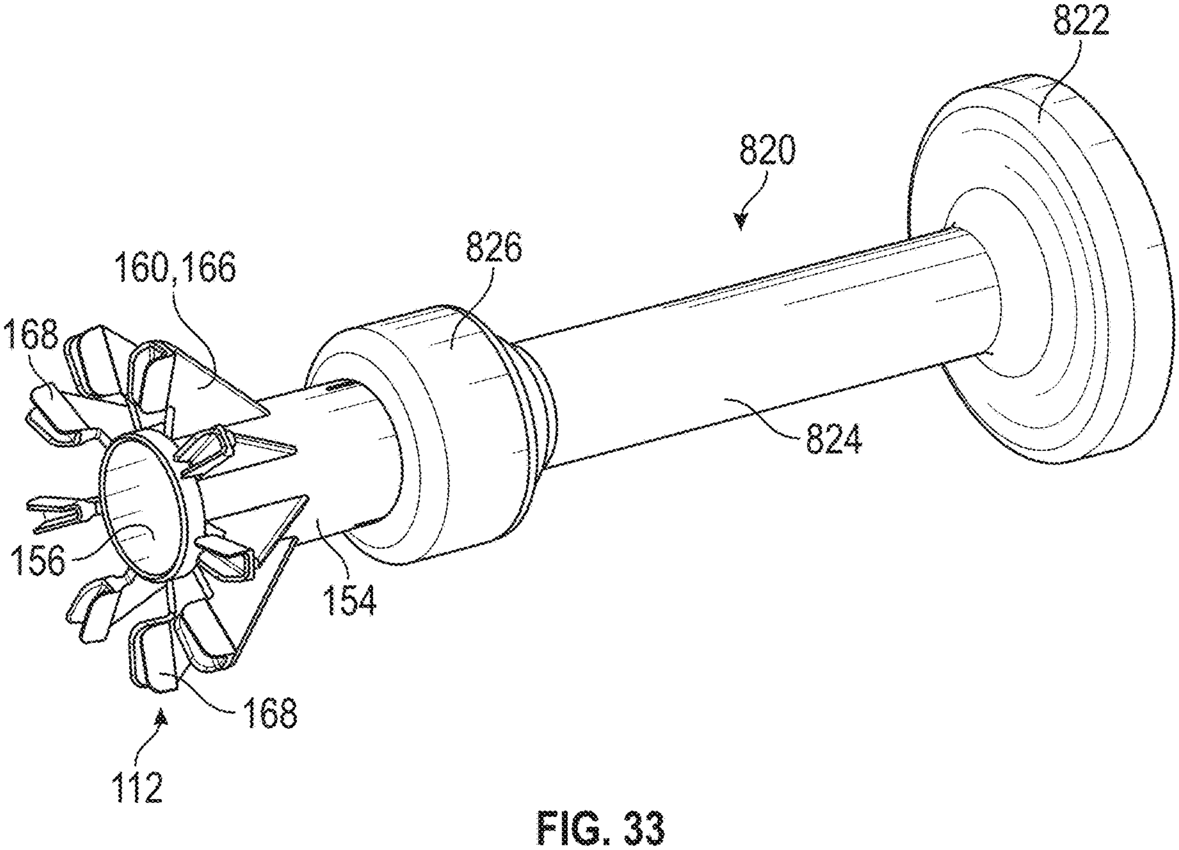
FIG. 33 is a perspective view of the extender and pusher member of the crimping device of FIG. 31.

All features described herein are independent of one another and, except where structurally impossible, can be used in combination with any other feature described herein. For example, elongated guides 608 as shown in FIGS. 26-27 can be used in combination with any of the crimping devices disclosed herein. In another example, an extender 820 as shown in FIGS. 32-33 can be used in combination with any of the crimping devices disclosed herein. Any of the disclosed crimping devices can be used in combination with the loading assembly 2400. Any of the disclosed trimming devices can be used in combination with the loading assembly 2400.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language. As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

EXAMPLES OF THE DISCLOSED TECHNOLOGY

Figure 36:
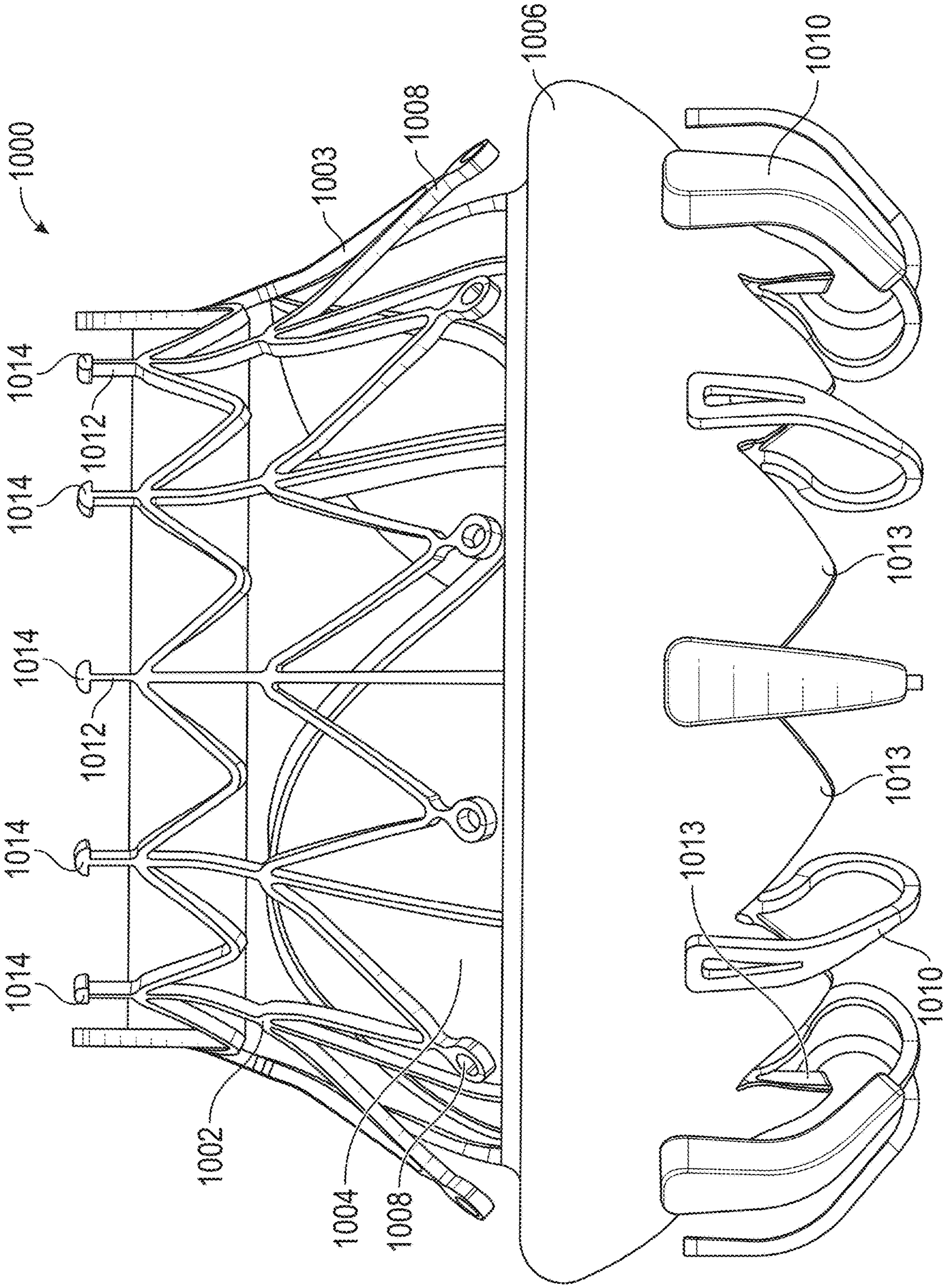
FIG. 36 is a side elevation view of an example of a prosthetic heart valve that can be crimped using any of the crimping devices disclosed herein.

FIGS. 1-10 show an exemplary system for at least partially crimping a prosthetic valve and other crimpable, implantable medical devices, such as stents, grafts, etc., and for securing said implantable medical devices to a delivery apparatus. The illustrated system generally comprises a crimping device 100 and a radially expandable and compressible prosthetic valve 1000 (FIG. 36). The crimping device 100 is configured to reduce the diameter of the prosthetic valve 1000 from a fully expanded configuration to a fully or partially radially compressed state for initial coupling with a delivery apparatus. Once the prosthetic valve 1000 has been coupled to the delivery apparatus, a separate loading assembly (e.g., loading assembly 2400 shown in FIG. 53) can be used to fully crimp the prosthetic valve and load it into a capsule or sheath of the delivery apparatus. FIG. 36 illustrates an exemplary prosthetic valve 1000 that can be used with any of the crimping devices disclosed herein.

As mentioned, the exemplary system shown in FIGS. 1-10 can further comprise a delivery apparatus 102 or a portion thereof. Referring to FIG. 2A, the delivery apparatus can comprise, for example, an inner shaft or catheter 104 (such as a guidewire shaft) and an outer sheath 106 (also called a capsule), which is sized to retain the prosthetic valve 1000 in the radially compressed configuration for delivery into a patient. The prosthetic valve 1000 can comprise any radially collapsible and expandable prosthetic valve, such as a prosthetic heart valve. The prosthetic valve 1000 can be radially collapsible and expandable between an expanded configuration and a delivery configuration (or any of various configurations in between). The prosthetic valve 1000 can be self-expandable or plastically expandable. A self-expandable valve can have a frame formed from a self-expanding metal (e.g., Nitinol). A plastically expandable valve can have a frame formed from a plastically deformable metal (e.g., stainless steel or cobalt chromium alloy).

Though the prosthetic valves shown herein are described as plastically deformable or self-expandable prosthetic valves, it should be noted that the crimping devices disclosed herein can be used with any type of prosthetic valve. For example, the crimping devices can be used with mechanically-expandable prosthetic heart valves in which the frame is radially expandable via one or more mechanical actuators (such as the prosthetic valves described in U.S. Pat. No. 10,603,165 and U.S. Publication No. 2023/0225863, each of which is incorporated herein by reference in its entirety). The frames of some mechanical valves can comprise pivotable junctions between the struts of the frame, while others can comprise a unitary lattice frame expandable and/or compressible via mechanical means. The crimping devices described herein can additionally be used with other types of transcatheter prosthetic valves, including balloon-expandable prosthetic heart valves in which the frame is made from a plastically deformable material such as is disclosed in U.S. Pat. Nos. 9,393,110 and 11,096,781, and U.S. Publication No. 2019/0365530, each of which is incorporated herein by reference in its entirety.

After the prosthetic valve 1000 is coupled to the delivery apparatus 102, the prosthetic valve 1000 can be removed from the crimping device 100. In some examples, the prosthetic valve 1000 and the delivery apparatus 102 can be advanced through an outlet of the crimping device 100 such that the crimping device 100 remains positioned around a portion of the delivery apparatus 102 that is distal to the prosthetic valve 1000. In other examples, the crimping device 100 or components thereof can be configured to separate into pieces or open, e.g., like a clam shell, such that the crimping device 100 can be removed laterally from the delivery apparatus 102 and prosthetic valve 1000, as further described below. After the prosthetic valve 1000 is removed from the crimping device 100, the prosthetic valve 1000 can be further crimped and loaded into the delivery apparatus 102, e.g., using a loading assembly.

Figure 1:
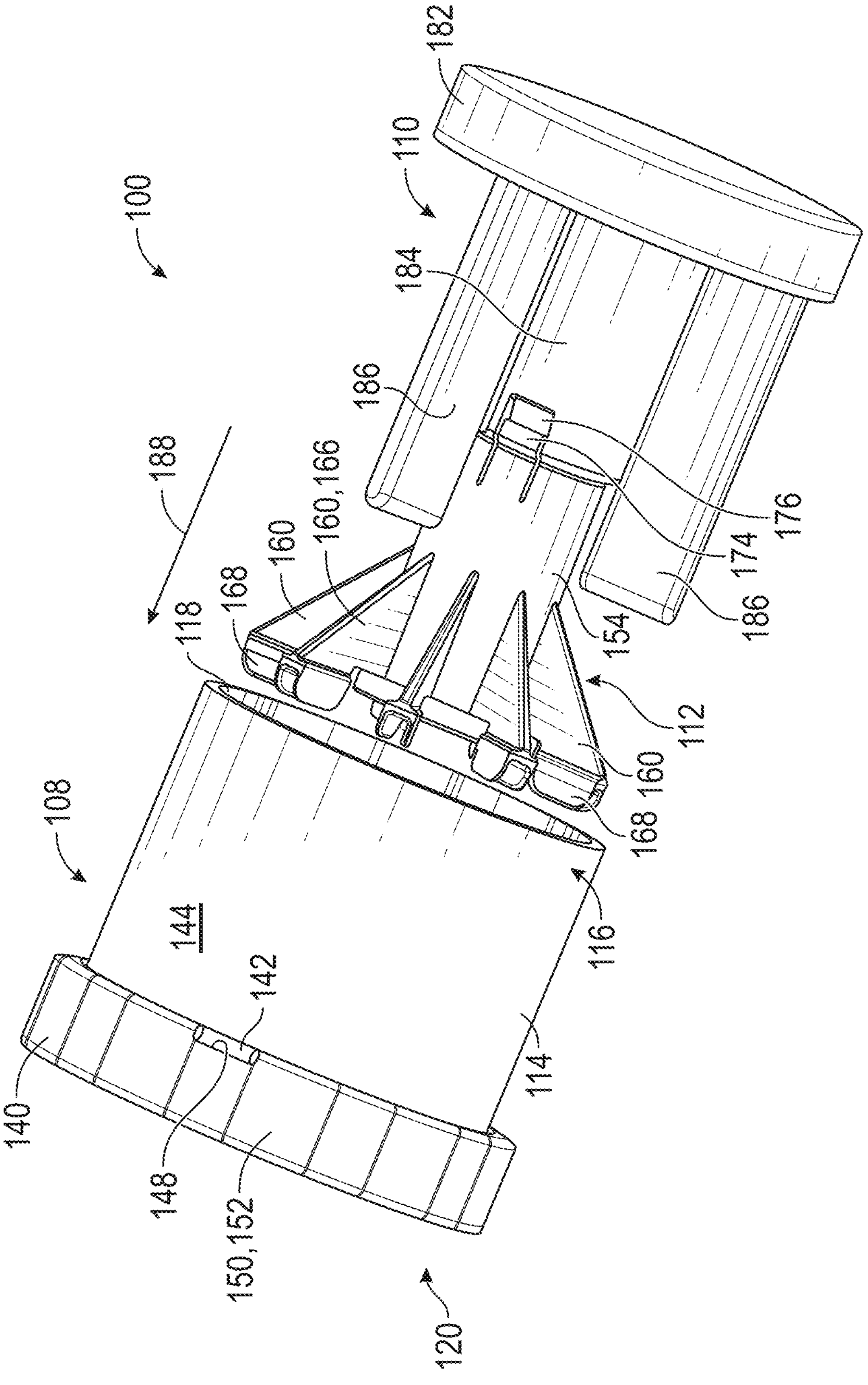
FIG. 1 is a perspective view of a crimping device, according to one example.

Referring to FIG. 1, an exemplary crimping device 100 can generally comprise a housing 108, an actuator 110, and a valve holder or pusher member 112 (also referred to as a pedestal member) removably coupled to the actuator 110. The actuator 110 and pusher member 112 can be axially movable relative to the housing 108. In some examples, the housing 108 can comprise first and second housing components or side portions 114 (see FIG. 4) that are separable from one another, and in other examples the housing 108 can be formed as a unitary piece.

Figure 2A:
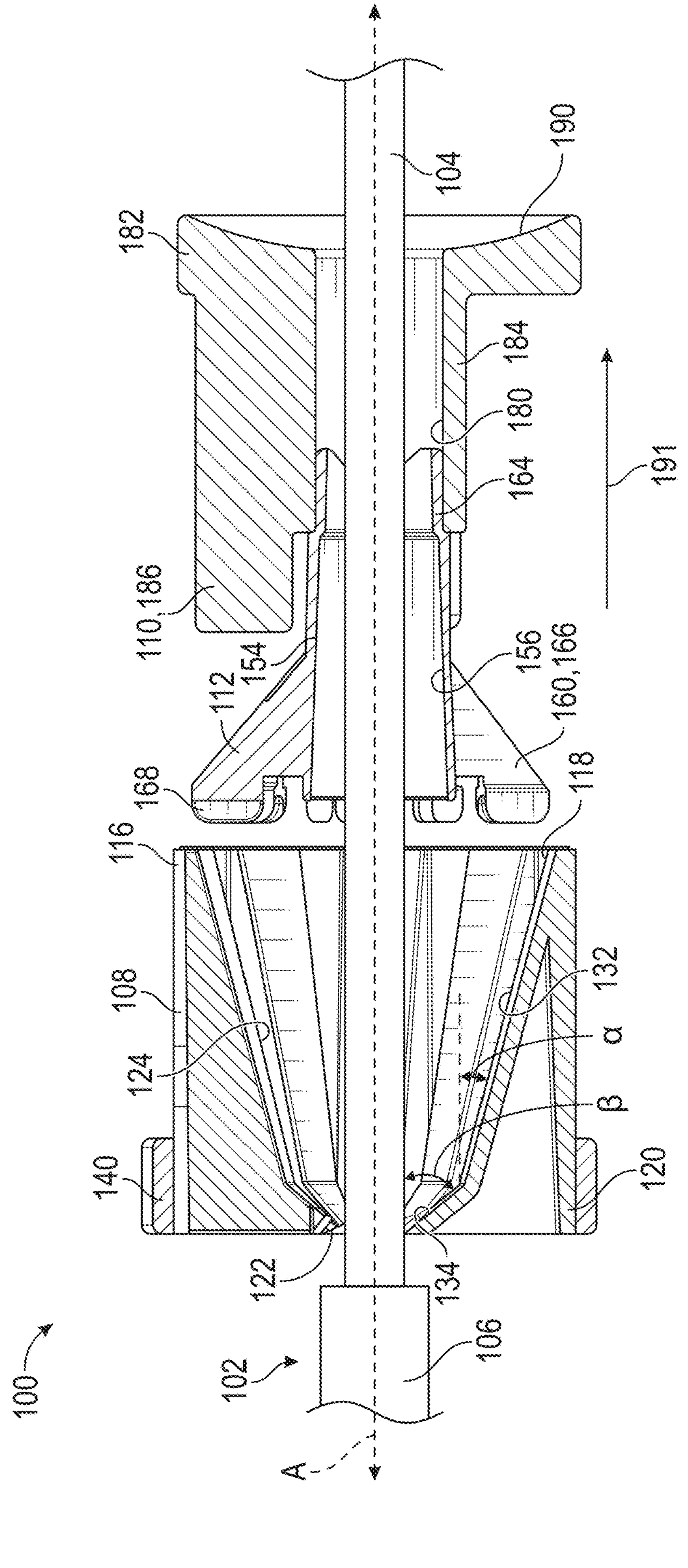
FIG. 2A is a cross-sectional side elevation view of the crimping device of FIG. 1 mounted on an exemplary delivery apparatus.

As shown in FIG. 2A, the housing 108 can comprise a distal or inlet end portion 116 comprising an aperture or inlet 118 and a proximal or outlet end portion 120 comprising an aperture or outlet 122. The housing 108 can have a generally cylindrical shape having an inner bore defining a tapered or funnel segment 124 that tapers from the inlet 118 to the outlet 122 and terminates at the outlet. In certain examples, the funnel segment 124 can be defined by a plurality of rib members 128 extending inwardly from an interior surface of the housing as described in greater detail below. The funnel segment 124 can taper from a first, greater diameter adjacent the inlet 118 to a second, smaller diameter adjacent the outlet 122. The diameter of the outlet 122 can be approximately the specified diameter of the prosthetic valve 1000 in the radially compressed, delivery configuration. In some examples, such as shown in FIGS. 2-4, the outlet 122 can be flush with/defined by an outer rim portion 126 (FIG. 4) at the outlet end portion 120 but in other examples the outlet 122 can be recessed with respect to or extend beyond the rim portion 126.

Figure 3A:
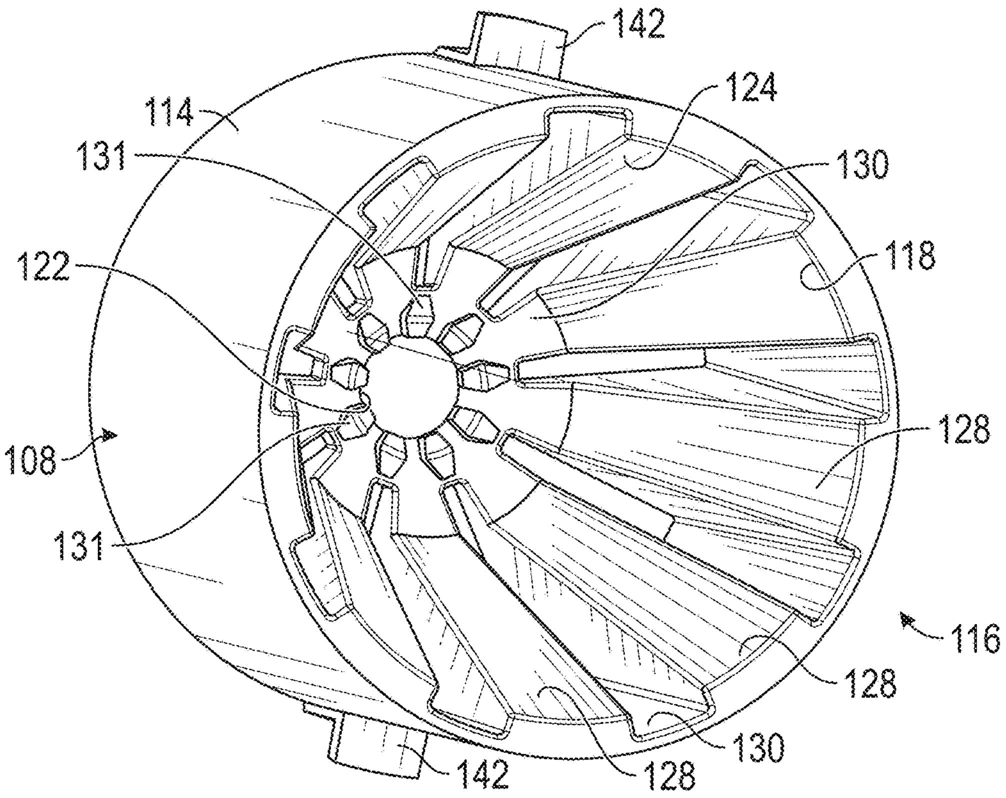
FIG. 3A is a perspective view of the housing of the crimping device of FIG. 1.
Figure 3B:
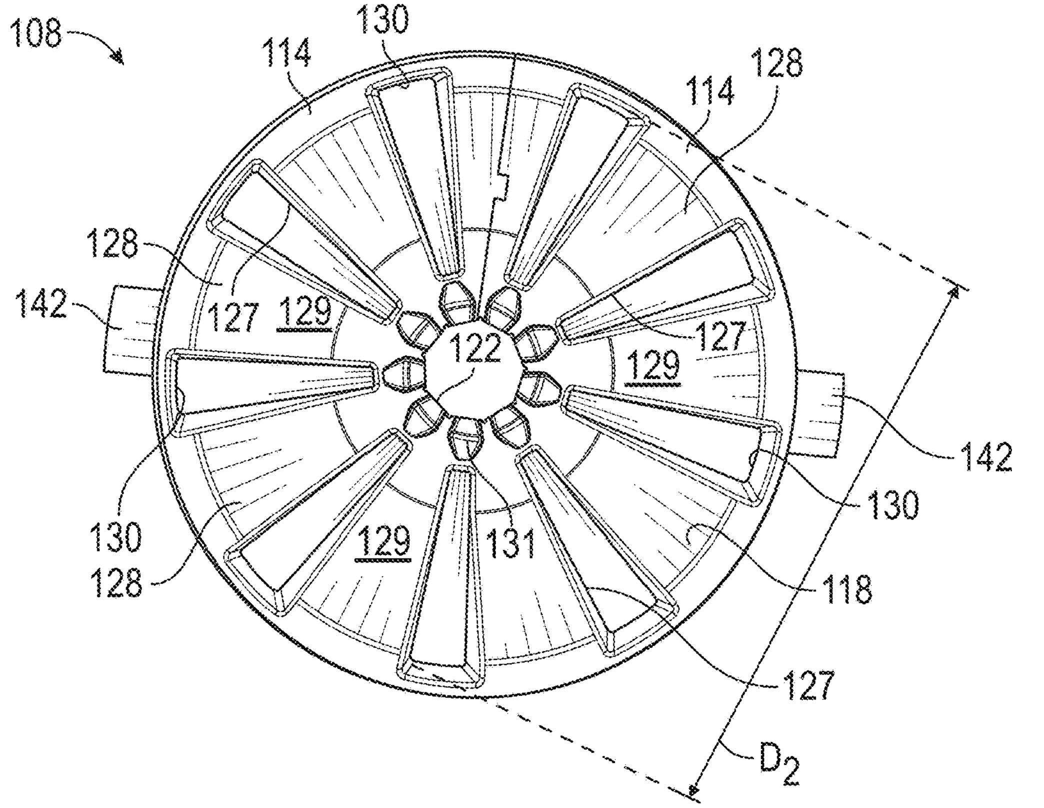
FIG. 3B is an end-on view of the housing of the crimping device of FIG. 1.
Figure 4:
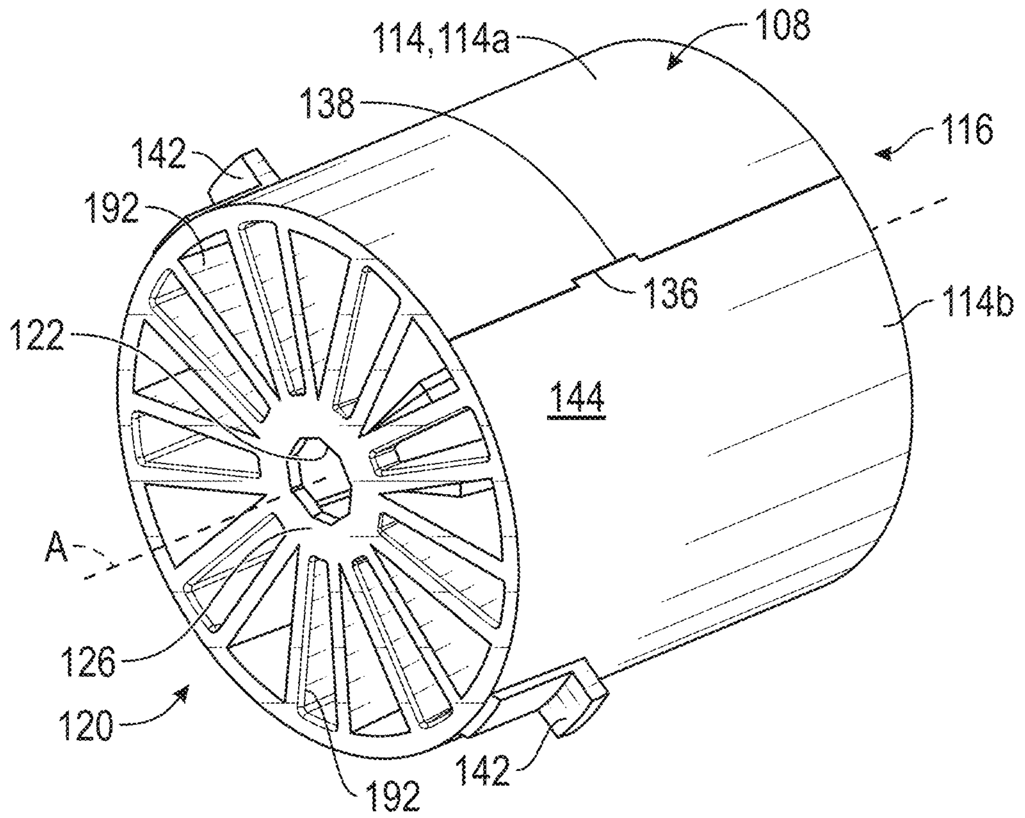
FIG. 4 is a perspective view of the housing of the crimping device of FIG. 1.

Referring to FIG. 3A, the funnel segment 124 can comprise a plurality of circumferentially spaced ramp members and/or ribs 128 extending longitudinally along at least a portion of the length of the housing 108 and extending radially inwardly toward a longitudinal axis A (FIG. 4) extending through the housing 108. The radially inner surfaces 129 of the ribs 128 can define the funnel segment 124. The thickness of the ribs 128 (the thickness being the dimension extending from the inner wall 130 of the housing 108 toward the longitudinal axis A) can increase along their length from a smaller thickness adjacent the inlet end portion 116 to a greater thickness adjacent the outlet end portion 120. Stated differently, a radial distance r measured between the axis A and the inner surfaces 129 of the ribs 128 can decrease from the inlet end portion 116 in a direction toward the outlet 122. Thus, the diameter of the funnel segment 124 can decrease in a direction toward the outlet 122. The ribs 128 function to prevent or at least minimize axial deformation of a prosthetic valve (such as prosthetic valve 1000 shown in FIG. 36) during radial compression and/or assist in alignment of the connection features of the prosthetic valve with mating features of the delivery apparatus. As the prosthetic valve advances along the funnel segment 124 (e.g., when pushed by the pusher member 112), the tapered ribs 128 gradually crimp the prosthetic valve into the compressed configuration.

Referring to FIG. 2A, in some examples, the funnel segment 124 can define a first tapered section 132 and a second tapered section 134 that can crimp the prosthetic valve at different rates due to the different tapering angles of the two sections. In the illustrated example, for example, the first section 132 is tapered at a smaller angle α relative to the longitudinal axis A than the angle β of the second section 134. For example, in some particular examples, each angle can be between 0 and 90 degrees. In certain examples, the angle α can be 1° to 90°, 1° to 70°, 1° to 60°, 1° to 40°, 1° to 30°, 1° to 20°, 5° to 30°, 5° to 20°, 40° or less, 30° or less, 20° or less, etc. In the illustrated example, the angle α can be 15°. In certain examples, the angle β can be 10° to 90°, 20° to 70°, 30° to 70°, 30° to 60°, 40° to 60°, 90° or less, 70° or less, 60° or less, 50° or less, etc. In the illustrated example, the angle β can be 50°. Accordingly, the first section 132 can begin to radially compress a prosthetic valve from the fully expanded diameter to a partially crimped diameter before it enters the second section 134 where it is then crimped from the partially crimped diameter to a further partially crimped diameter for attachment to a delivery apparatus and/or loading into a delivery apparatus (e.g., delivery apparatus 102). In other examples, the first section 132 can be tapered at the same angle as the second section 134, or at a greater angle than the second section 134.

Figure 2B:
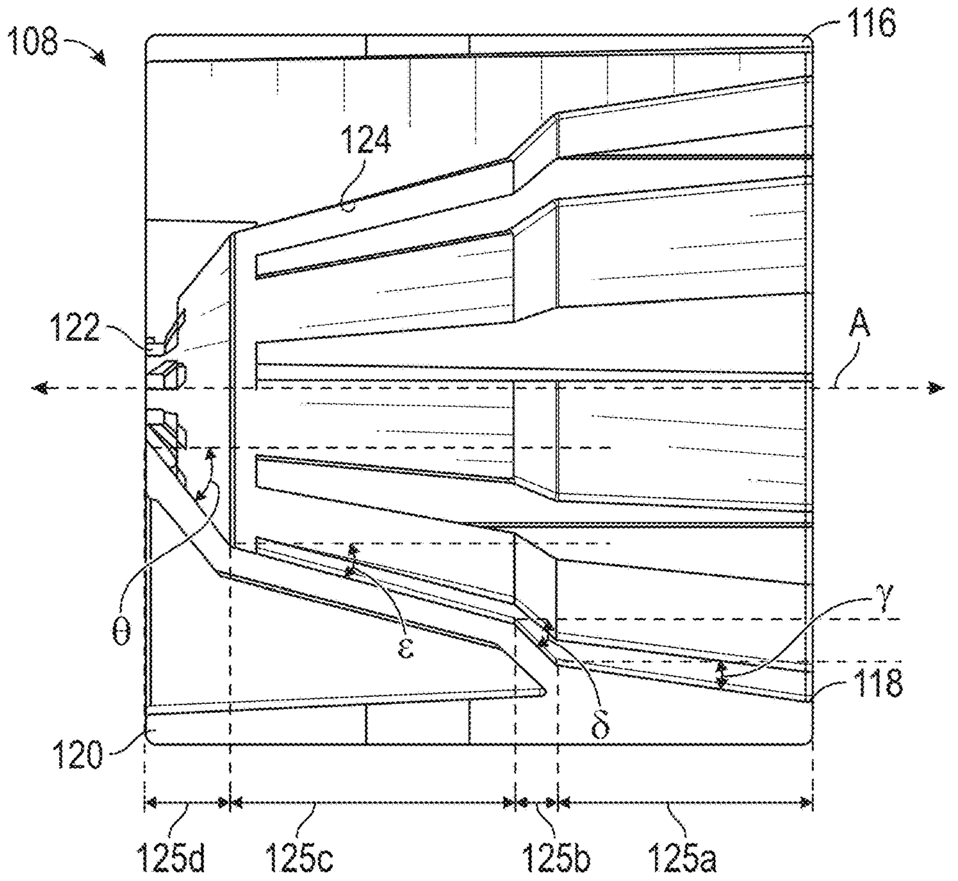
FIG. 2B is a cross-sectional side elevation view of another example of a housing for a crimping device.
Figure 2C:
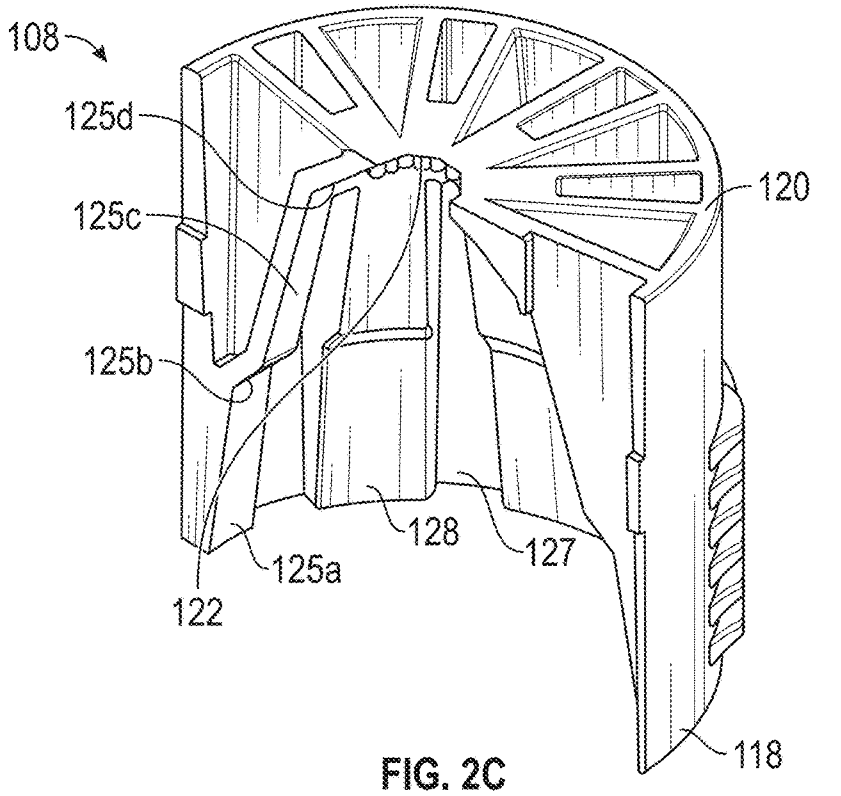
FIG. 2C is a perspective view of a portion of the housing of FIG. 2B.

In other examples, the funnel segment 124 can define one or more additional tapered sections that can crimp the prosthetic valve at different rates due to the different tapering angles of the sections. For example, FIGS. 2B-2C illustrate a funnel segment 124 having four tapered sections **125*a*, 125*b*, 125*c*, and 125*d*. The first section 125*a* can be tapered at a first angle γ relative to a line parallel to the longitudinal axis A of the housing 108, the second section 125*b* can be tapered at a second angle δ, the third section 125*c* can be tapered at a third angle ε, and the fourth section 125*d* can be tapered at a fourth angle θ. In the illustrated example, the second angle δ can be greater than the first and third angles γ, ε such that the second section 125*b* forms a step between the first and third sections 125*a*, 125*c*. In the illustrated example, the fourth angle θ can be greater than the second angle β, which can be greater than the third angle ε, which is greater than the first angle γ. Accordingly, sections 125*a*-125*d* can crimp the prosthetic valve 1000 from a fully expanded diameter to a partially crimped diameter as the prosthetic valve is advanced through the housing 108. In other examples, one or more sections can have the same angle. For example, in some particular examples, each angle can be between 0 and 90 degrees. In certain examples, the angle δ can be 1° to 90°, 1° to 75°, 1° to 65°, 1° to 45°, 1° to 35°, 1° to 25°, 5° to 35°, 5° to 25°, 45° or less, 35° or less, 25° or less, etc. In the illustrated example, the angle δ can be 45°. In certain examples, the angle γ can be 1° to 90°, 1° to 70°, 1° to 50°, 1° to 40°, 10° or less, 20° or less, 30° or less, etc. In the illustrated example, the angle γ can be 7° or less. In certain examples, the angle ε can be 1° to 90°, 1° to 50°, 1° to 40°, 1° to 30°, 1° to 20°, 10° or less, 20° or less, 30° or less, etc. In the illustrated example, the angle ε can be 15° or less. In certain examples, the angle θ can be 1° to 90°, 1° to 75°, 1° to 65°, 1° to 55°, 1° to 45°, 60° or less, 50° or less, 40° or less, etc. In the illustrated example, the angle θ can be 55° or less. In the illustrated example, the angle γ can be 10° or less. In some examples, the first angle γ and the second angle δ can be configured to follow the contour of the prosthetic valve 100. Accordingly, the first and second sections 125*a* and 125*b* can be configured to receive the prosthetic valve 1000 prior to crimping, and as the prosthetic valve is advance through the third and fourth sections 125*c*, 125*d*, it can be compressed by the third angle ε and the fourth angle θ. Such a configuration advantageously allows the prosthetic valve 1000 to be easily inserted into the funnel segment 124**.

Referring to FIG. 4, each side portion 114 of the housing 108 can comprise a half-cylinder such that when they are placed together they form a generally cylindrical or tubular shape. The side portions 114*a*, 114*b* can each include mating features that allow the side portions to be coupled to one another. For example, as shown in FIG. 4, the first side portion 114*a* can comprise one or more recesses 136 such as diametrically opposed recesses formed in the longitudinal edges of the first side portion 114*a*, and the second side portion 114*b* can comprise corresponding protrusions or tabs 138 extending from the longitudinal edges of the second side portion 114*b*. As shown, the protrusions 138 can sit within the recesses 136 when the side portions 114 are coupled together.

The first and second side portions 114 can be held or locked together in the assembled state while a prosthetic valve is being crimped and then separated from each other to facilitate removal of the crimping device 100 from the delivery apparatus 102 after the prosthetic valve is loaded onto the delivery apparatus. As shown in FIG. 1, the first and second side portions 114 can be coupled together via a retaining member or retaining ring 140, which can encircle the side portions 114 and releasably retain them together.

In some examples, such as the example illustrated in FIG. 3A, the housing 108 can further comprise one or more alignment features 131 disposed on the internal surface 130 of the housing 108. The alignment features 131 can be configured as protrusions or nubs shaped to guide and/or orient portions of a prosthetic valve to assist in alignment of the connection features of the prosthetic valve (e.g., enlarged end portions 1014 of arms 1012 shown in FIG. 36) with mating features of the delivery apparatus.

Figure 5:
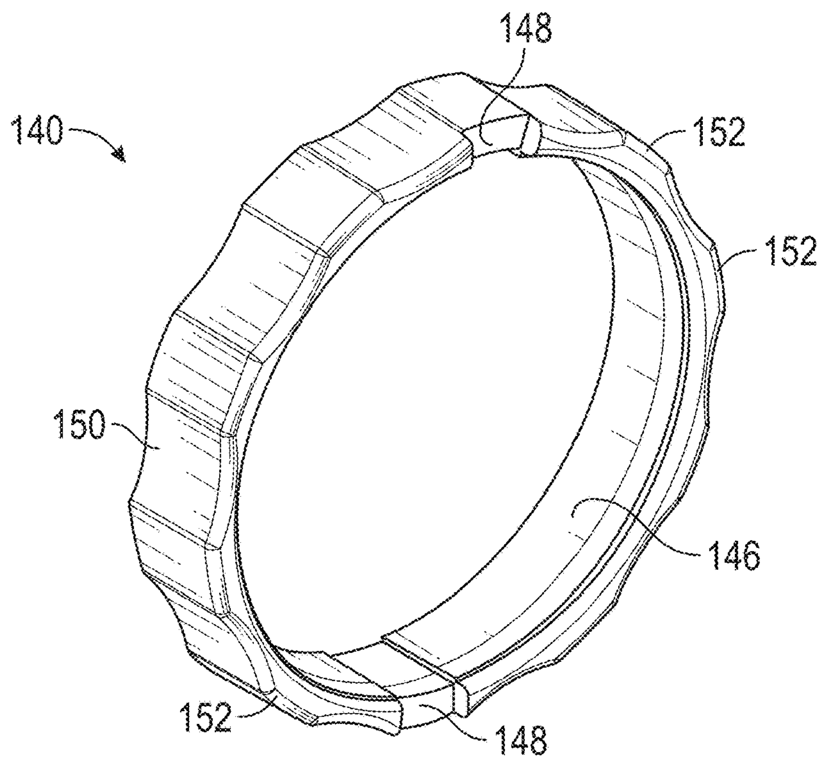
FIG. 5 is a perspective view of the retaining ring of the crimping device of FIG. 1.

Referring to FIG. 5, the retaining member 140 can include an internal annular surface 146 that can be sized to slide over an outer surface 144 (FIG. 4) of the housing 108 and form a frictional fit with, for example, the outlet end portions 120 of the housing side portions 114, such that retaining member 140 can hold the side portions 114 together during use but can be easily removed by a user when it is desired to disassemble the housing assembly 108 and remove it from the delivery apparatus 102. In other examples, the retaining ring 140 can be disposed on the inlet end portion 116 of the housing 108. The side portions 114 can comprise one or more tabs 142 (see e.g., FIG. 4) configured to engage the retaining member 140 and restrain the retaining member 140 against movement along the outer surface of the housing 108 past a selected point. In some examples, the retaining ring 140 can comprise one or more recesses 148 configured (e.g., sized and shaped) such that the tabs 142 can sit within the recesses 148. The retaining member 140 can include a gripping interface 150 for easy gripping and use by a user. The gripping interface 150 can include, for example, a plurality of circumferentially spaced ridges 152. Further details of the housing and the retaining member can be found, for example, in U.S. Pat. No. 10,639,147, which is incorporated by reference herein in its entirety.

In other examples, the side portions 114 can be releasably coupled together using a variety of alternative or additional techniques or mechanisms, for example, the side portions can be configured to form a snap-fit connection, or each side portion can include an integral mating feature configured to mate with a corresponding mating feature of the remaining side portion (e.g., a bayonet mount). In still other examples, the housing 108 can be a unitary component configured as a cylindrical housing component or member rather than multiple, separable components.

Figure 6:
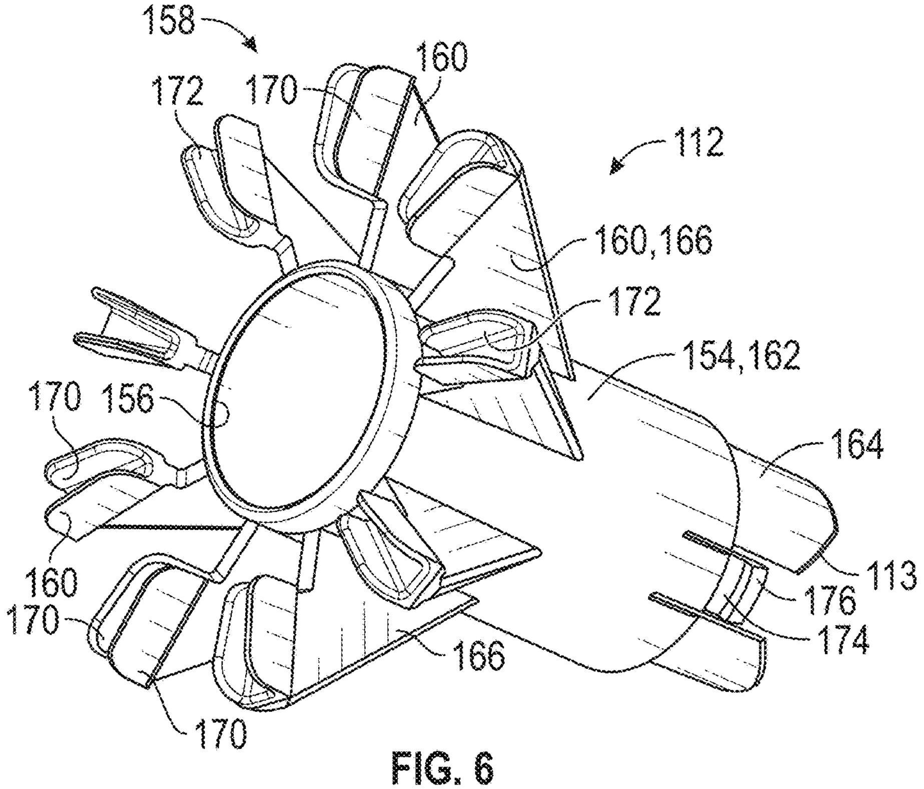
FIGS. 6-7 are perspective views of the pusher member of the crimping device of FIG. 1.
Figure 7:
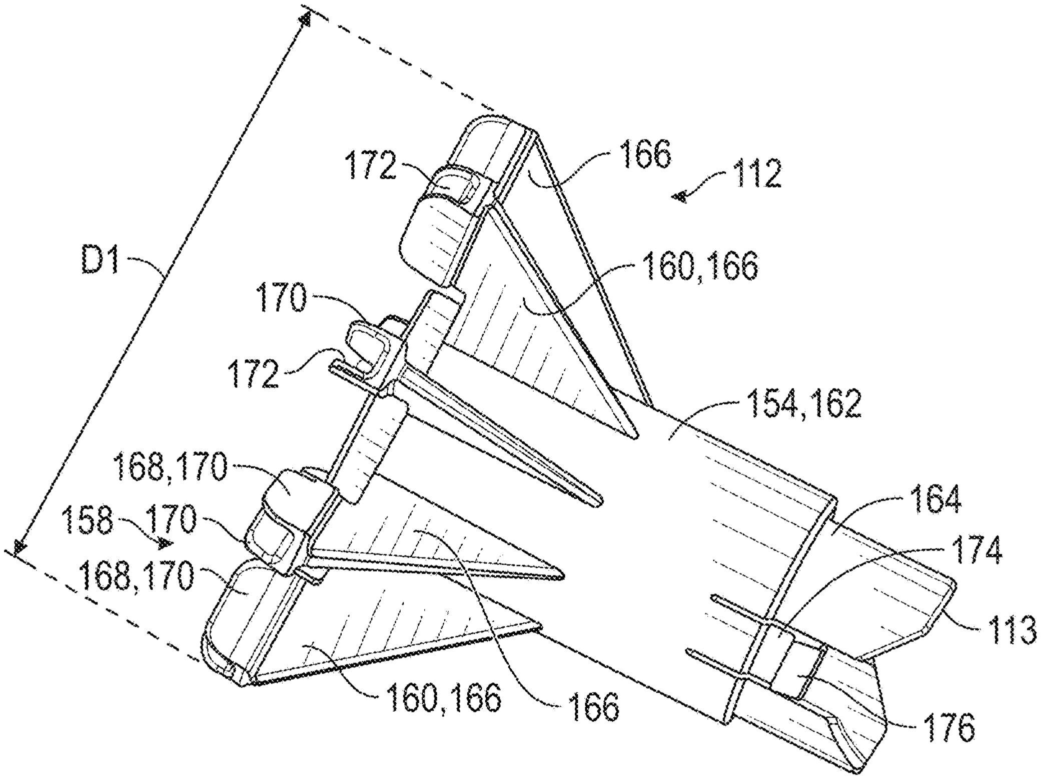
Figure 8:
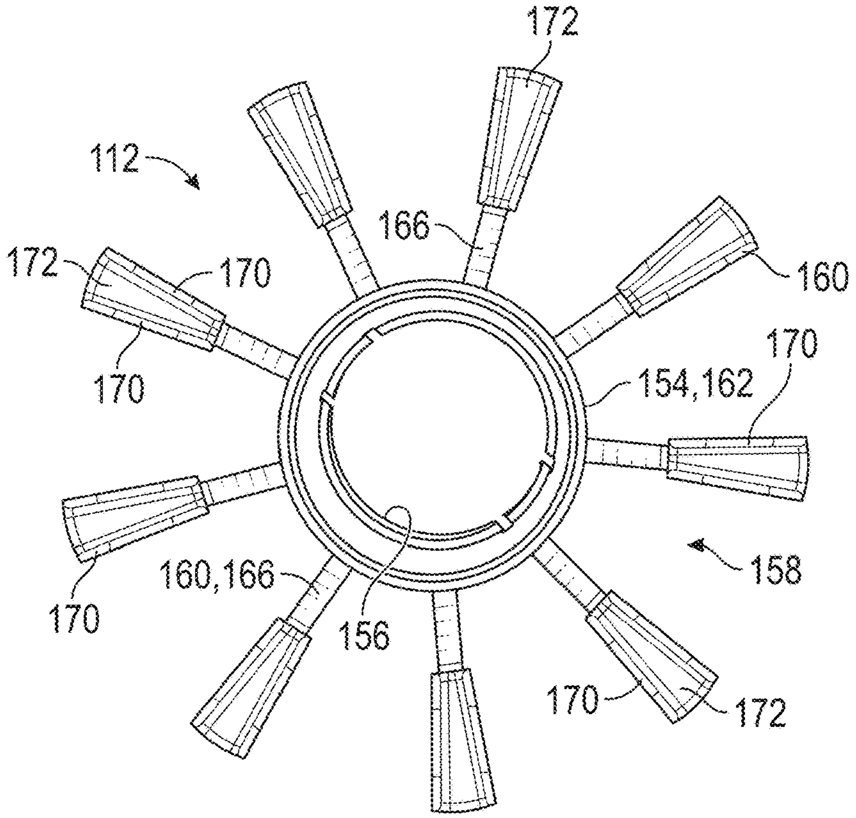
FIG. 8 is an end-on view of the pusher member of the crimping device of FIG. 1.
Figure 9:
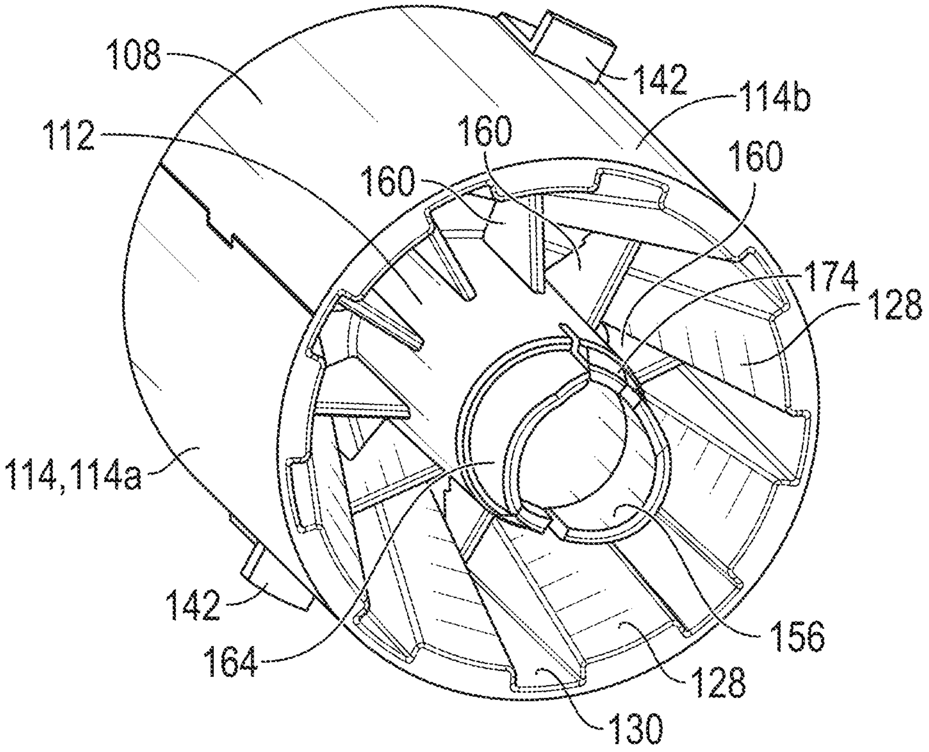
FIG. 9 is a perspective view of the housing of the crimping device of FIG. 1 with the pusher member disposed therein.

As mentioned, the crimping device 100 can further comprise a valve holder or pusher member 112 that is releasably couplable to the actuator 110. Referring to FIGS. 6-8, the pusher member 112 can comprise a generally cylindrical or tubular main body or stem 154 including an inner bore 156, and a holding portion 158 comprising a plurality of circumferentially spaced, radially extending members referred to herein as arms 160. The arms 160 can be configured to be slidably disposed between the ribs 128 of the housing 108, as shown in FIG. 9, such that as the pusher member 112 moves axially with respect to the housing 108, the arms 160 travel and/or slide through gaps/slots 127 defined between the ribs 128. The pusher member 112 can have an outer diameter $D_1$ (FIG. 7) less than an inner diameter $D_2$ (FIG. 3B) defined by the inner surface 130 of the housing 108 in the gaps between the ribs 128 such that the pusher member 112 can be disposed within the housing 108. In certain examples, the gaps/slots 127 can also facilitate insertion of a tool into the funnel portion to guide the implant (e.g., the frame of the implant) and prevent the implant from catching on the interior edges of the funnel portion as the implant is compressed.

The stem 154 can have a first end portion 162 having a first diameter and a second end portion 164 having a second diameter less than the first diameter. The second end portion 164 can be sized to extend into a portion of the actuator 110. The arms 160 can extend from the first end portion 162. Each arm 160 can have a substantially triangular base portion 166 and a seat 168 comprising, for example, first and second walls 170 defining a recess or channel 172 between them. Thus, in the illustrated example, the pusher member 112 can comprise a plurality of seats 168 arrayed circumferentially around the first end portion 162 with channels 172 open in the direction of advancement of the pusher member during a valve crimping operation. The seat 168 can be configured to hold or engage a portion of the prosthetic valve (e.g., the anchors 1010 of prosthetic valve 1000, shown in FIG. 36), for example, to prevent the prosthetic valve from being displaced relative to the pusher member 112 and/or align portions of the prosthetic valve with the ribs 128. For example, the anchors 1010 can sit within the channels 172 of the seats 168. As best seen in FIG. 8, the seats 168 can taper from a first width/thickness adjacent a radially outer edge of the pusher member 112 (e.g., at the radially outermost ends of the seats 168) to a second width/thickness, less than the first thickness, adjacent the stem 154 so as to generally correspond to the shape of the spaces between the ribs 128 of the housing 108.

The second end portion 164 of the stem 154 can comprise one or more resilient locking features 174 (e.g., two diametrically opposed locking features in the illustrated example) configured to releasably couple the pusher member 112 to the actuator 110 such that the actuator 110 can be used to advance the pusher member 112 (and therefore the prosthetic valve) within the housing 108. For example, in the illustrated example, the locking features 174 are configured as resilient latch members having a protrusion or lip 176 that can mate with a corresponding feature (e.g., an opening or ledge) in the actuator 110. In the example shown in FIGS. 1-10, the actuator 110 comprises one or more openings 178 (FIG. 10) which can engage the locking features 174. The locking features 174 can be deflected inwardly when the second end portion 164 of the pusher member 112 is advanced into an inner bore 180 of the actuator 110 and can deflect outwardly once the within the openings 178, coupling the pusher member 112 and the actuator 110 together with a snap-fit connection.

Figure 10:
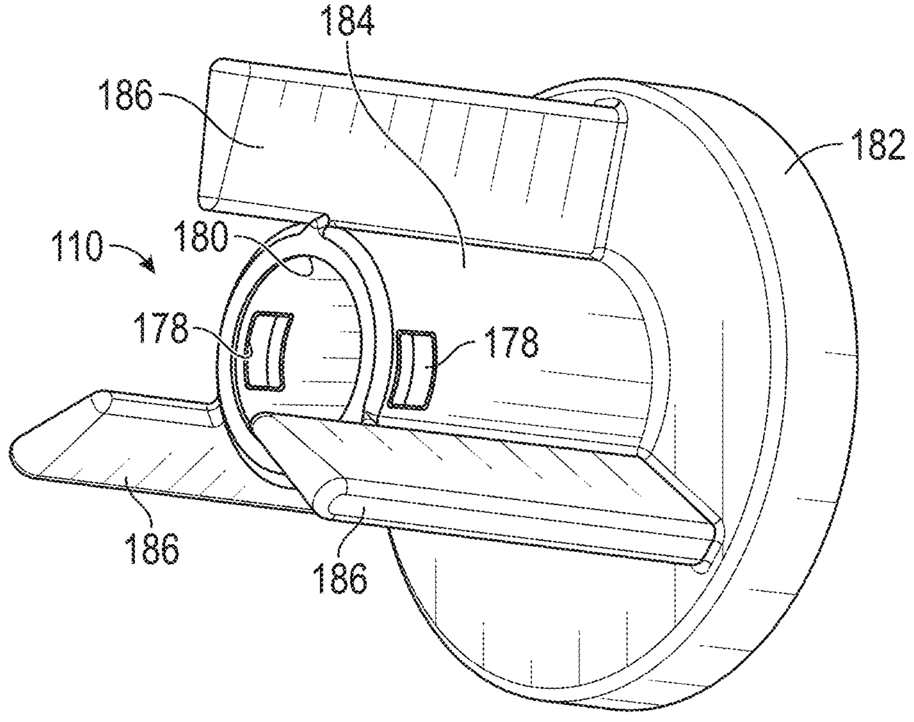
FIG. 10 is a perspective view of the actuator of the crimping device of FIG. 1.

Referring to FIG. 10, the actuator 110 can comprise a grasping portion or base 182 from which one or more extension portions/members 184, 186 can extend. The extension members can comprise a central extension member 184 (which can include the corresponding locking feature(s) such as openings 178) and one or more guide members referred to herein as linear guide members 186 (e.g., three linear guide members in the illustrated example). The central extension member 184 can be configured as a cylindrical protrusion/tube having an inner lumen or bore 180, and the linear guide members 186 can be elongated rectangular protrusions extending from the base 182 and arrayed circumferentially around the central extension member 184. The linear guide members 186 can taper from a first thickness adjacent a radially outer edge of the actuator 110 to a second thickness, less than the first thickness, along the radially inner edges of the linear guide members adjacent the central extension member 184 so as to generally correspond to the shape of the spaces between the ribs 128 of the housing 108. A user can grip the base 182 and apply a pushing force to the actuator 110 to push the pusher member 112 into the housing 108, as represented by arrow 188 in FIG. 1. In some examples, the base 182 can comprise a gripping interface similar to gripping interface 150 of the retaining ring 140. As best seen in FIG. 2, in some examples the base 182 can comprise a recess 190 extending into a thickness of the base 182.

Though in the illustrated examples the crimping device 100 is shown with components that are substantially circular in cross-section, in other examples, the components can have any of various shapes in cross-section (e.g., square, rectangular, ovoid, triangular, etc.).

In use, the crimping device 100 can be used to crimp a prosthetic valve (e.g., prosthetic valve 1000 shown in FIG. 36) in the following exemplary manner. The prosthetic valve 1000 can be inserted into the housing 108. The pusher member 112 and actuator 110 can be aligned with the prosthetic valve 1000 so as to engage an adjacent end portion of the prosthetic valve 1000. As shown in FIG. 2, the housing 108, pusher member 112, and actuator 110 can be positioned co-axially around the shaft 104 of the delivery apparatus 102. The actuator 110 (and therefore the pusher member 112) can be advanced axially forward into the housing 108 by the user, for example, by pressing the housing and the actuator together in the axial direction. As the actuator 110 is advanced relative to the housing 108, the pusher member 112 is advanced into the housing 108, which in turn pushes the prosthetic valve 1000 through the funnel segment 124 of the housing 108 in the direction of the outlet 122. As prosthetic valve 1000 is pushed through the funnel segment 124, the prosthetic valve is at least partially radially compressed and pushed outwardly through the outlet 122.

In the example of FIGS. 1-10, the actuator and pusher member are advanced into the housing by axially directed force applied to the actuator by the user (e.g., by hand, or with a pressing device such as a vise), and without significant rotation of the actuator relative to the housing. In certain examples, insertion of the guide members 186 of the actuator into the channels between the ribs 128 of the housing can prevent or substantially prevent rotation of the actuator relative to the housing as the valve is crimped (e.g., the housing and actuator rotate relative to each other by 10° or less, such as by 5 degrees or less, as they are advanced together). Stated differently, the guide members can maintain an angular alignment between the housing 108 and the actuator 110 during the crimping operation. In some examples, the prosthetic valve 1000 can be pushed directly from the crimping device 100 into a sheath of a delivery apparatus (such as sheath 106 shown in FIG. 2). In other examples, the prosthetic valve 1000 can be coupled to a valve retaining member, for example valve retaining member 1110 of delivery apparatus 1100, and a separate loading assembly (such as loading assembly 2400 shown in FIG. 53) can be used to crimp the prosthetic valve 1000 to its fully crimped configuration and load it into a sheath/capsule of the delivery apparatus. This additional crimping and loading step is described in more detail with respect to FIGS. 60-69.

In some examples, the actuator 110 and/or the pusher member 112 can further comprise an engagement mechanism configured to releasably engage a corresponding engagement mechanism on the housing 108 such that the actuator 110 (and/or the pusher member 112) and the housing 108 can be locked together once the prosthetic valve 1000 has reached a selected crimped configuration (e.g., partially or fully crimped). This allows a user to release the actuator 110 without the resilient spring-force of the prosthetic valve 1000 pushing the pusher member 112 out of the housing 108 and allowing the prosthetic valve to resiliently return to the uncrimped or partially crimped configuration. For example, the linear guide members 186 of the actuator 110 can comprise one or more resilient latches (similar to latches 174 described previously) configured to mate with one or more corresponding openings in the housing 108 to lock the housing and actuator together at the selected location (e.g., when the prosthetic valve is partially or fully crimped). In other examples, various other types of engagement mechanisms can be used. In some examples, the housing 108 and actuator 110 can lock together at a selected position wherein the prosthetic valve is disposed within the outlet 122 (in other words, such that the prosthetic valve has only partly advanced through the outlet). Such a configuration allows the user to release the crimping device 100 to connect the connection features of the prosthetic valve to the mating features of the delivery apparatus without the prosthetic valve resiliently expanding and pushing the pusher member 112 out of the inlet end portion 116.

Any or all of the crimping devices disclosed herein can advantageously allow for a one-person operation of the crimping device and a repeatable, predictable procedure for crimping and loading a prosthetic valve/coupling a prosthetic valve to a delivery apparatus. Some examples of the prosthetic valve can include connection features that form a releasable connection with mating features of the delivery apparatus (the connection features are located at the end of the prosthetic valve opposite the end in engagement with the pusher member) (e.g., see connecting arms 1012 of prosthetic valve 1000, described in further detail below). In certain examples, the connection features of the prosthetic valve can be radially compressed while maintaining rotational alignment with the mating features of the delivery apparatus. The crimping device, such as device 100, allows a single operator to control crimping of the prosthetic valve while maintaining the rotational alignment of the connection features of the prosthetic valve with the mating features of the delivery apparatus. As the prosthetic valve is advanced out of the outlet 122 of the crimping device 100, the operator can connect the connection features of the prosthetic valve to the mating features of the delivery apparatus.

In some examples, such as the example shown in FIG. 2, the prosthetic valve can be advanced through the outlet 122 of the crimping device 100 and into the sheath 106 of the delivery apparatus 102. The sheath 106 can be a tubular structure configured to contain the prosthetic valve in the delivery configuration. The crimping device 100 can then be removed from the delivery apparatus 102 by sliding it distally off the inner shaft 104 (in the direction of arrow 191), or by removing the retaining ring 140 and separating the side portions 114 of the housing 108. The pusher member

112 and actuator 110 can have inner bores large enough to allow them to be slid off of the delivery apparatus 102, for example, by sliding them distally relative to the inner shaft 104 until they are removed from the distal end of the delivery apparatus.

Figure 37:
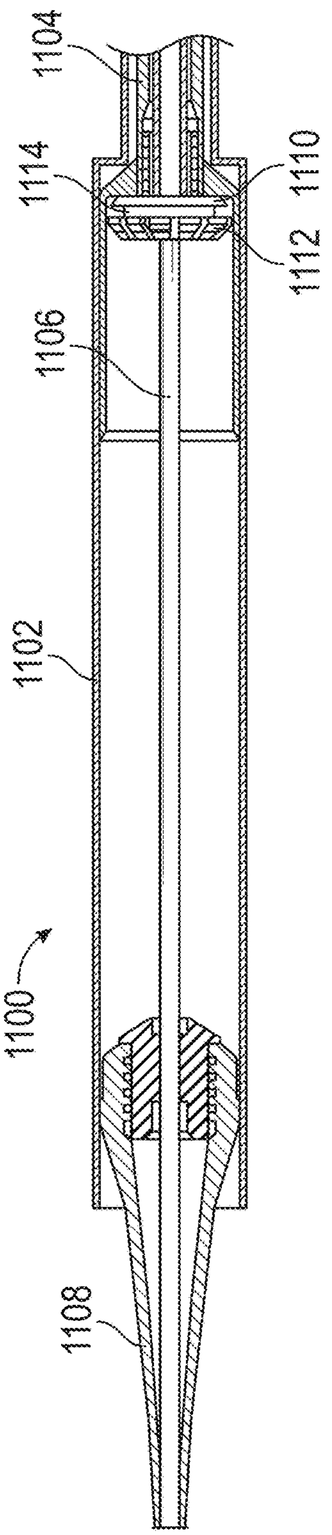
FIG. 37 is a cross-sectional side elevation view of a distal end portion of an example of a delivery apparatus that can be used to deliver and implant the prosthetic valve of FIG. 36.

In other examples, such as described with respect to FIG. 37, the prosthetic valve can be advanced through the outlet 122 of the crimping device 100 and can be coupled to a valve retaining member (e.g., member 1110 of delivery apparatus 1100). So coupled, the crimping device 100 can be removed from the delivery apparatus (e.g., by sliding it distally off the inner shaft 104 (in the direction of arrow 191), or by removing the retaining ring 140 and separating the side portions 114 of the housing 108), and a separate crimping and loading assembly (e.g., loading assembly 2400) can be used to advance the prosthetic valve into the capsule/sheath of the delivery apparatus.

Once the prosthetic valve 1000 has been loaded into the delivery apparatus, the delivery apparatus 102 can be inserted into the vasculature of a patient and used to deliver the prosthetic valve 1000 percutaneously to the desired implantation location using conventional techniques. The distal end of the delivery apparatus 102 can be inserted into another device, such as an introducer sheath, which has been already inserted into a patient, to facilitate insertion of the delivery apparatus 102 into the patient.

In some examples, a system comprising a crimping device (e.g., crimping device 100), a delivery apparatus 102, and a prosthetic valve (e.g., prosthetic valve 1000) can be packaged and shipped from the manufacturer to the end user with the prosthetic valve pre-loaded inside of the fully assembled crimping device coaxially mounted on the delivery apparatus. In some examples, the system can further comprise a sterile package enclosing the crimping device mounted on the distal end portion of the delivery apparatus, the prosthetic valve pre-loaded in the crimping device, and the entire the delivery apparatus or just the distal end portion of the delivery apparatus on which the crimping device and the prosthetic valve are mounted. In other examples, the system can further comprise another device, such as an introducer sheath, to assist in inserting the delivery apparatus 102 into a patient once the prosthetic valve has been loaded into the sheath 106. In some examples, the system can further comprise a crimping and loading assembly (e.g., crimping and loading assembly 2400 shown in FIG. 53) packaged with the other components.

In some examples, the prosthetic valve (such as prosthetic valve 1000) can be in a partially crimped configuration prior to being disposed within the crimping device 100 (or any of the other crimping devices disclosed herein). For example, the prosthetic valve can be pre-crimped to the partially crimped configuration using another crimping instrument, prior to being assembled into crimping device 100. In the partially crimped configuration, the prosthetic valve has an outer diameter that is between that of the expanded configuration and that of the delivery configuration. In some examples, the prosthetic valve can have an outer diameter in the partially crimped configuration that is closer to the outer diameter in the delivery configuration than to the outer diameter in the expanded configuration. For example, the prosthetic valve 1000 in the partially crimped configuration can be crimped about 75% of the way from the expanded configuration to the delivery configuration. The crimping device 100 can also be configured to crimp the prosthetic valve to the delivery configuration from the expanded configuration without first pre-crimping the prosthetic valve to an intermediate partially crimped configuration.

Figure 11:
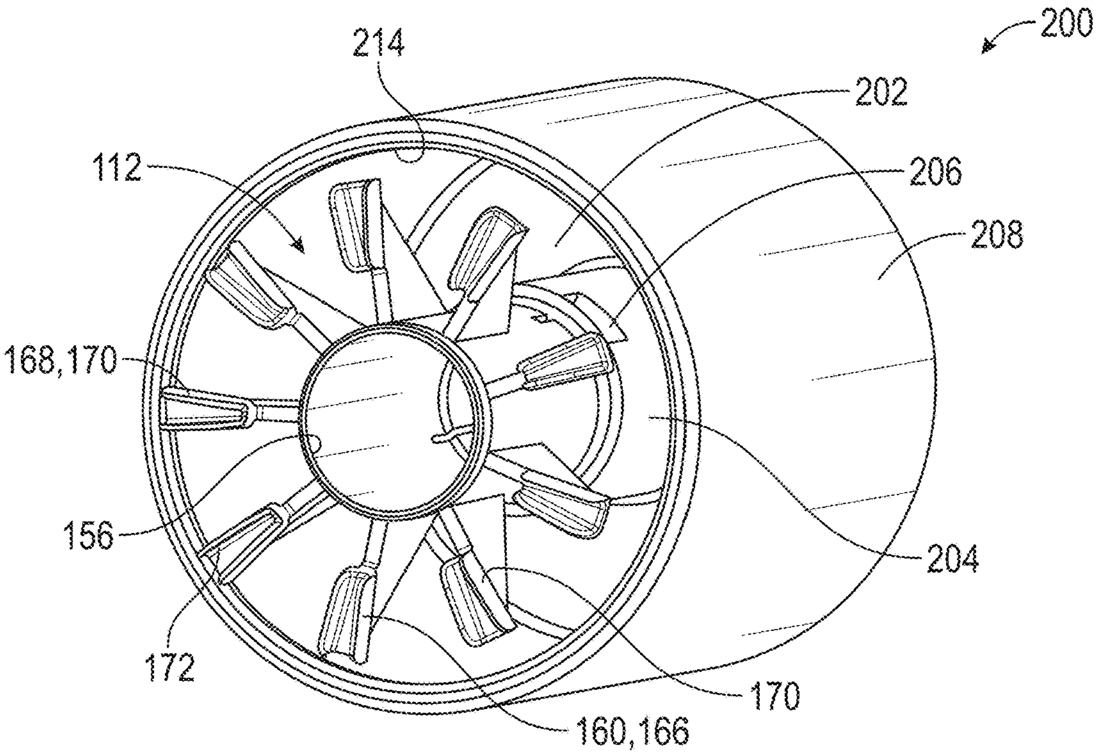
FIG. 11 is a perspective view of another example of an actuator coupled to the pusher member of the crimping device of FIG. 1.
Figure 12:
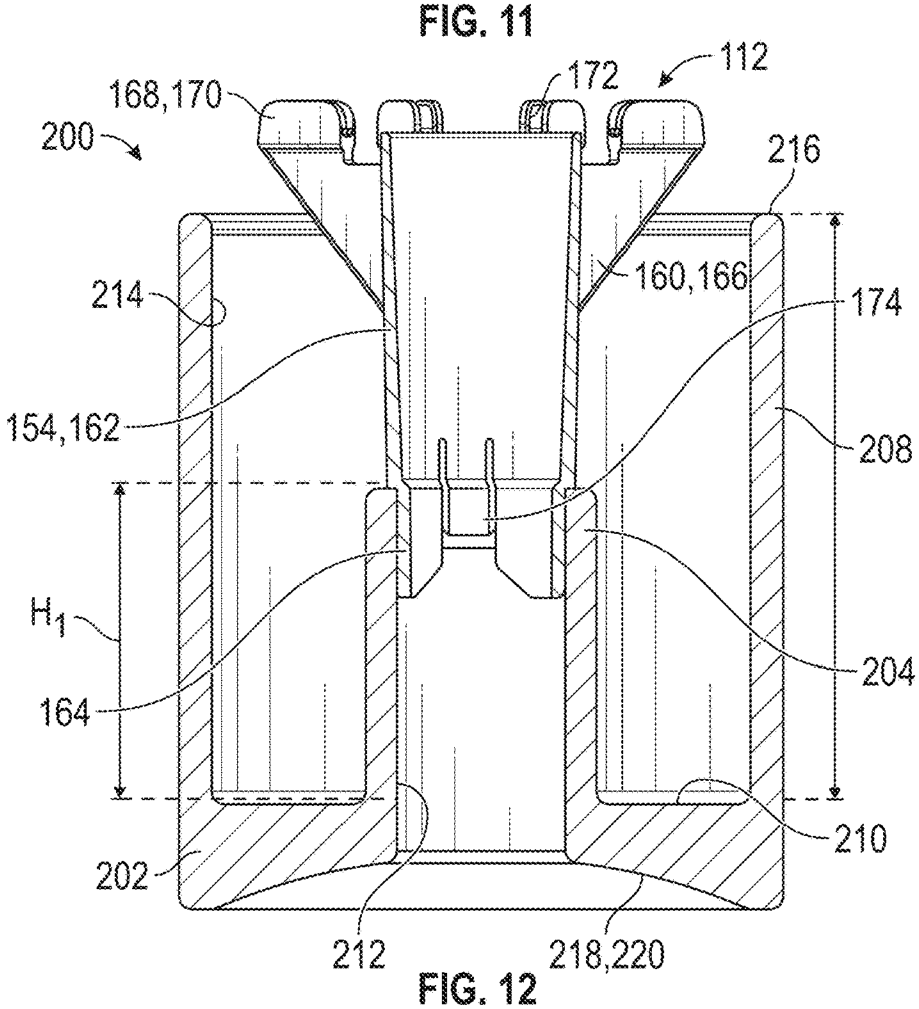
FIG. 12 is a cross-sectional side elevation view of the actuator and pusher member of FIG. 11.

FIGS. 11-12 illustrate another example of an actuator 200 that can be used in lieu of or in addition to actuator 110 described previously. Actuator 200 can comprise a base plate/member 202, a first extension member/portion 204 extending axially from a first surface 210 of the base member 202 and comprising one or more openings 206 configured to mate with the resilient locking features 174 of the pusher member 112. The actuator 200 can further comprise a second extension member/portion 208 extending from the first surface 210 and positioned coaxially around the first extension member 204. Thus, in the illustrated example the first extension member 204 can be configured as an inner extension member and the second extension member 208 can be configured as an outer extension member disposed about an outer perimeter of the base member 202. In certain examples, an inner diameter of the second extension portion 208 can be greater than an outer diameter of the housing 108. In the example shown in FIGS. 11-12, each extension member 204, 208 can be a cylindrical/tubular extension member comprising respective inner bores 212 (FIG. 12), 214. In other examples, the extension members 204, 208 can have any of various other shapes in cross section, such as square, rectangular, ovoid, triangular, etc.

As shown in FIG. 12, the first cylindrical extension member 204 can have a height $H_1$ less than a height $H_2$ of the second cylindrical extension member 208 measured relative to the first surface 210. The pusher member 112 can be removably coupled to the first cylindrical extension member 204 in the same manner as described previously for central portion 184. In some examples, such as the illustrated example, the first end portion 162 of the pusher member 112 can extend past a first/open end portion 216 of the second cylindrical extension member 208. As shown, a second surface 218 of the base member 202 can include a recess 220, for example, a hemispherical recess. The recess 220 can provide an ergonomic face for a user to place their fingers on the actuator 200 in order to advance the actuator 200.

The actuator 200 can be used in combination with pusher member 112 and housing 108 to compress a prosthetic valve (e.g., prosthetic valve 1000) in the same manner as described previously for actuator 110. For example, as the actuator 200 and the housing 108 are advanced together, the housing 108 can be at least partially received within the second cylindrical extension portion 208. Such a configuration advantageously allows the pusher member 112 to be centered along the longitudinal axis A (FIG. 2B) of the housing such that it is aligned with the prosthetic valve during crimping.

Figure 13:
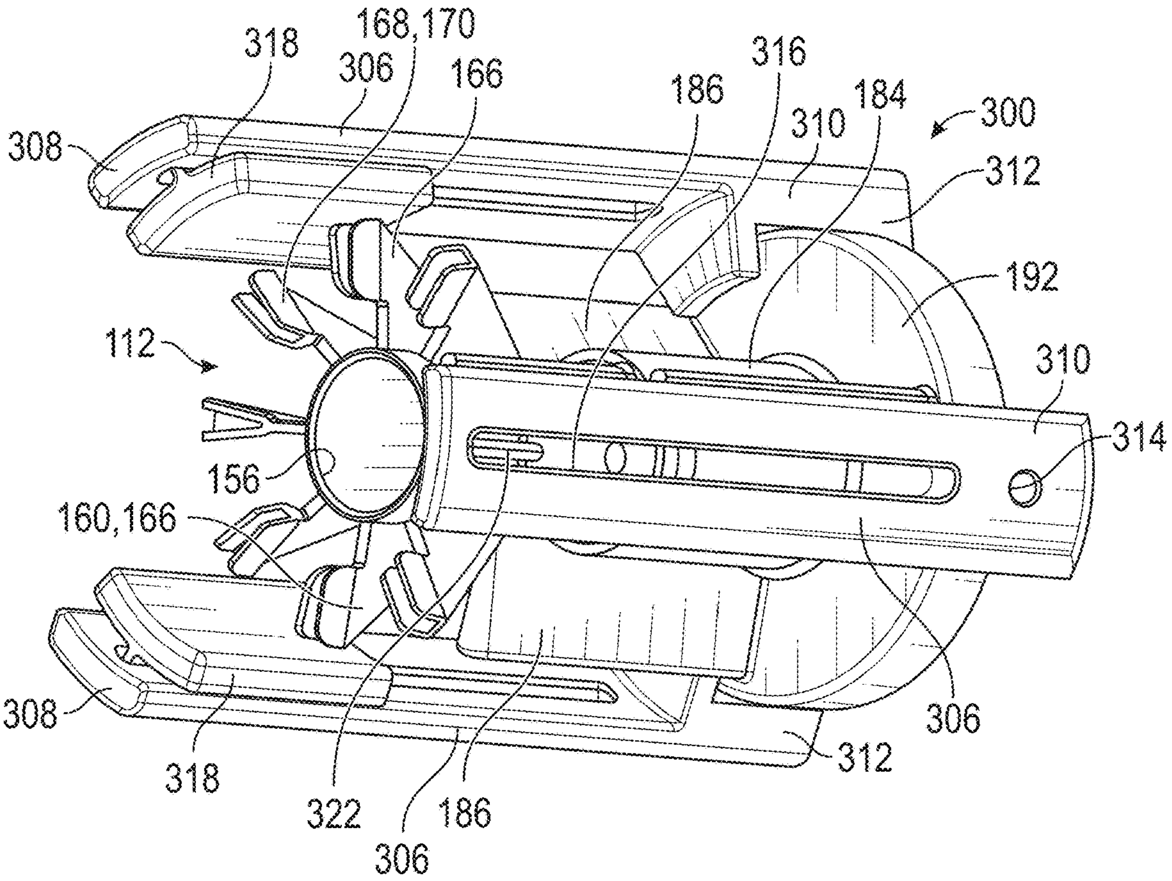
FIG. 13 is a perspective view of another example of an actuator coupled to the pusher member of the crimping device of FIG. 1.
Figure 14:
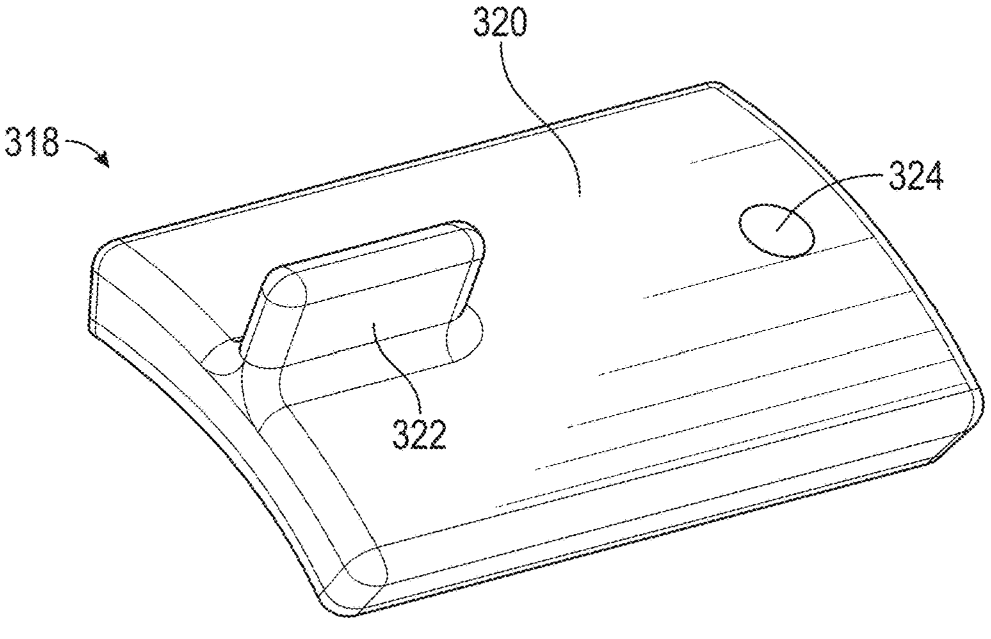
FIG. 14 is a perspective view of the slidable member of FIG. 13.
Figure 15:
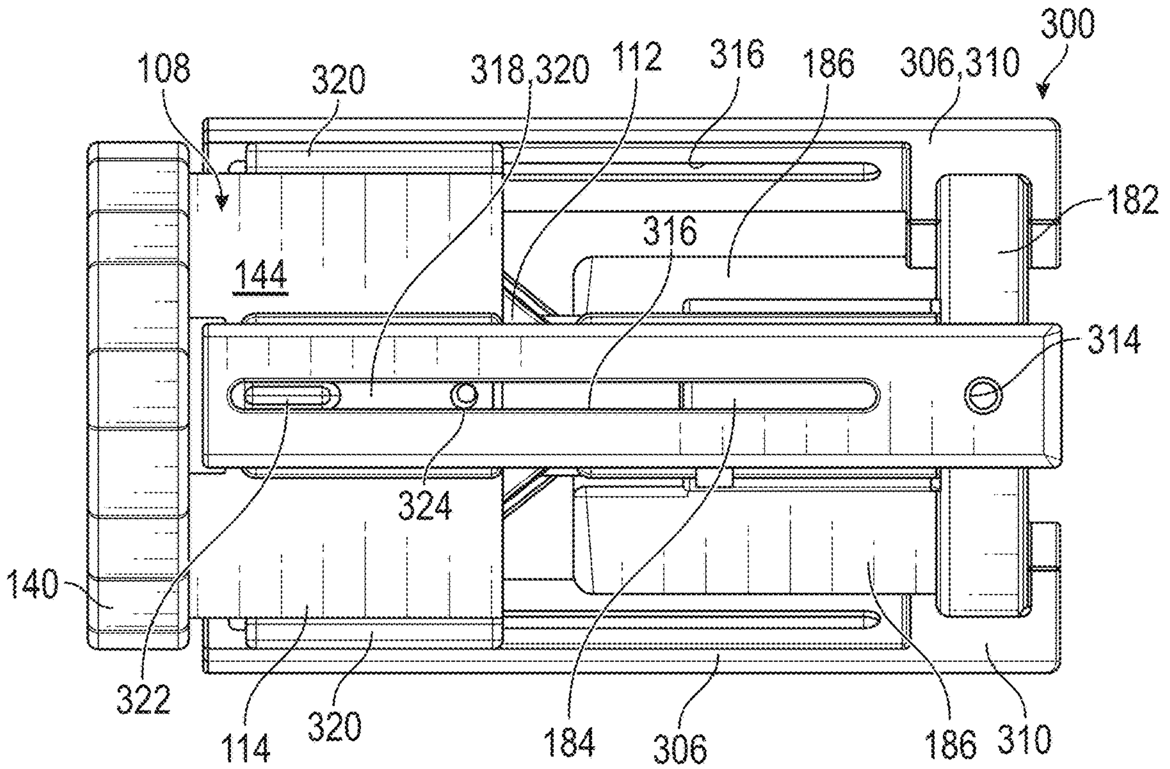
FIG. 15 is a side elevation view of the actuator and pusher member of FIG. 13 coupled to a housing.
Figure 16:
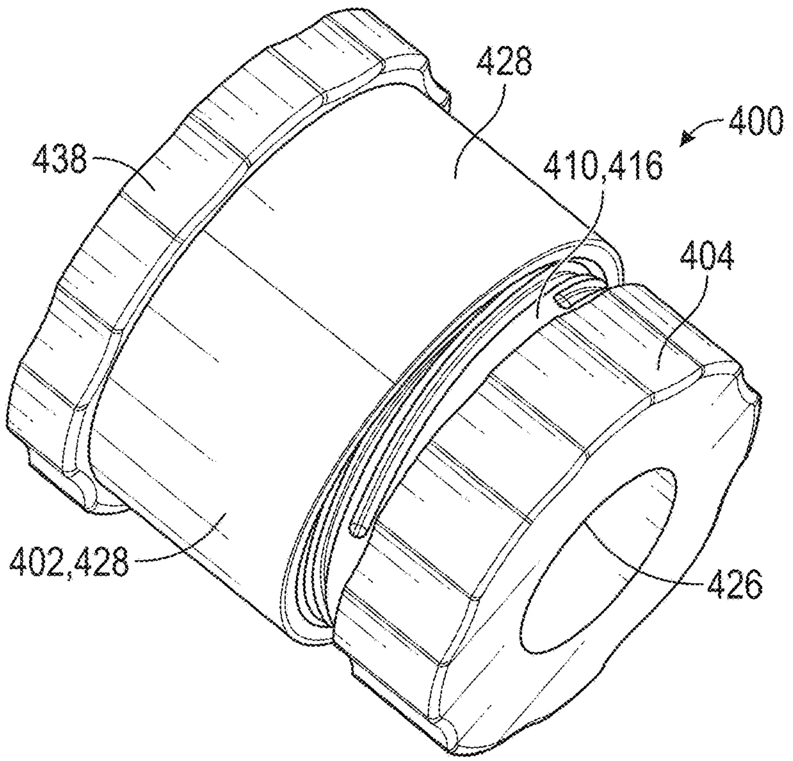
FIGS. 16-17 are perspective views of another example of a crimping device.

FIGS. 13-15 illustrate another example of an actuator 300 that can be used in lieu of or in addition to actuator 110 described previously. Actuator 300 can be similar to the actuator 110 described previously (e.g., comprising a base 182, central extension 184 with openings 178, and linear guide members 186), except that actuator 300 further comprises guide members such as guides 306.

The guides 306 can be configured as elongated members coupled to and extending from the base portion/member 302. Each guide 306 can comprise a first end portion 308 and a second end portion 310, which is adjacent the base member 302. The second end portion 310 can be removably coupled to the base member 302 via a coupling portion configured as a bracket 312 having an opening sized such that the base member 302 can be received within the opening. One or more apertures 314 can be disposed in the second end portion 310 such that a fastener can extend through the aperture to couple a respective guide 306 to the base member 302. The guides 306 can each comprise an elongated opening or slot 316 extending at least partially along the length of the guide 306.

The actuator 300 can further comprise one or more slidable members 318 (also referred to as spacer members) each paired with a respective guide 306. Referring to FIG. 14, a slidable member 318 can comprise a main portion 320 and a projection or protrusion 322. The protrusion 322 can be sized to extend into and sit within the slot 316 of a respective guide 306, as shown in FIG. 13, such that the slidable member 318 can slide axially relative to the guide 306. Each slidable member 318 can comprise an aperture or opening 324 into which a fastener can be disposed to couple the slidable member 318 to the housing 108, as shown in FIG. 15. For example, an end portion of the fastener can engage an outer surface 144 of the housing 108, and/or the fastener can extend into a corresponding aperture in the outer surface 144 of the housing 108. As shown in FIG. 13, each guide 306 and slidable member 318 can have a curved shape in cross-section, such as corresponds to the curved outer circumference of the housing 108.

As shown in FIGS. 13-15, in the illustrated example, the actuator 300 can have three guides 306 equally spaced from one another about the circumference of the base member 302. In other examples, the actuator 300 can have a greater or fewer number of guides 306 and the guides 306 can be spaced at any locations and/or interval about the circumference of the base member 302.

In use, once the prosthetic valve 1000 has been inserted into the housing 108, the actuator 300 can be aligned with the housing 108 such that the slidable members 318 are disposed adjacent an outer surface of the housing 108 and such that the pusher member 112 engages an adjacent end portion of the prosthetic valve 1000. Thus aligned, fasteners can be tightened through the apertures 324 of the slidable members 318 to couple the actuator 300 to the housing 108. As a force (e.g., a pushing force) is applied to the actuator by a user, the housing 114 and the actuator 300 move toward each other such that protrusions 322 of the slidable members 318 slide/travel along the slots 316, and such that the pusher member 112 advances axially forward into the housing 108. The pusher member 112 can continue to be advanced through the housing 108, thereby advancing the prosthetic valve 1000 through the housing 108. The protrusions of the slidable members 318 traveling along the slots of the guide members can maintain the angular orientation of the housing and the actuator as they are pressed together, preventing rotation of one relative to the other. As prosthetic valve 1000 is pushed through the funnel segment 124, the prosthetic valve is radially compressed and pushed outwardly through the outlet 122. The prosthetic valve 1000 can then be coupled to a valve retaining member 1110 of the delivery apparatus 1100, as described in more detail with respect to FIG. 37 or can be loaded directly into the sheath of the delivery apparatus as described previously with respect to crimping device 100.

In some examples, the guides 306 can further comprise an engagement or locking mechanism configured to lock the sliding members 318 against movement relative to the slot 316 once the prosthetic valve 1000 has reached the fully crimped position (e.g., once the pusher member 112 has been fully advanced into the housing 108). This can allow a user to release the actuator 300 without the resilient spring-force of the prosthetic valve 1000 pushing the pusher member 112 out of the housing (which may allow the prosthetic valve to resiliently return to the uncrimped or partially crimped configuration). For example, the slot 316 can comprise one or more latches or tabs (e.g., angled teeth) that allow movement of the protrusion 322 past the tabs in a first direction (e.g., to advance the pusher member 112 into the housing 108) and prevent movement of the protrusion 322 past the tabs in a second direction opposite the first direction (e.g., to retract the pusher member 112 from the housing 108). In another example, the guides 306 can comprise one or more set screws configured to allow the user to 'pause' the crimping procedure at any point. Set screws in the apertures 324 can also be used for this purpose, and/or the guide members can include any of various other fixation means including detents, cam lobes, etc., to create discrete increments of travel along the guide members.

Figure 17:
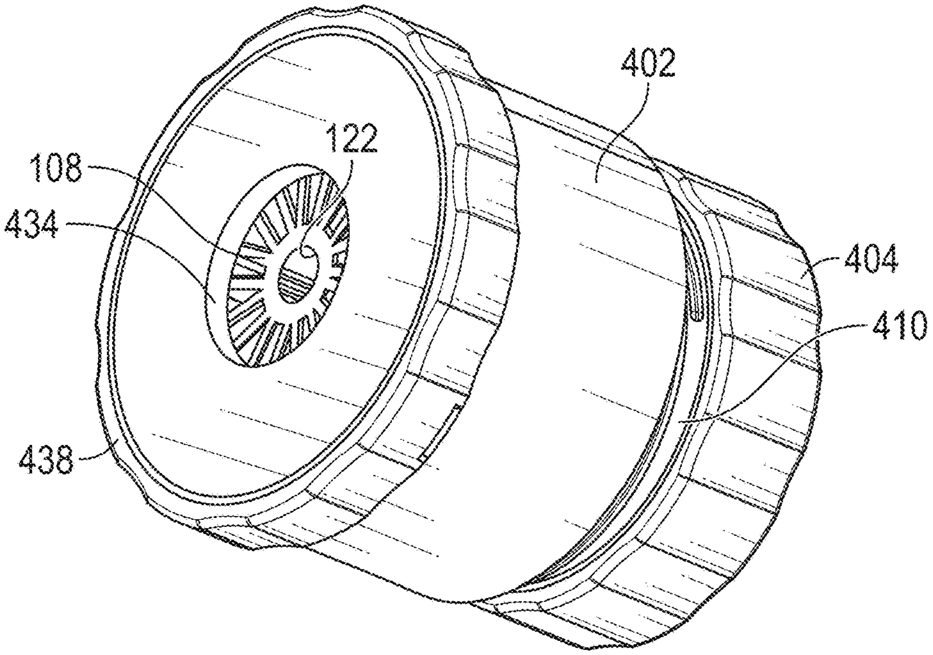
Figure 18:
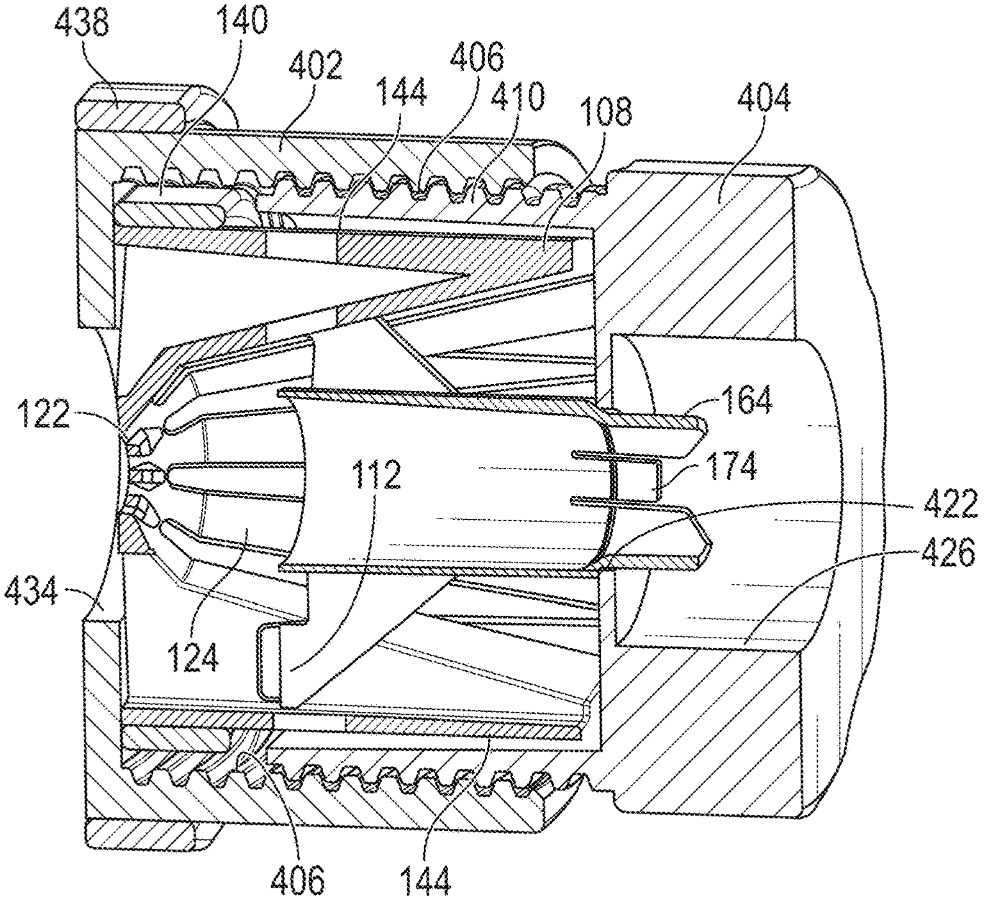
FIG. 18 is a cross-sectional perspective view of the crimping device of FIG. 16.

FIGS. 16-22 illustrate another example of a crimping device 400. Crimping device 400 can generally comprise a housing 108 (as described previously), an outer housing or shell 402, and an actuator 404 including a pusher member 112 (as described previously). As shown in FIG. 18, the housing 108 can be disposed within the outer shell 402. A portion of the actuator 404 can be received between an inner surface 406 of the shell 402 and an outer surface 144 of the housing 108 and can advance by, for example, threads on the exterior surface of the actuator 404 and complementary threads on the interior surface of the shell 402.

Figure 19:
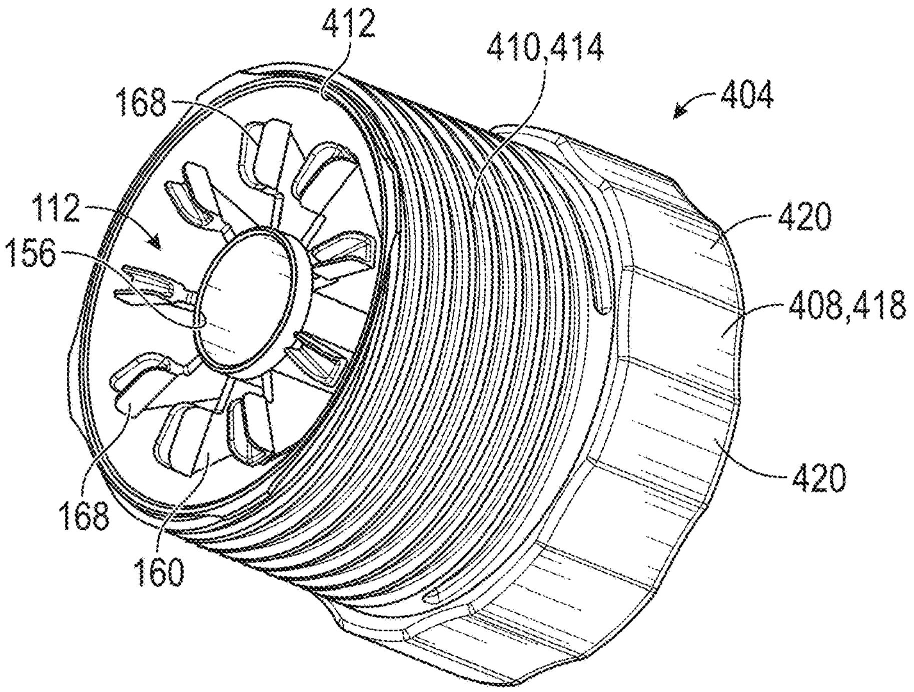
FIG. 19 is a perspective view of the actuator and pusher member of the crimping device of FIG. 16.
Figure 20:
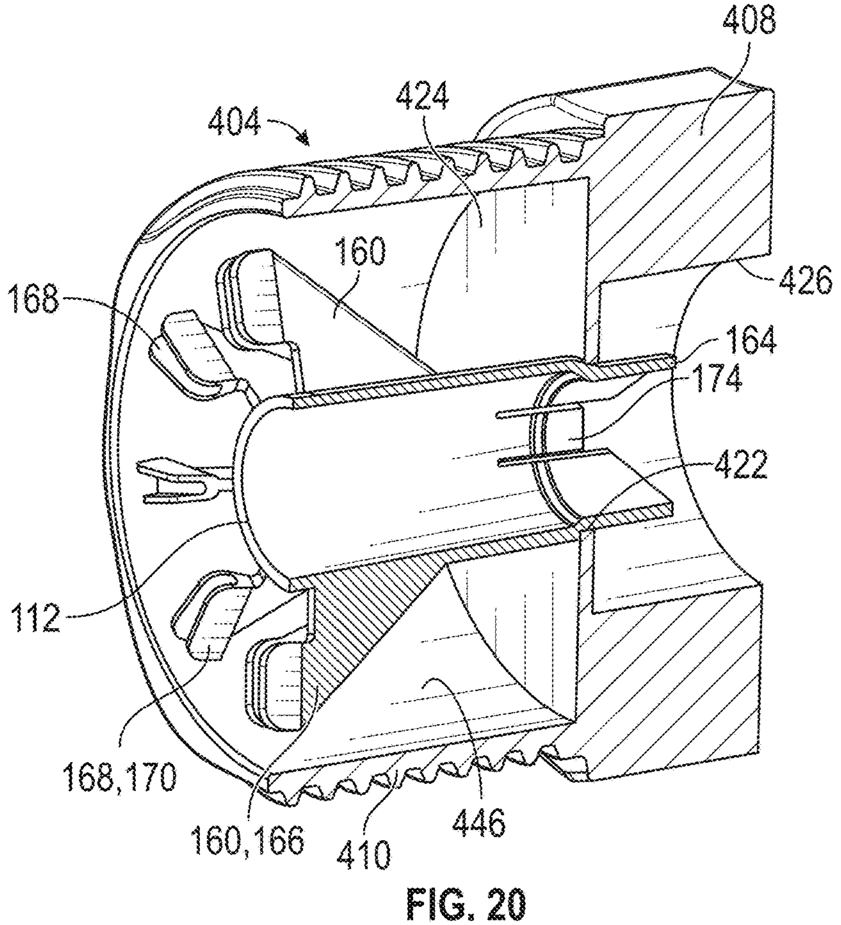
FIG. 20 is a cross-sectional perspective view of the actuator and pusher member of the crimping device of FIG. 16.

Referring to FIGS. 19-20, the actuator 404 can comprise a base 408, and an extension portion 410 extending from the base 408. The extension portion 410 can be configured as a cylindrical extension portion defining an inner bore 412. An outer surface of the extension portion 410 can comprise a threaded portion 414 (e.g., external threads) configured to interface with a correspondingly threaded portion 416 (e.g., internal threads) disposed on the inner surface 406 of the shell 402.

The base 408 can include a gripping interface 418 for easy gripping and use by a user. The gripping interface 418 can include, for example, a plurality of circumferentially spaced ridges 420. As shown in FIG. 20, the base 408 can also include an opening or aperture 422 into which the second end portion 164 of the pusher member 112 can extend. The aperture 422 can be surrounded by an annular surface/shoulder/flange referred to hereinafter as a ledge 424. The pusher member 112 can be removably coupled to the base 408 via the resilient locking features 174. For example, as mentioned previously, the locking features can be resilient latches having a lip 176 (see e.g., FIG. 7). The locking features 174 can deflect inwardly as the second end portion 164 is inserted into the aperture 422 and then resiliently return such that the lips 176 can engage the ledge 424, thereby forming a snap-fit connection between the base 408 and the pusher member 112. The connection between the pusher member 112 and the actuator 404 can be configured to allow rotation of the actuator 404 without causing corresponding rotation of the pusher member 112 (e.g., when the arms 160 of the pusher member 112 are disposed between the ribs 128 of the housing portion). Stated differently, as the actuator 404 is rotated, the pusher member 112 moves axially with the actuator 404 but does not rotate because the lips 176 are configured to slip or rotate relative to the ledge 424. The base 408 can further comprise a recess 426 into which the second end portion 164 of the pusher member 112 can extend when the pusher member and actuator are releasable coupled together. The recess 426 can be sized to allow a user to access the resilient locking features 174 in order to decouple the pusher member 112 from the base 408.

Figure 21:
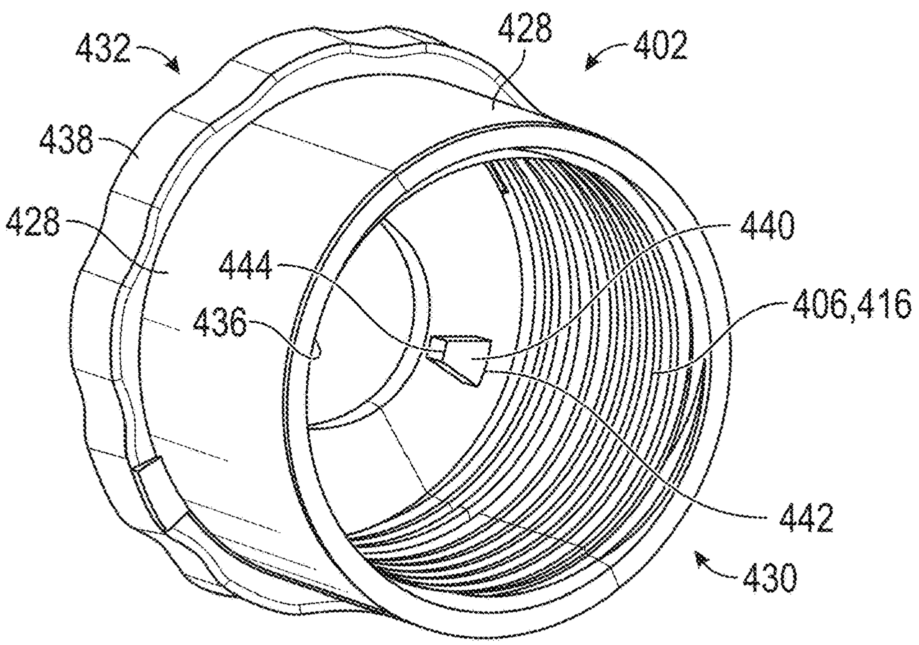
FIG. 21 is a perspective view of the shell of the crimping device of FIG. 16.

Referring to FIG. 21, in the illustrated example, the shell 402 can comprise first and second side portions 428 that are separable from one another, similar to the first and second side portions 114 of the housing 108. In other examples, the shell 402 can have more than two separable portions, or can be formed as a unitary piece. The shell 402 can comprise an inlet end portion 430 and an outlet end portion 432. The outlet end portion 432 can comprise an aperture or outlet 434 (FIG. 17) configured to align with the outlet 122 of the housing 108 when the housing is disposed within the shell. As shown in FIG. 17, the outlet 434 can have a diameter greater than the outlet 122 of the housing 108, for example, so that the sheath 106 of the delivery apparatus 102 can directly abut the outlet end portion of the housing and surround the outlet 122.

The shell 402 can have a generally cylindrical shape having an inner bore. As mentioned previously, an inner surface 406 of the shell 402 can comprise a threaded portion 416 configured to interface with the correspondingly threaded portion 414 of the actuator 404. In the illustrated example, each side portion 428 of the shell 402 can comprise a half-cylinder such that when they are placed together they form a generally cylindrical or tubular shape. The first and second side portions 428 can be coupled together via a retaining member or retaining ring 438 (e.g., similar to retaining ring 140 of the housing 108), which can encircle the side portions 428 and releasably retain them together (FIGS. 17 and 18). The retaining member 438 can be sized to slide over and form a frictional fit with the proximal end portions of the housing side portions 428 (e.g., axially aligned with the outlet 434) to hold them in the assembled position.

Figure 22:
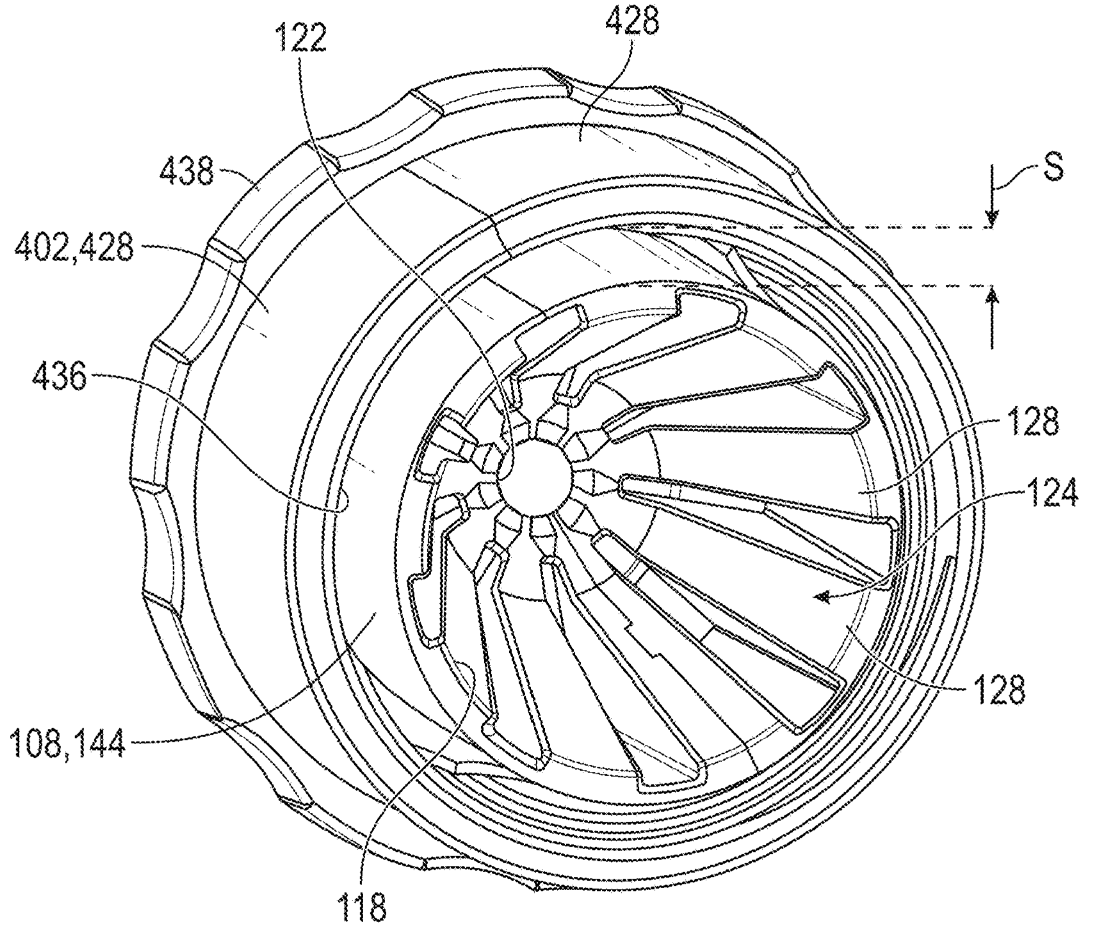
FIG. 22 is a perspective view of the shell and housing of the crimping device of FIG. 16.

Referring to FIG. 21, each side portion 428 of the shell 402 can comprise one or more alignment features 440 configured to prevent or mitigate rotation of the housing 108 relative to the shell 402 when the housing 108 is received in the shell 402. In the illustrated example, each alignment feature 440 can be a protrusion disposed on an inner surface of the shell 402 and extending toward the inlet 436. The alignment feature 440 can have a wedge shape that tapers from a first width at the radially outer end 442 to a second, smaller width at the radially inner end 444 such that the alignment feature 440 can extend into a corresponding recess 192 (FIG. 4) in an outlet end portion the housing 108. The recesses 192 can be defined between the ribs 128 and/or defined by the ribs 128 (e.g., can extend into a hollow interior of the ribs 128). As shown in FIG. 22, when the housing 108 is disposed within the shell 402 and aligned with the alignment feature(s), a circumferentially extending space S can be defined between the outer surface 144 of the housing 108 and the inner surface 406 of the shell 402. As shown in FIG. 18, the threads of the actuator extension portion 410 can engage the threads of the shell 402 such that the actuator 404 can advance within the space S, thereby advancing the pusher member 112 into the housing 108. Accordingly, the actuator 404 is not coupled to the housing 108 (which includes the valve-compressing funnel segment 124), but rather an inner surface 446 (FIG. 20) of the actuator extension portion 410 can travel axially relative to the outer surface 144 of the housing 108 as the actuator 404 and the shell 402 are threaded together.

In use, the housing 108 can be disposed within the shell 402 such that it engages the alignment features 440 and the prosthetic valve 1000 can be inserted into the housing 108. The pusher member 112 can be aligned with the prosthetic valve 1000 (e.g., between the ribs 128 of the housing 108) so as to engage an adjacent end portion of the prosthetic valve 1000. Thus aligned, the extension portion 410 of the actuator 404 can be inserted into the space S such that the threaded portion 414 of the actuator engages the threaded portion 416 of the shell 402. As the actuator 404 is rotated, the threaded portions 414, 416 convert the rotation into axial movement (e.g., translation/pushing), allowing the pusher member 112 to advance axially forward into the housing 108. The actuator 404 can continue to be advanced relative to the shell 402, which advances the pusher member 112 and therefore pushes the prosthetic valve 1000 through the housing 108. As prosthetic valve 1000 is pushed through the funnel segment 124, the prosthetic valve is radially compressed and pushed outwardly through the outlet 122. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100. In certain examples, the actuator 404 does not directly contact the housing 108 during the crimping process.

Figure 23:
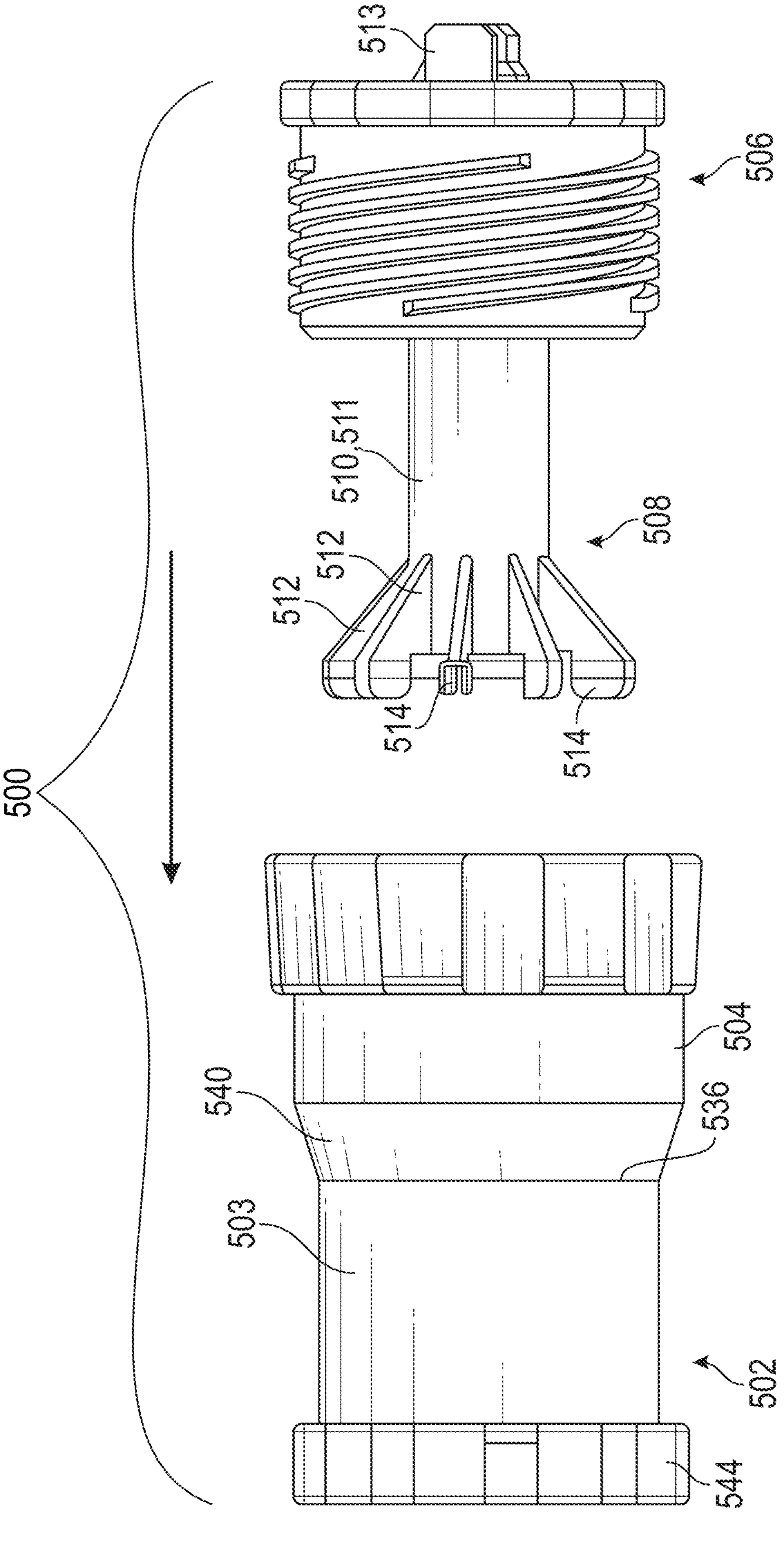
FIG. 23 is a side elevation view of another example of a crimping device.
Figure 24:
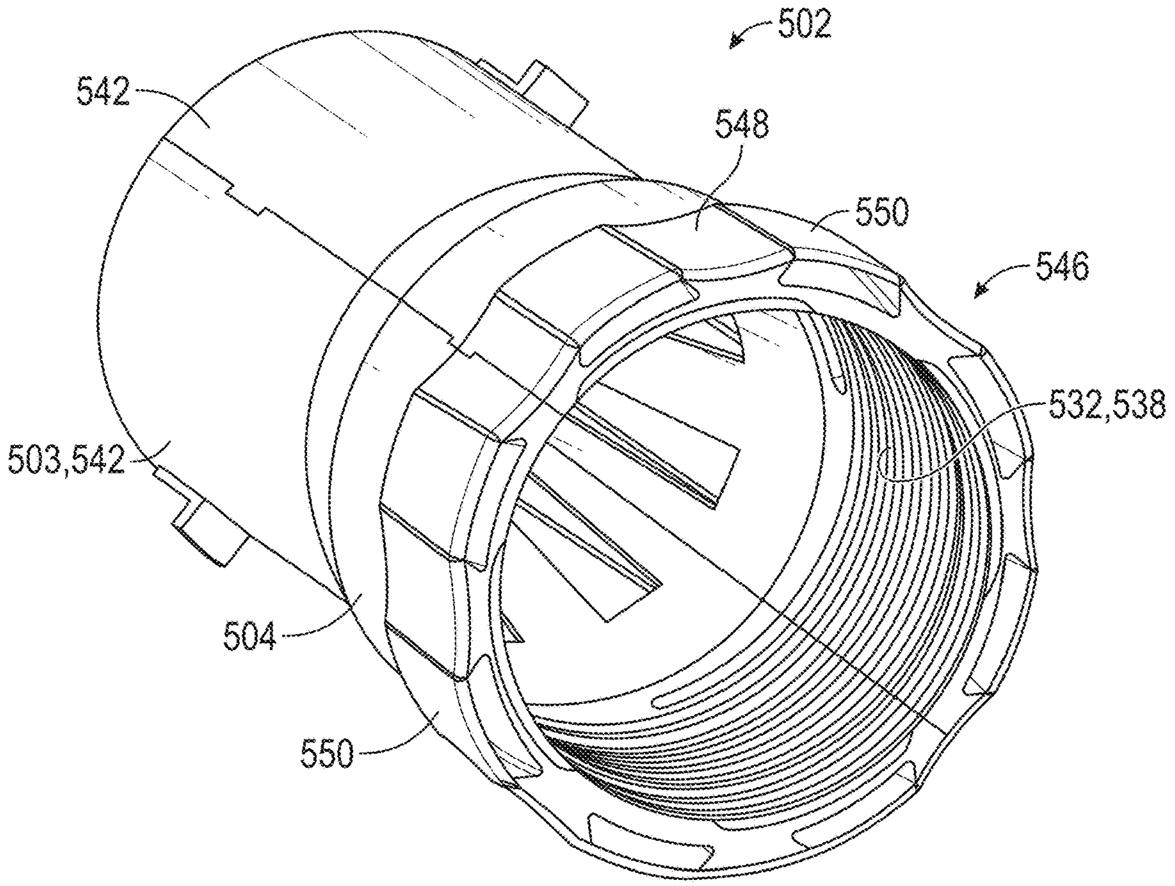
FIG. 24 is a perspective view of the housing of the crimping device of FIG. 23.
Figure 25:
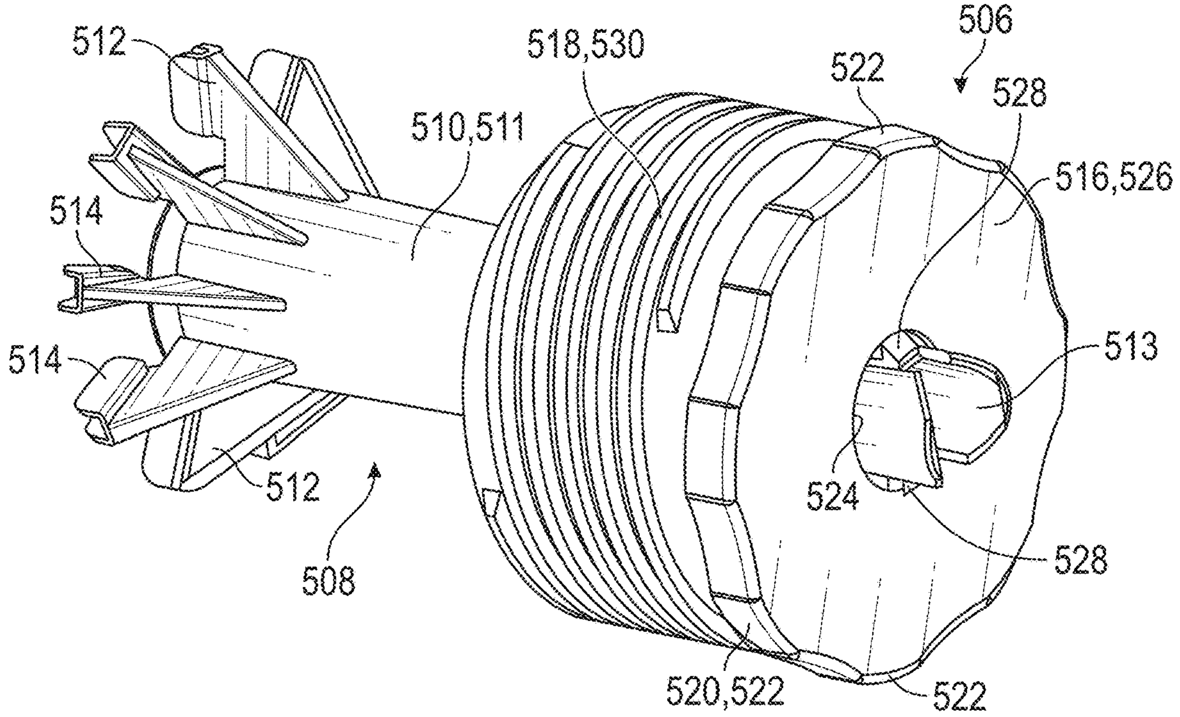
FIG. 25 is a perspective view of the actuator and pusher member of the crimping device of FIG. 23.

FIGS. 23-25 illustrate another example of a crimping device 500. Crimping device 500 can generally comprise a housing 502 including a main body 503 (also referred to as a valve crimping portion) and an extender portion 504 (also referred to as a driver or actuator coupling portion), an actuator 506, and a pusher member 508 removably coupled to the actuator. The pusher member 508 can be the same as pusher member 112 described previously (e.g., comprising a stem 510 having a first end portion 511 and a second end portion 513, and a plurality of arms 512 each having a seat 514) except that pusher member 508 has an elongated stem 510 when compared to pusher member 112.

Referring to FIG. 25, the actuator 506 (shown coupled to pusher member 508) can comprise a base 516, and an extension portion/member 518 extending from the base 516. The base 516 can include a gripping interface 520 for gripping by a user. The gripping interface 520 can include, for example, a plurality of circumferentially spaced ridges 522. As shown, the base 516 can also include an opening or aperture 524 into which the second end portion 513 of the pusher member 508 can extend. The aperture 524 can be surrounded by a surface/shoulder/ledge 526 which can engage the resilient locking features 528 (as described previously with respect to resilient locking features 174) to releasably couple the pusher member to the actuator 506. The extension portion 518 can be configured as a cylindrical extension portion defining an inner bore 519 (FIG. 76) into which the pusher member 508 can extend. An outer surface of the extension member 518 can comprise a threaded portion 530 configured to interface with a correspondingly threaded portion 532 disposed on an inner surface of the extender portion 504 of the housing 502 (FIG. 24).

Figure 74:
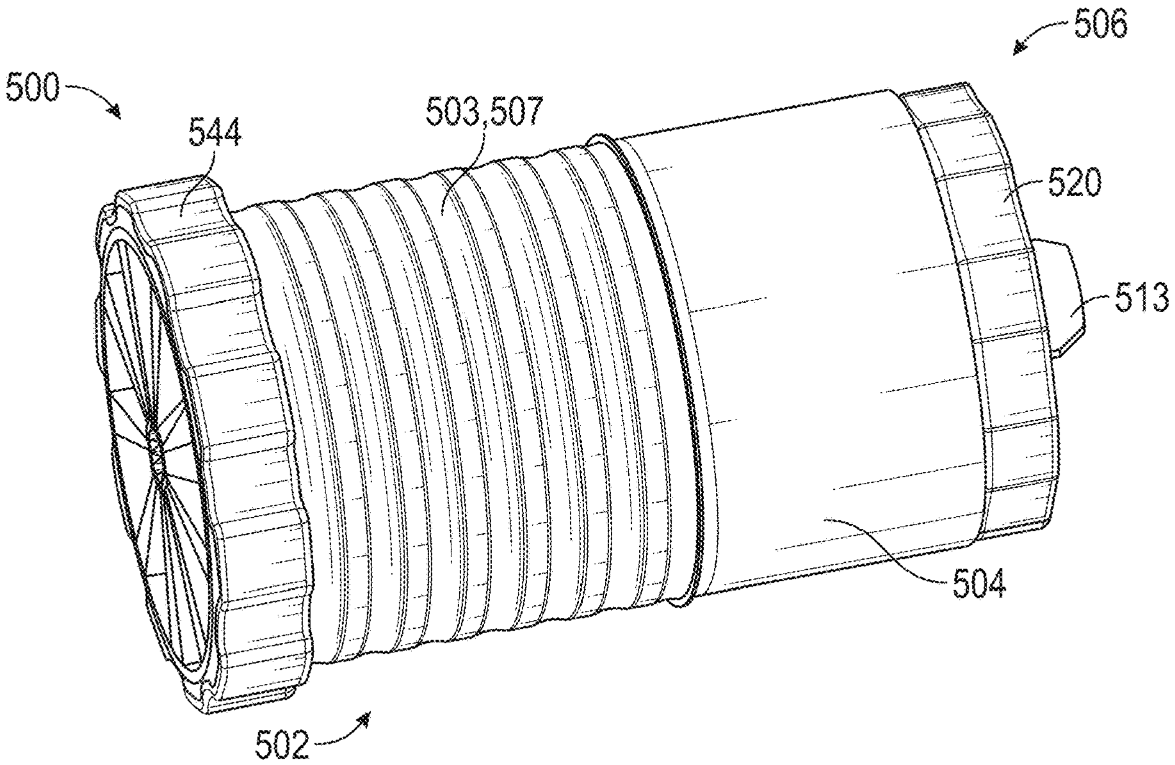
FIG. 74 is a perspective view of another example of a crimping device.
Figure 75:
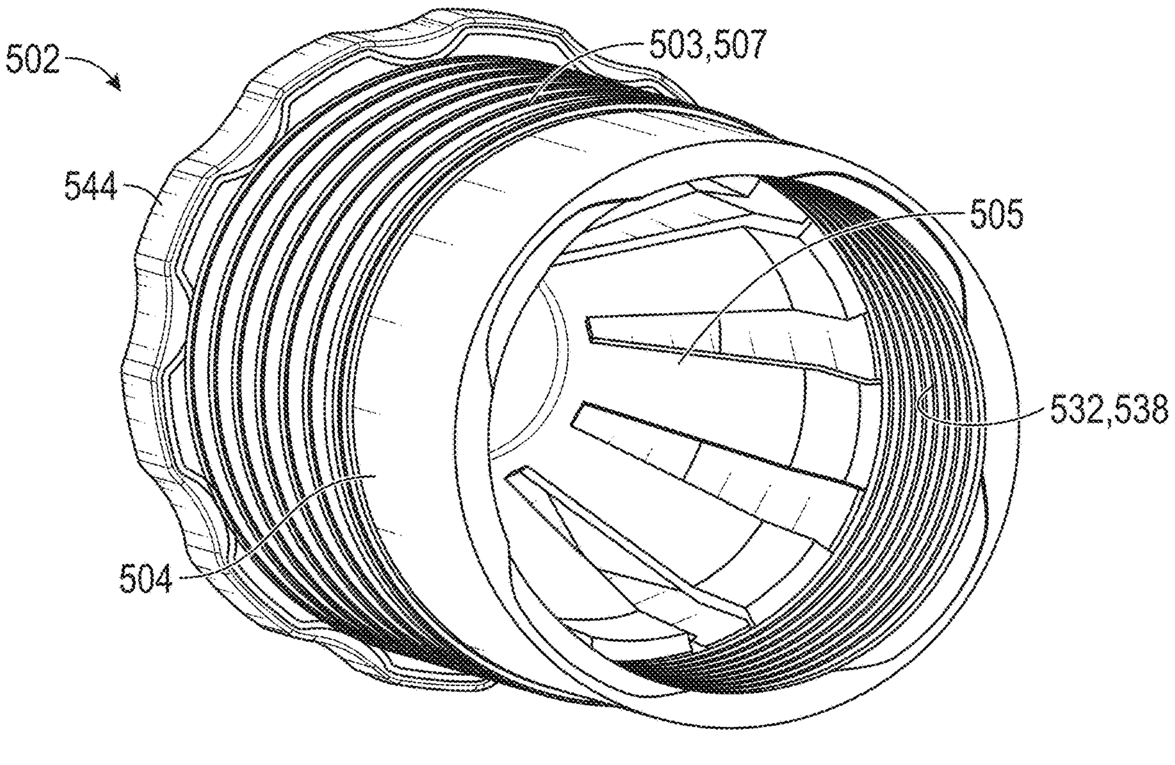
FIG. 75 is a perspective view of the housing of the crimping device of FIG. 74.
Figure 76:
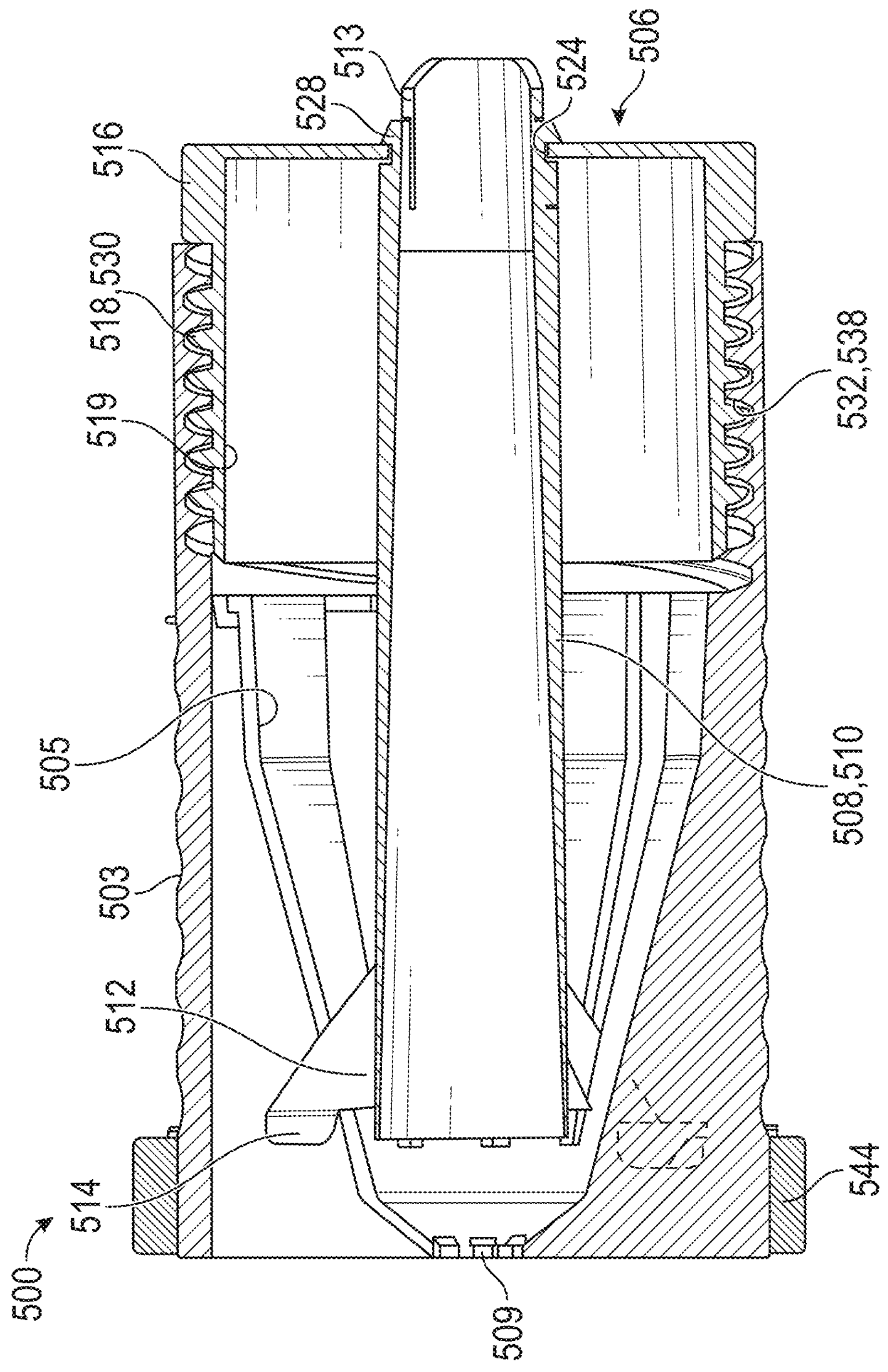
FIG. 76 is a cross-sectional view of the crimping device of FIG. 74.

Referring to FIG. 24, the main body 503 of the housing 502 can be similar to housing 108 described previously (e.g., comprising an inner funnel segment 505 (FIG. 76) and a plurality of ribs), except that the main body 503 comprises or is coupled to an extender portion 504 extending from an inlet end 536 (FIG. 23) of the main body 503. The extender portion 504 can be a substantially cylindrical member including an inner bore 538. In the illustrated example, the extender portion 504 has a diameter greater than a diameter of the main body 503. However, in other examples, such as shown in the example of FIGS. 74-76, the diameter of the extender portion 504 can be substantially equal to the diameter of the main body 503. In the example illustrated in FIG. 23, the extender 504 can comprise a tapered portion 540 that tapers from the diameter of the extender portion 504 to the diameter of the main body 503.

The housing 502 can comprise first and second side portions 542 (FIG. 24), which can be coupled/held together via a retaining ring 544 (FIG. 23) configured to encircle the side portions 542 and releasably retain them together, as described previously with respect to retaining ring 140 and side portions 114. The inlet end portion 546 of the extender portion 504 can comprise a gripping interface 548 for gripping and use by a user. The gripping interface 548 can include, for example, a plurality of circumferentially spaced ridges 550.

As mentioned previously, an inner surface of the extender portion 504 can comprise a threaded portion 532 configured to interface with the threaded portion 530 of the actuator. In use, once the prosthetic valve 1000 has been inserted into the main body 503 of the housing 502, the pusher member 508 can be aligned with the prosthetic valve 1000 so as to engage an adjacent end portion of the prosthetic valve 1000. Thus aligned, the pusher member 508 can be inserted into the housing 502 through the extender portion 504 until the threads 530 of the actuator 506 engage the threads 532 of the extender portion 504. Thus engaged, the actuator 506 can be rotated and the threaded portions can translate the rotation into axial movement (e.g., pushing) of the pusher member 508, allowing the pusher member to advance axially forward into the main body 503 thereby pushing the prosthetic valve 1000 through the main body 503. As prosthetic valve 1000 is pushed through the funnel segment of the main body, the prosthetic valve is radially compressed and pushed outwardly through the outlet 509 (FIG. 76). The prosthetic valve 1000 can then be coupled to a valve retaining member 1110 of the delivery apparatus 1100, as described in more detail with respect to FIG. 37 or can be loaded directly into the sheath of the delivery apparatus as described previously with respect to crimping device 100.

As mentioned previously, FIGS. 74-76 illustrate another example of a crimping device 500 wherein the extender portion 504 (also referred to as a driver or actuator coupling portion) of the housing 502 has an outer diameter substantially equal to the outer diameter of the main body 503. Referring to FIG. 76, the main body 503 of the housing 502 can be similar to housing 108 (e.g., including an inner funnel segment 505 having a plurality of ribs) except that the main body 503 comprises an extender portion 504. In the illustrated example, the extender portion 504 is formed integrally with the main body 503. However, in other examples, the extender portion 504 can be formed separately from the main body and either permanently or releasably coupled to the main body.

The extender portion 504 can be a substantially cylindrical member including an inner bore 538. In the example shown in FIGS. 74-76, the extender portion 504 has an outer diameter that is substantially equal to the outer diameter of the main body 503. The inner surface of the extender portion 504 can comprise a threaded portion 532 configured to interface with correspondingly threaded portion 530 on an outer surface of the actuator 506.

In some examples, as shown in FIGS. 74-76, the outer surface of the main body 503 can comprise a plurality of circumferentially extending ridges 507. The ridges 507 can facilitate gripping by a user. In certain examples, the housing 502, or portion(s) thereof, can be transparent to facilitate viewing of the prosthetic valve as it is pushed through the funnel.

FIGS. 26-29 illustrate another example of a crimping device 600. Crimping device 600 can generally comprise a housing 108 (as described previously), an actuator 602, and a pusher member 112 (as described previously) removably coupled to the actuator 602.

Referring to FIG. 27, the actuator 602 can comprise a threaded guide member configured as a base member 604 including a central aperture 606, a plurality of extension members 608 extending from the base member 604 and disposed about a circumference of the base member, and an actuator member configured as an elongated threaded member referred to hereinafter as a thumbscrew 610. In the illustrated example, the actuator 602 comprises three extension members 608 evenly spaced about the circumference. However, in other examples, the actuator 602 can comprise a greater or fewer number of extension members and they can be spaced in any configuration.

Each extension member 608 can be an elongated member having a first end portion 612 and a second end portion 614 coupled to the base member. The first end portion 612 can comprise means for coupling the actuator 602 to the housing 108, as shown in FIG. 26. For example, in the illustrated example, the first end portion 612 can comprise an aperture 616 through which a fastener 618 can extend to couple actuator 602 to the housing 108. As shown in FIG. 26, the extension members 608 can be disposed adjacent an outer surface 144 of the housing 108 and the fasteners 618 can extend through the extension members 608 to contact or engage the surface of the housing 108 and thereby restrain the actuator 602 from movement relative to the housing 108. In some examples, the apertures 616 and the fasteners 618 can be threaded such that the fasteners can be advanced and/or retracted relative to the extension members 608 by rotating the fasteners. Each fastener 618 can further comprise a gripping portion or handle 620 (e.g., a loop) configured to allow a user to actuate the fastener 618. In some examples, the outer surface 144 of the housing 108 can comprise openings or recesses into which the fasteners 618 can extend to further secure the housing 108 and the actuator 602 relative to one another. In other examples, for example, each extension member 608 can comprise an integral protrusion or hooked end portion configured to engage a corresponding aperture or recess in the housing 108. In such examples, the extension members 608 can be resiliently flexible such that a user can bend them to remove the protrusions from the aperture/recess of the housing to decouple the actuator 602 from the housing 108.

As mentioned, the base member 604 of the actuator 602 can comprise a central aperture 606 (FIG. 27) extending through a thickness of the base member 604. The aperture 606 can comprise a threaded portion (e.g., the inner surface) configured to engage a correspondingly threaded portion 622 of a thumbscrew 610. The thumbscrew 610 can be an elongated member having a first end portion 624, a second end portion 626, and an external surface comprising a threaded portion 622. The second end portion 626 can include a gripping interface 628 for easy gripping and use (e.g., rotation) by a user. The gripping interface 628 can include, for example, a plurality of circumferentially spaced ridges 630.

Figure 28:
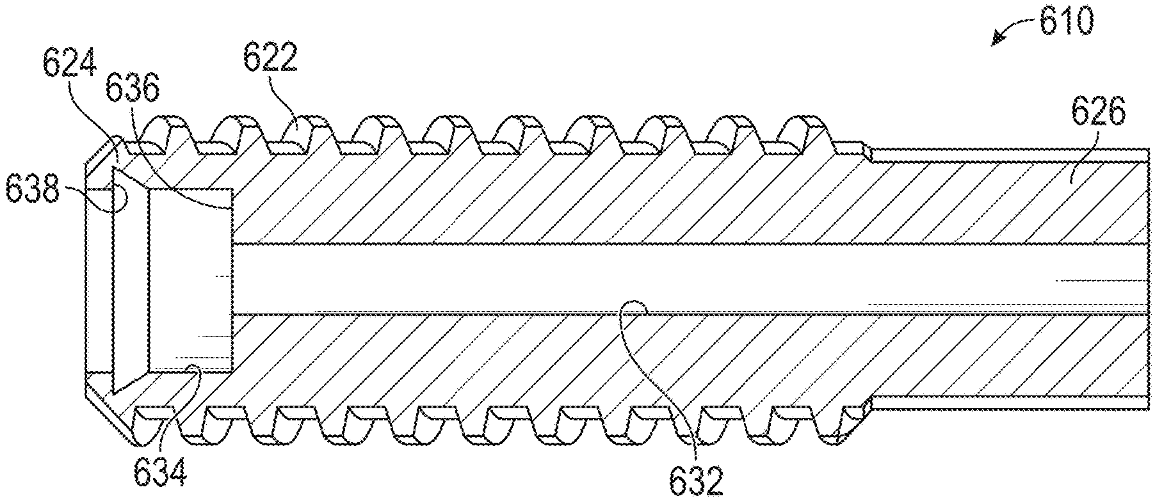
FIG. 28 is a cross-sectional side elevation view of the thumbscrew of the actuator of FIG. 27.
Figure 29:
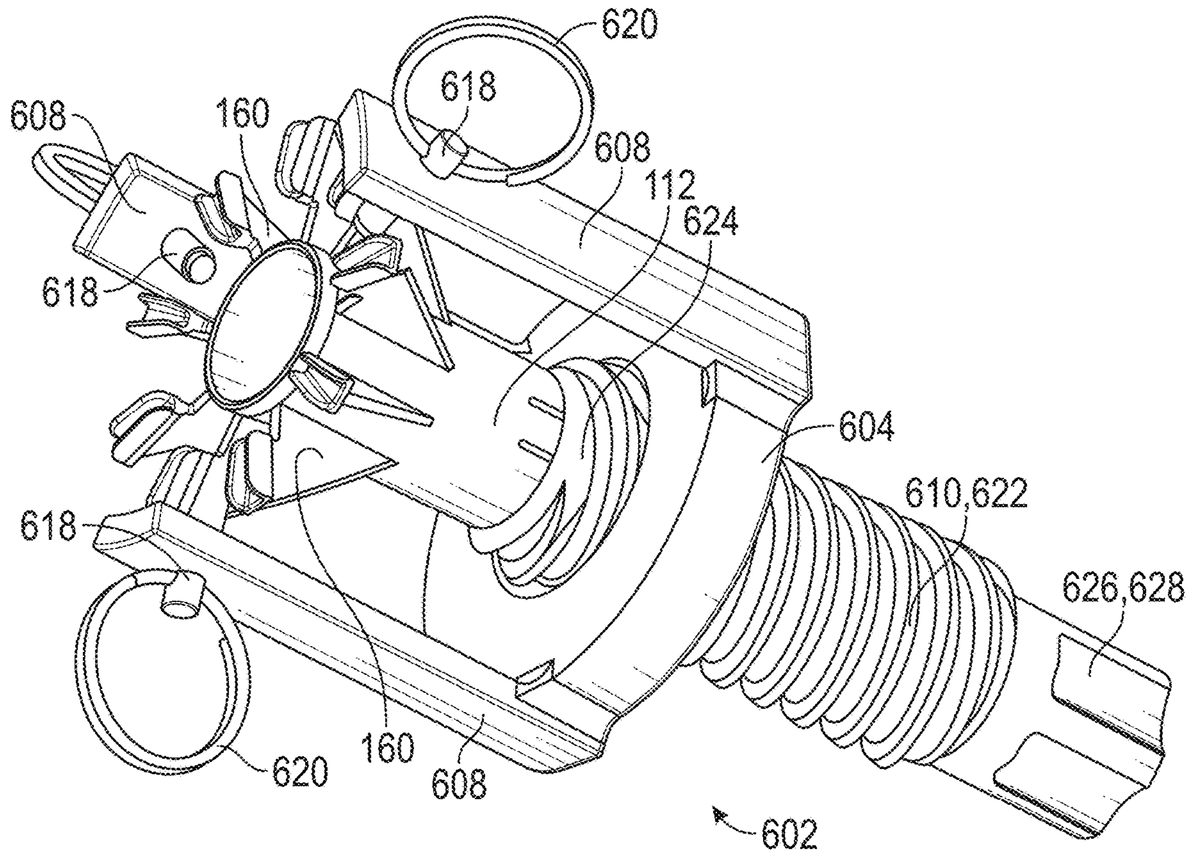
FIG. 29 is a perspective view of the actuator and pusher member of the crimping device of FIG. 26.

Referring to FIG. 28, the thumbscrew 610 can have an inner bore 632 that extends axially along a length of the thumbscrew 610, such that a portion of the delivery apparatus (e.g., inner shaft 104 of delivery apparatus 102) can extend through the inner bore 632 when the crimping device 600 is disposed on the delivery apparatus 102. The first end portion 624 of the thumbscrew can comprise a recess 634 into which the second end portion 164 of the pusher member 112 can extend. The recess 634 can include an first annular shoulder 636 against which a distal edge 113 (FIG. 7) of the pusher member 112 can abut, and a second annular shoulder 638 configured to engage the resilient locking features 174 on the pusher member 112 to retain the second end portion of the pusher member within the recess 634. The protrusions or lips 176 of the resilient locking features 174 can engage the second annular shoulder 638 such that they allow rotational motion of the thumbscrew 610 relative to the pusher member 112 but prevent or mitigate axial movement of the pusher member 112 relative to the thumbscrew 610. This configuration allows the pusher member 112 to remain in the same rotational orientation while the thumbscrew 610 is rotated (aided by the engagement of the pusher member arms 160 with the ribs 128 of the housing 108), while allowing the thumbscrew 610 to axially advance the pusher member 112 into the housing 108.

In use, the crimping device 600 can be used to crimp a prosthetic valve (e.g., prosthetic valve 1000 shown in FIG. 36) in the following exemplary manner. The prosthetic valve 1000 can be inserted into the housing 108. As show in FIG. 26, the extension members 608 of the actuator 602 can be disposed adjacent the outer surface 144 of the housing 108 and the fasteners 618 can be actuated to couple the actuator 602 to the housing 108. So coupled, the pusher member 112 can be aligned with the prosthetic valve 1000 so as to engage an adjacent end portion of the prosthetic valve 1000. A user can rotate the thumbscrew 610 and the threaded portions of the thumbscrew and base member 604 can translate the rotation into axial movement (e.g., pushing) of the thumbscrew 610 and therefore the pusher member 112, allowing the pusher member 112 to advance axially forward into the housing 108. The advancement of the pusher member 112 into the housing 108 pushes the prosthetic valve 1000 through the funnel segment 124 of the housing 108 such that the prosthetic valve is radially compressed and pushed outwardly through the outlet 122 for coupling to the delivery apparatus. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100.

Figure 30A:
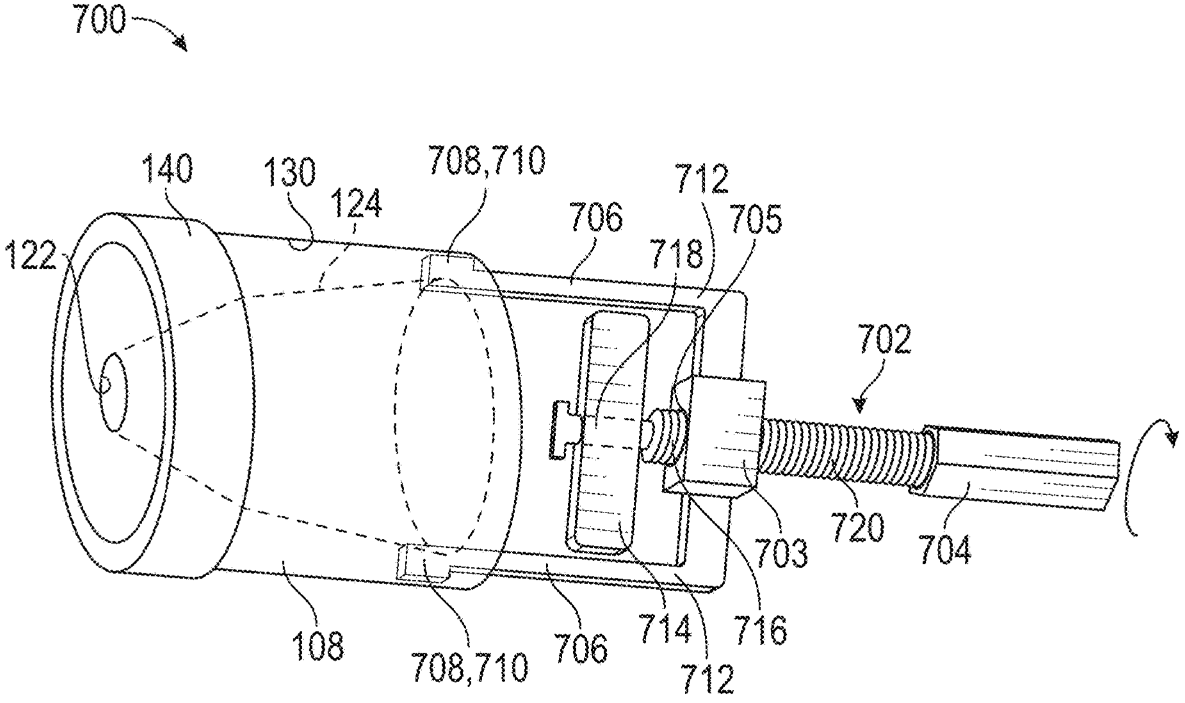
FIG. 30A is a perspective view of another example of a crimping device.
Figure 30B:
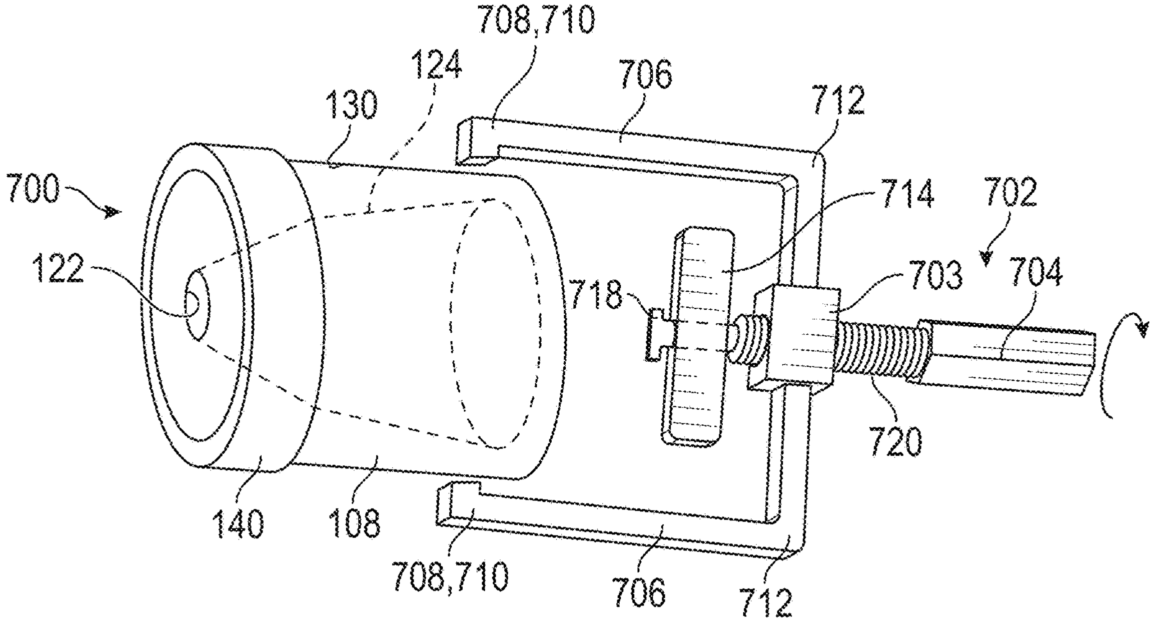
FIG. 30B is a perspective view of another example of a crimping device.

FIGS. 30A-30B illustrate another example of a crimping device 700. The crimping device 700 can be similar to device 600 described previously (e.g., including a housing 108 and an actuator 702 comprising a thumbscrew 704), except where specifically noted.

The actuator 702 can comprise a base member 703 (e.g., a guide member) having a threaded aperture 705, and one or more extension members 706 extending from the base member 703. The extension members can have a first end portion 708 and a second end portion 712. In certain examples, the extension members 706 can engage or couple to an inner surface 130 of the housing. For example, the extension members 706 can each comprise a protrusion 710 configured to extend into a corresponding opening in the inner surface 130 of the housing 108. In other examples, the extension members 706 can be biased radially outwardly such that they form a friction-fit with an inner surface 130 of the housing 108 to couple the actuator 702 to the housing 108. In yet other examples, the members 706 can engage the exterior of the housing 108 to couple the housing to the actuator 702, such as shown in FIG. 30B.

In some examples, the crimping device 700 can comprise a pushing element 714, for example, a plate member, configured to push against an adjacent portion of a prosthetic valve to advance the prosthetic valve through the housing 108. In some examples, the pushing element 714 can be a pusher member, such as pusher member 112 described previously. The first end portion 716 of the thumbscrew 704 can comprise an engagement member 718 (e.g., a pin member) configured to extend through a central aperture in the pushing element 714 to couple the pushing element 714 and the thumbscrew 704 together. The engagement member 718 can be coupled to the pushing element 714 such that the rotation of the thumbscrew 704 does not cause corresponding rotation of the pushing element 714.

The thumbscrew 704 can comprise a threaded portion 720 configured to interface with the correspondingly threaded aperture 705 such that rotation of the thumbscrew causes axial advancement of the pushing element 714 relative to the base member 703. The crimping device 700 can be used to crimp a prosthetic valve in a similar manner as described previously for crimping device 600.

Figure 31:
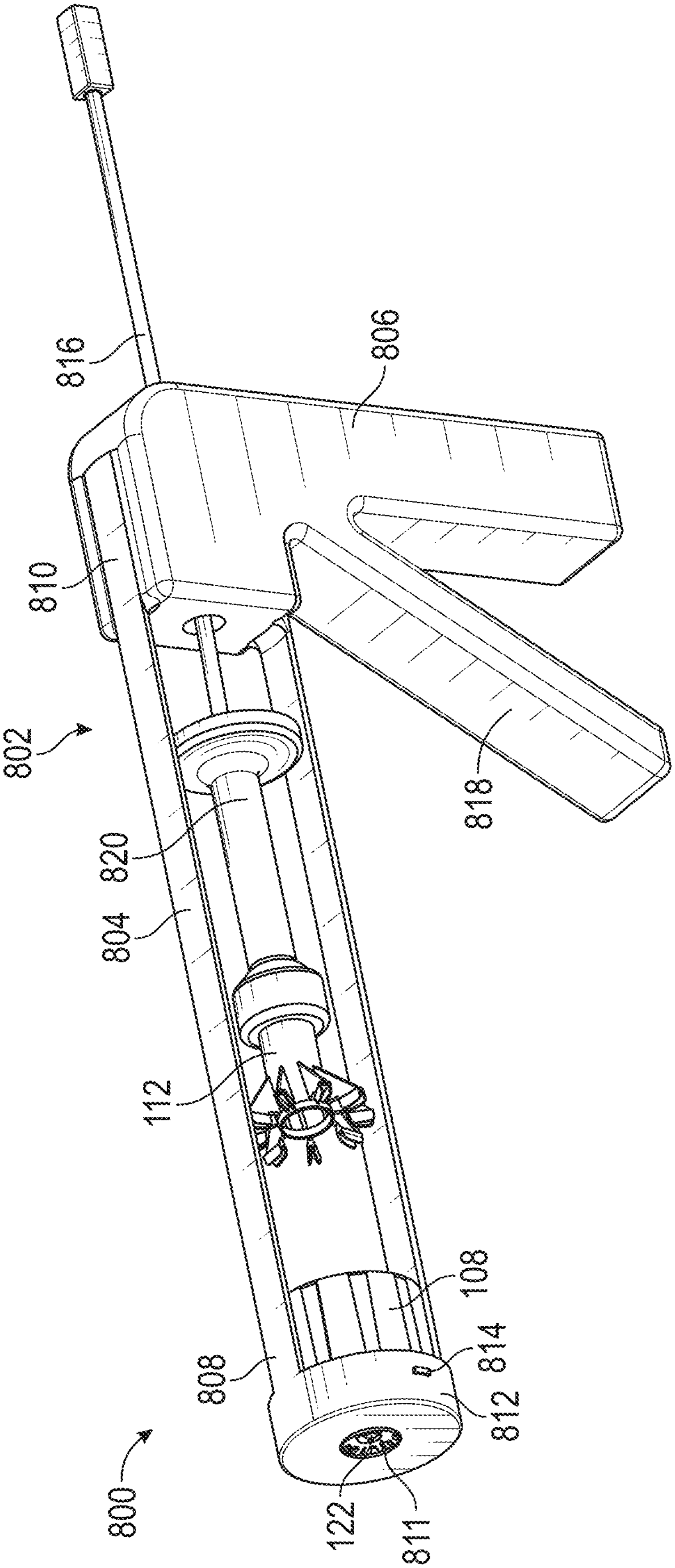
FIG. 31 is a perspective view of another example of a crimping device.

FIGS. 31-33 illustrate another example of a crimping device 800. Crimping device 800 can comprise a housing 108 (as described previously), a pusher member 112 (as described previously), and an actuator 802.

The actuator 802 can be a plunger-type actuator (e.g., a caulk gun or other similar device) having a holder/frame/barrel portion 804 coupled to a handle 806. The barrel portion 804 can have a first end portion 808 and a second end portion 810 coupled to the handle 806. The first end portion 808 can comprise a retaining member 812 configured to releasably couple the housing 108.

In the illustrated example, the retaining member 812 can have an annular shape corresponding to the circumference of the housing 108. However, in other examples the retaining member 812 can have any shape configured to correspond to an outer perimeter of the housing. In some examples, the housing and the retaining member can comprise corresponding engagement features that allow the two components to be releasably coupled together. For example, the housing 108 can comprise one or more protrusions 814 configured to extend into recesses or apertures in the retaining member 812, and/or the retaining member 812 can comprise protrusions configured to extend into recesses or apertures in the housing 108. In other examples, the housing 108 can be held by the retaining member using a friction fit. In some examples, the retaining member 812 can be used in lieu of or in addition to the retaining ring 140. The retaining member 812 can further comprise an aperture or outlet 811 configured to align with the outlet 122 of the housing 108. As shown in FIG. 31, the outlet 811 can have a diameter greater than the outlet 122 of the housing 108, for example, so that the sheath 106 of the delivery apparatus 102 can directly abut the outlet end portion of the housing and surround the outlet 122.

The handle 806 can comprise an actuator member 816 configured as a plunger, and a trigger member 818. For example, in some examples, the handle 806 can be similar to that of a caulking gun. The trigger 818 can be configured to advance the actuator member 816 when actuated (e.g., pulled) by a user. For example, each time the trigger is pulled, the actuator member 816 can incrementally advance in a first direction (e.g., toward the housing 108) and be restrained against movement in a second, opposite direction (e.g., away from the housing 108). In some examples, the trigger can advance and/or retract the actuator member. For example, when the trigger is held down, a user can pull the actuator member in a direction away from the housing to retract the actuator member. In certain examples, the actuator member 816 can be permanently or releasably coupled to an extender 820 configured to releasably couple the pusher member 112.

Referring to FIG. 32, the extender 820 can comprise a base portion 822, a central extension member 824, a pusher member holder 826, and an inner bore 828 extending along the length of the extender 820. The base portion 822 can be coupled to the actuator member 816, as shown in FIG. 31. The pusher member holder 826 can comprise an inner recess 830 into which the second end portion 164 of the pusher member 112 can extend. The recess 830 can include an first annular shoulder 832 against which a distal edge 113 (FIG. 7) of the pusher member 112 can abut, and a second annular shoulder 834 configured to engage the resilient locking features 174 on the pusher member 112 to retain the second end portion of the pusher member within the recess 830. The protrusions or lips 176 of the resilient locking features 174 can engage the second annular shoulder 834. The pusher member 112 can rotate within the extender 820 such that a user can manually align the arms 160 of the pusher member 112 with the prosthetic valve so as to engage an adjacent end portion of the prosthetic valve. As the actuator member 816 is advanced using the trigger 818, it advances the extender 820 (and therefore the pusher member 112) relative to the housing 108.

In use, the crimping device 800 can be used to crimp a prosthetic valve (e.g., prosthetic valve 1000 shown in FIG. 36) in the following exemplary manner. The prosthetic valve 1000 can be inserted into the housing 108, and the housing 108 can be inserted into the retaining member 812 of the actuator. The user can actuate the trigger 818 to advance the actuator member 816 (and thus the extender 820 and pusher member 112) until the pusher member 112 engages an adjacent end portion of the prosthetic valve 1000. The user can continue to actuate the trigger 818 to advance the pusher member through the housing 108, which in turn advances the prosthetic valve. As prosthetic valve 1000 is pushed through the funnel segment 124 of the housing, the prosthetic valve is radially compressed and pushed outwardly through the outlet 122. The prosthetic valve 1000 can then be coupled to a valve retaining member 1110 of the delivery apparatus 1100, as described in more detail with respect to FIG. 37 or can be loaded directly into the sheath of the delivery apparatus as described previously with respect to crimping device 100. In certain examples, the extender member 820 or portions thereof (e.g., the pusher member holder 826) can be an integral part of the plunger member 816, such as an end portion of the plunger member 816.

Figure 34:
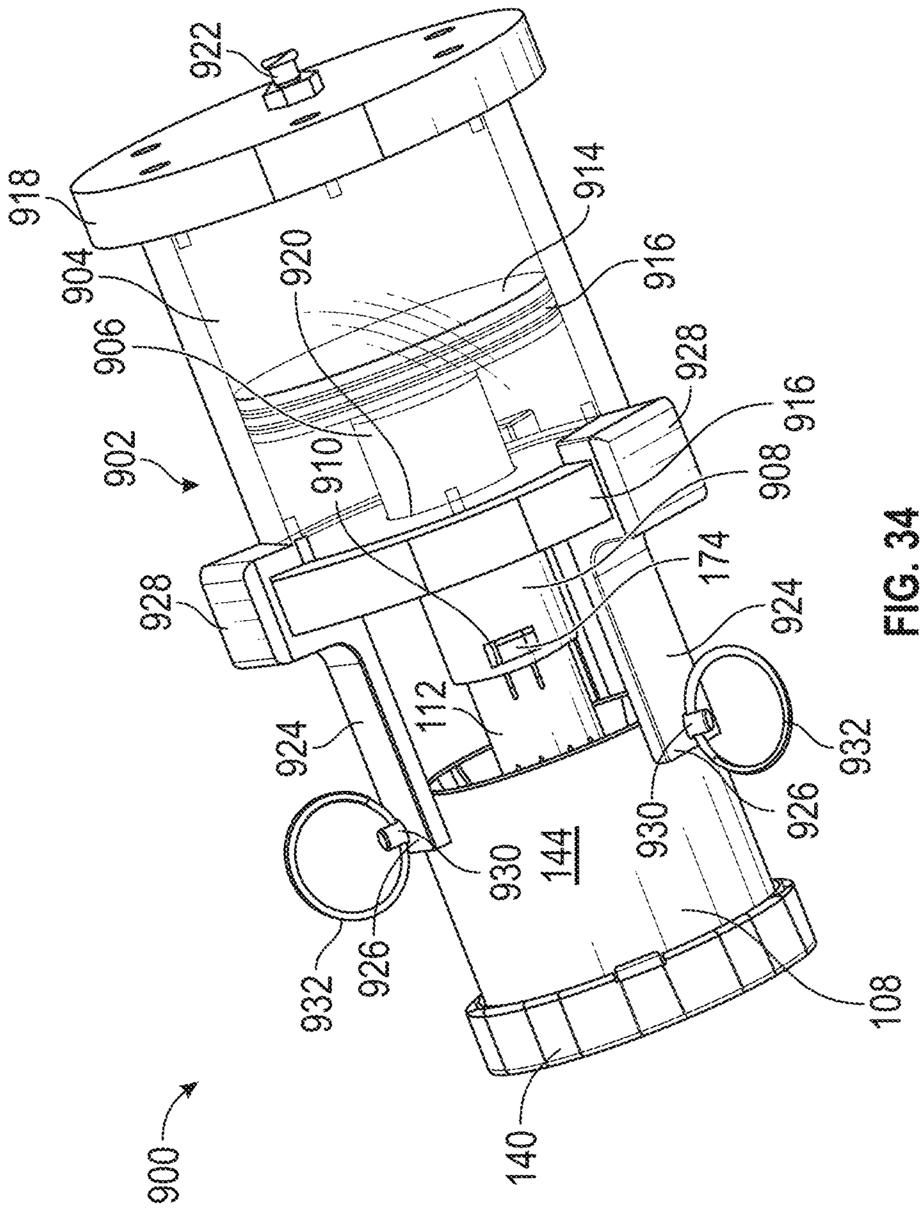
FIG. 34 is a perspective view of another example of a crimping device.
Figure 35:
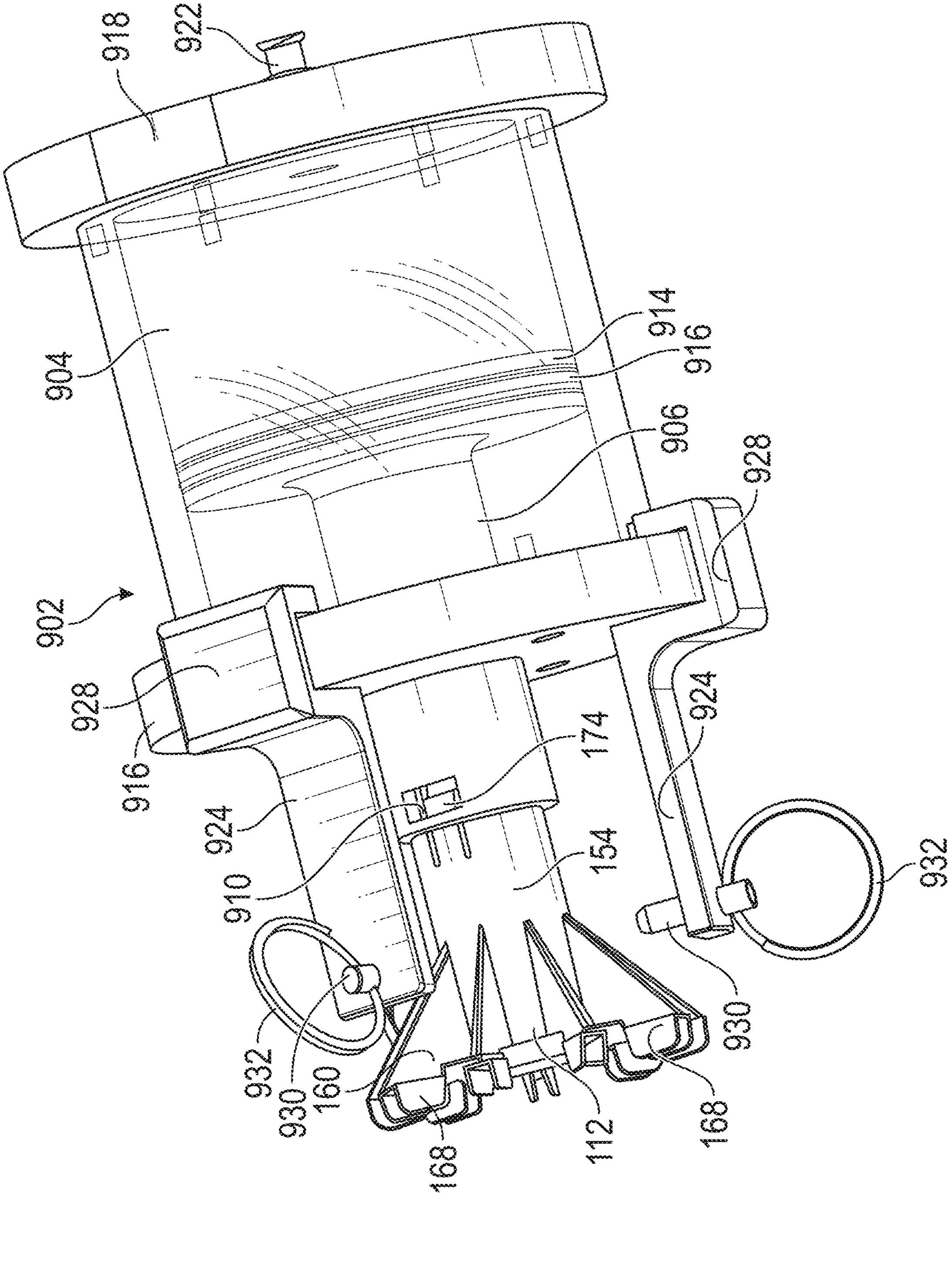
FIG. 35 is a perspective view of the actuator and pusher member of the crimping device of FIG. 34.

FIGS. 34-35 illustrate another example of a crimping device 900. Crimping device 900 can comprise a housing 108 (as described previously), a pusher member 112 (as described previously), and an actuator 902. The actuator 902 can be configured as a hydraulic actuator configured to advance the pusher member 112 into the housing 108 using pressurized hydraulic fluid. In certain examples, the hydraulic fluid can be pumped into the actuator 902, such as with a syringe.

The actuator 902 can comprise a fluid chamber 904 and a piston 906. The piston 906 can have a first end portion 908 (e.g., on a shaft member of the piston) having one or more openings 910 configured to mate with the resilient locking features 174 of the pusher member 112 to releasably couple the pusher member and piston to one another. The second end portion 912 of the piston 906 can be configured as a disc-shaped piston head 914 having an outer perimeter that corresponds to the shape of the fluid chamber 904. The piston head 914 can be sized such that it can move within the fluid chamber 904 but forms a seal with the chamber walls such that fluid cannot pass around the piston head 914. In other words, the outer diameter of the piston head 914 can be substantially equal to the inner diameter of the fluid chamber 904. In some examples, the piston head 914 can further comprise one or a plurality of O-rings or other sealing members 915 disposed around an outer circumference of the piston head 914 to aid in sealing the piston head to prevent fluid from passing around it.

The fluid chamber 904 can comprise a first end portion 916 and a second end portion 918. In the illustrated example, the chamber 904 is cylindrical, however, in other examples, the fluid chamber can have any of various shapes. The first end portion 916 can comprise an opening or aperture 920 configured to allow the first end portion 908 of the piston 906 to extend through it, as shown in FIGS. 34-35. The second end portion 918 can comprise an inlet 922 configured to be fluidly coupled (e.g., using flexible tubing) to a fluid dispensing device, fluid reservoir, or pump for example, a syringe, such as a high-pressure syringe (see e.g., syringe 2208 shown in FIG. 51). In particular examples, the syringe can be an Atrion QL® syringe.

The fluid chamber 904 can further comprise a plurality of extension members 924 extending from and disposed about a circumference of the first end portion 916. In the illustrated example, the actuator 902 comprises three extension members 924 evenly spaced about the circumference. However, in other examples, the actuator 902 can comprise a greater or fewer number of extension members and they can be spaced in any configuration.

Each extension member 924 can be an elongated member having a first end portion 926 and a second end portion 928 coupled to the fluid chamber 904. The first end portion 926 can comprise means for coupling the actuator 902 to the housing 108. For example, in the illustrated example, the first end portion 926 can comprise an aperture through which a fastener 930 can extend to couple the first end portion 926 to the housing 108. As shown in FIG. 34, the extension members 924 can be disposed adjacent an outer surface 144 of the housing 108 and the fasteners 930 can extend through the extension members 924 and into corresponding recesses or openings in the housing 108 and thereby restrain the actuator from movement relative to the housing. In other examples, the fasteners can extend through the extension members to frictionally contact or engage the outer surface of the housing 108. Each fastener 930 can further comprise a gripping portion or handle 932 (e.g., a loop) configured to allow a user to actuate/turn the fastener 930. In other examples, for example, each extension member 924 can comprise an integral protrusion or hooked end portion configured to engage a corresponding aperture or recess in the housing 108. In such examples, the extension members 924 can be resiliently flexible such that a user can bend them to remove the protrusions from the aperture/recess of the housing 108 to decouple the actuator 902 from the housing 108. In some examples, the apertures in the extension members 924 and the fasteners 930 can be threaded such that the fasteners 930 can be advanced and/or retracted relative to the extension members 924 by rotating the fasteners.

In use, the crimping device 900 can be used to crimp a prosthetic valve (e.g., prosthetic valve 1000 shown in FIG. 36) in the following exemplary manner. The prosthetic valve 1000 can be inserted into the housing 108. The extension members 924 of the actuator 902 can be disposed adjacent the external surface 144 of the housing 108 and the fasteners 930 can be actuated (e.g., using the handles 932) to couple the actuator 902 to the housing. So coupled, the pusher member 112 can be aligned with the prosthetic valve 1000 so as to engage an adjacent end portion of the prosthetic valve 1000. The user can actuate the fluid reservoir (e.g., by depressing the plunger of a syringe or activating a pump) to dispense fluid (e.g., saline solution) into the fluid chamber 904 via the inlet 922. As the fluid chamber 904 fills with fluid, the pressure causes the piston 906 to advance, thereby advancing the pusher member 112 axially forward into the housing 108. The advancement of the pusher member into the housing pushes the prosthetic valve 1000 through the funnel segment 124 of the housing 108 such that the prosthetic valve is radially compressed and pushed outwardly through the outlet 122. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100. In certain examples, the working fluid can be a liquid, such as an aqueous liquid (e.g., saline solution), or a gas (e.g., a compressed inert gas such as nitrogen, carbon dioxide, etc.).

In some examples, all components of the crimping devices disclosed herein (e.g., crimping devices 100, 200, 300, 400, 500, 600, 700, 800, 900, etc.) can be disposable. In other examples, one or more components of any of the crimping devices described herein can be configured to be reusable. For example, the actuator of each crimping device (e.g., the hydraulic actuator 902 and the plunger-type actuator 802) can be configured such that it can be reused numerous times with a plurality of prosthetic valves.

Any or all of the crimper device assembly components described herein can be made from polymeric materials, such as injection molded plastic. In certain examples, one or more components can also be made by three-dimensional printing or other additive manufacturing processes. In certain examples, components subject to high stress, friction, or the like, or portions of such components, can comprise other materials such as metal, ceramic, etc., depending upon the particular characteristics sought.

FIG. 36 is a side elevation view of an exemplary prosthetic valve 1000 that can be crimped using any of the crimping devices disclosed herein. The prosthetic valve 1000 comprises a radially expandable and compressible metal frame 1002 supporting a plurality of leaflets 1004 inside of the frame. In some examples, the frame 1002 can comprise an inner frame portion and an outer frame portion. The prosthetic valve 1000 can also include a sealing member 1006 (e.g., a fabric skirt) secured on the outside of the frame 1002 and configured to create a seal against a native valve annulus. In certain examples, the prosthetic valve 1000 is self-expandable with the frame 1002 being formed from a self-expanding metal (e.g., Nitinol). In other examples, as mentioned previously, the prosthetic valve 1000 can be balloon-expandable or mechanically expandable.

The frame 1002 can comprise a main body 1003, a first set of anchors 1008 and a second set of anchors 1010 extending toward each other from opposing portions of the main body 1003. In some particular examples, the prosthetic valve 1000 is a prosthetic mitral valve and the first anchors 1008 are part of an atrial portion of the valve and configured to help anchor the prosthetic valve 1000 in the left atrium, while the second anchors 1010 are part of a ventricular portion of the valve and are configured to help anchor the prosthetic valve 1000 in the left ventricle. The second anchors 1010 can be disposed between a plurality of apices 1013 of the frame 1002. The end of the frame 1002 opposite the second anchors 1010 can include a plurality of connecting arms 1012 having enlarged end portions 1014. The end portions 1014 are configured to engage mating features of a delivery apparatus to form a releasable connection between the prosthetic valve and the delivery apparatus. Further details of the prosthetic valve can be found, for example, in U.S. Pat. No. 10,639,143, which is incorporated by reference herein in its entirety.

As noted above, the plurality of ribs 128 within the housing of any of the disclosed crimping devices can aid in the alignment of the prosthetic valve 1000. For example, the prosthetic valve 1000 can be aligned within a respective crimping device such that one or both of the first and second set of anchors 1008 and 1010 are disposed between the plurality of ribs 128, thereby ensuring that the enlarged end portions 1014 are positioned for engagement with the mating features of the delivery apparatus to form a releasable connection between the prosthetic valve and the delivery apparatus. As the prosthetic valve is pushed out of the outlet 122, the second set of anchors 1010 can be radially compressed against the main body 1003 of the frame 1002 of the prosthetic valve 1000. In alternative examples, the second tapered portion 134 (FIG. 2) of the funnel segment 124 can be adapted to cause the anchors 1010 to bend away from the main body 1003 into a substantially straightened configuration extending 180 degrees from the main body 1003 as the prosthetic valve 1000 moves through the funnel segment 124.

Figure 53:
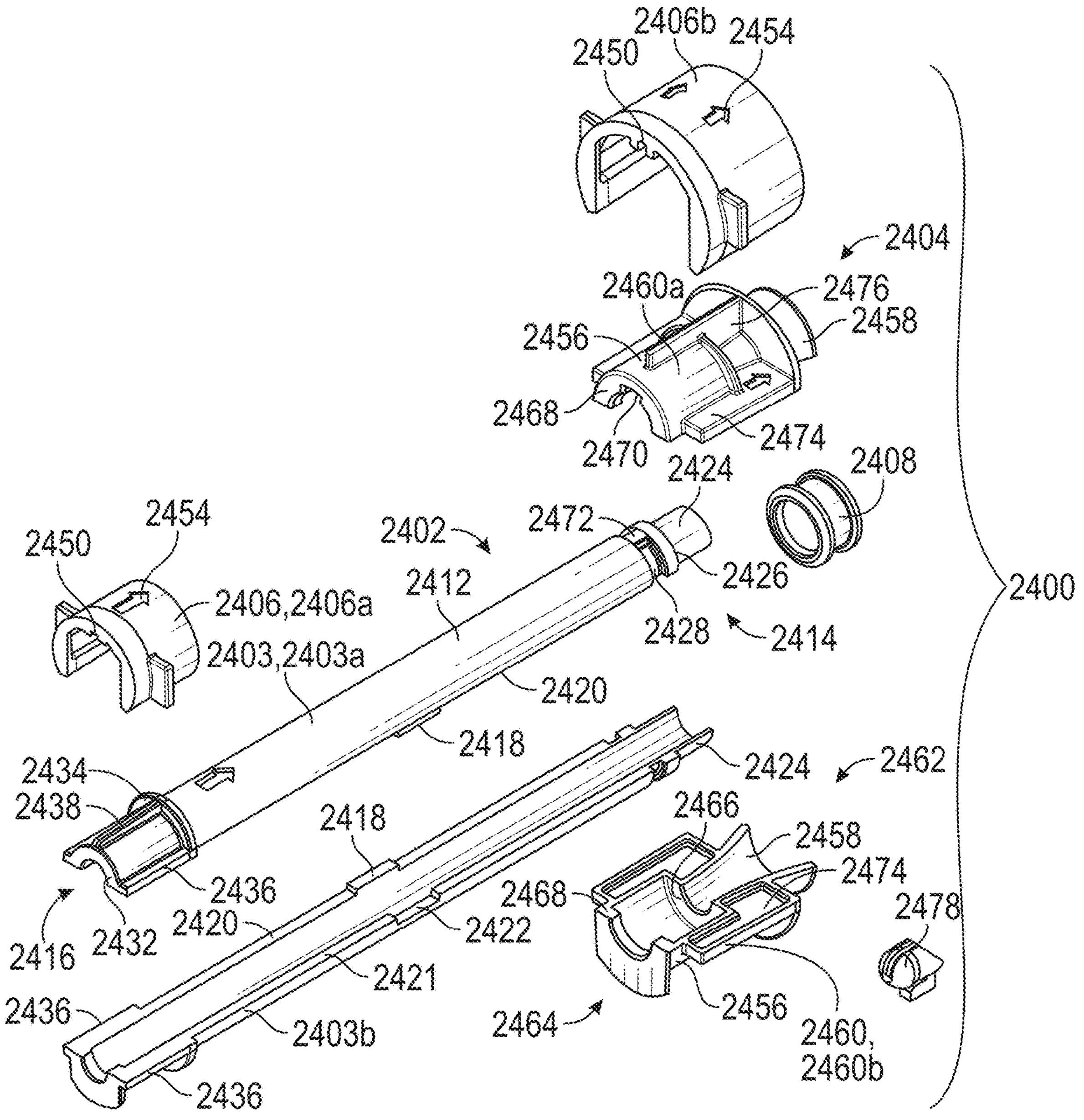
FIG. 53 is an exploded perspective view of a loading assembly, according to one example.

FIG. 37 shows the distal end portion of an exemplary delivery apparatus 1100 that can be used to deliver and implant the prosthetic valve 1000 in a patient's body. Any of the crimping devices disclosed herein can be used to crimp the prosthetic valve 1000 at least partially and couple it to the valve retaining member 1110. After the prosthetic valve 1000 is coupled to the valve retaining member 1110, it can be further crimped and loaded into the delivery apparatus using a separate loading assembly 2400 (FIG. 53).

As shown in FIG. 37, the delivery apparatus 1100 generally comprises an outer sheath 1102, a first shaft 1104 extending coaxially through the sheath 1102, and a second shaft 1106 extending coaxially through the first shaft 1104. A nose cone 1108 can be attached to the distal end portion of the second shaft 1106. Although not shown, the proximal end portions of the sheath 1102, the first shaft 1104, and the second shaft 1106 can be coupled to a handle and each of these components can be moveable axially relative to each other.

A valve-retaining member 1110 can be connected to the distal end portion of the first shaft 1104 and can include a plurality of circumferentially spaced slots 1112 sized to receive the connecting arms 1012 of the prosthetic valve 1000. During the crimping process, the valve-retaining member 1110 initially can be outside of the sheath 1102. As the prosthetic valve 1000 is initially pushed out of the outlet 122 of the housing 108, the connecting arms 1012 can be placed within respective slots 1112 of the valve-retaining member 1110. The enlarged end portions 1014 can be positioned within an annular slot 1114 proximal to slots 1112 to prevent axial separation of the prosthetic valve from the valve-retaining member. Further details of the loading and engagement of the prosthetic valve with the delivery apparatus can be found, for example, in U.S. Patent Publication No. 2018/0055629.

In some examples, once the prosthetic valve is coupled to the valve-retaining member 1110, the crimping device can be removed from the delivery apparatus and a separate crimping and loading assembly (such as loading assembly 2400) can be used to compress the prosthetic valve 1110 to the delivery configuration and load the prosthetic valve into the sheath 1102. In other examples, as the prosthetic valve is further advanced from the crimping device, the sheath 1102 can be advanced distally over the valve-retaining member 1110 and the prosthetic valve 1000. After the delivery apparatus 1100 is inserted into a patient's vasculature and the distal end portion is positioned at or adjacent the desired implantation site (e.g., the native mitral valve), the sheath 1102 can be retracted proximally to deploy the prosthetic valve 1000 from the sheath 1102, allowing the prosthetic valve to expand under its own resiliency. When the sheath 1102 is retracted proximally beyond the valve-retaining member 1110, the connecting arms 1012 can expand radially away from their engagement with the slots 1112, thereby de-coupling the prosthetic valve from the delivery apparatus.

Figure 38:
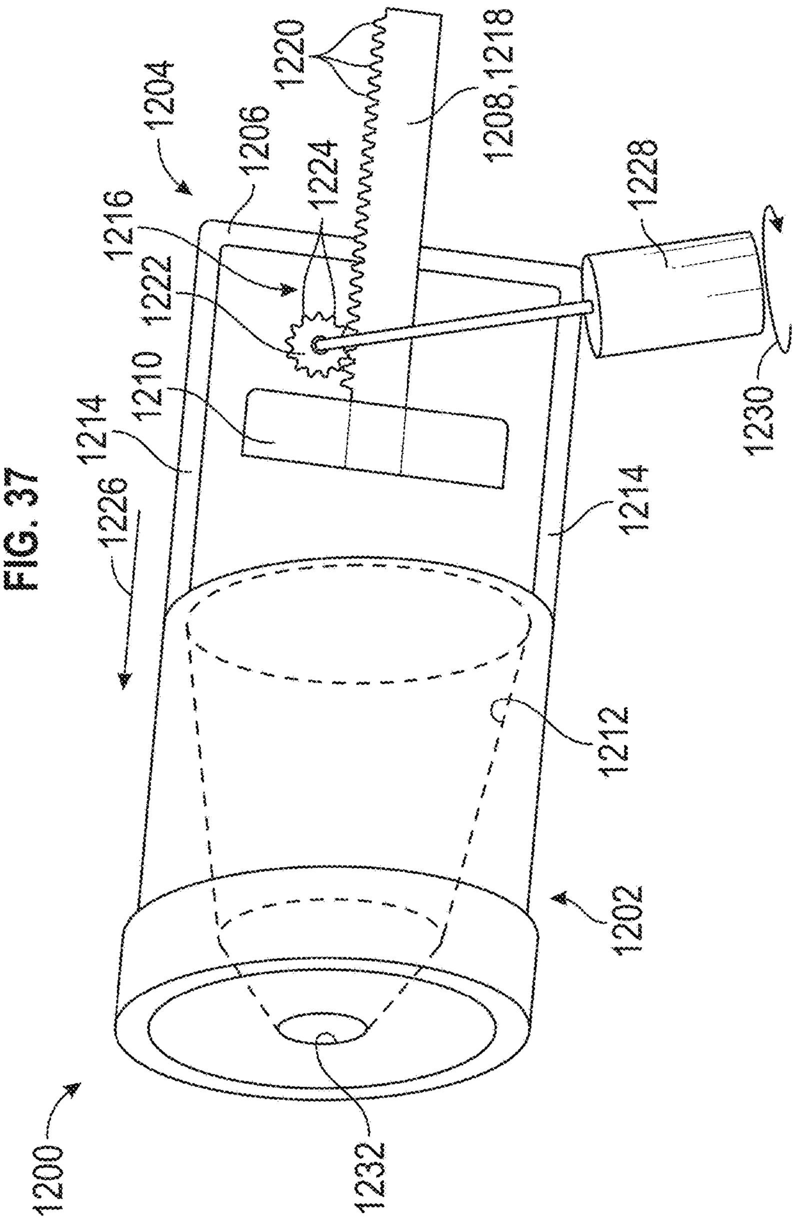
FIG. 38 is a perspective view of an example of a crimping device.

FIG. 38 schematically illustrates another example of a crimping device 1200 comprising a housing 1202 and an actuator 1204. The housing 1202 can be the same as previously described housing 108, except where specifically noted. The actuator 1204 can comprise a base member/plate 1206 and a movable portion 1208. The movable portion 1208 can be releasably coupled to a pusher member 1210, such as or similar to pusher member 112 described previously, for holding a prosthetic valve (e.g., prosthetic valve 1000) and advancing the prosthetic valve through a funnel segment 1212 of the housing 1202. The pusher member 1210 can be coupled to the movable portion 1208 of the actuator.

The base member 1206 can comprise one or more extension members 1214 (e.g., elongated members) configured to releasably couple the actuator 1204 to the housing 1202. For example, in some examples, the extension members 1214 can be similar to extension members 608 or 924 described previously. In other examples, the extension members 1214 can engage an internal surface of the housing 1202 (e.g., via a friction-fit and/or via an engagement feature (e.g., fasteners, etc.) configured to couple a corresponding engagement feature and/or opening on the housing).

The movable portion 1208 can comprise a rack and pinion assembly 1216 comprising a linear rack member 1218 having a plurality of teeth 1220 and a circular gear or pinion member 1222 comprising a corresponding plurality of teeth 1224 configured to engage the teeth 1220 of the linear rack 1218. The two sets of teeth 1220, 1224 can be configured to engage each other such that rotation of the pinion 1222 in a first direction causes corresponding axial movement of the linear rack 1218 in a first direction (e.g., represented by arrow 1226) and rotation of the pinion in a second direction causes corresponding axial movement of the linear rack 1218 in a second direction opposite the first direction. In some examples, the teeth 1220 of the linear rack 1218 can be angled such that the rack can move axially relative to the pinion 1222 in the first direction but is prevented from moving relative to the pinion in the second direction. In other words, in some examples, the rack and pinion assembly 1216 can comprise or function as a ratcheting mechanism.

The pinion 1222 can be coupled to an actuator member 1228 (such as a knob or lever) configured to rotate the pinion 1222. In some examples, the pinion 1222 can be bevel gear, and the actuator can comprise a corresponding head portion configured to engage the bevel gear. Rotation of the actuator member 1228 in a first direction (e.g., as represented by arrow 1230) can cause corresponding rotation of the pinion 1222 in a first direction, and thereby advance the linear rack 1218 and the pusher member 1210 relative to the housing 1202. Rotation of the actuator member 1228 in a second direction (e.g., opposite the first direction) can cause corresponding rotation of the pinion 1222 in the second direction and thereby retract the linear rack 1218 relative to the housing 1202.

In use, the crimping device 1200 can be used to crimp a prosthetic valve (e.g., prosthetic valve 1000 shown in FIG. 36) in the following exemplary manner. The prosthetic valve 1000 can be inserted into the funnel segment 1212 of the housing 1202. The actuator 1204 can be coupled to the housing 1202 using the extension members 1214. So coupled, the pusher member 1210 can be aligned with the prosthetic valve 1000 so as to engage an adjacent end portion of the prosthetic valve 1000. The user can actuate the actuator member 1228 (e.g., by rotating the knob) to rotate the pinion 1222 and cause corresponding axial motion of the linear rack 1218, thereby advancing the pusher member 1210 axially forward into the housing 1202. The advancement of the pusher member 1210 into the housing pushes the prosthetic valve 1000 through the funnel segment 1212 of the housing 1202 such that the prosthetic valve is radially compressed and pushed outwardly through the outlet 1232. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100.

Figure 39:
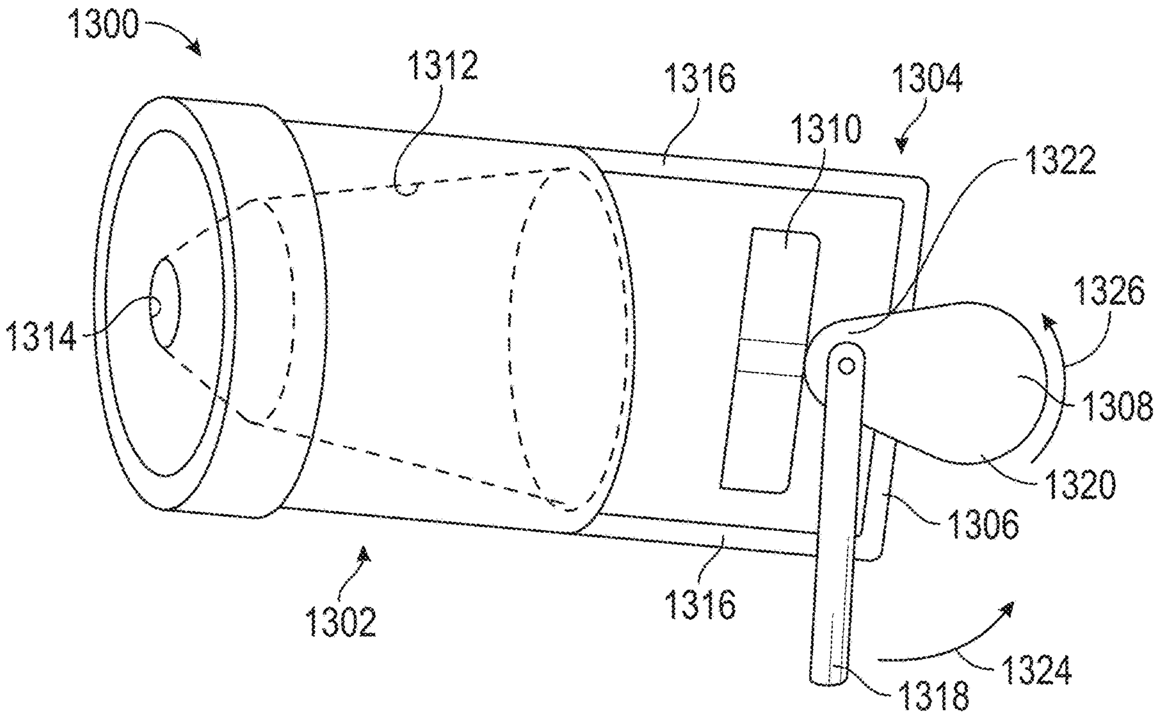
FIG. 39 is a perspective view of another example of a crimping device.

FIG. 39 schematically illustrates another example of a crimping device 1300 comprising a housing 1302 and an actuator 1304. The housing 1302 can be similar to previously described housing 108, except where specifically noted. The actuator 1304 can comprise a base member or plate 1306 and a movable portion 1308. The movable portion 1308 can be releasably coupled to a pusher member 1310, such as or similar to pusher member 112 described previously, for holding a prosthetic valve (e.g., prosthetic valve 1000) and advancing the prosthetic valve through the funnel segment 1312 of the housing 1302 to the outlet 1314.

The base member 1306 can comprise one or more extension members 1316 (e.g., elongated members) configured to releasably couple the actuator 1304 to the housing 1302. For example, in some examples, the extension members 1316 can be similar to extension members 608 or 924 described previously. In other examples, the extension members 1316 can engage an internal surface of the housing 1302 (e.g., via a friction-fit and/or via an engagement member configured to couple a corresponding engagement member and/or opening on the housing). The movable portion 1308 can comprise a lever 1318 and a cam element 1320. The cam element 1320 can be pivotably coupled to the base member 1306 and rigidly attached to the lever 1318, for example at pin 1322, such that rotation of the lever 1318 (represented by arrow 1324) causes corresponding rotation of the cam element 1320 (represented by arrow 1326). In other examples, the lever 1318 can be a knob or other type of actuation mechanism configured to cause rotational movement of the cam element 1320.

The cam element 1320 can be configured such that rotation of the cam element 1320 applies an actuation force in a first direction to the pusher member 1310, advancing the pusher member axially into the housing 1302. For example, the cam element 1320 can have lobe shape configured to contact the pusher member and apply the actuation force to the pusher member 1310 when the lever 1318 is actuated. In some particular examples, less than 1 inch of movement is needed to fully advance the pusher member 1310 into the housing 1302 (e.g., such that the prosthetic valve is at least partially advanced through the outlet). In such examples, only one rotation of the lever 1318 (e.g., one movement of between about 90 degrees and about 180 degrees) may be needed to at least partially advance the prosthetic valve through the outlet. In other examples, the lever 1318 can be actuated multiple times to advance the prosthetic valve into/through the outlet. In such examples, the crimping device 1300 can further comprise a stop or ratchet mechanism configured to prevent the pusher member 1310 from sliding backwards out of the housing 1302 in between actuations of the lever 1318.

In use, the crimping device 1300 can be used to crimp a prosthetic valve (e.g., prosthetic valve 1000 shown in FIG. 36) in the following exemplary manner. The prosthetic valve 1000 can be inserted into the funnel segment 1312 of housing 1302. The actuator 1304 can be coupled to the housing 1302 using the extension members 1316. So coupled, the pusher member 1310 can be aligned with the prosthetic valve 1000 so as to engage an adjacent end portion of the prosthetic valve 1000. The user can actuate the lever 1318 (e.g., by rotating it between about 90 degrees and about 180 degrees) to rotate the cam element 1320, which can contact the pusher member 1310 and cause corresponding axial motion of pusher member 1310 to advance the pusher member 1310 axially forward into the housing 1302. The advancement of the pusher member 1310 into the housing 1302 pushes the prosthetic valve 1000 through the funnel segment 1312 of the housing 1302 such that the prosthetic valve is radially compressed and pushed outwardly through the outlet 1314. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100.

Figure 40:
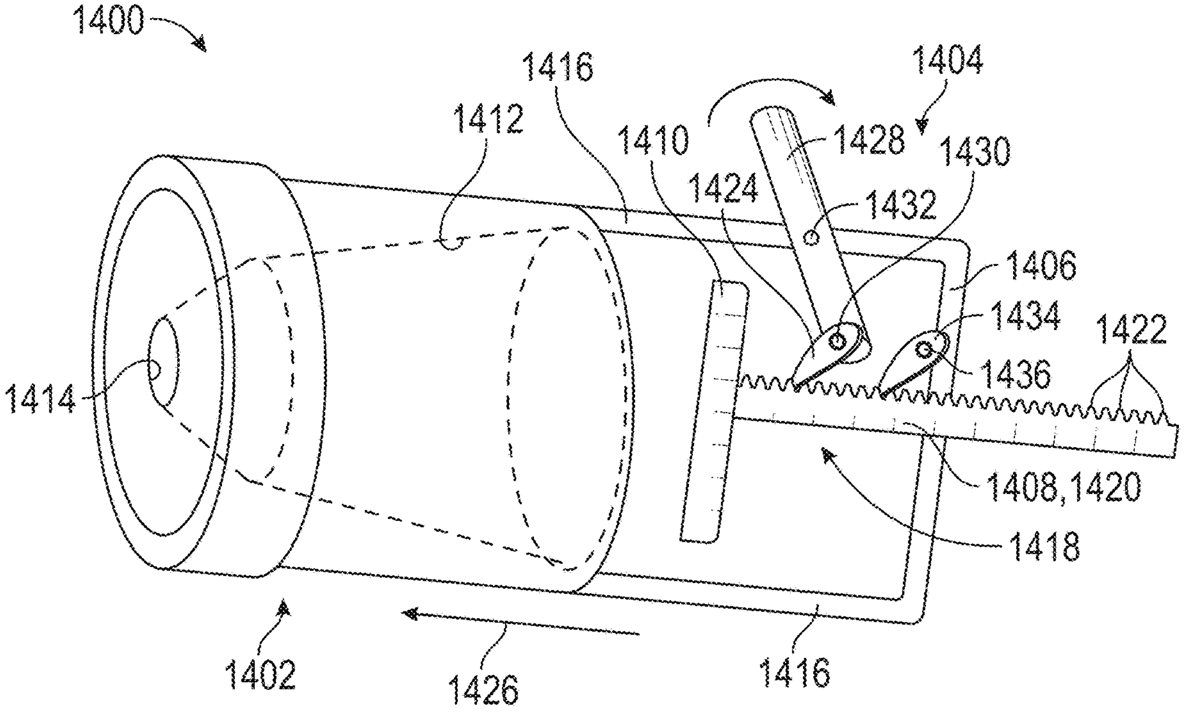
FIG. 40 is a perspective view of a still another example of a crimping device.

FIG. 40 illustrates another example of a crimping device 1400 comprising a housing 1402 and an actuator 1404. The housing 1402 can be similar to previously described housing 108, except where specifically noted. The actuator 1404 can comprise a base member/plate 1406 and a movable portion 1408. The movable portion 1408 can be releasably coupled to a pusher member 1410, such as or similar to pusher member 112 described previously, for holding a prosthetic valve (e.g., prosthetic valve 1000) and advancing the prosthetic valve through the funnel segment 1412 of the housing 1402 and through the outlet 1414.

The base member 1406 can comprise one or more extension members 1416 (e.g., elongated members) configured to releasably couple the actuator 1404 to the housing 1402. For example, in some examples, the extension members 1416 can be similar to extension members 608 or 924 described previously. In other examples, the extension members 1416 can engage an internal surface of the housing (e.g., via a friction-fit and/or via an engagement member configured to couple a corresponding engagement member and/or opening on the housing).

The movable portion 1408 can comprise a ratchet mechanism or ratchet assembly 1418 comprising a linear rack member 1420 having a plurality of teeth 1422 and a pawl member 1424 configured to engage the teeth 1422 of the linear rack 1420. The pawl 1424 and the teeth 1422 are configured such that when the pawl 1424 is engaged with the rack 1420, the linear rack 1420 (and therefore the pusher member 1410) can move relative to the base member 1406 in a first axial direction (e.g., represented by arrow 1426), but is prevented from moving relative to the base member 1406 in a second, opposite axial direction. This configuration allows compression/crimping of the prosthetic valve while preventing resilient expansion of the prosthetic valve from pushing the pusher member 1410 out of the housing 1402.

The pawl 1424 can be coupled to an actuator member 1428 via a pivot or rotatable pin 1430. The pin 1430 can be spring biased such that the pawl 1424 remains engaged with the teeth 1422 of the linear rack 1420. The actuator member 1428 can be pivotably coupled to a respective extension member 1416 and/or the base member 1406, for example, via a pin 1432, such that a user can actuate the actuator member 1428 to cause movement of the linear rack 1420 relative to the base member 1406 (e.g., to advance the pusher member 1410 into the housing 1402). The actuator 1404 can further comprise a locking member 1434 (e.g., an additional pawl) configured to further restrain the linear rack 1420 from movement in the second axial direction (e.g., away from the housing 1402). The locking member 1434 can be pivotably coupled to the base member 1406 via a pin 1436. Though the actuator member 1428 is shown as a lever in the illustrated example, in other examples, the actuator member 1428 can be, for example, a knob or other mechanism configured to move the pawl 1424 relative to the linear rack 1420 when actuated.

In use, the crimping device 1400 can be used to crimp a prosthetic valve (e.g., prosthetic valve 1000 shown in FIG. 36) in the following exemplary manner. The prosthetic valve 1000 can be inserted into the funnel segment 1412 of the housing 1402. The actuator 1404 can be coupled to the housing 1402 using the extension members 1416. So coupled, the pusher member 1410 can be aligned with the prosthetic valve 1000 so as to engage an adjacent end portion of the prosthetic valve 1000. The user can actuate the actuator member 1428 (e.g., by pivoting the lever) to actuate the pawl 1424 and cause axial motion of the linear rack 1420 in a first axial direction, thereby advancing the pusher member 1410 axially forward into the housing 1402. The advancement of the pusher member 1410 into the housing 1402 pushes the prosthetic valve 1000 through the funnel segment 1412 of the housing 1402 such that the prosthetic valve is radially compressed and pushed outwardly through the outlet 1414. The prosthetic valve 1000 can then be coupled to a valve retaining member 1110 of the delivery apparatus 1100, as described in more detail with respect to FIG. 37 or can be loaded directly into the sheath of the delivery apparatus as described previously with respect to crimping device 100.

Figure 41:
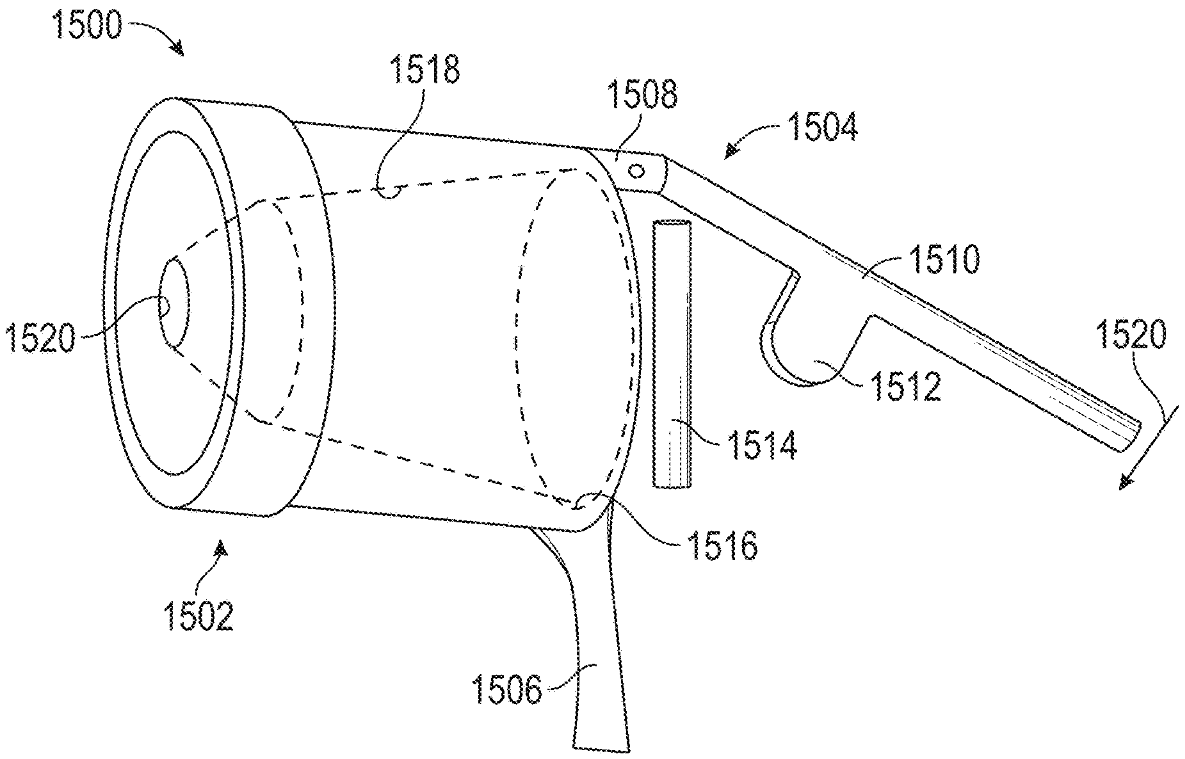
FIG. 41 is a perspective view of an example of a crimping device.

FIG. 41 illustrates another example of a crimping device 1500 comprising a housing 1502 and an actuator 1504. The housing 1502 can be similar to previously described housing 108, except where specifically noted. The housing 1502 can have a gripping portion or handle 1506 coupled to the housing 1502 such that a user can hold the housing 1502 via the handle 1506. The handle 1506 can be permanently or releasably coupled to the housing.

The actuator 1504 can comprise an extension member 1508 coupled to the housing 1502. The extension member 1508 can be pivotably coupled to a movable portion configured as a lever member 1510. As shown in FIG. 41, the lever 1510 can comprise a pushing member or protrusion 1512 configured to advance a prosthetic valve into the housing 1502. In the illustrated example, the protrusion 1512 acts on a pusher member configured as a flat member or plate member 1514 disposed at the inlet end portion 1516 of the housing 1502. In some examples, the plate member 1514 can comprise a plurality of recesses or openings configured to interface with ribs (e.g., such as ribs 128 described previously) within the housing 1502 such that the plate member 1514 can be inserted into the housing and advanced within the housing to crimp the prosthetic valve. In other examples, the plate member 1514 can be coupled to a pusher member, such as pusher member 112 described previously. In still other examples, in lieu of a plate 1514, a pusher member 112 can be releasably coupled to the protrusion 1512 or disposed within the inlet end portion 1516. In some examples, the handle 1506 and the lever 1510 can comprise corresponding locking features configured to releasably lock the handle 1506 and lever 1510 together when the lever 1510 is actuated, thereby locking the crimping device 1500 with the prosthetic valve 1000 in the crimped position.

In use, the crimping device 1500 can be used to crimp a prosthetic valve (e.g., prosthetic valve 1000 shown in FIG. 36) in the following exemplary manner. The prosthetic valve 1000 can be inserted into the funnel segment 1518 of the housing 1502, and the plate 1514 and/or pusher member 112 can be aligned with the prosthetic valve 1000 so as to engage an adjacent end portion of the prosthetic valve 1000. The user can pivot the lever 1510 (e.g., as shown by arrow 1520) such that the protrusion 1512 engages the plate 1514 and advances the plate 1514 (and thereby the prosthetic valve 1000) axially forward into the housing 1502. The advancement of the plate 1514 into the housing pushes the prosthetic valve 1000 through the funnel segment 1518 of the housing 1502 such that the prosthetic valve is radially compressed and pushed outwardly through the outlet 1520. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100.

Figure 42:
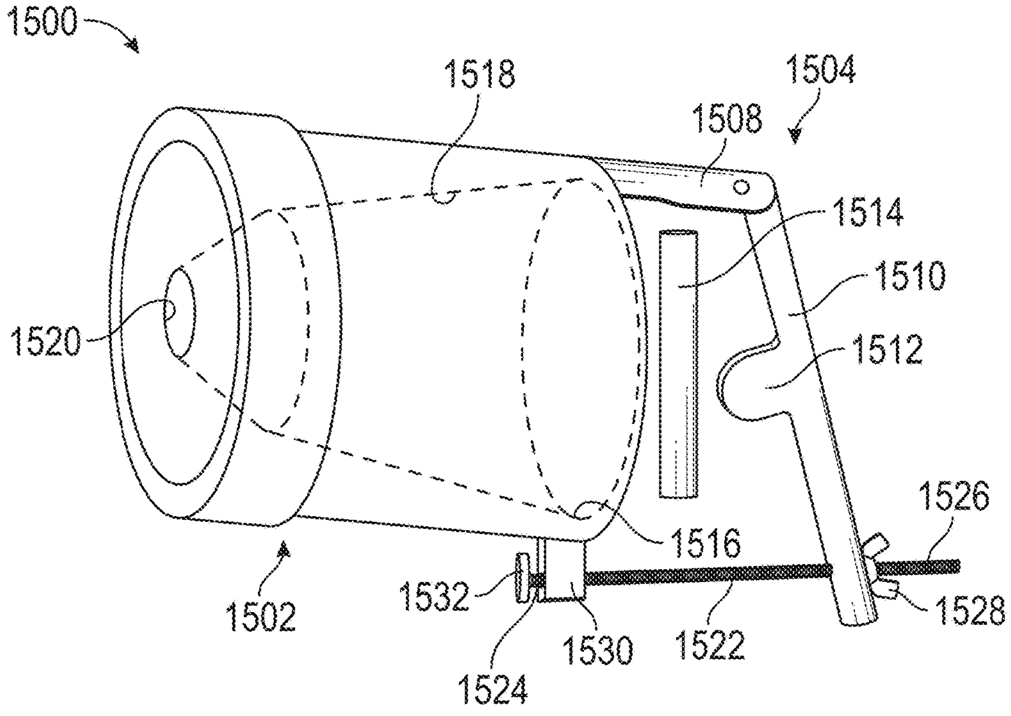
FIG. 42 is a perspective view of another example of a crimping device.

In some examples, as shown in FIG. 42, in lieu of the handle 1506, the crimping device 1500 can comprise an actuator member 1522 coupled to the lever 1510 and configured to allow a user to actuate the lever 1510. The actuator member 1522 can be an elongated, threaded member having a first end portion 1524 coupled to the housing 1502. In the illustrated example, the actuator member 1522 is coupled to an outer surface of the housing 1502, however, in other examples, the actuator member 1522 can be coupled to an inner surface of the housing 1502, for example, at the inlet portion 1516. The first end portion 1524 can be coupled to the housing 1502 via a member configured as a mounting member, protrusion, boss, and/or block 1530 having an aperture though which the actuator member 1522 extends. The first end portion 1524 can comprise a stop or cap 1532 configured to prevent the actuator member 1522 from being pulled free of the block 1530.

The actuator member 1522 can have a second end portion 1526 that extends through an aperture in the lever 1510. A driver member, configured as a threaded wingnut 1528 (also referred to as a fastener), can be disposed on the second end portion 1526 of the actuator member 1522 adjacent the lever 1510. In some examples, both the aperture and the fastener can be threaded, in other examples, only one of the two components is threaded. In use, once the prosthetic valve and plate 1514 are disposed within the housing, the user can actuate the fastener 1528 (e.g., by rotating it along the threads of the actuator member 1522) to advance the lever 1510 relative to the housing 1502. Such a configuration advantageously lessens the amount of force that the user must apply to crimp the prosthetic valve. The threaded engagement of the wingnut 1528 and the actuator member 1522 mitigates or prevents movement of the lever 1510 in a second direction (e.g., away from the housing 1502) thereby allowing the user to release the actuator 1504 during the crimping process without having the prosthetic valve resiliently uncrimp and push the lever 1510 out of the housing.

Figure 43A:
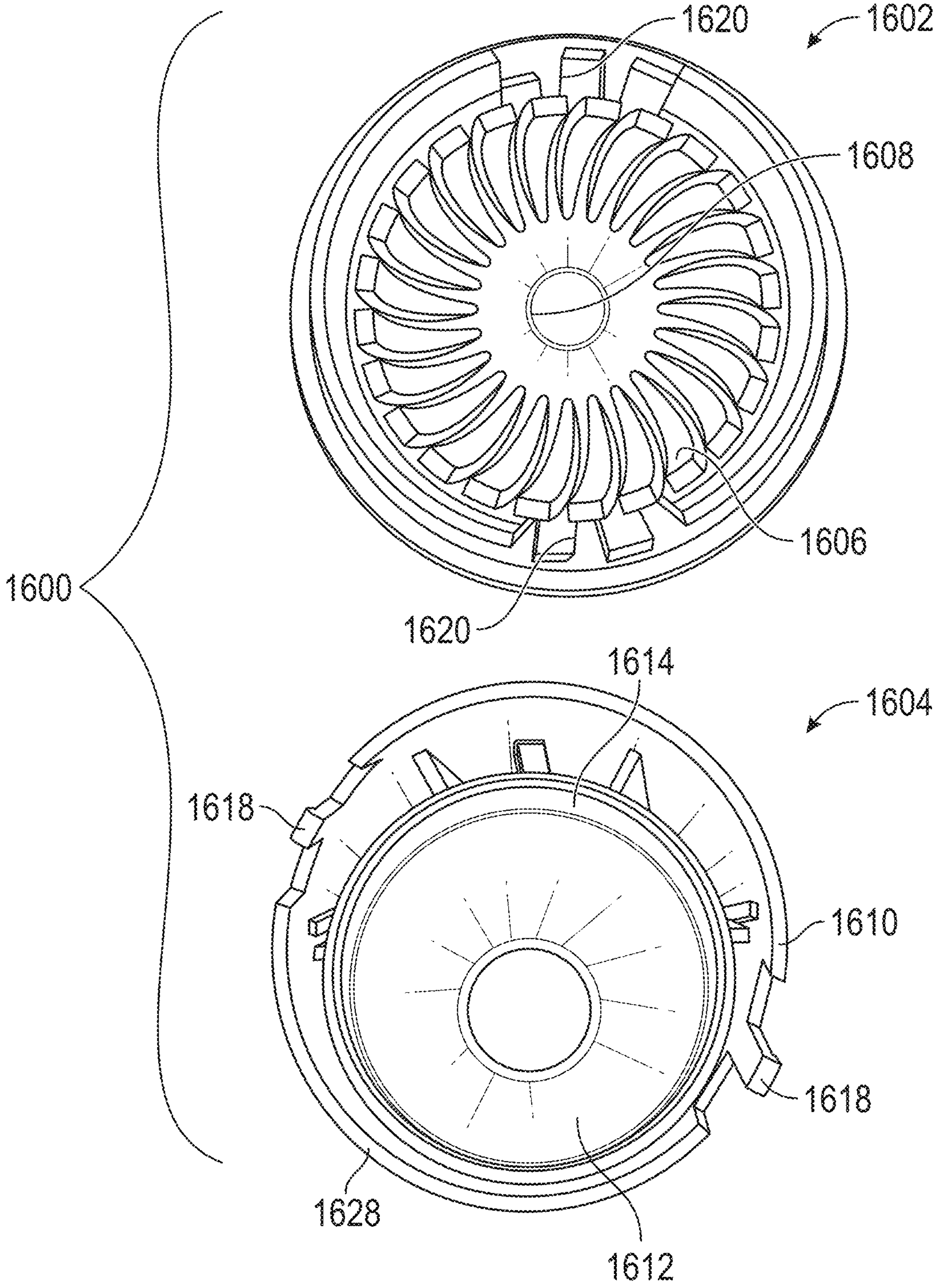
FIG. 43A is a perspective view of another example of a crimping device, with the housing shown in a bottom up view and the actuator shown in a top down view.
Figure 43B:
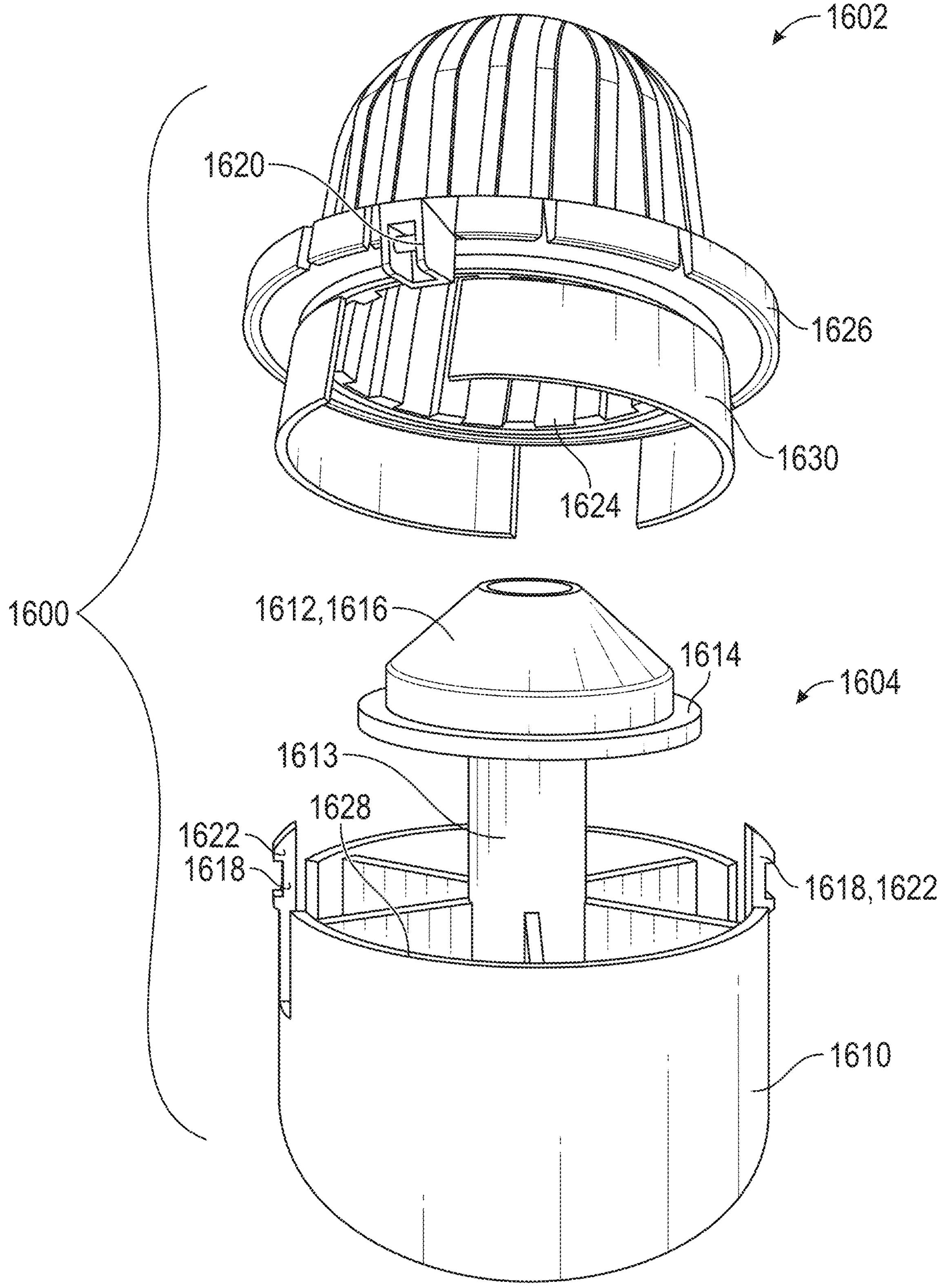
FIG. 43B is a perspective view of the crimping device of FIG. 43A.
Figure 43C:
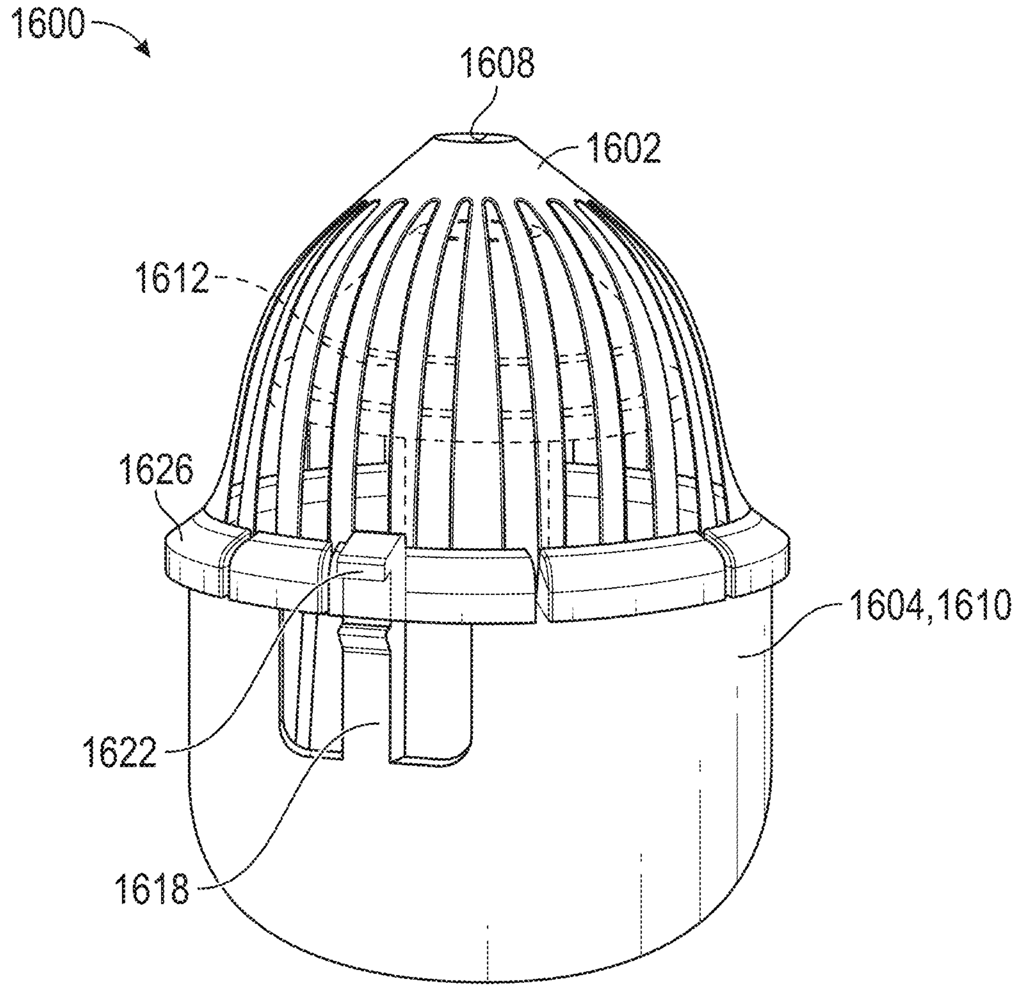
FIG. 43C is a perspective view of the crimping device of FIG. 43A.

FIGS. 43A-43C, illustrate another example of a crimping device 1600 comprising a housing 1602 and an actuator 1604. The housing 1602 can have a hemispherical or cupped shape defining an internal funnel segment 1606 and can include an outlet 1608. The actuator 1604 can comprise a base portion 1610 and a pusher member 1612, for holding a prosthetic valve (e.g., prosthetic valve 1000) and advancing the prosthetic valve the through the funnel segment 1606 and through the outlet 1608.

As shown in FIG. 43B, the pusher member 1612 can comprise a stem 1613, an annular lip or shoulder 1614, and a domed central protrusion 1616. The prosthetic valve 1000 can be disposed on the pusher member such that an edge portion of the prosthetic valve 1000 (e.g., an inflow edge portion) sits on the annular lip 1614 and such that the central protrusion 1616 sits within the prosthetic valve 1000. The base portion 1610 of the actuator 1604 can comprise one or more engagement features 1618 configured to releasably couple corresponding engagement features 1620 (FIG. 43A) on the housing 1602 such that the actuator 1604 and the housing 1602 can be locked together once the prosthetic valve 1000 has reached a selected crimped configuration (e.g., partially or fully crimped). This allows the user to release the actuator 1604 without the resilient spring-force of the prosthetic valve pushing the pusher member 1612 out of the housing 1602.

In the illustrated example, the engagement features 1618 are configured as resilient latches (e.g., two diametrically opposed resilient latches) comprising a protrusion or tooth 1622 (FIG. 43B) that can mate with a corresponding feature 1620 (e.g., an opening) in the housing 1602. The engagement features 1618 can deflect radially inwardly as the actuator 1604 is advanced relative to the housing 1602 and can deflect radially outwardly once within the openings 1620, coupling the actuator 1604 and the housing 1602 together with a snap-fit connection.

In the illustrated example, the pusher member 1612 and base portion 1610 are formed as a unitary piece, however, in other examples the pusher member 1612 and base portion 1610 can be formed as separate pieces and can be releasably or permanently coupled together (e.g., as described previously with respect to pusher member 112 and actuator 110).

As shown, the housing 1602 can comprise a ridged interior surface 1624 configured to assist in alignment of the prosthetic valve 1000 with the mating features of the delivery apparatus during compression of the prosthetic valve and advancement through the funnel segment 1606. The housing 1602 can comprise an annular lip or shoulder 1626 disposed around an external circumference of the housing and configured to selectively abut a distal edge 1628 of the base portion 1610 of the actuator 1604 (as shown in FIG. 43C). The housing 1602 can further comprise an extension portion 1630 having a diameter less than a diameter of the base portion 1610 of the actuator 1604 such that when the actuator 1604 and housing 1602 are coupled together, the extension portion 1630 sits within the actuator 1604. As mentioned previously and as shown in FIG. 43C, the shoulder 1626 can comprise one or more engagement features 1620 (e.g., openings/apertures) configured to engage the engagement features 1618 on the actuator 1604.

In use, the crimping device 1600 can be used to crimp a prosthetic valve (e.g., prosthetic valve 1000 shown in FIG. 36) in the following exemplary manner. The prosthetic valve 1000 can be inserted into the funnel segment 1606 of the housing 1602. The actuator 1604 can be disposed such that the pusher member 1612 is aligned with an adjacent end portion of the prosthetic valve 1000 (e.g., such that the inflow end portion of the prosthetic valve 1000 is disposed on the annular lip 1614 of the pusher member 1612). The user can actuate the actuator member 1604 (e.g., by manually pushing the actuator) to advance the pusher member 1612 axially forward into the housing 1602. The advancement of the pusher member 1612 into the housing 1602 pushes the prosthetic valve 1000 through the funnel segment 1606 of the housing 1602 such that the prosthetic valve is radially compressed and pushed outwardly through the outlet 1608. The prosthetic valve 1000 can then be coupled to a valve retaining member 1110 of the delivery apparatus 1100, as described in more detail with respect to FIG. 37 or can be loaded directly into the sheath of the delivery apparatus as described previously with respect to crimping device 100.

Figure 44:
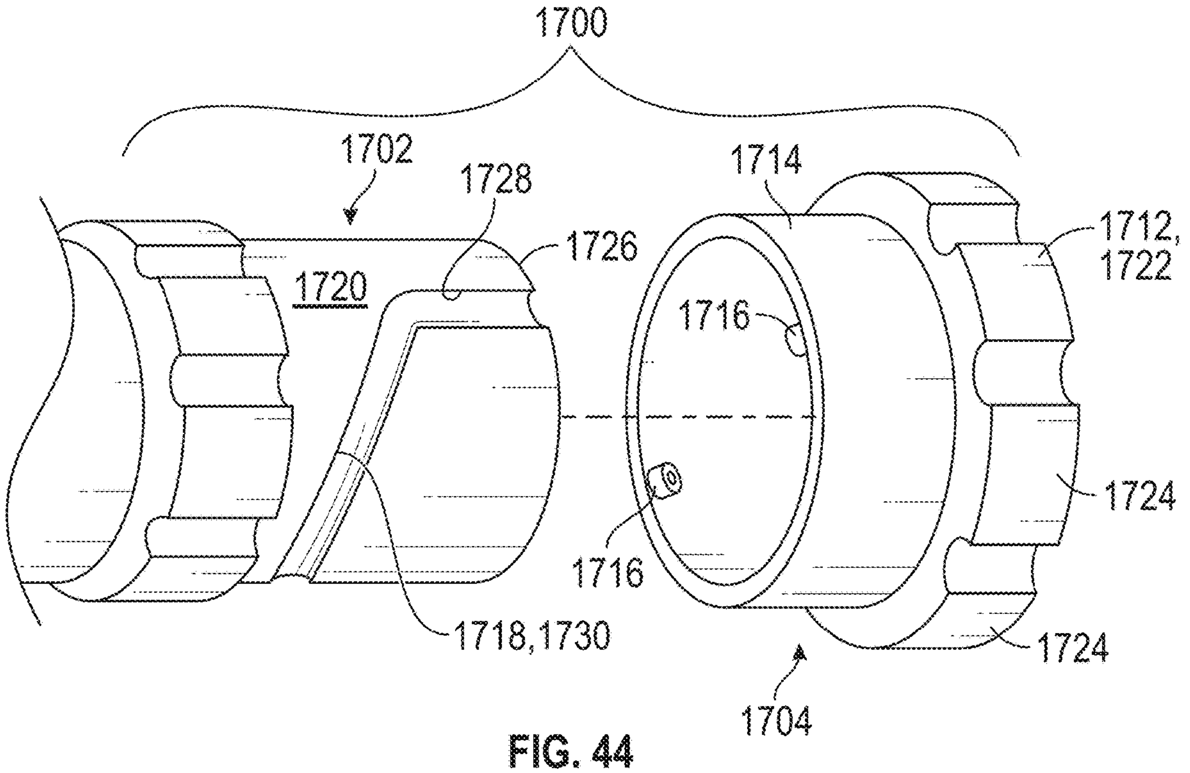
FIGS. 44-45 are perspective views of another example of a crimping device.
Figure 45:
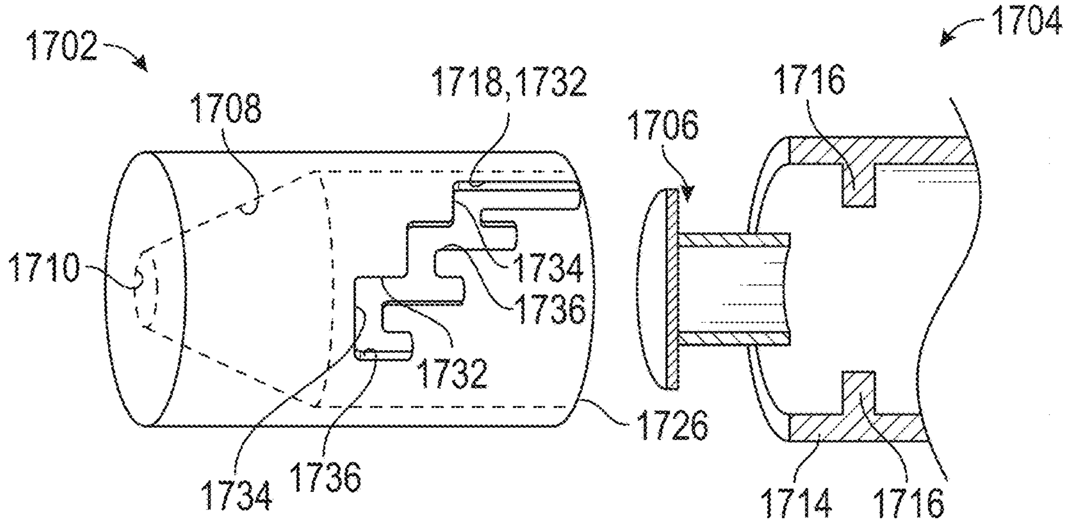

FIGS. 44-45, illustrate another example of a crimping device 1700 comprising a housing 1702, an actuator 1704, and a pusher member 1706 (FIG. 45). The pusher member 1706 can be the same as or similar to pusher member 112 described previously, for holding a prosthetic valve (e.g., prosthetic valve 1000) and advancing the prosthetic valve 1000 through the funnel segment 1708 (FIG. 45) of the housing 1702 to the outlet 1710 (FIG. 45).

The actuator 1704 can comprise a base member 1712 and a cylindrical extension member 1714 having an internal diameter wider than an external diameter of the housing 1702 such that the actuator 1704 can be advanced axially over the housing 1702. The extension member 1714 can comprise one or more protrusions/projections/pins 1716 extending radially inwardly from an inner surface of the extension member 1714 and configured to engage one or more channels/recesses/tracks 1718 disposed in an outer surface 1720 of the housing 1702.

In some examples, the actuator 1704 can further comprise a gripping interface 1722 for easy gripping and use by a user (e.g., on the base member 1712). The gripping interface 1722 can include, for example, a plurality of circumferentially spaced ridges 1724.

The housing 1702 can be similar to previously described housing 108, except that housing 1702 comprises one or more channels/recesses/tracks 1718 (e.g., two diametrically opposed channels) disposed in the outer surface 1720 of the housing 1702. As the actuator 1704 is advanced over the housing 1702 the pins 1716 can advance within the channels 1718. In some examples, the channels 1718 can extend only partially through the thickness of the wall of the housing 1702, but in other examples, the channels 1718 can extend entirely through the wall to form a slot. The channels 1718 can extend from an inlet or mouth 1726 of the housing 1702 along at least a portion of the length of the housing.

In some examples, such as shown in FIG. 44, the channels 1718 can comprise a first, axially extending portion 1728 and a second, angled portion 1730. In such examples, the pins 1716 of the actuator 1704 can be advanced within the axially extending portion 1728, and then the actuator 1704 can be twisted or rotated to continue to advance the pins 1716 within the angled portion 1730. In other examples, such as shown in FIG. 45, the one or more channels 1718 can comprise a plurality of stepped portions each comprising an axially extending portion 1732 and a laterally extending portion 1734. In some examples, the stepped portions can further include stops or rests 1736. In such examples, the pins 1716 can be advanced within an axially extending portion 1732 until a laterally extending portion 1734 is reached, the actuator 1704 and/or the housing 1702 can then be twisted/rotated such that the pins slide laterally along the laterally extending portion 1734. The stops or rests 1736 provide a distinct stopping points such that the user can release the force applied to the actuator 1704 and/or housing 1702 without the resilient spring-force of the prosthetic valve pushing the actuator 1704 off of the housing. The stepped portions allow the prosthetic valve 1000 to be incrementally compressed as the actuator 1704 is advanced over the housing 1702.

In use, the crimping device 1700 can be used to crimp a prosthetic valve (e.g., prosthetic valve 1000 shown in FIG. 36) in the following exemplary manner. The prosthetic valve 1000 can be inserted into the funnel segment 1708 of the housing 1702. The actuator 1704 can be disposed such that the pusher member 1706 (FIG. 45) is aligned with an adjacent end portion of the prosthetic valve 1000, and such that the pins 1716 are aligned with the channels 1718. The user can then actuate the actuator member 1704 (e.g., by manually pushing on the actuator) to advance the pins 1716 within the channels 1718 and thereby advance the pusher member 1706 axially forward into the housing 1702. The advancement of the pusher member 1706 into the housing 1702 pushes the prosthetic valve 1000 through the funnel segment 1708 of the housing 1702 such that the prosthetic valve is radially compressed and pushed outwardly through the outlet 1710. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100.

Figure 46:
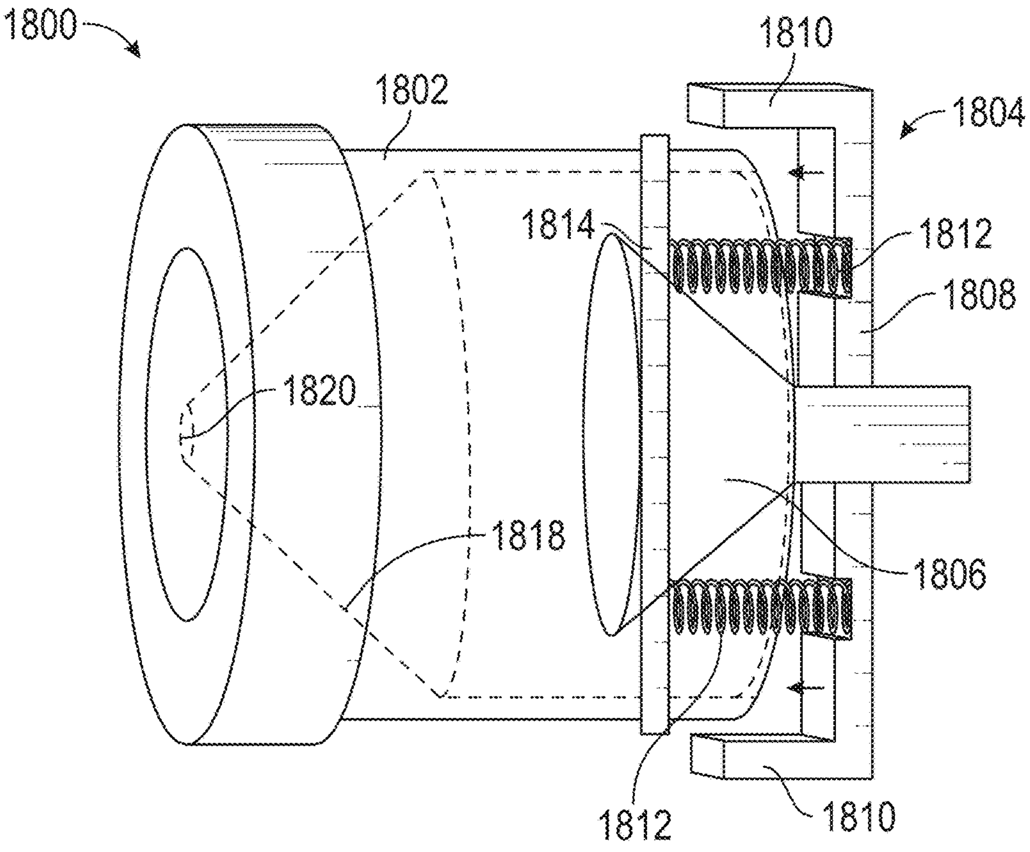
FIG. 46 is a perspective view of another example of a crimping device.

FIG. 46 illustrates another example of a crimping device 1800 comprising a housing 1802, an actuator 1804, and a pusher member 1806. The housing 1802 can be similar to previously described housing 108, except where specifically noted. The actuator 1804 can comprise a base portion 1808 including one or more extension members or arms 1810, one or more springs 1812 (e.g., compression springs), and a stopping member 1814. The actuator 1804 can be movably coupled to a pusher member 1806, such as or similar to pusher member 112 described previously, for holding a prosthetic valve (e.g., prosthetic valve 1000) and advancing the prosthetic valve through the funnel segment 1818 of the housing 1802 and through the outlet 1820.

The pusher member 1806 can be coupled to the actuator 1804 via the one or more springs 1812. In certain examples, the springs 1812 can be tension springs. The springs 1812 can be preloaded (e.g., in an extended state) such that contraction of the springs 1812 as they return to their natural state advances the pusher member 1806 (and thereby the prosthetic valve 1000 disposed within the housing) into the housing 1802. The springs 1812 can have a stiffness such that they provide a pushing force greater than a resilient spring-force provided by the prosthetic valve 1000. In other words, the springs 1812 can be strong enough to advance the pusher member 1806 into the housing 1802 and compress the prosthetic valve 1000 despite the opposing spring-force of the prosthetic valve 1000.

As mentioned, the actuator 1804 can further comprise a locking/stopping member 1814 configured to selectively retain the pusher member 1806 against movement relative to the housing 1802. For example, the stopping member 1814 can be an elongated rod that extends between the arms of the pusher member 1806 (in examples where pusher member 1806 is configured like pusher member 112), a flat plate that extends over the distal end of the pusher member 1806, or an annular plate that extends over the distal end of the pusher member 1806 but includes an opening such that the pusher member can contact a prosthetic valve disposed within the housing. Stopping member 1814 can remain in place while base portion 1808 advances the pusher member 1806 forward (i.e., due to the compression of springs 1812).

In use, the crimping device 1800 can be used to crimp a prosthetic valve (e.g., prosthetic valve 1000 shown in FIG. 36) in the following exemplary manner. The prosthetic valve 1000 can be inserted into the funnel segment 1818 of the housing 1802. The actuator 1804 can be disposed adjacent an inlet of the housing 1802 and the springs 1812 can be placed into tension (e.g., by pulling the base member 1808 in a direction away from the prosthetic valve 1000). The user can then release the base member 1808, allowing the springs 1812 to compress back to a zero-load state in order to advance the pusher member 1806 axially forward into the housing 1802. The advancement of the pusher member 1806 into the housing 1802 pushes the prosthetic valve 1000 through the funnel segment 1818 of the housing 1802 such that the prosthetic valve is radially compressed and pushed outwardly through the outlet 1820. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100.

Figure 47:
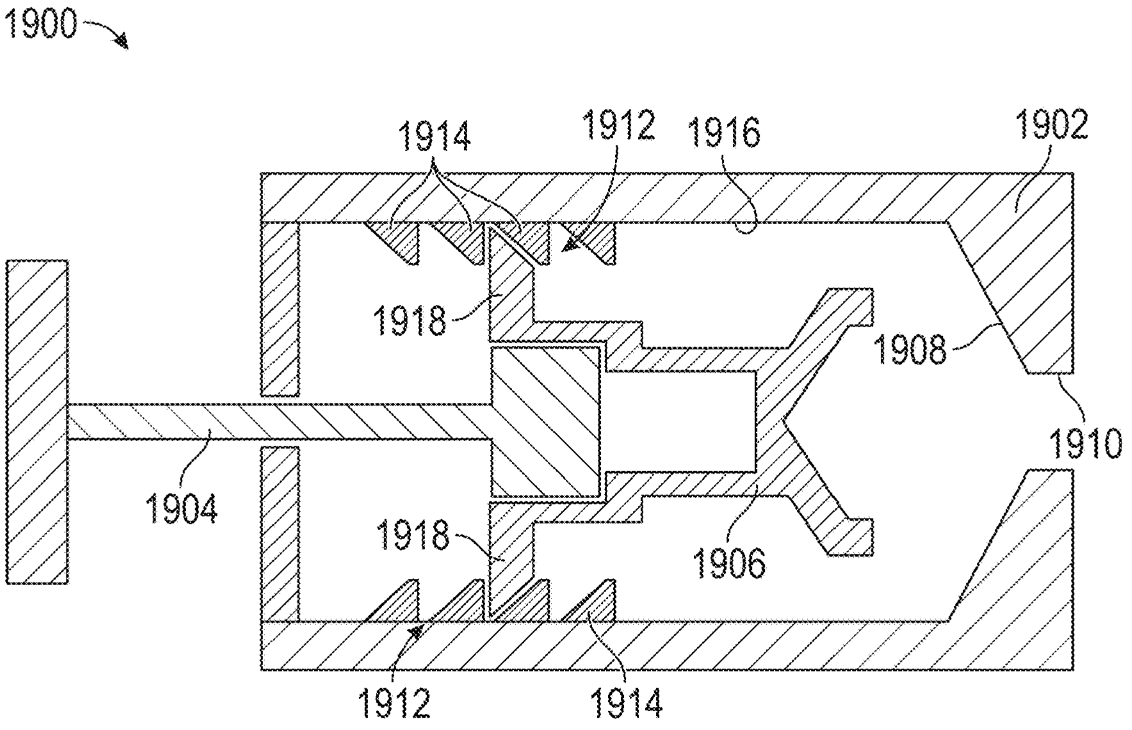
FIG. 47 is a perspective view of another example of a crimping device.

FIG. 47 illustrates another example of a crimping device 1900 comprising a housing 1902 and an actuator 1904. The housing 1902 can define an internal funnel segment 1908 ending in an outlet 1910 and can comprise one or more linear racks 1912 comprising a plurality of angled teeth 1914 extending axially along at least a portion of the inner surface 1916 of the housing 1902.

The actuator 1904 can be releasably or permanently coupled to a pusher member 1906, such as or similar to pusher member 112. The pusher member 1904 and/or actuator 1906 can comprise one or more pawl members 1918 configured to engage the angled teeth 1914 of the housing 1902. The engagement of the one or more pawls 1918 with the teeth 1914 of the housing 1902 allow the actuator 1904 and pusher member 1906 to be advanced relative to the housing 1902 in a first axial direction but prevent the actuator and pusher member from moving relative to the housing in a second, opposite axial direction. This configuration allows for compression/crimping of the prosthetic valve while preventing resilient expansion of the prosthetic valve from pushing the pusher member 1906 out of the housing 1902.

In use, the crimping device 1900 can be used to crimp a prosthetic valve (e.g., prosthetic valve 1000 shown in FIG. 36) in the following exemplary manner. The prosthetic valve 1000 can be inserted into the housing 1902. The pusher member 1906 and actuator 1904 can then be advanced into the housing 1902 until the pawl member(s) 1918 engage the plurality of teeth 1914 and such that the pusher member 1906 is aligned with the prosthetic valve 1000 so as to engage an adjacent end portion of the prosthetic valve 1000. The user can then continue to advance the actuator 1904 (and thereby the pusher member 1906) axially into the housing. The advancement of the pusher member 1906 into the housing 1902 pushes the prosthetic valve 1000 through the funnel segment 1908 such that the prosthetic valve is radially compressed and pushed outwardly through the outlet 1910. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100.

Figure 48:
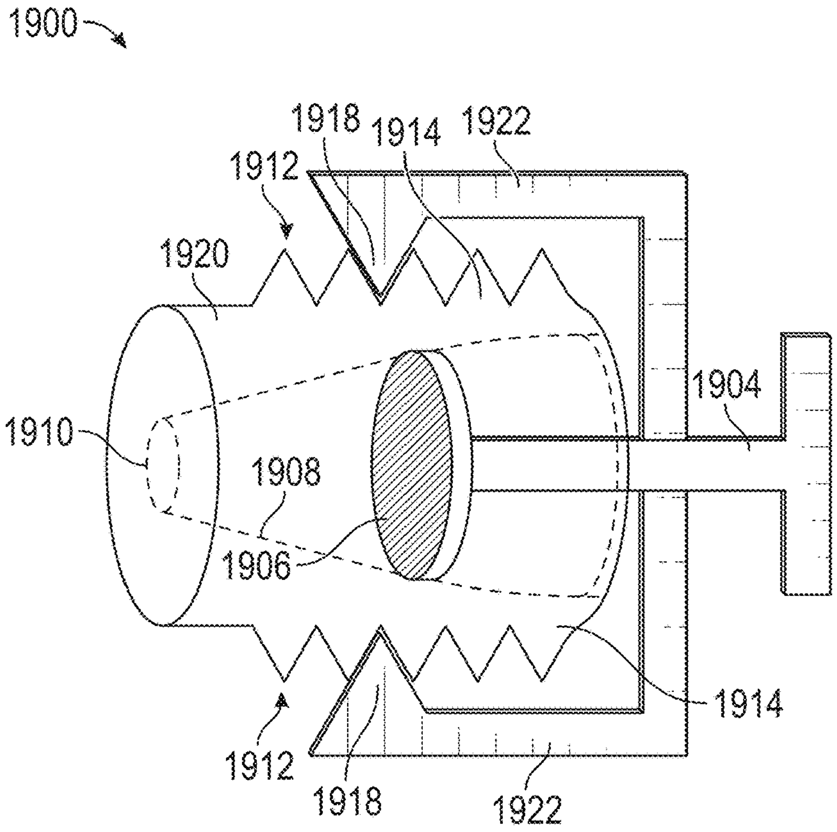
FIG. 48 is a perspective view of another example of a crimping device.

Referring to FIG. 48, in another example, the one or more linear racks 1912 can be disposed on an outer surface 1920 of the housing 1902 instead of an inner surface 1916. In such examples, the corresponding one or more pawls 1918 can be disposed on extension members or arms 1922 extending from the actuator 1904.

Figure 49A:
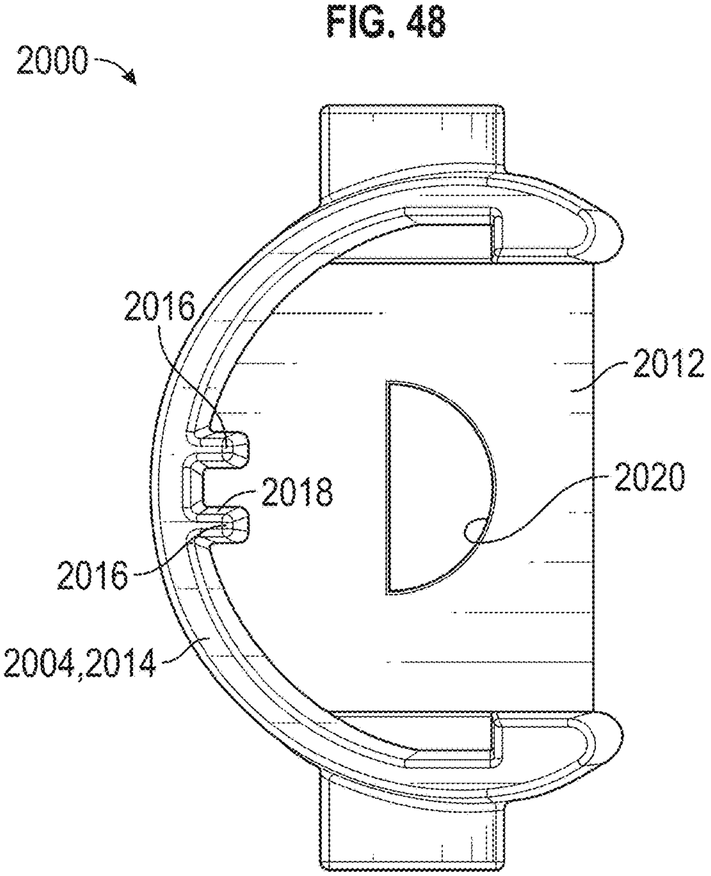
FIG. 49A is a top down view of an actuator of a crimping device, according to one example.
Figure 49B:
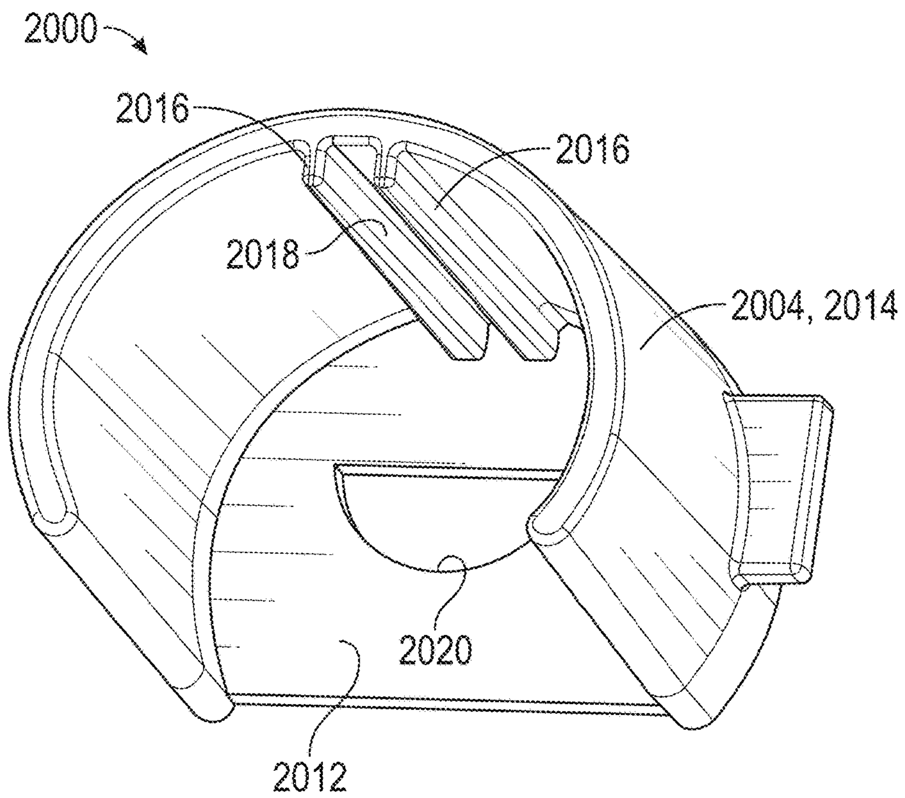
FIG. 49B is a perspective view of the actuator of FIG. 49A.
Figure 49C:
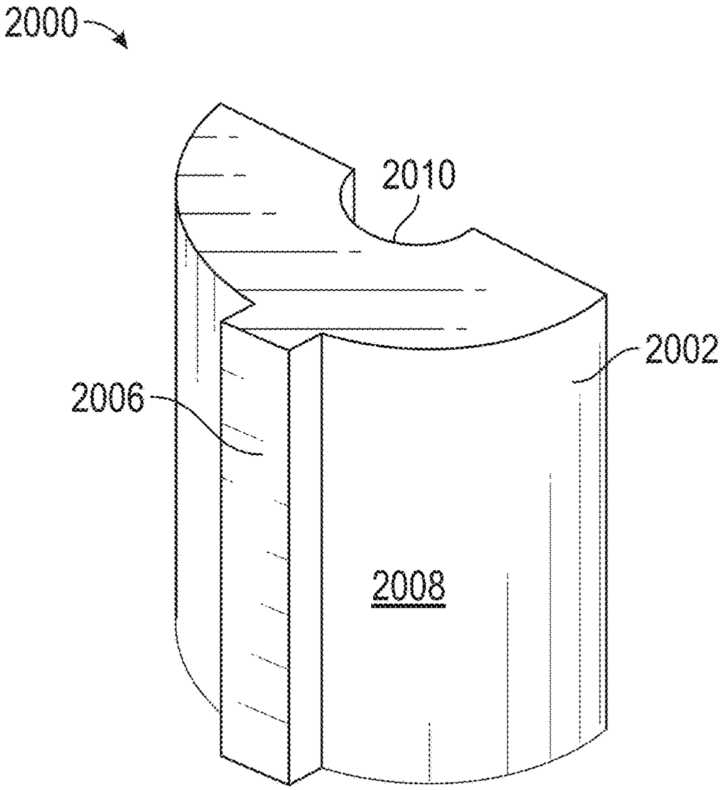
FIG. 49C is a perspective view of a portion of a housing that with the actuator shown in FIG. 49A forms a crimping device.

FIGS. 49A-49C illustrate another example of a crimping device 2000. The crimping device 2000 can comprise a housing 2002 (one half of which is shown in FIG. 49C) and an actuator 2004 (FIGS. 49A-49B). The housing 2002 can be similar to housing 108 described previously, except that housing 2002 comprises an outer rib 2006 disposed on an outer surface 2008 of the housing 2002. Though the illustrated example shows a housing 2002 that comprises two halves (only one of which is illustrated), in other examples, the housing may be formed as a unitary piece. Housing 2002 can define an inner funnel segment (not shown) leading to an outlet 2010.

Referring to FIGS. 49A-49B, the actuator 2004 can comprise a base member or floor 2012, a C-shaped extension member 2014, and one or more ribs 2016 disposed on an internal surface of the extension member 2014 and defining a channel 2018 between them. The actuator 2004 can be configured as a clamp member such that when the actuator 2004 is advanced over the first and second side portions of the housing 2002 the actuator 2004 retains the side portions together in an assembled configuration.

The actuator can further comprise an aperture 2020 extending through the thickness of the floor 2012. The aperture 2020 can be configured to couple a pusher member such as or similar to pusher member 112. In the illustrated example, the aperture 2020 can have a non-circular shape (e.g., a D-shape). In such examples, the second end portion 164 of the pusher member 112 can have a corresponding non-circular shape in cross-section such that when the pusher member 112 is inserted into the aperture 2020 the pusher member 112 is restrained against rotation relative to the actuator 2004. The pusher member 112 can be retained within the aperture 2020 using one or more resilient locking features/latches 174 as described previously with respect to crimping device 100.

In use, the crimping device 2000 can be used to crimp a prosthetic valve (e.g., prosthetic valve 1000 shown in FIG. 36) in the following exemplary manner. The prosthetic valve 1000 can be inserted into the housing 2002 (the halves of which can be held together by the user, or by a collar or other means). The actuator 2004 can then be advanced over the housing 2002 such that the rib 2006 of the housing 2002 is disposed within the channel 2018 of the actuator 2004 and such that the pusher member 112 is aligned with the prosthetic valve 1000 so as to engage an adjacent end portion of the prosthetic valve 1000. The C-shape of the actuator 2004 holds the two halves of the housing together while housing 2002 is disposed within the actuator 2004. The user can then continue to advance the actuator 2004 axially along the outside of the housing 2002, thereby advancing the pusher member 112 axially into the housing. The advancement of the pusher member 112 into the housing 2002 pushes the prosthetic valve 1000 through the funnel segment of the housing 2002 such that the prosthetic valve is radially compressed and pushed outwardly through the outlet 2010. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100.

Figure 50:
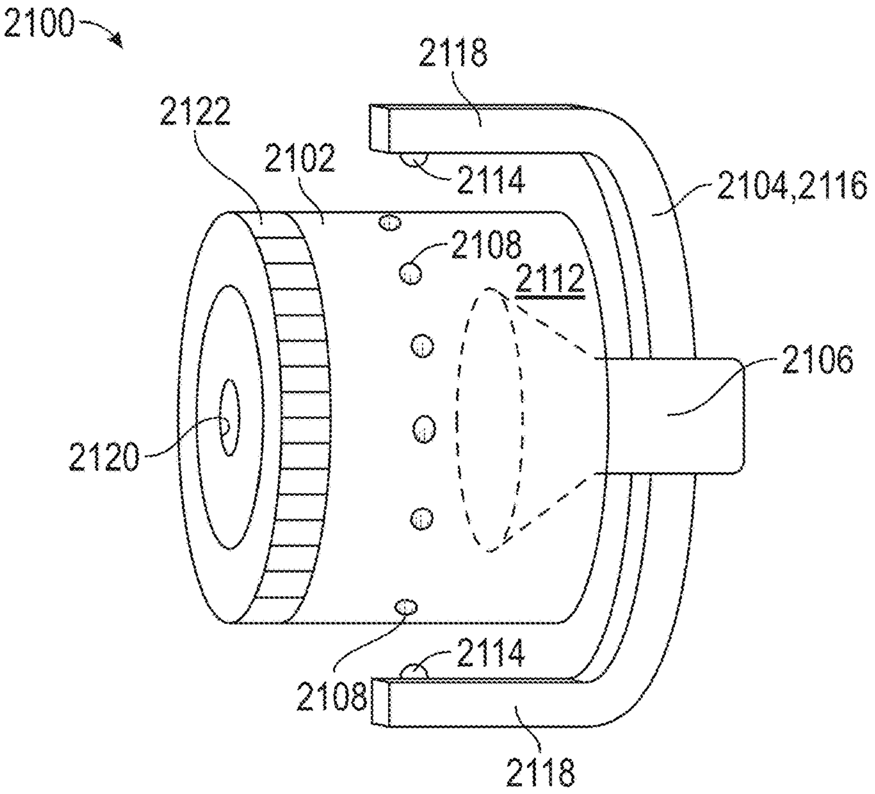
FIG. 50 is a perspective view of another example of a crimping device.

FIG. 50 illustrates another example of a crimping device 2100 comprising a housing 2102, an actuator 2104, and a pusher member 2106. The housing 2102 can be similar to previously described housing 108, except that housing 2102 comprises one or more engagement elements 2108 disposed on an outer surface 2112 of the housing and configured to engage corresponding engagement elements 2114 on the actuator 2104. For example, in some examples, the engagement elements 2108 can be divots/recesses/apertures/detents in the outer surface 2112 of the housing configured to receive corresponding protrusions/projections 2114 on the actuator 2104. In other examples, the engagement elements 2108 can be magnets configured to couple corresponding magnets 2114 on the actuator 2104.

The actuator 2104 can comprise a base member 2116 and one or more extension members 2118. The actuator 2104 can be coupled to a pusher member 2106, such as or similar to pusher member 112 described previously, for holding a prosthetic valve (e.g., prosthetic valve 1000) and advancing the prosthetic valve through the funnel segment of the housing 2102 to the outlet 2120. In some examples, the pusher member 2106 and actuator 2104 can be releasably coupled together, and in other examples, they can be formed as a unitary piece. As mentioned, the extension members 2118 can comprise corresponding engagement elements 2114 (e.g., protrusions/projections and/or magnets) configured to releasably couple the actuator to the housing 2102. The engagement elements 2108 on the housing 2102 can be disposed at a selected axial location along a length of the housing such that when the actuator 2104 and the housing 2102 are coupled together the prosthetic valve 1000 is at a selected crimped configuration (e.g., partially or fully crimped). In certain examples, the housing 2102 can comprise separable halves coupled together by a coupling member such as a ring or collar 2122. In other examples, the interaction of the engagement elements 2108 on the housing 2102 and the engagement elements 2114 on the actuator 2104 (e.g., physical engagement or magnetic engagement) can couple the halves of the housing together. In certain examples, the housing 2102 can also comprise a plurality of circumferentially arranged rows of engagement elements 2108 spaced apart axially along the length of the housing 2102 to allow the housing and the actuator 2104 to be releasably coupled together with the pusher member 2106 at different axial positions within the housing.

In use, the crimping device 2100 can be used to crimp a prosthetic valve (e.g., prosthetic valve 1000 shown in FIG. 36) in the following exemplary manner. The prosthetic valve 1000 can be inserted into the funnel segment of housing 2102. The actuator 2104 can then be advanced relative to the housing 2102 such that the pusher member 2106 advances axially forward into the housing and the extension members 2108 are advanced along an outer surface 2112 of the housing. In certain examples, the actuator 2104 can be advanced into the housing 2102 without rotation, or substantially without rotation, of the components. The advancement of the pusher member 2106 into the housing 2102 pushes the prosthetic valve 1000 through the funnel segment of the housing 2102 such that the prosthetic valve is radially compressed and pushed outwardly through the outlet 2120. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100.

Once the pusher member 2106 advances into the housing 2102 by a selected amount (e.g., once the prosthetic valve 1000 is at least partially advanced through the outlet) the engagement elements 2114 on the extension members 2118 can engage the engagement elements 2108 on the housing 2102, thereby releasably locking the actuator 2104 and housing 2102 together. Such a configuration allows the user to release (e.g., let go of) the crimping device 2100 to connect the connection features of the prosthetic valve to the mating features of the delivery apparatus without the prosthetic valve resiliently expanding and pushing the pusher member 2106 out of the housing 2102.

Figure 51:
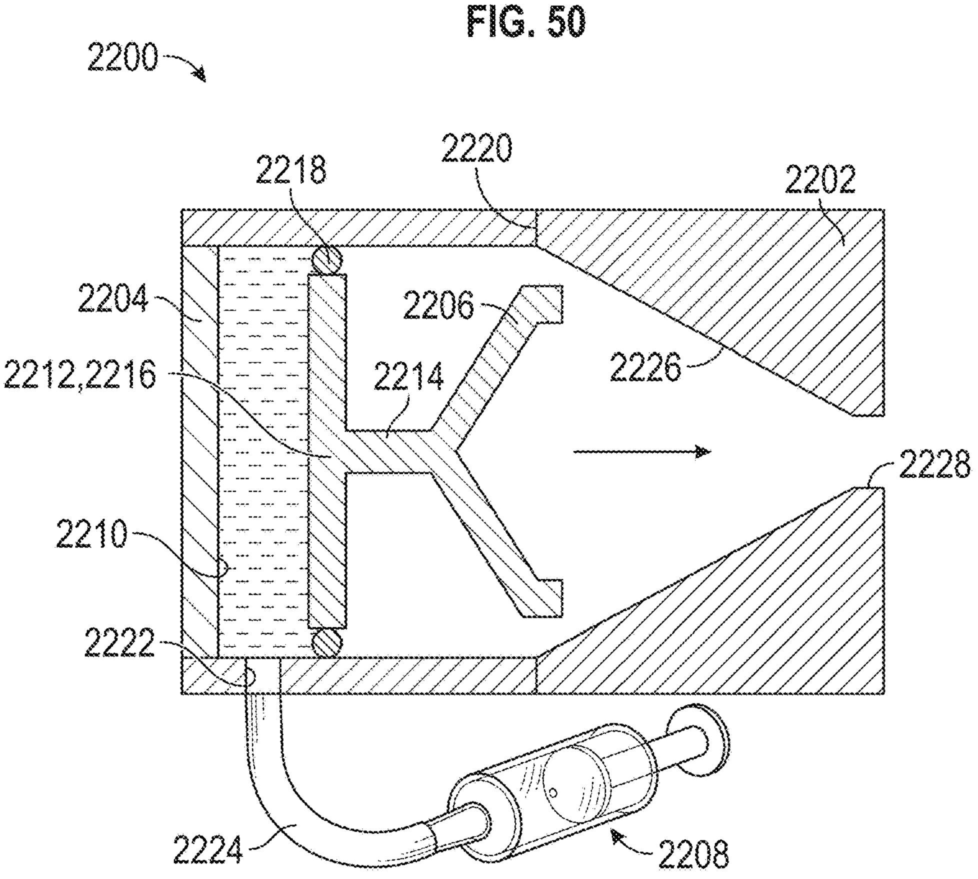
FIG. 51 is a cross-sectional view of another example of a crimping device.

FIG. 51 illustrates another example of a crimping device 2200. Crimping device 2200 can comprise a housing 2202, an actuator 2204, and a pusher member 2206. The actuator 2204 can be configured as a hydraulic actuator (e.g., similar to actuator 902) configured to advance the pusher member 2206 within the housing 2202 using pressurized hydraulic fluid (e.g., water, oil, etc.). In certain examples, the hydraulic fluid can be pumped into the actuator 2202 using a fluid dispensing device 2208, such as a syringe.

The actuator 2204 can comprise a fluid chamber 2210 and a piston 2212. The piston 2212 can have a first end portion or shaft member 2214 coupled to the pusher member 2206, and a second end portion configured as a disc-shaped piston head 2216 having an outer perimeter that corresponds to the shape of the fluid chamber 2210. The piston head 2216 can be sized such that it can move within the fluid chamber 2210 and forms a seal with the chamber walls such that fluid cannot pass around the piston head 2216. In other words, the outer diameter of the piston head 2216 can be substantially equal to the inner diameter of the fluid chamber 2210. In some examples, the piston head 2216 can further comprise one or a plurality of O-rings or other sealing members 2218 disposed around an outer circumference of the piston head 2216 to aid in sealing the piston head to prevent fluid from passing around it. The fluid chamber 2210 of the actuator 2204 can be coupled to an inlet portion 2220 of the housing 2202

In the illustrated example, the chamber 2210 and housing 2202 are cylindrical, however, in other examples, the fluid chamber can have any of various shapes. The fluid chamber 2210 can comprise an inlet 2222 configured to be fluidly coupled (e.g., using flexible tubing 2224) to a fluid dispensing device 2208, fluid reservoir, or pump for example, a syringe, such as a high-pressure syringe. In particular examples, the syringe can be an Atrion QL® syringe.

In use, the crimping device 2200 can be used to crimp a prosthetic valve (e.g., prosthetic valve 1000 shown in FIG. 36) in the following exemplary manner. The prosthetic valve 1000 can be inserted into the housing 2202. The actuator 2204 can be coupled to the housing 2202. So coupled, the pusher member 2206 can be aligned with the prosthetic valve 1000 so as to engage an adjacent end portion of the prosthetic valve 1000. The user can actuate the fluid reservoir 2208 (e.g., by depressing the plunger of a syringe or activating a pump) to dispense fluid (e.g., saline solution) into the fluid chamber 2210 via the inlet 2222. As the fluid chamber 2210 fills with fluid, the pressure causes the piston 2212 to advance, thereby advancing the pusher member 2206 axially forward into the housing 2202. The advancement of the pusher member into the housing pushes the prosthetic valve 1000 through the funnel segment 2226 of the housing 2202 such that the prosthetic valve is radially compressed and pushed outwardly through the outlet 2228. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100. In certain examples, the working fluid can be a liquid, such as an aqueous liquid (e.g., saline solution), or a gas (e.g., a compressed inert gas such as nitrogen, carbon dioxide, etc.).

Figure 52:
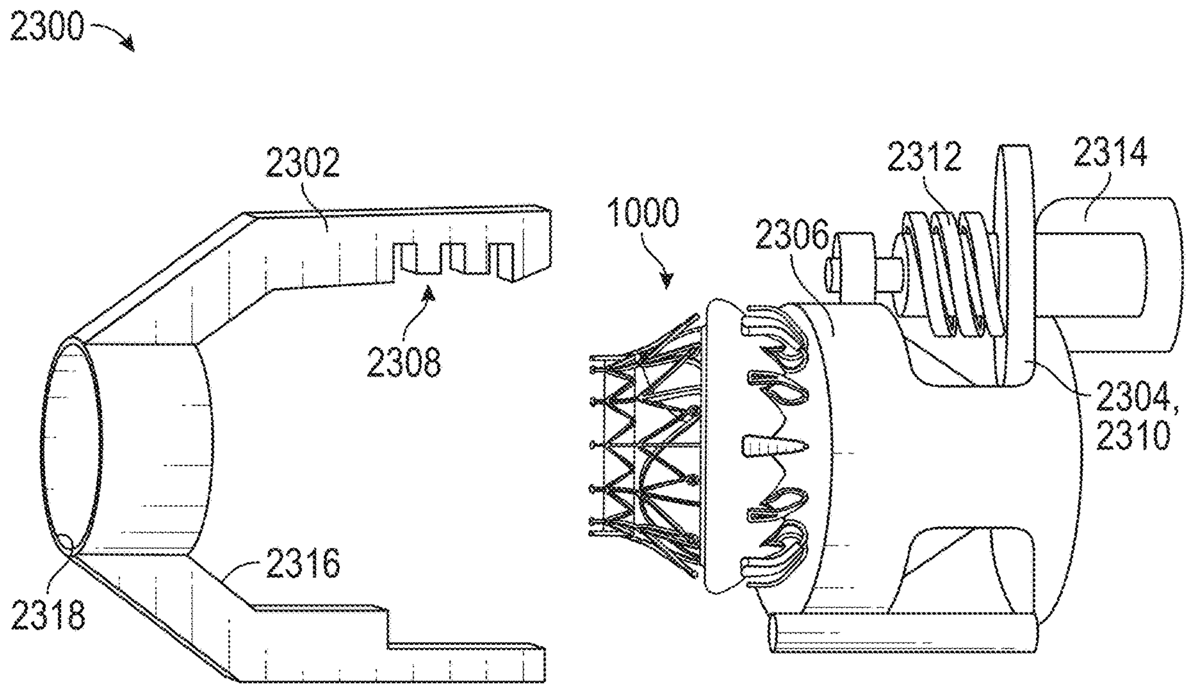
FIG. 52 is a perspective view of another example of a crimping device.

FIG. 52 illustrates another example of a crimping device 2300. Crimping device 2300 can comprise a housing 2302, an actuator 2304, and a pusher member 2306 (similar to or the same as pusher member 112 described previously) coupled to the actuator 2304. The actuator 2304 can be configured to advance the pusher member 2306 into the housing 2302.

The housing 2302 can be similar to housing 108 described previously except that housing 2302 comprises a threaded portion 2308 disposed on an inner surface of the housing 2302. The actuator 2304 can comprise a base member 2310 and a thumbscrew/threaded rod/actuator member 2312 configured to interface with the threaded portion 2308 of the housing 2302. The actuator member 2312 can be positioned such that it is radially offset from the longitudinal axis of the pusher member 2306 and can be configured such that the actuator member 2312 can rotate about a longitudinal axis extending through the actuator member 2312.

In use, the crimping device 2300 can be used to crimp a prosthetic valve (e.g., prosthetic valve 1000 shown in FIG. 36) in the following exemplary manner. The prosthetic valve 1000 can be inserted into the housing 2302. The pusher member 2306 can be aligned with the prosthetic valve 1000 so as to engage an adjacent end portion of the prosthetic valve 1000, and such that the actuator member 2312 is aligned with the threaded portion 2308 of the housing 2302. A user can then rotate the actuator member 2312 (e.g., using a gripping portion 2314) such that it engages the threaded portion 2308 of the housing 2302. The engagement of the threads can translate the rotation into axial movement (e.g., pushing) of the actuator 2304 and therefore the pusher member 2306, advancing the pusher member 2306 axially forward into the housing 2302. The advancement of the pusher member 2306 into the housing 2302 pushes the prosthetic valve 1000 through the funnel segment 2316 of the housing 2302 such that the prosthetic valve is radially compressed and pushed outwardly through the outlet 2318 for coupling to the delivery apparatus. The prosthetic valve 1000 can then be coupled to a valve retaining member 1110 of the delivery apparatus 1100, as described in more detail with respect to FIG. 37, or can be loaded directly into the sheath of the delivery apparatus as described previously with respect to crimping device 100.

Figure 56:
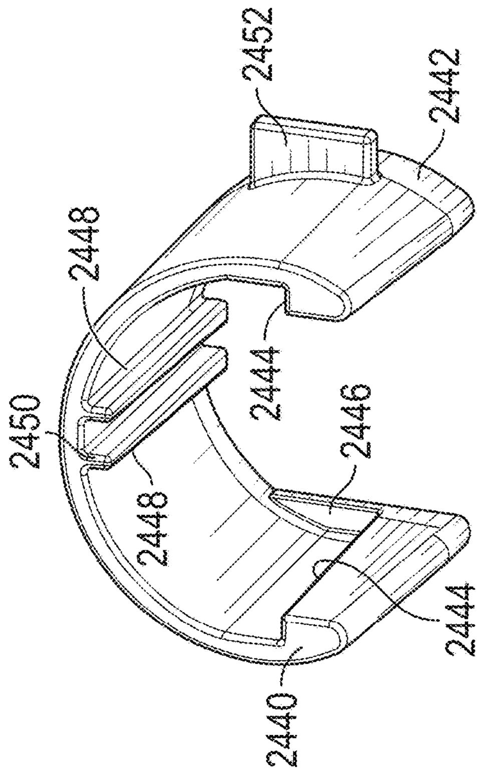
FIG. 56 is a perspective view of a clamp member of the loading assembly of FIG. 53.
Figure 57:
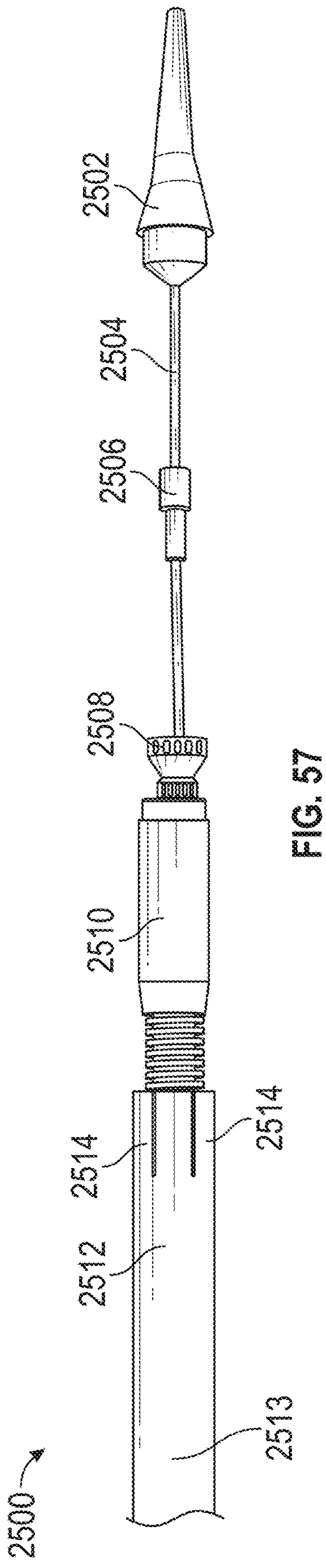
FIG. 57 is a side view of a distal end portion of an exemplary delivery apparatus that can be used with the loading assembly shown of FIG. 53.

Referring to FIGS. 53-63, as mentioned previously, once the prosthetic valve 1000 has been initially coupled to the delivery apparatus (e.g., to a valve retaining member), a separate loading assembly 2400 can be used to fully crimp the prosthetic valve and load it into a capsule or sheath of the delivery apparatus (e.g., sheath 2512 of delivery apparatus 2500 shown in FIG. 57).

Referring to FIG. 53, the loading assembly 2400 can generally comprise a support tube 2402, a loader member/funnel member 2404, one or more fasteners/clamps 2406, and an annular tab ring/holder member 2408. The loading assembly 2400 or components thereof can be configured to separate into pieces or open, e.g., like a clam shell, such that the loading assembly 2400 can be placed or assembled on and removed from the delivery apparatus.

Figure 55:
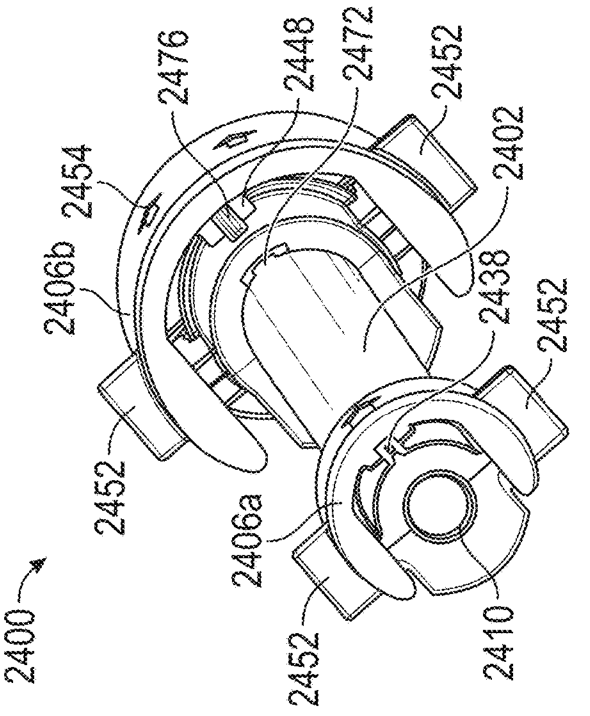

The support tube 2402 can comprise a first lateral side portion 2403*a* and a second lateral side portion 2403*b*. Each side portion 2402 can comprise a half-cylinder such that when they are placed together they form a generally cylindrical or tubular shape defining an inner bore 2410 (FIG. 55). The support tube 2402 can have a main body 2412 having a first or inlet end portion 2414 and a second end portion 2416. The side portions 2402 can each include mating features that assist with coupling the side portions to one another. For example, as shown in FIG. 53, each side portion 2402 can comprise a protrusion/tab 2418 extending from a longitudinal edge 2420 of the side portion and a diametrically opposed recess 2422 formed in the opposing longitudinal edge 2421. Each tab 2418 can sit within a corresponding recess 2422 when the side portions 2402 are coupled together.

The inlet end portion 2414 can comprise an extension portion 2424 having an outer diameter less than an outer diameter of the main body 2412. The extension portion 2424 can be separated from the main body 2412 by an annular shoulder 2426. The inlet end portion 2414 can further comprise a recess 2428 configured such that an annular shoulder 2468 of the funnel member 2404 can be disposed within the recess 2428 when the funnel member is assembled onto the support tube 2402. In the illustrated example, the recess 2428 can have an arced shape extending around a portion of the perimeter of the support tube 2402.

The second end portion 2416 can comprise a first annular shoulder 2432 and a second annular shoulder 2434 extending radially from an outer surface of the main body 2412. Each side portion 2403 can comprise diametrically opposed flanges 2436 such that when the side portions are disposed adjacent one another the inner surfaces of the flanges 2436 on the first side portion 2403*a* can contact the inner surfaces of the flanges 2436 on the second side portion 2403*b*. The second end portion 2416 can further comprise one or more ribs 2438 (e.g., one rib in the illustrated example) extending longitudinally between the first and second shoulders 2432, 2434.

The first and second side portions 2403*a*, 2403*b* can be placed over a shaft of a delivery apparatus (e.g., shaft 2512) and then can be held or locked together using a first clamp 2406*a*. The side portions 2403 can be held in the assembled state while a prosthetic valve (e.g., prosthetic valve 1000) is crimped and loaded into a capsule or sheath of the delivery device, and then can be separated from each other to facilitate removal of the loading assembly 2400 from the delivery apparatus after the prosthetic valve has been loaded.

Referring to FIG. 56, each clamp 2406 can be a C-shaped member having a first end portion 2440 and a second end portion 2442. The clamp 2406 can have one or more ledges 2444 (e.g., two opposed ledges) extending radially inwardly from inner walls of the free edge portions of the clamp 2406, and extending along at least a portion of the length of the clamp. The second end portion 2442 can comprise a stopping surface 2446 extending radially inwardly toward a longitudinal axis of the clamp 2406. The clamp 2406 can further comprise first and second ribs 2448 extending radially inwardly from an inner surface of the clamp and extending longitudinally along the length of the clamp. The first and second ribs 2448 can define a channel 2450 between them. The channel 2450 can function as an alignment feature (e.g., with the rib 2438 (FIG. 53) of the second end portion 2416 of portion 2403*a* of the support tube) to orient the clamp member 2406 relative to the support tube 2402.

Each clamp 2406 can further comprise one or more tabs 2452 extending radially outwardly from an outer surface of the clamp 2406. In the illustrated example, the tabs 2452 are diametrically opposed rectangular tabs, however, in other examples, the tabs 2452 can have any of various shapes and can be positioned at any location about the outer perimeter of the clamp. Force can be applied to the tabs 2452 (e.g., manually by a user) to advance the clamp 2406 over a portion of the support tube 2402 and/or other component of the loading assembly 2400. In some examples, the clamps 2406 can include indicia 2454 (such as arrows) indicating in which direction the clamp 2406 should be advanced over the components.

Figure 54:
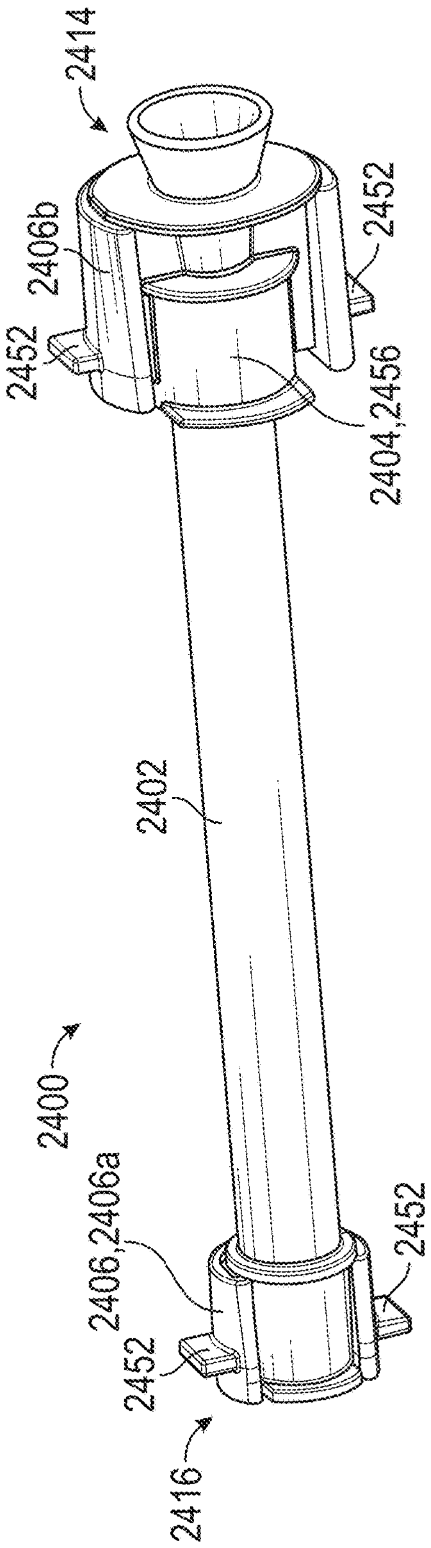
FIGS. 54-55 are perspective views of the loading assembly of FIG. 53.

A first clamp member 2406*a* (see e.g., FIG. 53) can be used to hold or lock the side portions 2403 of the support tube 2402 in the assembled position. The first clamp 2406 can be aligned with the second end portion 2416 of the support tube 2402 such that the rib 2438 is aligned with the channel 2450. The first clamp 2406*a* can then be axially advanced over the second end portion 2416 of the support tube 2402 until the flanges 2436 engage the stopping surface 2446. The ledges 2444 can retain the flanges 2436 together to retain the side portions 2403 within the clamp 2406*a*, thereby locking the side portions 2403 in the assembled position, as shown in FIGS. 54-55.

Figure 58:
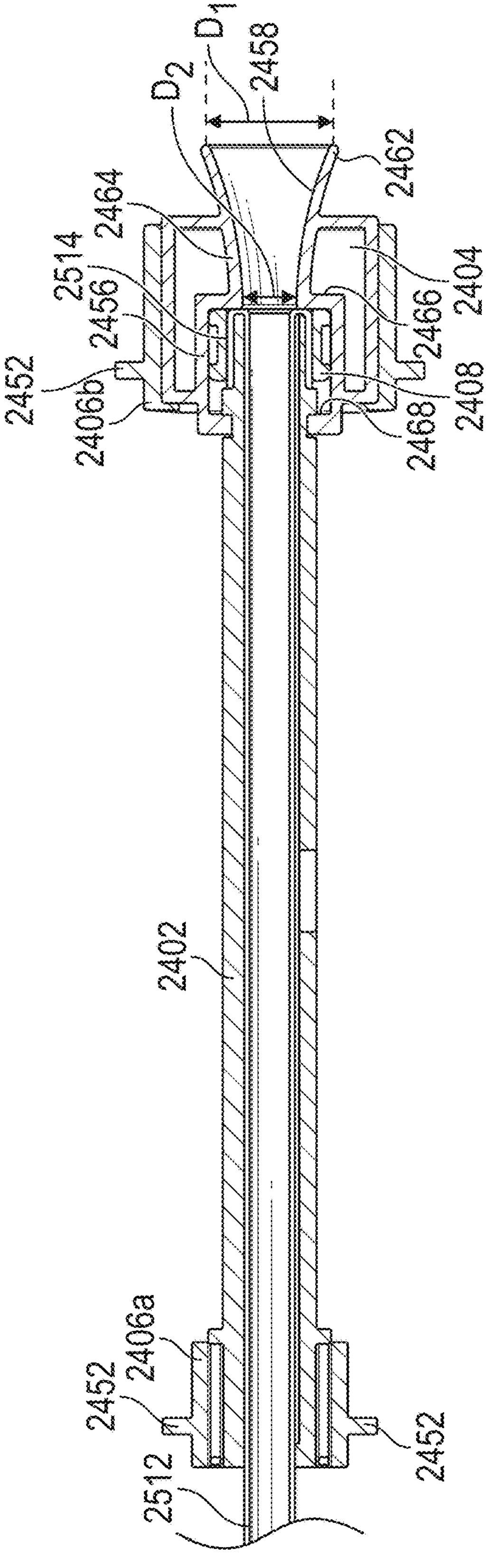
FIG. 58 is a cross-sectional side view of a distal end portion of a shaft of the delivery apparatus of FIG. 57 with the loading assembly of FIG. 53 disposed thereon.

Referring again to FIG. 53, as mentioned previously, the loading assembly 2400 can comprise a holder member 2408. The holder member 2408 can be an annular member sized to fit over the extension portion 2424 of the support tube 2402. When the support tube 2402 is disposed over a capsule/sheath of the delivery system, the holder member 2408 can be advanced over the extension portion 2424 to retain one or more tabs 2514 (FIG. 57) of the capsule 2512 in a folded-back position, as shown in FIG. 58. In some examples, the capsule 2512 can be formed from one or more materials such as PTFE, ePTFE, polyether block amide (Pebax®), polyetherimide (Ultem®), PEEK, urethane, Nitinol, stainless steel, and/or any other biocompatible material. In some particular examples, the capsule can comprise an outer polymer layer, a metal middle layer located on a radially inner surface of the outer polymer layer, and an inner liner located on a radially inner surface of the middle layer. The tabs 2514 can be defined by spaced axially extending cuts extending circumferentially around the distal end portion of the capsule 2512. The tabs 2514 can be folded back (proximally) over the capsule to facilitate insertion of the implant into the capsule and bending of the distal end portion. Further details of the capsule can be found, at least, in U.S. Pat. No. 10,813,757, which is incorporated by reference herein in its entirety. The holder member 2408 can advantageously hold the tabs 2514 (FIG. 57) of the sheath 2512 in tension to keep the capsule taut, thereby preventing or mitigating bending or deformation of the capsule during the insertion/loading of the prosthetic valve. The holder member 2408 further functions to help retain the side portions 2403 of the support tube 2402 in the assembled position.

The funnel member 2404 can comprise a body portion 2456 and a funnel portion 2458. The funnel member 2404 can comprise first and second side portions 2460, that when assembled together form the funnel member and define an inner bore extending along the length of the funnel member. The body portion 2456 can have a generally cylindrical shape when assembled. As shown in FIG. 58, the funnel portion 2458 can comprise an inlet end portion 2462 and an outlet end portion 2464 and can taper from a first diameter $D_1$ at the inlet end portion 2462 to a second, smaller diameter $D_2$ where it meets the body portion (e.g., at the outlet end portion 2464). When assembled on the support tube 2402, the outlet of the funnel member 2404 can be positioned adjacent (e.g., distally of) the capsule 2512 and in communication with the interior of the capsule 2512. The body portion 2456 can comprise a first annular shoulder 2466 where it meets the funnel portion 2458 and a second annular shoulder 2468. When assembled on the support tube 2402 the second annular shoulder 2468 can sit within the support tube recess 2428, which can restrain axial movement of the funnel member relative to the support tube. As best seen in FIG. 53, the second annular shoulder 2468 can comprise a cutout 2470 configured to align with an anti-rotation feature configured as a protrusion or rib 2472 of the recess 2428 to prevent rotation of the funnel member 2404 relative to the support tube 2402.

Each side portion 2460 can comprise diametrically opposed flanges 2474 such that when the side portions are disposed adjacent one another the inner surfaces of the flanges 2474 on the first side portion 2460*a* contact the inner surfaces of the flanges 2474 on the second side portion 2460*b*. The flanges 2474 can be clamped together using a clamp 2406 to retain the funnel member 2404 in the assembled state. The funnel member 2404 can further comprise one or more ribs 2476 (e.g., one rib in the illustrated example) extending longitudinally along at least a portion of the length of the funnel member 2404. The rib 2476 can serve as an alignment feature in combination with a channel 2450 of the second clamp member 2406*b* to orient the second clamp member 2406*b* relative to the funnel member 2404.

The second clamp member 2406*b* can be used to hold or lock the side portions 2460 of the funnel member 2404 in the assembled position, as shown in FIGS. 54-55. The second clamp 2406*b* can be aligned with the body portion 2456 of the funnel member 2404 such that the rib 2476 is aligned with the channel 2450. The second clamp 2406*b* can then be axially advanced over the body portion 2456 of the funnel member 2404 until the flanges 2474 contact the stopping surface 2446, as shown in FIG. 58. The ledge 2444 can engage an outer surface of one or more flanges 2474 to retain the side portions 2460 within the clamp 2406*b*, thereby locking the funnel member 2404 in the assembled position, as shown in FIGS. 54-55.

The loading assembly 2400 can be assembled on a sheath or capsule 2512 of a delivery apparatus 2500 (FIG. 57) and used to load a prosthetic valve (e.g., prosthetic valve 1000) into the capsule 2512 in the following exemplary manner. FIG. 57 illustrates a portion of an exemplary delivery apparatus 2500 having a nosecone/tapered tip 2502, a first shaft 2504 configured as a guidewire lumen, a guidewire shield 2506, a valve retaining member 2508, a tubular retaining member referred to hereinafter as an outer ring 2510 (which can be disposed on its own shaft), and an outer shaft 2513 (a distal end portion of which comprises capsule 2512 which has a plurality of tabs 2514). Further details of the delivery apparatus can be found, at least, in U.S. Pat. No. 10,813,757, which is incorporated by reference herein in its entirety. FIG. 58 shows the loading assembly 2400 disposed on the capsule 2512.

Referring to FIG. 58, the side portions 2403 of the support tube 2402 can be disposed over the capsule 2512 and the first clamp 2406*a* can be advanced over the second end portion 2416 of the support tube 2402 (e.g., in a direction toward the inlet end portion 2414 of the support tube) to retain the support tube 2402 in the assembled position. The holder member 2408 can be advanced (e.g., in a direction away from the inlet end portion 2414) over the extension portion 2424 (FIG. 53) of the support tube, folding the tab portions 2514 of the capsule 2512 back and retaining them between the holder member 2408 and the extension portion 2424. At this point in the assembly process, the loading assembly 2400 can be referred to as "partially assembled."

Figure 60:
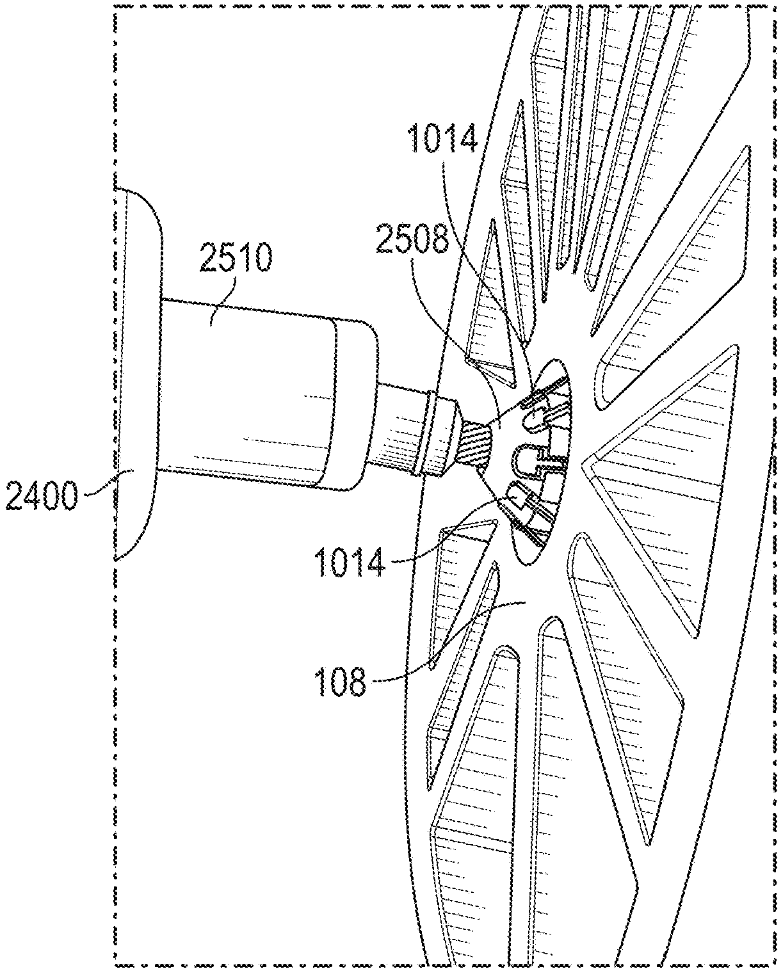
FIGS. 60-64B show an exemplary method of loading the prosthetic heart valve of FIG. 36 into the loading assembly of FIG. 53.
Figure 61:
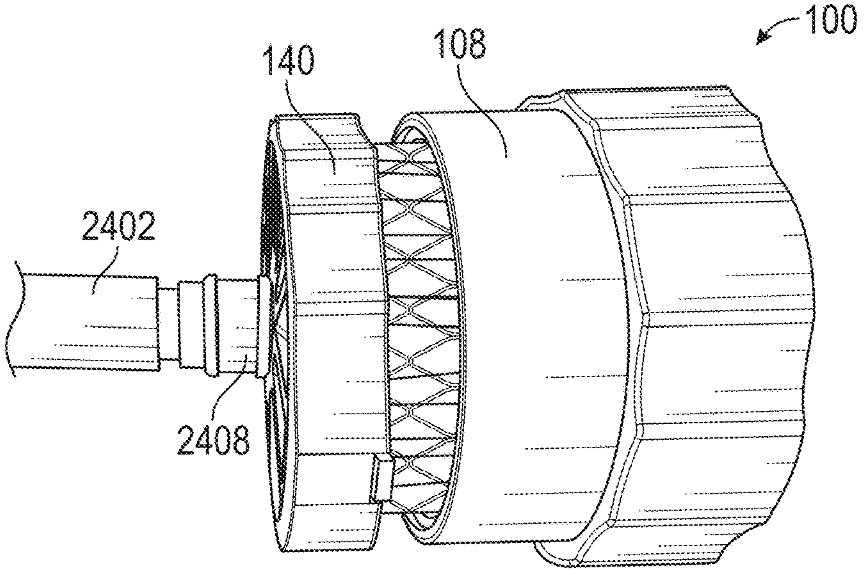
Figure 62:
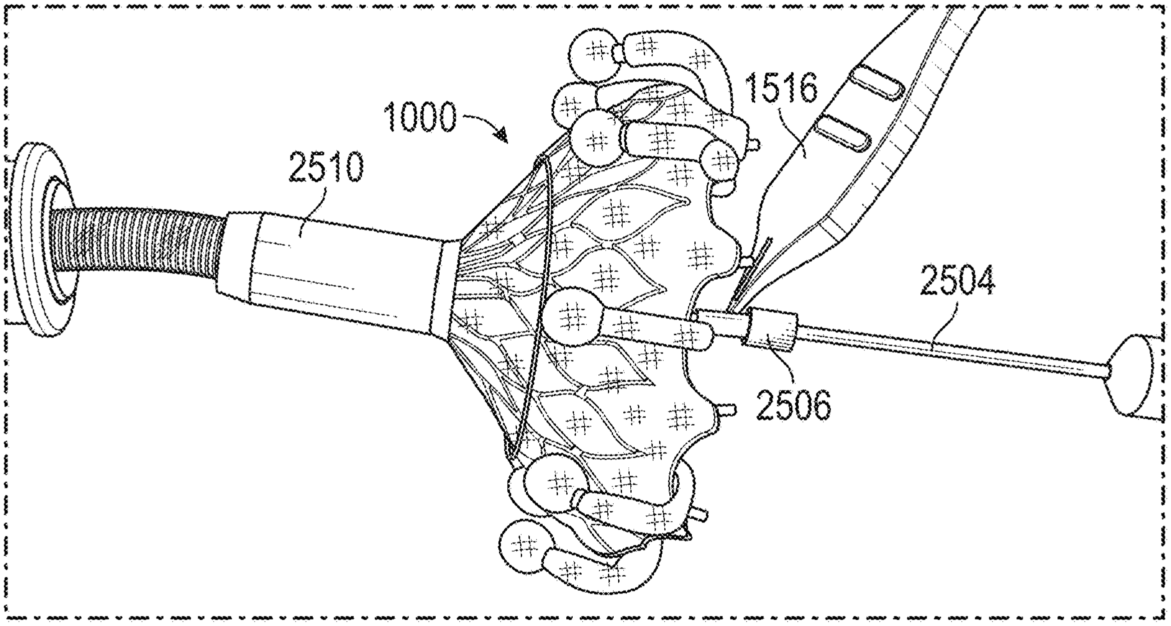

Referring to FIG. 60, once the loading assembly 2400 is partially assembled on the delivery apparatus 2500, a crimping device 100 (though crimping device 100 is shown, any of the crimping devices described previously can be used) can be used to couple the prosthetic valve 1000 with a valve retaining member 2508, as described previously. The capsule 2512 can be advanced (e.g., using the handle of the delivery apparatus 2500) until it contacts the crimping device 100 (see e.g., FIG. 61), and the prosthetic valve 1000 can be slowly drawn out from the crimping device 100. The capsule 2512 can then be retracted (e.g., using the handle of the delivery apparatus) to ensure that the prosthetic valve 1000 is properly coupled with the valve retaining member 2508 while the actuator of the crimping device is held in place. So coupled, the outer ring 2510 can be advanced (e.g., using the handle of the delivery apparatus) over the valve retaining member 2508 and a portion of the prosthetic valve 1000 within the valve retaining member 2508 (e.g., the arms 1012 with enlarged end portions 1014). In certain examples, the outer ring 2510 can prevent the enlarged end portions 1014 of the prosthetic valve frame from uncoupling from the valve retaining member 2508. The partially assembled loading assembly 2400 can then be advanced over the outer ring 2510 until the holding member 2408 is adjacent an outlet end of the crimping device 100, as shown in FIG. 61. The crimping device 100 can then be removed from the delivery apparatus, as shown in FIG. 62, and the guidewire shield 2506 can be advanced distally over the first shaft 2504 (e.g., using advancement tool 2516) adjacent the nose cone such that it is axially spaced from the prosthetic valve 1000.

Figure 59:
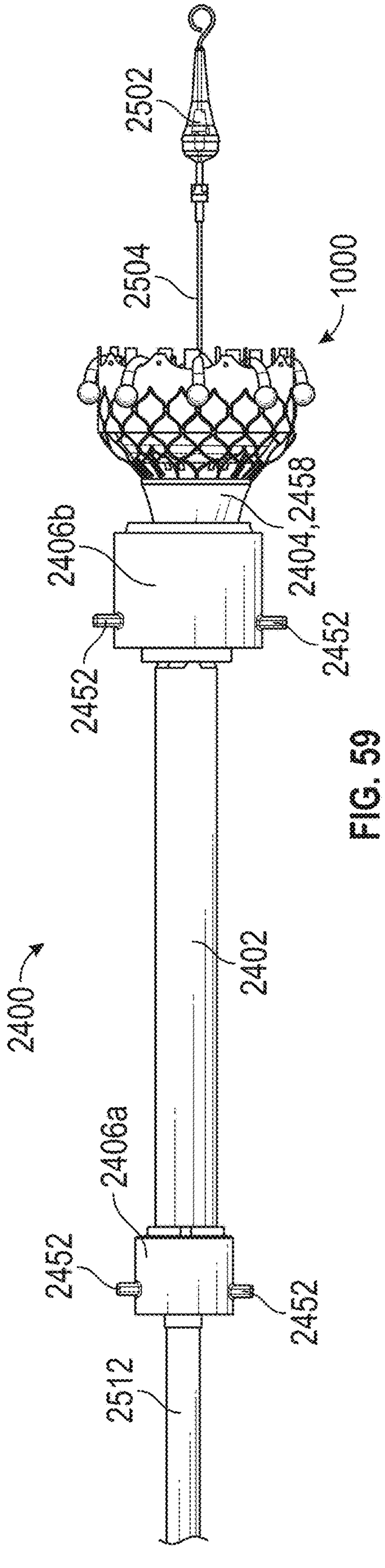
FIG. 59 is a side view of a distal end portion of the delivery apparatus of FIG. 57 with the loading assembly of FIG. 53 and the prosthetic heart valve of FIG. 36 disposed thereon.
Figure 63:
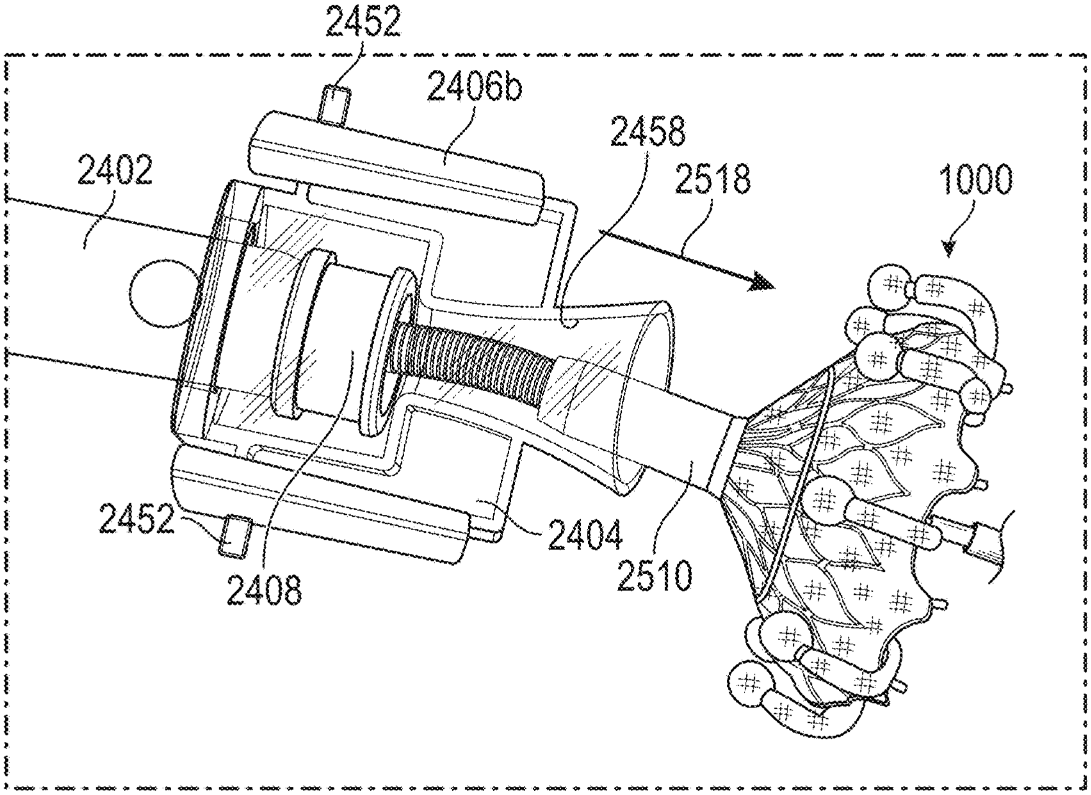

Referring to FIGS. 59 and 63, the side portions 2460 (FIG. 53) of the funnel member 2404 can then be disposed over the holder member 2408 such that the outer ring 2510 is disposed at least partially within the funnel portion 2458. At this point the loading assembly 2400 can be referred to as "fully assembled." The second clamp 2406*b* can be advanced over the funnel member 2404 (e.g., in a direction toward the inlet end portion 2414 of the support tube 2402) to retain the funnel member 2404 in the assembled position. The capsule 2512 (and therefore the attached loading assembly 2400) can then be advanced over the prosthetic valve 1000 in the direction shown by arrow 2518 using the handle of the delivery apparatus 2500 (or the prosthetic valve can be retracted inside the assembled capsule and loading assembly).

Figure 64A:
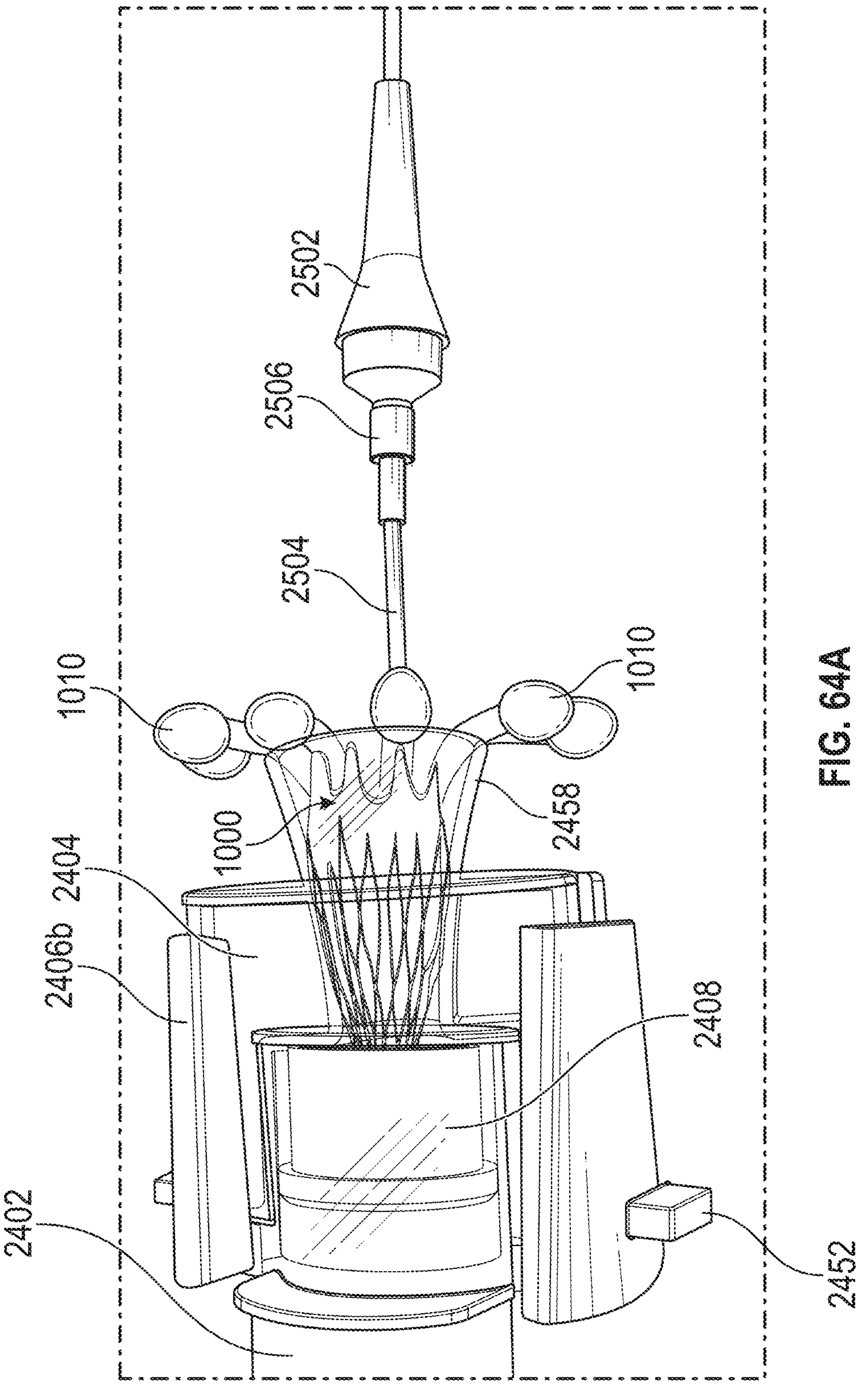

As shown in FIG. 64A, as the loading assembly 2400 is advanced over the prosthetic valve 1000, the funnel portion 2458 radially compresses the prosthetic valve 1000, allowing the prosthetic valve to be loaded into the capsule 2512. More particularly, as the capsule 2512 and loading assembly 2400 advances over the prosthetic valve 1000, the anchors 1010 of the prosthetic valve 1000 can contact and be inverted by the funnel portion 2458 such that the prosthetic valve 1000 moves into a substantially straightened configuration wherein the anchors 1010 extend distally from the main body 1003 rotated approximately 180° from their unrestrained configuration. With the tab members 2514 of the capsule 2512 folded back proximally over the capsule and held in place by the holder member 2408, the opening in the distal end portion of the capsule can be maintained as the implant is inserted into the capsule (e.g., by preventing the tab members 2514 from slipping past the holder member 2408). The capsule 2512 can be maintained in a tensioned or taut state during loading of the implant and prevented from buckling or bunching. The support tube 2402 can also provide can also provide structural support to the capsule 2512. In certain examples, the funnel portion 2458 can be filled with saline solution (e.g., supplied from a port in the handle of the delivery apparatus) during loading of the prosthetic valve. In certain examples, free apices of the frame of the prosthetic valve can be guided inside the funnel portion 2458, for example using the tool 1516.

Figure 64B:
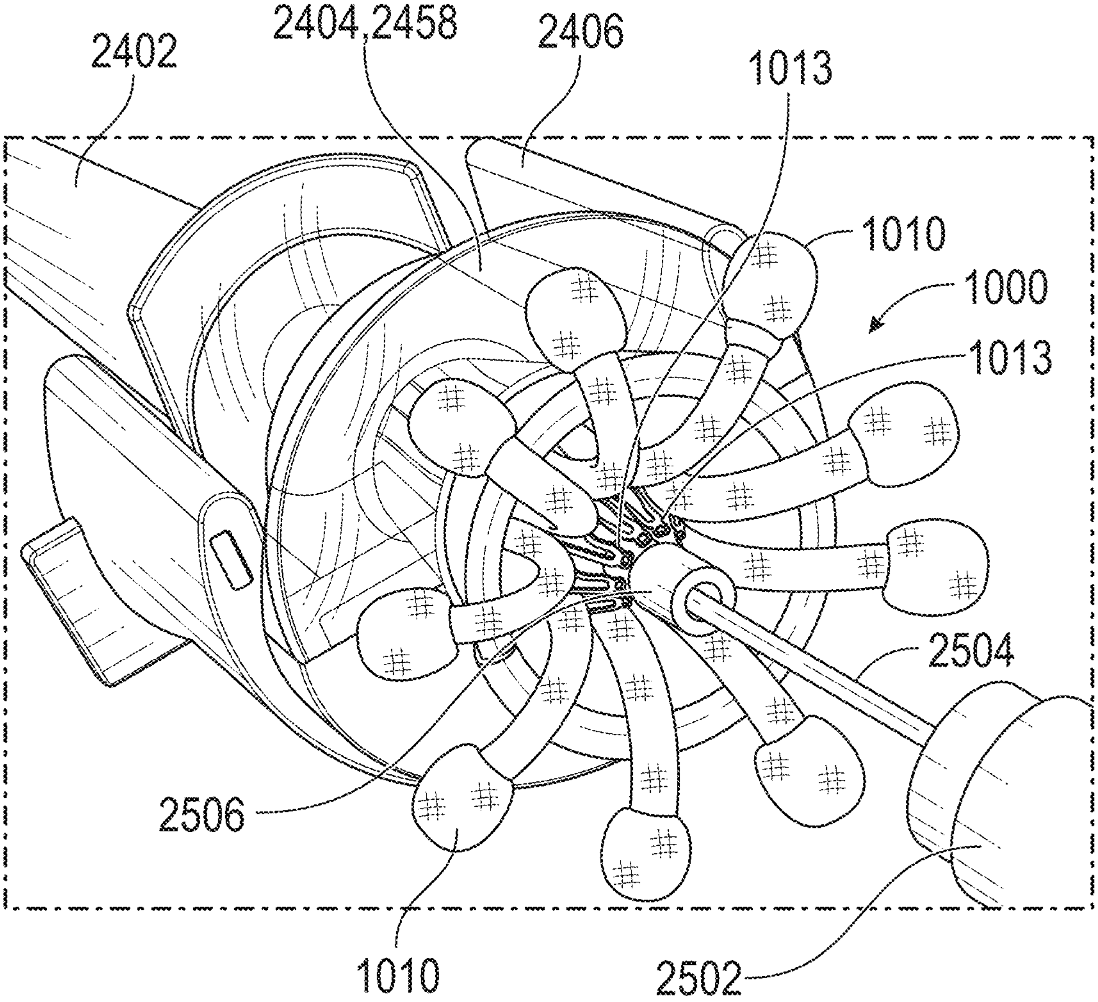

Referring to FIG. 64B, as the outflow apices 1013 of the frame of the prosthetic valve 1000 are received within the funnel portion 2458, the guidewire shield member 2506 can be advanced proximally along the guidewire shaft and positioned radially within the annular array of outflow apices 1013. In certain examples, the guidewire shield member 2506 can support the outflow apices 1013 of the prosthetic valve frame and maintain them at a selected orientation relative to the underlying guidewire shaft once the implant is fully crimped.

Once the prosthetic valve 1000 has been fully received within the capsule 2512, the loading assembly 2400 can be removed from the delivery apparatus 2500 (e.g., by removing the first and second clamps 2406, and removing the side portions 2460, 2403 of the funnel member 2404 and the support tube 2402.

Figure 65:
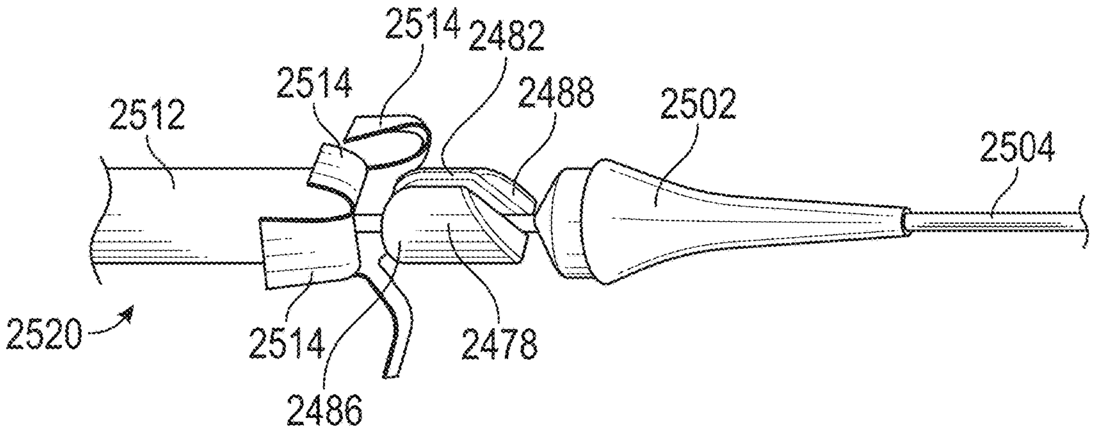
FIG. 65-69 show an exemplary method of trimming a sheath of the delivery apparatus of FIG. 57 using the trimming guide device of FIGS. 70-71.
Figure 67:
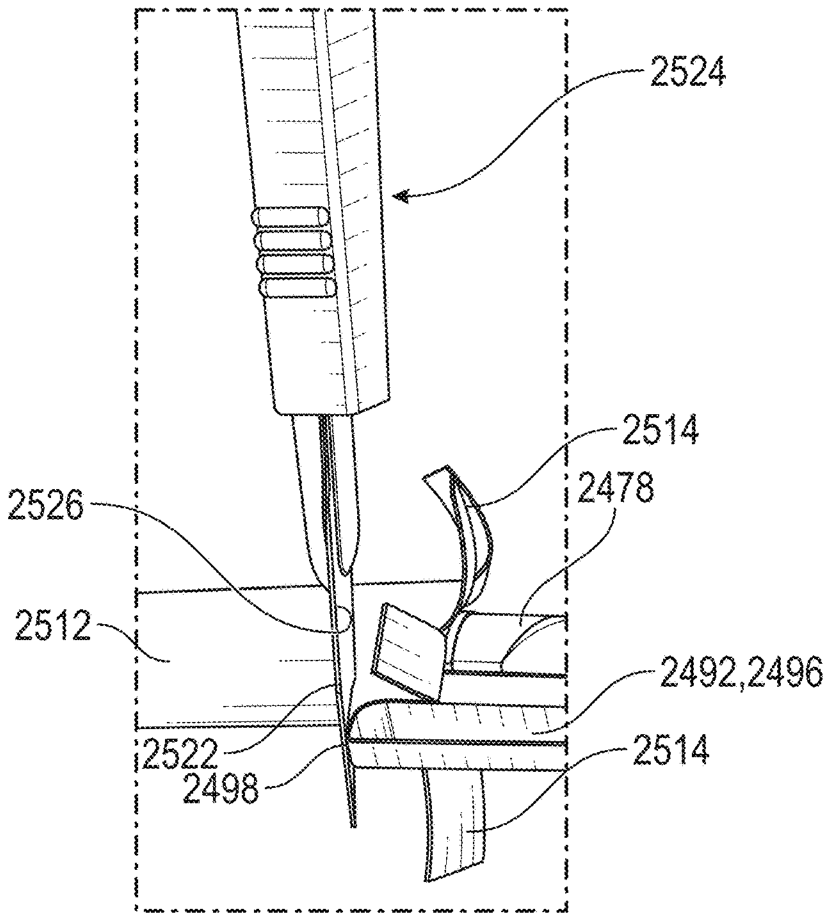
Figure 70:
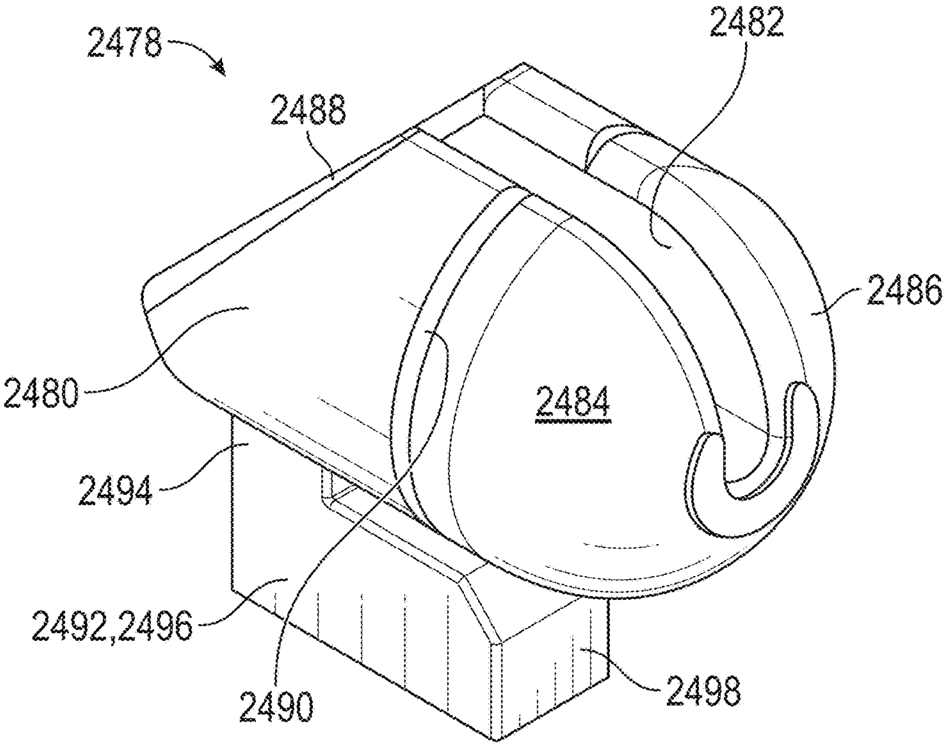
FIG. 70 is a perspective view of a trimming guide device, according to one example.
Figure 71:
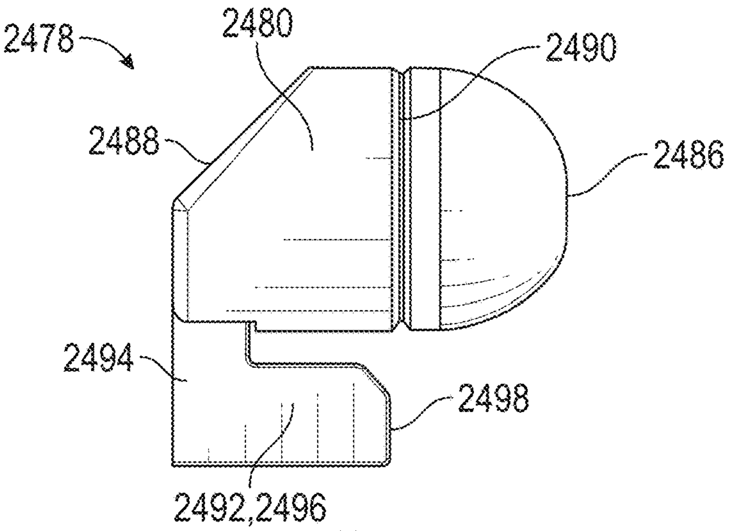
FIG. 71 is a side elevation view of the trimming guide device of FIG. 70.

Referring to FIG. 65, once the loading assembly 2400 has been removed from the delivery apparatus 2500, a trimmer guide member 2478 can be inserted into a distal end of the capsule 2512 to facilitate trimming of the capsule tabs 2514 at a selected axial location, as shown in FIG. 67. Referring to FIGS. 70-71, the trimmer guide member 2478 can comprise a main body 2480 including a slot 2482. The slot 2482 can extend from a longitudinal axis of the main body all the way to the radially outer surface 2484 of the main body. The main body 2480 can have a substantially cylindrical shape having a rounded end portion 2486 and an angled end portion 2488. The main body 2480 can comprise an annular notch or groove 2490 extending circumferentially around the main body 2480. The trimmer guide member 2478 can further comprise an arm member/guide arm 2492 having a radially-extending portion 2494 and an axially-extending portion 2496 that extends in the direction of the rounded end portion 2486. As best seen in FIG. 71, the axially-extending portion 2496 of the guide arm 2492 can have a length selected such that an end surface 2498 of the axially-extending portion 2496 is axially aligned with the groove 2490.

Figure 66:
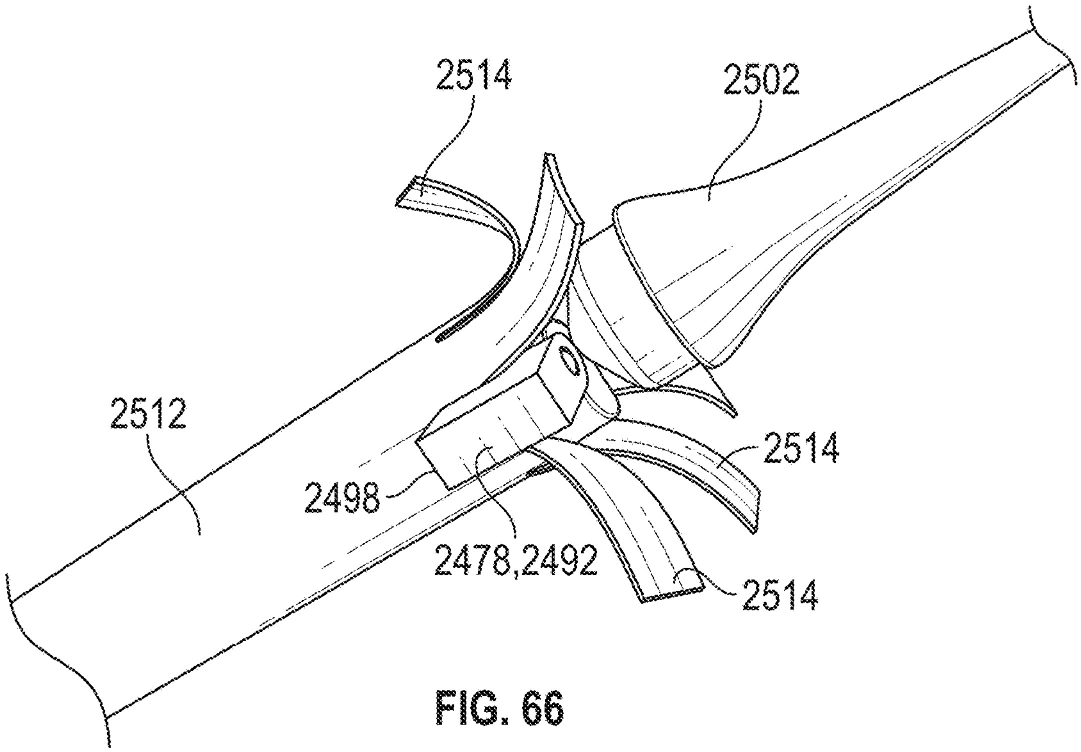
Figure 68:
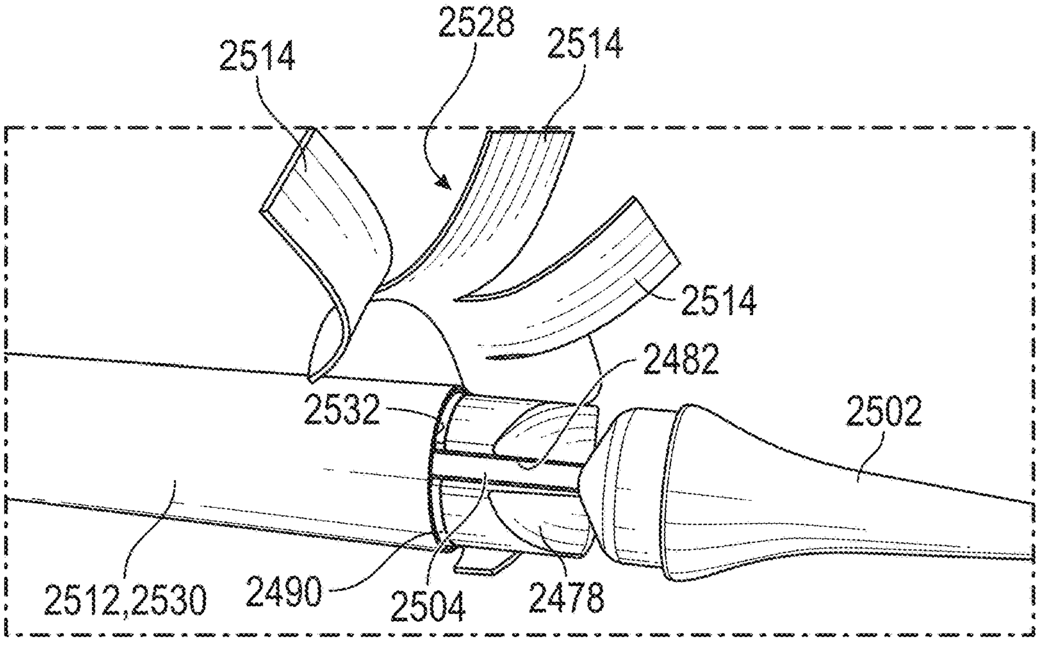

Referring to FIGS. 65-69, the trimming guide member 2478 (which can also be referred to as a 'trimmer device') can be disposed on the first shaft 2504 of the delivery apparatus 2500 by inserting the first shaft 2504 into the slot 2482. The trimming guide member 2478 can then be advanced into the distal end portion 2520 of the capsule 2512 until the rounded end portion 2486 abuts the guidewire shield member 2506 and/or the prosthetic valve 1000 within the capsule 2512. As shown in FIG. 66, the guide arm 2492 can extend over an outer surface of the capsule 2512 (e.g., between tabs 2514). As shown in FIG. 67, a user can position the blade 2522 of a cutting implement 2524 (e.g., a scalpel) such that a first surface 2526 (e.g., a side surface) of the blade 2522 contacts the end surface 2498 of the axially-extending portion 2496 of the guide arm 2492. With the blade 2522 contacting the end surface 2498, the user can advance the cutting edge of the blade radially inwardly toward a longitudinal axis of the capsule 2512 until the cutting edge is disposed within the groove 2490 of the trimming guide member 2478. The user can rotate the capsule 2512 relative to the blade 2522 (or vice versa) while retaining the cutting edge within the groove 2490 and applying cutting pressure in order to cut through the capsule 2512 and remove the tabs 2514, as shown in FIG. 68. This allows the user to cut through the capsule 2512 wall without damaging the interior components housed within the capsule.

The trimmed capsule segment 2528 including the plurality of tabs 2514 can then be removed from the remaining body 2530 of the capsule, for example, by manually tearing the trimmed segment 2528 from the remaining body 2530. The capsule 2512 can be re-trimmed if necessary (e.g., to clean up the distal edge 2532) using the cutting implement 2524 and trimmer guide member 2478. The trimmer guide member 2478 can then be removed.

Figure 69:
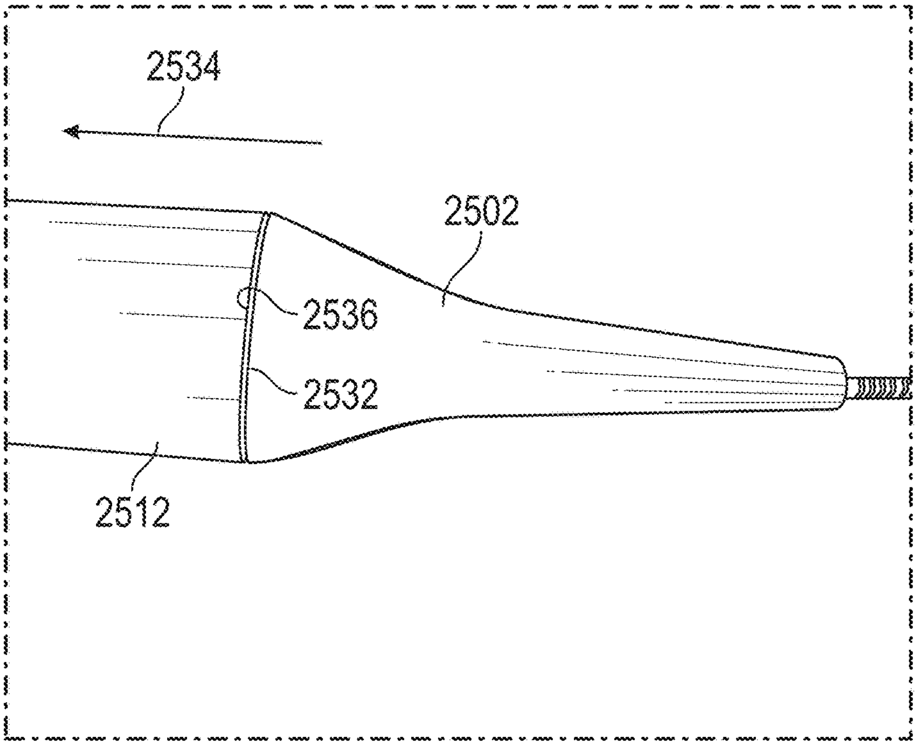

As shown in FIG. 69, the nosecone 2502 can be retracted proximally (as represented by arrow 2534) until a proximal edge 2536 of the nose cone 2502 abuts the distal edge 2532 of the capsule 2512. Use of the trimmer guide member 2478 advantageously minimizes any gaps between the capsule 2512 and the nosecone 2502 by using the end of the loaded prosthetic valve 1000 as the starting location for cutting the capsule 2512. Further, the trimmer guide member 2478 advantageously prevents or mitigates the risk of damage to the nosecone 2502, capsule 2512, and/or prosthetic valve 1000 during cutting.

Figure 72:
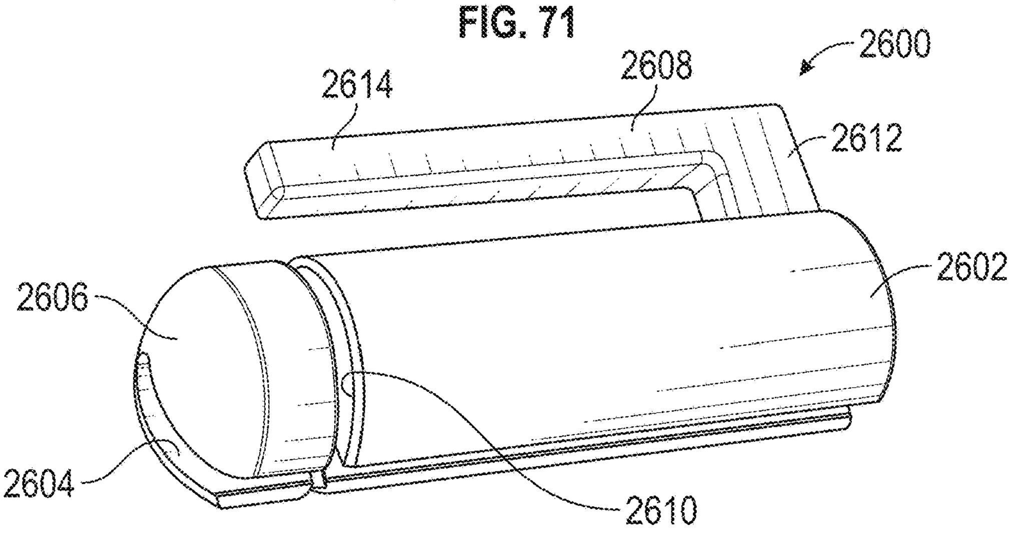
FIGS. 72-73 are perspective view of additional examples of trimming guide devices.

FIG. 72 illustrates an alternative example of a trimmer guide member 2600. The trimmer guide member 2600 can be similar to trimming guide member 2478 (e.g., having a main body 2602 with a slot 2604, a rounded end portion 2606, an annular groove 2610, and a guide arm 2608 having a radially extending portion 2612 and an axially extending portion 2614), except that trimmer guide member 2600 does not include the angled end portion. Trimmer guide member 2600 can have an elongated main body 2602 relative to the main body 2480 of trimmer guide member 2478.

Figure 73:
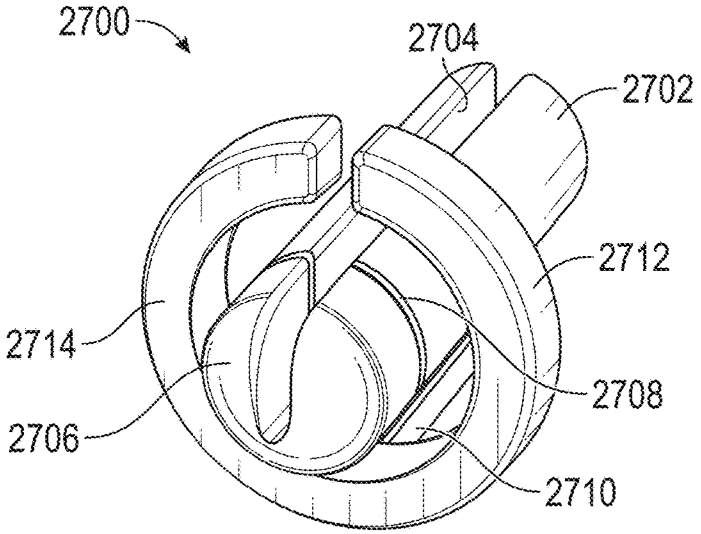

FIG. 73 illustrates another alternative example of a trimmer guide member 2700. Trimmer guide member 2700 can be similar to trimmer guide member 2478 (e.g., having a main body 2702 with a slot 2704, a rounded end portion 2706, an annular groove 2708, and a guide arm 2710) except that trimmer guide member 2700 further comprises an arc member 2712 coupled to the axially-extending portion of the guide arm 2710. The arc member 2712 can be a C-shaped member having a proximal surface 2714 that aligns with the groove 2708 in the main body 2702. This example advantageously allows the user to press the side surface of the blade against the arc member 2712 while cutting along the circumference of the capsule 2512 without having to rotate the capsule 2512 and/or the trimmer guide member 2700 relative to one another. Any of the trimmer guide member examples described herein can be used in combination with the crimper and loading assembly examples.

In certain examples, the halves of the support tube 2402 can be arranged in a parallel arrangement and serve as supports for the distal end of the delivery apparatus and/or the capsule 2512 during the cutting process described above.

Once the prosthetic valve 1000 is loaded into the capsule 2512 of the delivery system 2500, a surgeon can insert a guide wire into a patient to a selected treatment site, such as the native mitral valve. The delivery system can be introduced into the patient's vasculature and advanced over the guide wire to the native mitral valve. The surgeon can then position the capsule 2512 at a selected position relative to the annulus of the native mitral valve, and deploy the prosthetic valve in the native mitral valve annulus, for example by withdrawing the capsule from over the prosthetic valve and/or by advancing the prosthetic valve distally out of the capsule such that the prosthetic valve expands to its functional configuration and regulates blood flow through the mitral valve. In certain examples, the surgeon can manipulate the delivery apparatus to disconnect the prosthetic valve from the valve retention feature(s) at the distal end of the shaft. The delivery apparatus and the guide wire can then be withdrawn from the patient. The delivery apparatus and implant examples described herein can also be used to replace the function of other native heart valves such as the aortic valve, the tricuspid valve, or the pulmonary valve.

Figure 77:
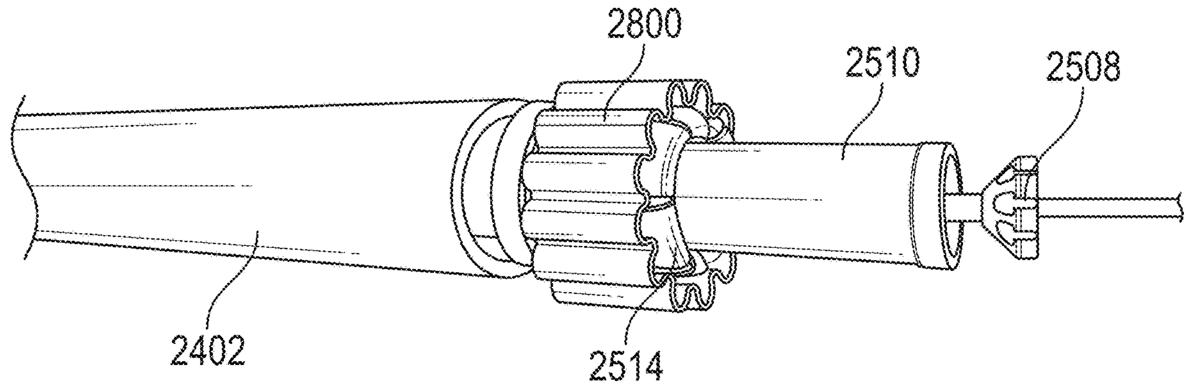
FIGS. 77-78 are perspective views of a distal end portion of a delivery apparatus including an example of a holder member.
Figure 78:
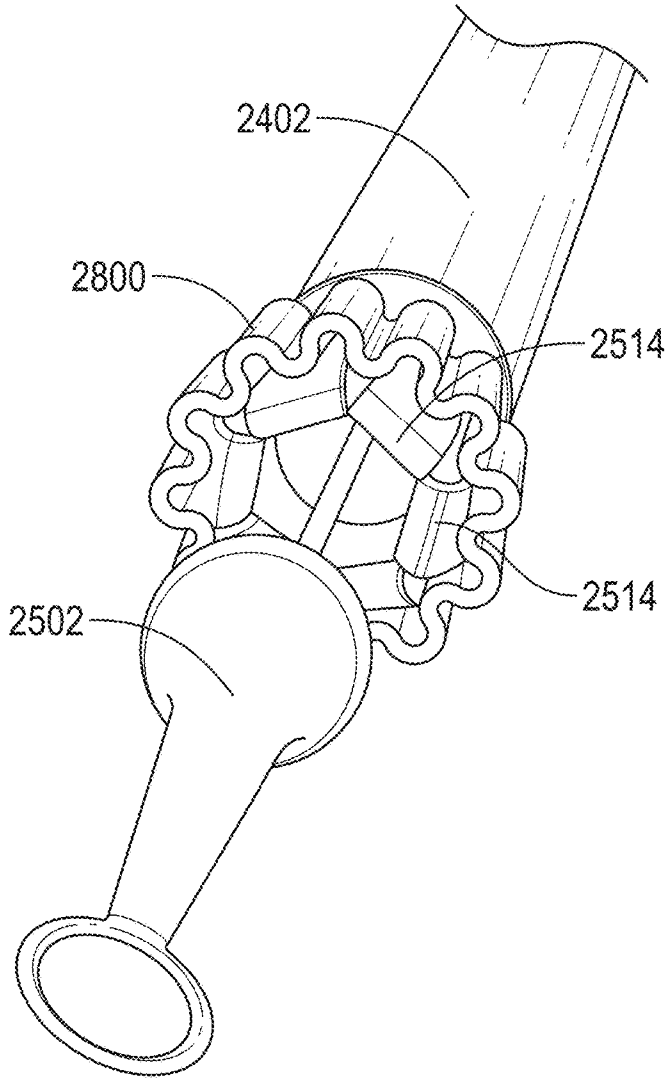
Figure 79:
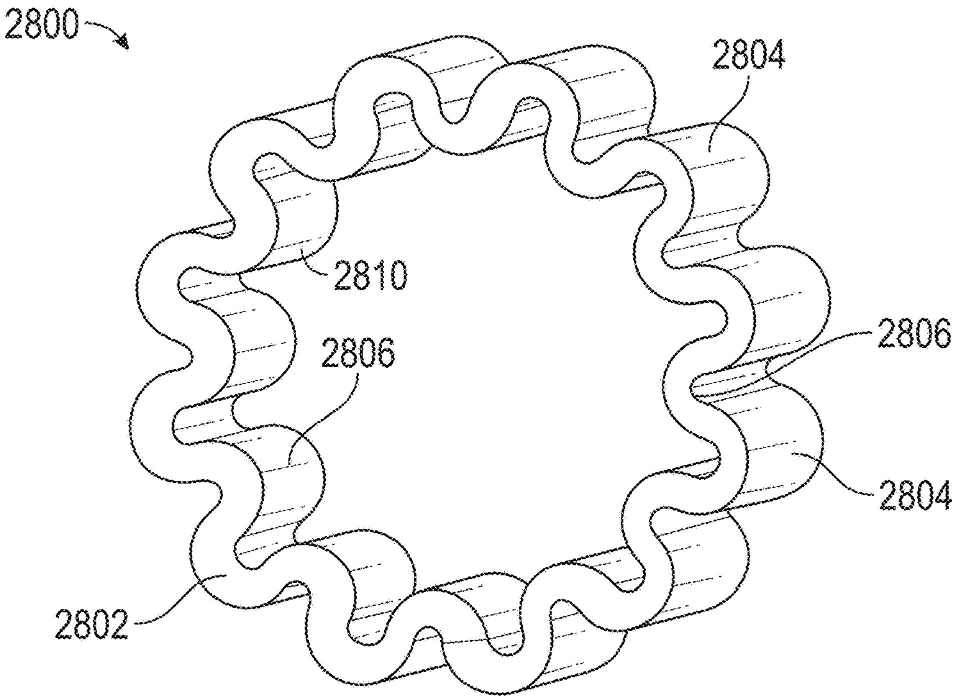
FIG. 79 is a perspective view of the holder member of FIGS. 77-78.
Figure 80:
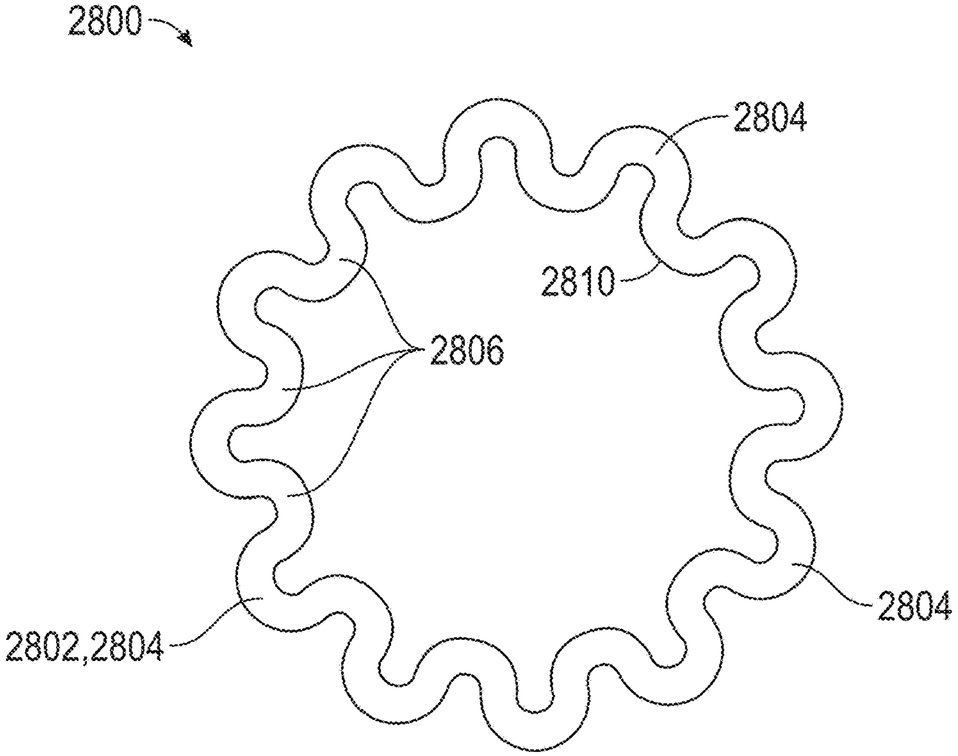
FIG. 80 is a top down view of the holder member of FIGS. 77-88.

Referring to FIGS. 77-80, in some examples of the loading assembly 2400, a flexible tab ring/holder member 2800 can be used in lieu of or in addition to the annular tab ring/holder member 2408. All other components of the loading assembly 2400 can remain the same unless noted otherwise. As shown in FIGS. 77-78, the flexible holder member 2800 can be used in the same manner as holder member 2408, namely, to fit over the extension portion 2424 (see FIG. 53) of the support tube 2402 to hold the tabs 2514 of the sheath/capsule 2512 in tension to retain the capsule 2512 in a taut position, thereby preventing or mitigating bending or deformation of the capsule during the insertion/loading of the prosthetic valve. The holder member 2800 further functions to help retain the side portions 2403 of the support tube 2402 in the assembled position.

The flexible holder member 2800 can be an annular member comprising a main body 2802 defining a lumen or bore 2810 extending therethrough. The main body 2802 having a sinusoidal/wavy shape in cross-section including a plurality of peaks 2804 and valleys 2806. In other examples, the flexible holder member 2800 can have a zig-zag shape. The shape of the flexible holder member 2800 allows the holder member 2800 to be inserted onto the extension portion 2424 and removed from the extension portion with less force than would be required for a rigid holder member. In some examples, the force required can be reduced by up to 50%. For example, if an insertion force of approximately 20 lbf and a removal force of approximately 12 lbf is required for a rigid holder member, the flexible holder member 2800 can be inserted with approximately 10 lbf and removed with approximately 6 lbf.

Figure 82:
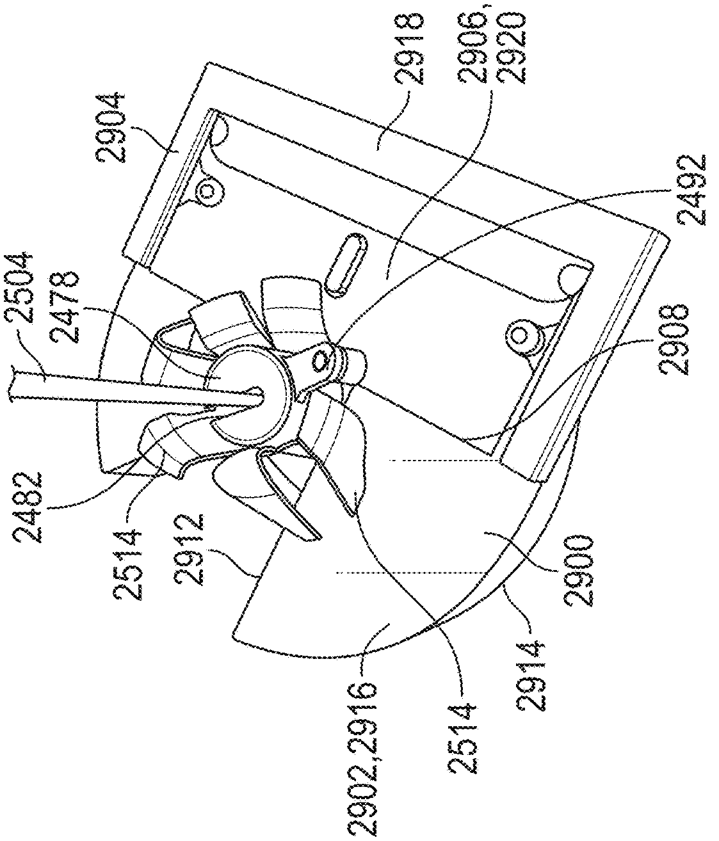
FIGS. 82-83 are perspective views of the trimming device of FIG. 81 disposed on a distal end portion of a delivery apparatus and including a trimmer guide member.
Figure 81:
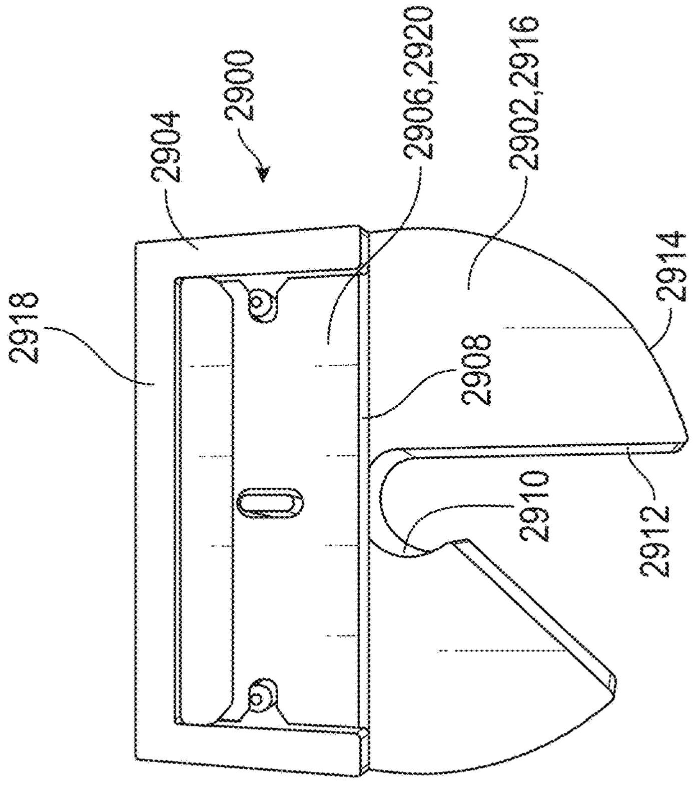
FIG. 81 is a perspective view of a trimming device, according to one example.
Figure 83:
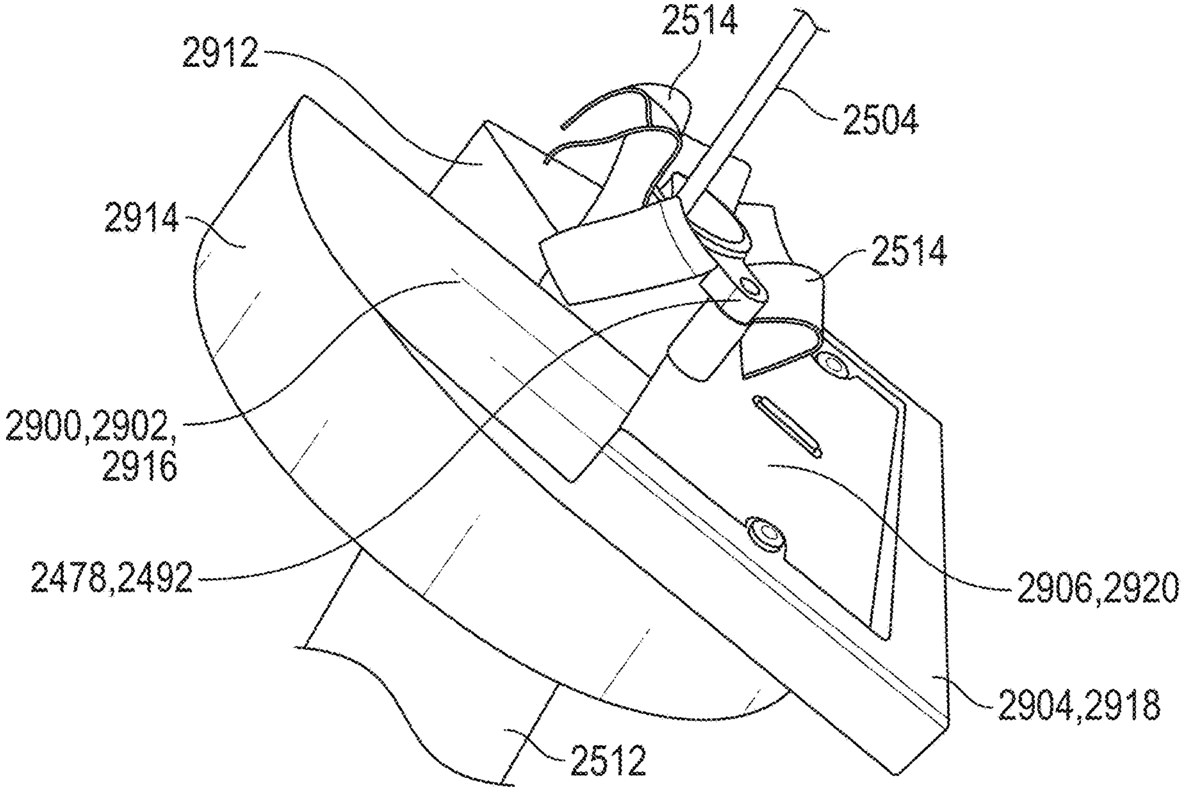

Referring to FIGS. 81-83, as mentioned previously, after loading of a prosthetic valve (such as prosthetic valve 1000 described previously) into a distal end of the capsule 2512, the capsule tabs 2514 can be trimmed off the capsule 2512, thus allowing the proximal edge 2536 of the nose cone 2502 to abut the distal edge 2532 of the capsule 2512, such as shown in FIG. 69. In some examples, a trimming device 2900 including an integrated cutting edge/blade can be used in lieu of a cutting implement such as the previously described scalpel. The trimming device 2900 can be used in conjunction with trimmer guide member 2478 to trim tabs 2514 from a capsule 2512, as shown in FIGS. 82-83. The trimming device 2900 is configured to be rotated around the capsule 2512, thus advantageously allowing a single operator to cut the capsule tabs 2514.

Referring to FIG. 81, the trimming device 2900 can comprise a main body 2902, a platform member 2904, and a removable blade 2906 having a cutting edge 2908. The main body 2902 can be an annular member defining a central lumen/bore 2910 extending through a thickness of the main body 2902. The central bore 2910 can be configured (e.g., sized and shaped) such that the capsule 2512 can be disposed within the central bore 2910, as shown in FIGS. 82-83. The main body 2902 can comprise a cutout 2912 extending from the central bore 2910 radially outward to a radially outer edge 2914 of the main body 2902. The platform member 2904 can be coupled to a first surface 2916 of the main body, and the blade 2906 can be disposed on the platform member

2904. The platform member 2904 can include a lip or edge portion 2918 configured to retain the blade 2906 on the platform member 2904 and position the blade 2906 such that the cutting edge 2908 extends slightly into the central bore 2910. In some examples, the platform member 2904 can be configured (e.g., sized and shaped) to be compatible with a standard razor blade, which allows the blade 2906 to be easily removed and replaced when desired.

In use, as shown in FIGS. 82-83, the trimmer guide member 2478 can be disposed on the first shaft 2504 by inserting the first shaft 2504 into the slot 2482 (FIG. 82). The trimmer guide member 2478 can then be advanced into the distal end portion of the capsule 2512 until the rounded end portion 2486 (FIG. 65) abuts the guidewire shield member 2506 and/or the prosthetic valve 1000 within the capsule 2512. As shown in FIG. 82, the guide arm 2492 can extend over an outer surface of the capsule 2512 (e.g., between tabs 2514).

As shown in FIGS. 82-83, a user can position the trimming device 2900 such that a first surface 2920 of the blade 2906 contacts the end surface 2498 of the guide arm 2492. The trimming device 2900 can then be advanced toward the capsule 2512 until the cutting edge 2908 of the blade 2906 is disposed within the groove 2490 (FIG. 70) of the trimmer guide member 2478. The user can rotate the trimming device 2900 relative to the capsule 2512 (or vice versa) while retaining the cutting edge 2908 within the groove 2490 and applying cutting pressure in order to cut through the capsule 2512 and remove the tabs 2514. This allows the user to cut through the capsule 2512 wall without damaging the interior components housed within the capsule. This configuration advantageously allows a single user to easily trim the tabs 2514 from the capsule, for example, by holding the capsule 2512 in one hand while rotating the trimming device 2900 with the other hand. Further, this configuration advantageously allows the tabs 2514 to be removed with a single 360-degree rotation of the trimming device 2900 around the capsule 2512.

The trimmed capsule segment including the plurality of tabs 2514 can then be removed from the remaining body of the capsule 2512, for example, by manually tearing the trimmed segment 2528 from the capsule. The capsule 2512 can be re-trimmed if necessary (e.g., to clean up the distal edge), by using the trimming device 2900 a second time. The trimmer guide member 2478 can then be removed.

Referring to FIGS. 84-87, in some examples, the tabs 2514 of the capsule 2512 can be removed using a trimming device 3000 that does not require use of trimmer guide member 2478 or a separate cutting implement such as a scalpel. After a prosthetic valve (e.g., prosthetic valve 1000 described previously) has been loaded into the capsule 2512, trimming device 3000 can be used to remove the capsule tabs 2514 from the capsule 2512, thus allowing the proximal edge 2536 of the nose cone 2502 to abut the distal edge 2532 of the capsule 2512, such as shown in FIG. 69. The capsule 2512 can, in some examples, comprise a compliant composite material having lubricious characteristics, for example, expanded polytetrafluorochtylene EPTFE. This can make the capsule difficult to cut without creating strands/remnant edges/leftover flashing/particulate. The trimming devices described here (including those described previously) prevent and/or mitigate these problems.

Figure 84:
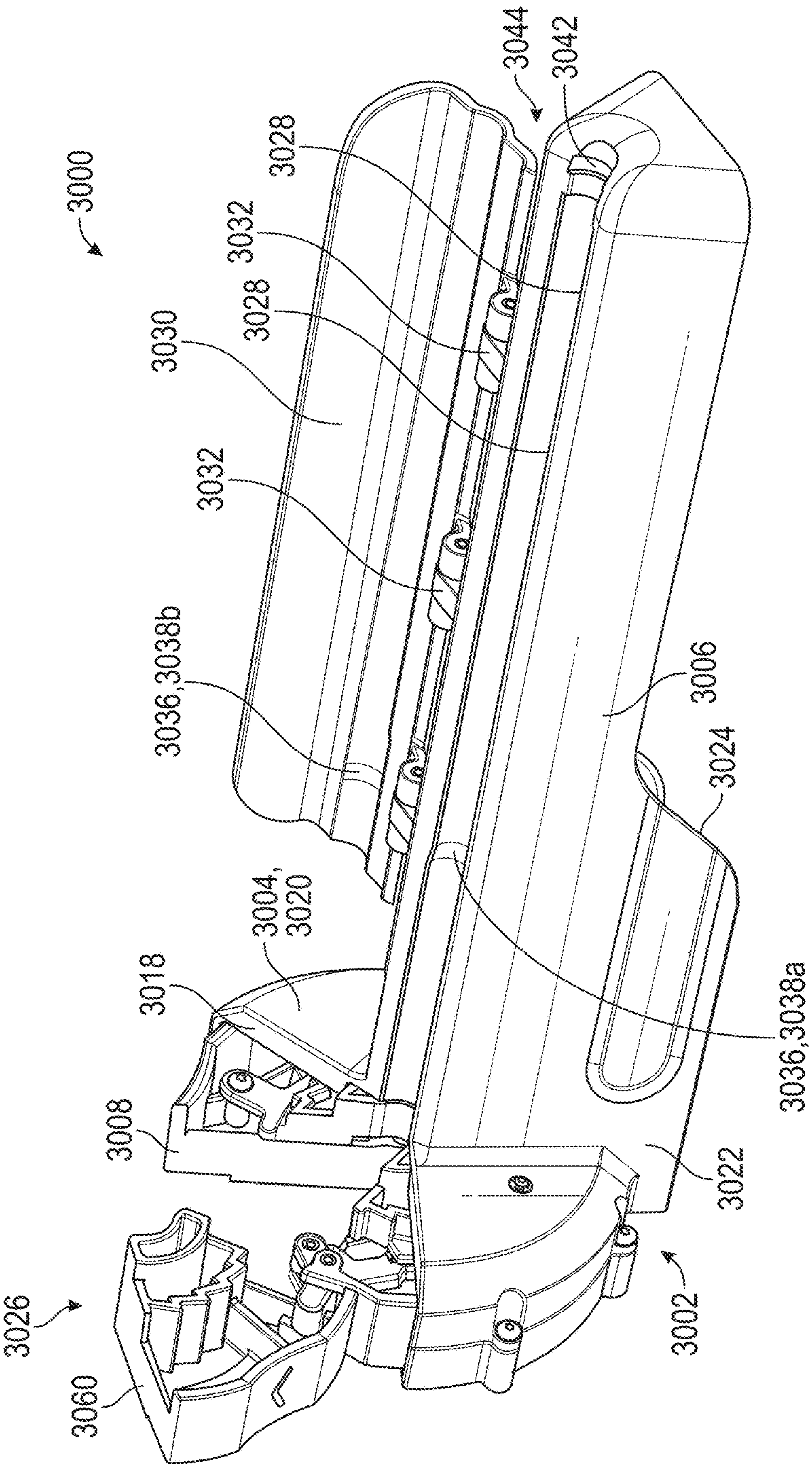
FIG. 84 is a perspective view of a trimming device, according to another example.
Figure 86:
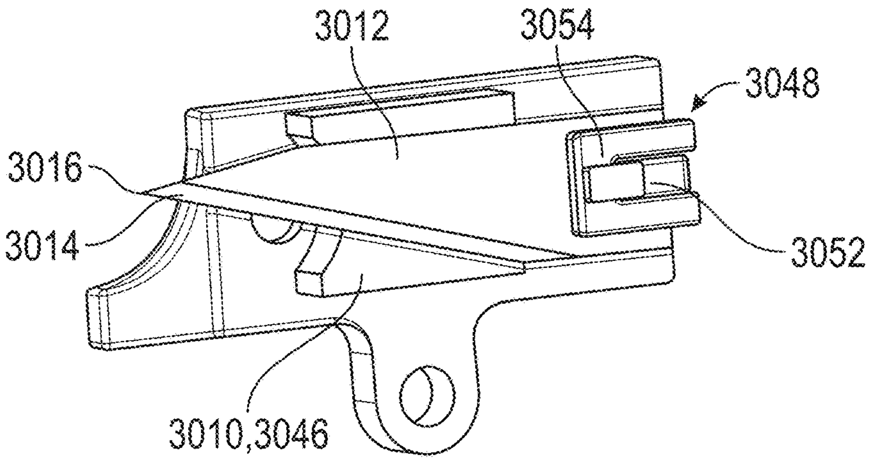
FIG. 86 is a perspective view of the blade holder of the trimming device of FIG. 84.

Referring to FIG. 84, the trimming device 3000 can generally comprise a housing 3002 including a main body 3004 and a support extension 3006, a rotatable member 3008, and a blade holder 3010 (FIG. 86) coupled to the rotatable member 3008. As shown in FIG. 86, the blade holder 3010 can be configured to hold a blade 3012 having a cutting edge 3014 including a point 3016.

Referring still to FIG. 84, the main body 3004 can comprise an overall cylindrical shape defining an annular inner chamber in which the rotatable member 3008 is disposed. The main body 3004 can comprise a cutout 3018 through which the rotatable member 3008 is visible and actuatable when within the main body 3004. The cutout 3018 can, in some examples, be shaped like a cylindrical sector.

As mentioned, the housing 3002 can further comprise a support extension 3006. The support extension 3006 can be coupled to and extend from a first surface 3020 of the main body 3004. In some examples, such as the illustrated examples, the support extension 3006 can comprise one or more legs or support members 3022. The support members 3022 can allow the trimming device 3000 to be disposed on a work surface, such as a table etc., thereby facilitating use by a single operator. In some examples, the support members 3022 can comprise an angled portion 3024. The angled portion 3024 can be configured to allow a distal end portion 3026 of the trimming device (including the main body 3004 and rotatable member 3008) to be positioned on a second surface to extend the working length of the device. In some examples, such as shown in FIG. 84, the support members 3022 can comprise a recessed portion in the outer surface configured to allow a user to position their thumb (or other finger) within the recess to facilitate holding the trimming device 3000 during use.

Figure 85:
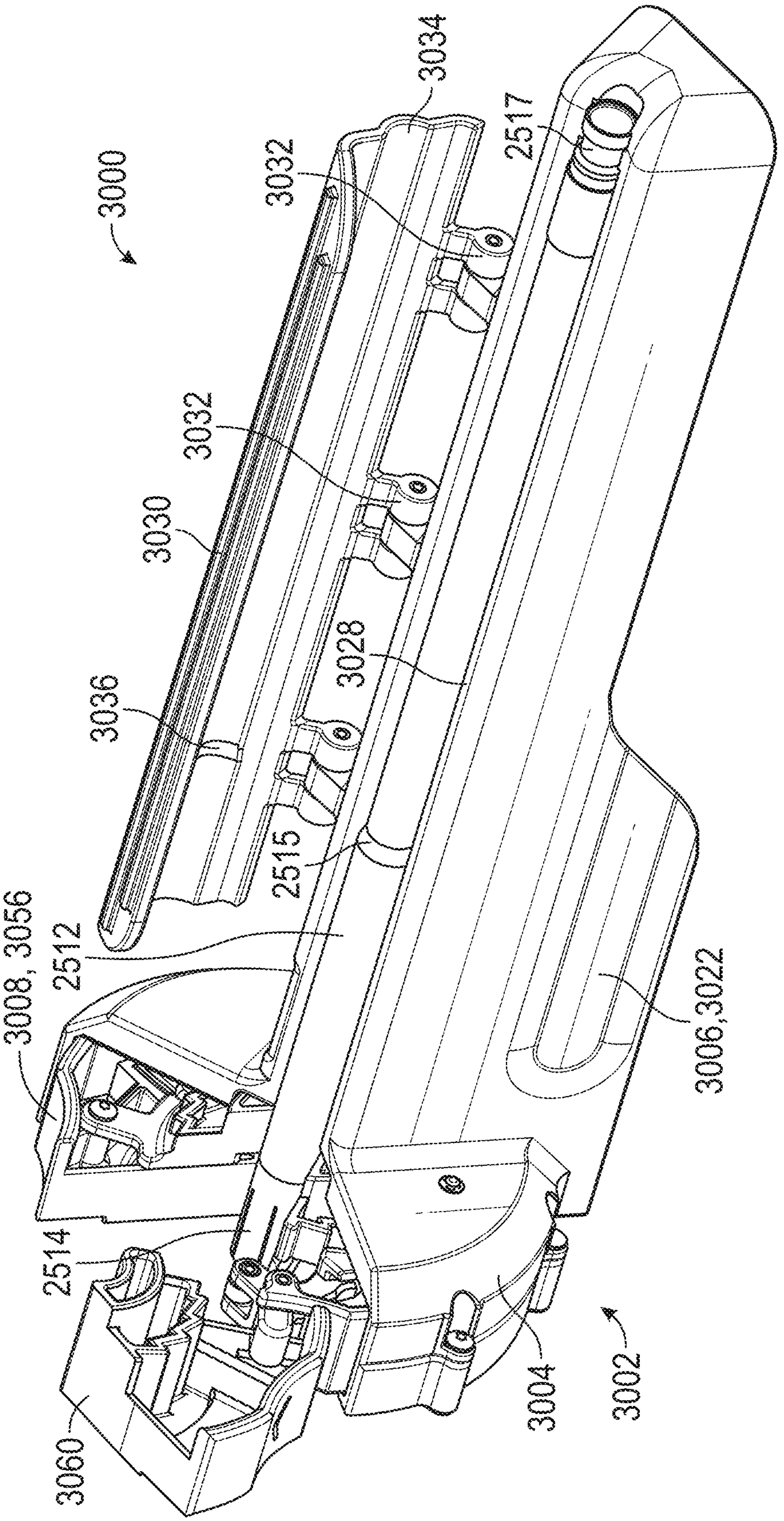
FIG. 85 is a perspective view of the trimming device of FIG. 84, showing a distal end portion of a delivery system disposed within the device.

As shown in FIG. 84, the support extension 3006 can comprise a central channel or recess 3028. The central recess 3028 can be configured (e.g., sized and shaped) such that a capsule 2512 can be disposed within the recess 3028, such as shown in FIG. 85. The trimming device 3000 can further comprise a lid member or clamp member 3030 pivotably coupled to the support extension 3006 via one or more hinges 3032. The clamp member 3030 can be movable between an open position (FIG. 84) and a closed position in which the clamp member 3030 is configured to mitigate movement of the capsule 2512 relative to the support extension 3006. The clamp member 3030 can comprise a central channel or recess 3034 such that when the clamp member 3030 is in the closed position the capsule 2512 is disposed withing the recess 3028 and the recess 3034.

The trimming device 3000 can comprise one or more alignment features 3036 configured to align with a corresponding locating feature(s) 2515 on the capsule 2512 such that when the capsule 2512 is disposed within the recess 3028 a selected cutting location at the distal end portion of the capsule 2512 is aligned with the blade 3012. As shown in FIG. 84, the recess 3028 and clamp member 3030 can together comprise a first alignment feature 3036. In the illustrated example, the alignment feature 3036 can comprise first and second laterally extending grooves/channels 3038*a*, 3038*b*, disposed in the recess 3028 and clamp member 3030, respectively. In some examples, the alignment feature 3036 can be, for example, a gripping member configured to frictionally engage an outer surface of the capsule 2512.

As shown FIG. 85, when the capsule 2512 is disposed within the recess 3028 the locating feature 2515 (e.g., a flared/tapered portion of the capsule 2512) sits within the alignment feature 3036. The alignment feature 3036 thus locates the capsule 2512 so that the selected cutting location (e.g., proximal to the tabs 2514) is aligned with the blade 3012. The clamp member 3030 can then be moved to the closed position to prevent or mitigate movement of the capsule 2512 during the cutting process.

In some examples, such as the illustrated example, the trimming device 3000 can comprise a second alignment feature 3042. The second alignment feature 3042 can be disposed at a proximal end portion 3044 of the trimming device 3000 and can be configured to engage a connector 2517 (FIG. 85) of the capsule 2512. The second alignment feature 3042 can prevent movement of the capsule 2512 relative to the trimming device 3000 and/or can help ensure that the capsule 2512 is positioned within the trimming device with the selected cutting location aligned with the blade 3012. In the illustrated example, the second alignment feature 3042 (FIG. 84) is a laterally extending groove/channel sized such that a portion of the connector 2517 can sit within the channel. However, in other examples the second alignment feature can be, for example, a gripping member disposed within the recess and/or the clamp member and/or an additional clamp member and configured to frictionally engage an outer surface of the connector 2517 and/or an outer surface of the capsule 2512.

Referring now to FIG. 86, the blade holder 3010 can comprise a main body 3046 comprising a blade engagement member 3048 and an aperture 3050. The blade engagement member 3048 comprises a first member 3052 extending from a surface of the main body and a removable second member 3054 configured to be disposed between the first member 3052 and the blade 3012 to retain the blade 3012 against the main body 3046 of the blade holder 3010. Such a configuration allows the blade 3012 to be easily replaced when the cutting edge 3014 has dulled. The first and second members 3052, 3054 can interlock with one another to prevent movement of the second member 3054 or the blade 3012 relative to the blade holder 3010. For example, as shown in FIG. 86, the second member 3054 can have a U-shape allowing it to slide under and around the first member 3052, however, in other examples, the first and second members 3052, 3054 can have any of various interlocking shapes.

Figure 87:
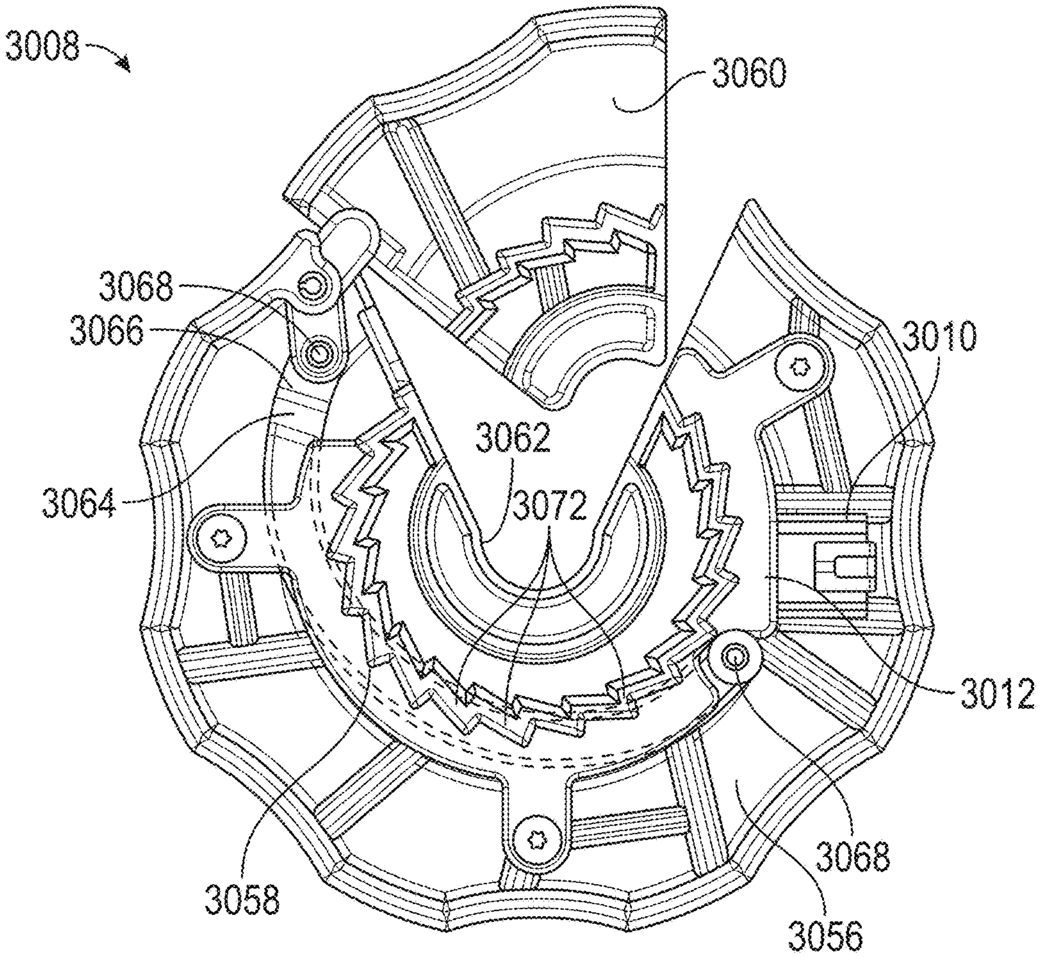
FIG. 87 is a front view of the rotatable member of the trimming device of FIG. 84, with the door member shown in the open position.
Figure 88:
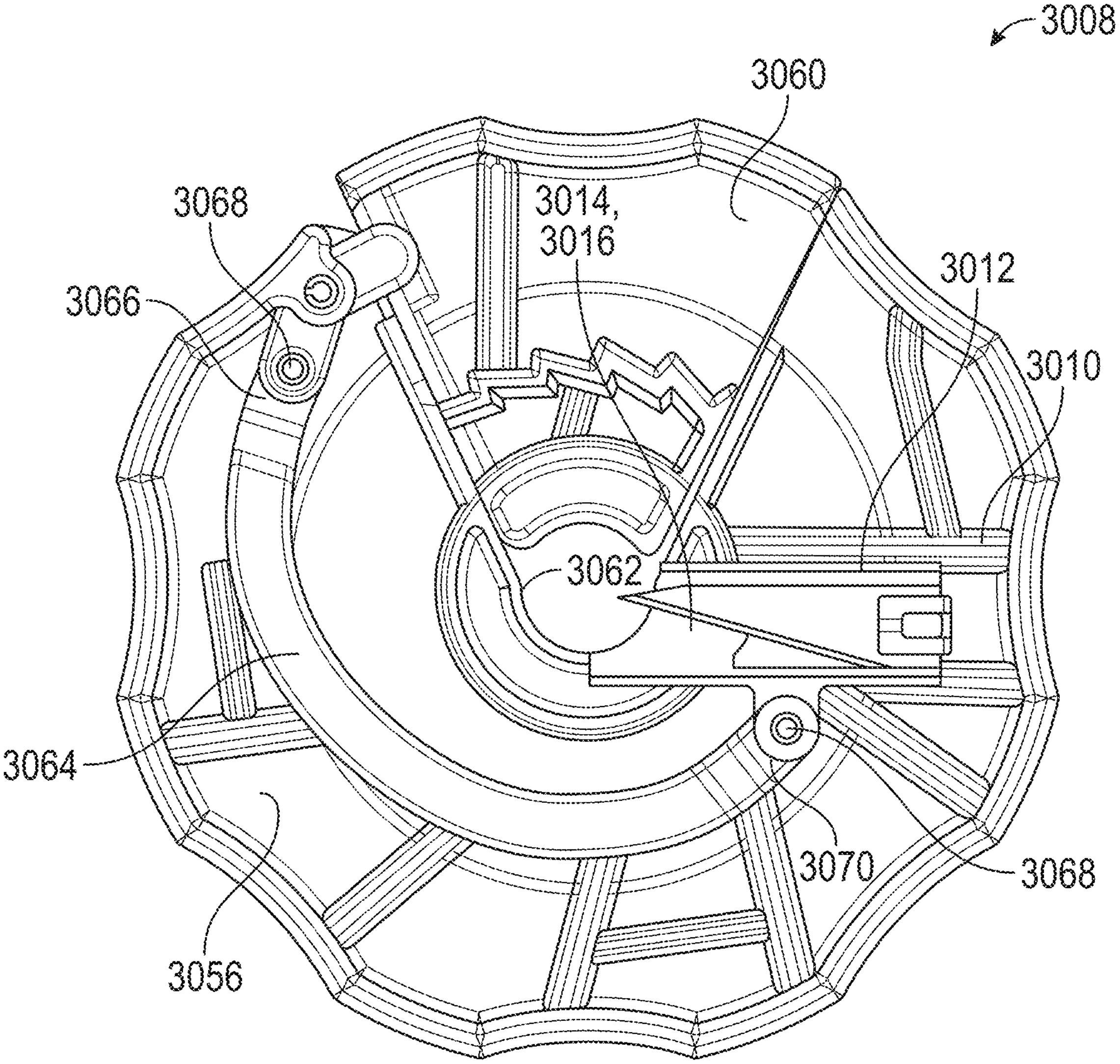
FIG. 88 is a front view of the rotatable member of the trimming device of FIG. 84, with the door member shown in the closed position and with the ratchet member removed.

FIGS. 87-88 illustrate the rotatable member 3008 and the blade holder 3010 with the other components of the trimming device 3000 removed for purposes of illustration. As shown in FIG. 87, the rotatable member 3008 can generally comprise a main body 3056, a ratchet member 3058, and a door member 3060. The rotatable member 3008 can define a central lumen or bore 3062 extending through a thickness of the main body. The central bore 3062 can be configured (e.g., sized and shaped) to allow a distal end portion of the capsule 2512 to be positioned within the bore 3062 such that a selected cutting location is aligned with the blade 3012.

The door member 3060 can be movable between an open position (FIG. 87) and a closed position (FIG. 88). The rotatable member 3008 can be configured such that movement of the door member 3060 from the open position to the closed position causes movement of the blade 3012 from a first, safety/non-cutting/retracted position (FIG. 87) to a second cutting/extended/use position (FIG. 88) wherein a cutting edge 3014 of the blade 3012 extends into the central bore 3062, as shown in FIG. 88. For example, the door member 3060 can be coupled to the blade holder 3010 via a cam member 3064. The cam member 3064 can have an elongated C-shape and can be pivotable coupled to the door member 3060 at a first end portion 3066 (e.g., via a fastener 3068) and to the blade holder 3010 at a second end portion 3070, for example, using a fastener 3068 extending through the aperture 3050 in the blade holder 3010.

In some examples, the door member 3060 can further comprise a locking member. The locking member can be actuatable between a locked position wherein the door member is retained in either the closed or open position, and an unlocked position wherein the door member is movable between the locked and unlocked positions.

As shown in FIGS. 87-88, as the door member 3060 moves from the open position to the closed position the first end portion 3066 of the cam member 3064 moves radially away from the central bore 3062 thus causing corresponding movement of the second end portion 3070 of the cam member 3064 thereby moving the blade holder 3010 from the retracted position (FIG. 87) to the use position (FIG. 88). Such a configuration advantageously prevents injury to the user and can prevent inadvertent damage to the capsule by ensuring that the cutting edge 3014 of the blade 3012 does not contact the capsule 2512 until the door is closed. This can prevent accidental cutting when the capsule is not in the selected location. In other examples, the blade holder 3010 can be coupled to a manually actuatable member, such as a button, such that a user can select when to move the blade from the retracted position to the use position. FIGS. 89-95 illustrate one such example.

Referring again to FIG. 87, the ratchet member 3058 can be coupled to the main body 3056 of the rotatable member 3008 and can comprise a plurality of teeth 3072. The teeth 3072 can be disposed circularly about a circumference of the ratchet member 3058. The plurality of teeth 3072 can be configured to engage a pawl of the main body 3004 (see e.g., pawl 3150 of the example shown in FIG. 91, which serves a similar function) such that the rotatable member 3008 can rotate in a first direction (e.g., clockwise in the orientation shown in FIG. 87) but is prevented from rotating in a second direction (e.g., counterclockwise in the orientation shown in FIG. 87). In some examples, the pawl can comprise a biasing member such as a spring configured to bias the pawl against the plurality of teeth 3072.

Referring to FIG. 85, in use, the capsule 2512 can be positioned within the trimming device 3000 such that the locating feature 2515 of the capsule 2512 aligns with the first alignment feature 3036 and the connector 2715 aligns with the second alignment feature 3042 (FIG. 84). The clamp member 3030 can then be actuated from the open position (FIG. 85) to the closed position to retain the capsule in position. This positions the selected cutting location (for example, proximal to the tabs 2514) such that it is aligned with a cutting edge 3014 of the blade 3012. So aligned, the door member 3060 can be moved from the open position (FIG. 87) to the closed position (FIG. 88) thereby actuating the cam member 3064 to move the blade holder 3010 (and therefore the blade 3012) from the retracted position to the use position, inserting a point 3016 of the blade 3012 through the wall of the capsule 2512. The rotatable member 3008 can then be rotated 360 degrees in order to cut through the capsule 2512 and remove the tabs 2514. The positioning of the blade 3012 as determined by the movement of the cam member 3064 allows the user to cut through the capsule 2512 wall without damaging any interior components housed within the capsule. This configuration advantageously allows a single user to easily trim the tabs 2514 from the capsule, for example, by positioning the capsule 2512 within the trimming device 3000 and rotating the rotatable member 3008. Further, this configuration advantageously allows the tabs 2514 to be removed with a single 360-degree rotation of the rotatable member 3008, thus expediting the process and avoiding the need for further trimming.

FIGS. 89-95 illustrate another example of a trimming device 3100. Trimming device 3100 can be similar to trimming device 3000 described previously except where indicated otherwise. That is, trimming device 3100 can generally comprise a housing 3102 including a main body 3104 and a support extension 3106, a rotatable member 3108, and a blade holder 3110 (FIG. 91) coupled to the rotatable member 3108 and including a blade 3112. It should be noted that any of the features described herein for trimming device 3100 can be adapted for use with trimming device 3000, and vice versa.

Figure 95:
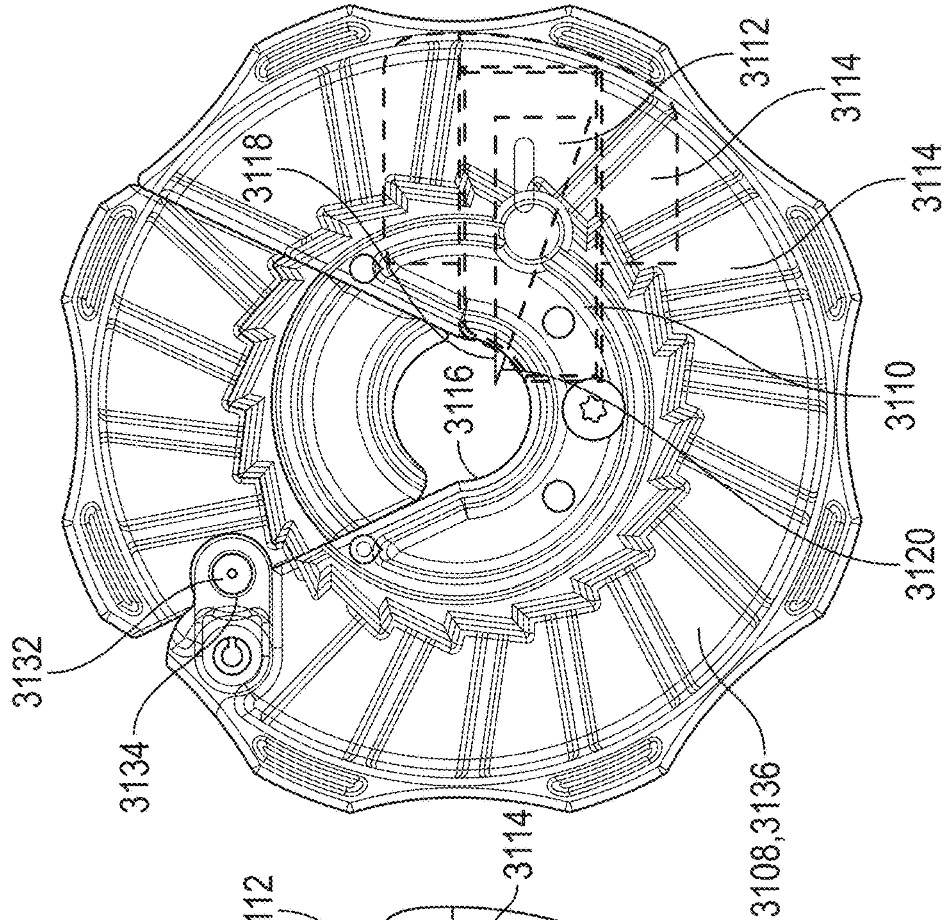
FIG. 95 is a front view of the rotatable member of the trimming device of FIG. 89, with the blade shown in the use position.
Figure 94:
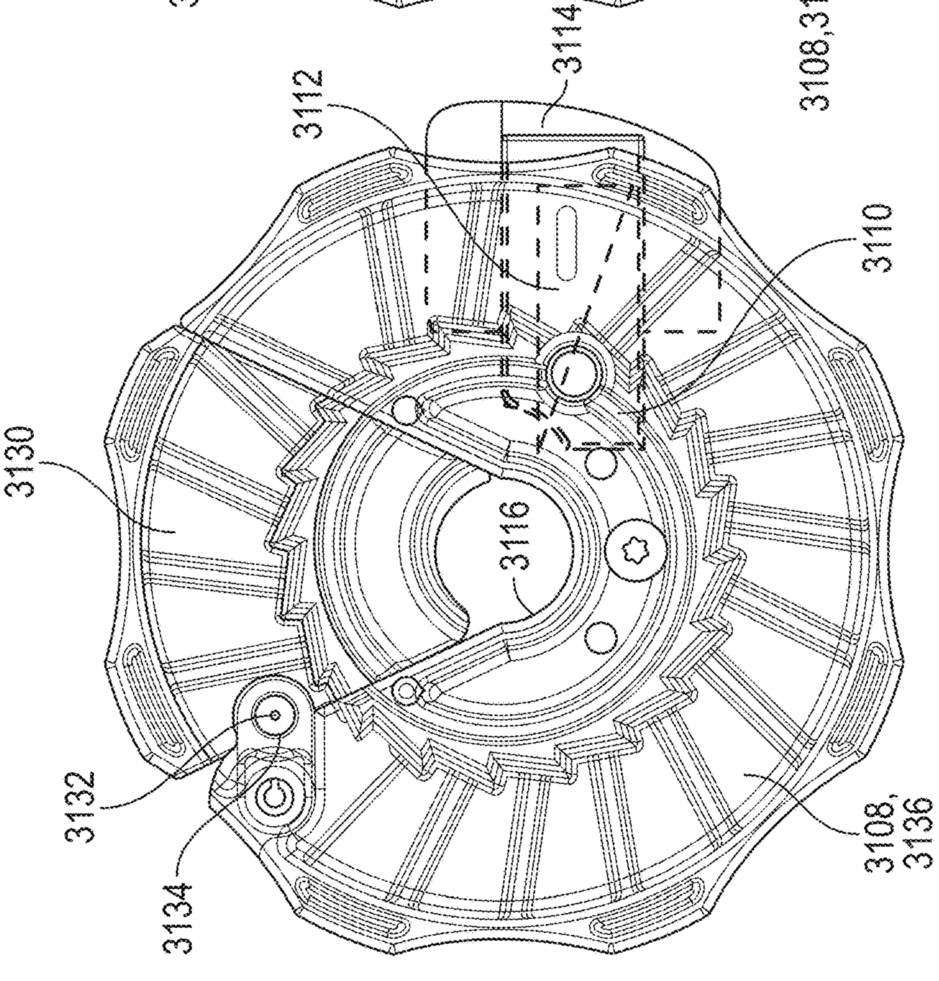
FIG. 94 is a front view of the rotatable member of the trimming device of FIG. 89, with the blade shown in the retracted position.

In lieu of cam member 3064 described previously, which positions blade holder 3010 based on the position of the door member 3060, trimming device 3100 includes an actuator member 3114, such as a button, that allows the position of the blade holder 3110 to be determined manually, such as by a user. Referring to FIGS. 94-95, the actuator member 3114 can be positioned adjacent a central lumen 3116 of the rotatable member 3108 and can be coupled to the blade holder 3110. The actuator member 3114 can be movable between a first position wherein the blade holder 3110 is in a safety/non-cutting/locked/retracted position (FIG. 94) to a second position wherein the blade holder (and therefore the blade 3112) is in a cutting/extended/use position (FIG. 95). When in the use position, a cutting tip 3118 and cutting edge of the blade 3120 extend into the central bore 3116 of the rotatable member 3108. In some examples, the actuator member 3114 can comprise a biasing member (such as a spring) configured to bias the actuator member 3114 into the first position.

Figure 91:
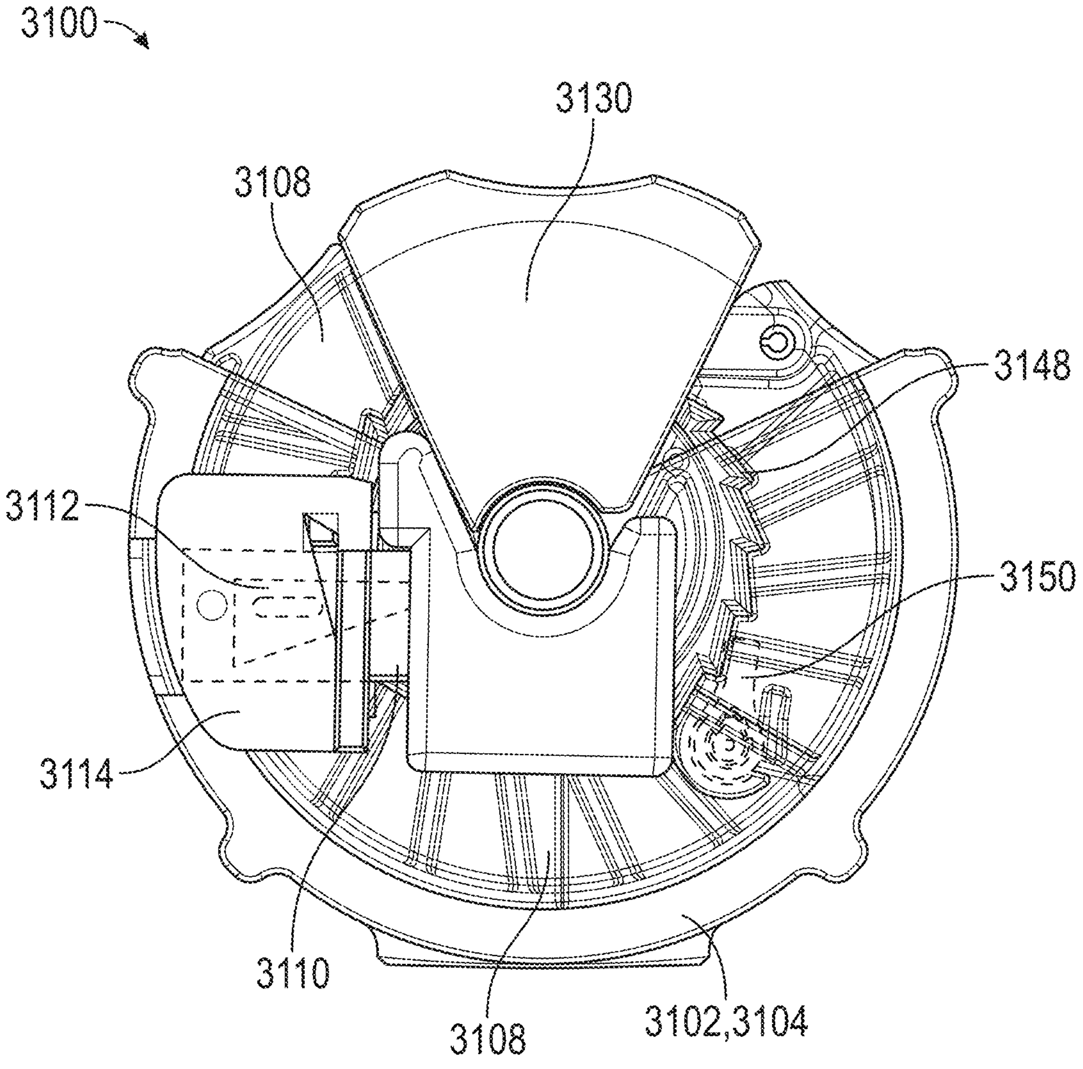
FIG. 91 is a front view of the trimming device of FIG. 89, with the door member shown in the closed position.
Figure 92:
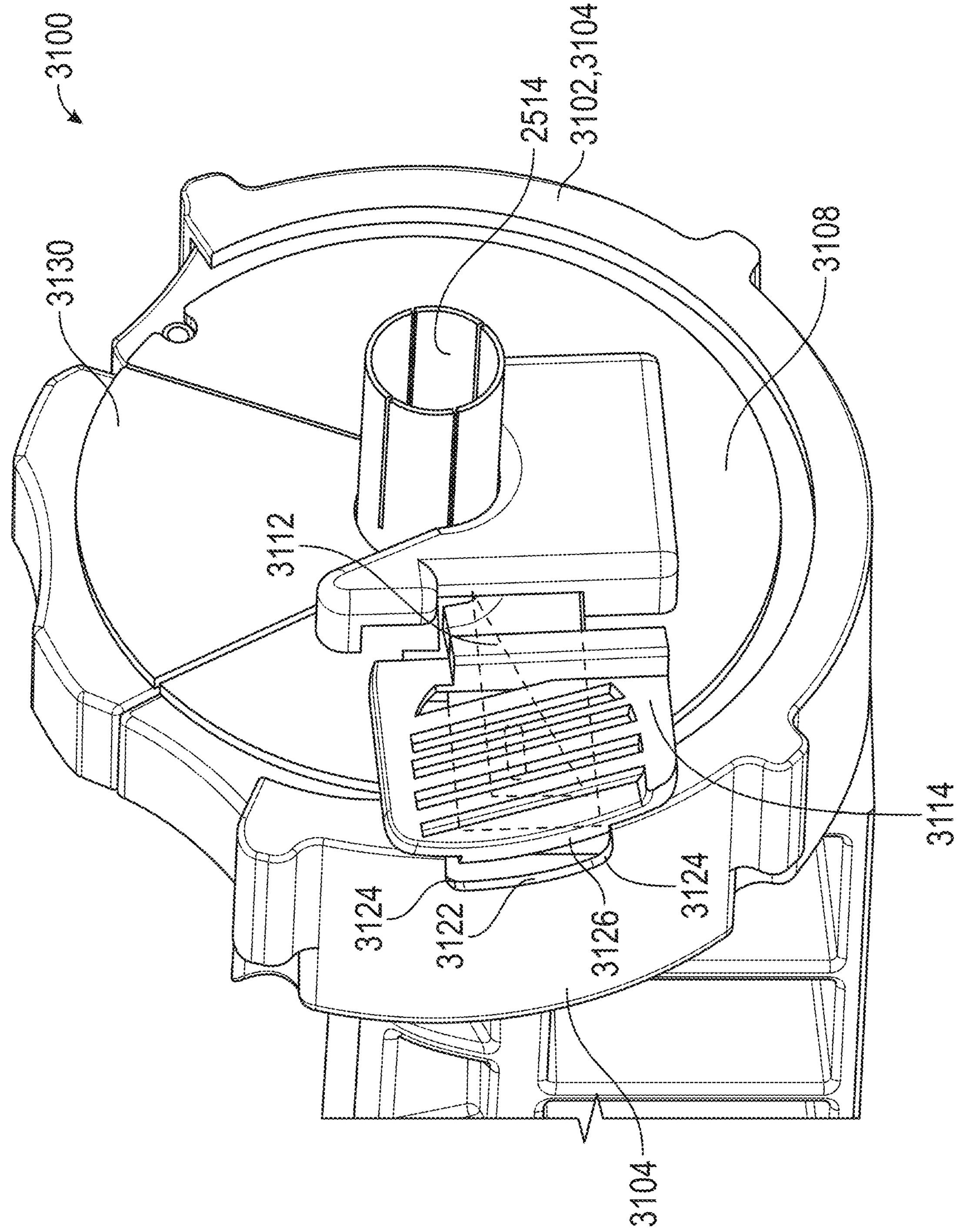
FIG. 92 is a perspective view of an end portion of the trimming device of FIG. 89.

Referring to FIGS. 91-92, in some examples, when in the first position (also referred to as the locked position), the actuator member 3114 can prevent rotation of the rotatable member 3108. Such a configuration advantageously prevents inadvertent rotation of the rotatable member 3108, thus making it easier to load the capsule 2512 into the trimming device 3100. For example, the main body 3104 of the housing 3102 can comprise a cutout 3122 defining one or more shoulders 3124. The actuator member 3114 (which is slidably coupled to the rotatable member 3108) can comprise a projection 3126 that sits within the cutout 3122 when the actuator member 3114 is in the first position, as shown in FIG. 92. Engagement of the projection 3126 with the one or more shoulders 3124 prevents rotation of the rotatable member 3108 relative to the main body 3104. When the actuator member 3114 moves from the first position (FIG. 94) to the second position (FIG. 95; also referred to as the unlocked position), the projection 3126 is no longer disposed within the cutout 3122 and the rotatable member 3108 can rotate relative to the main body 3104.

Figure 90:
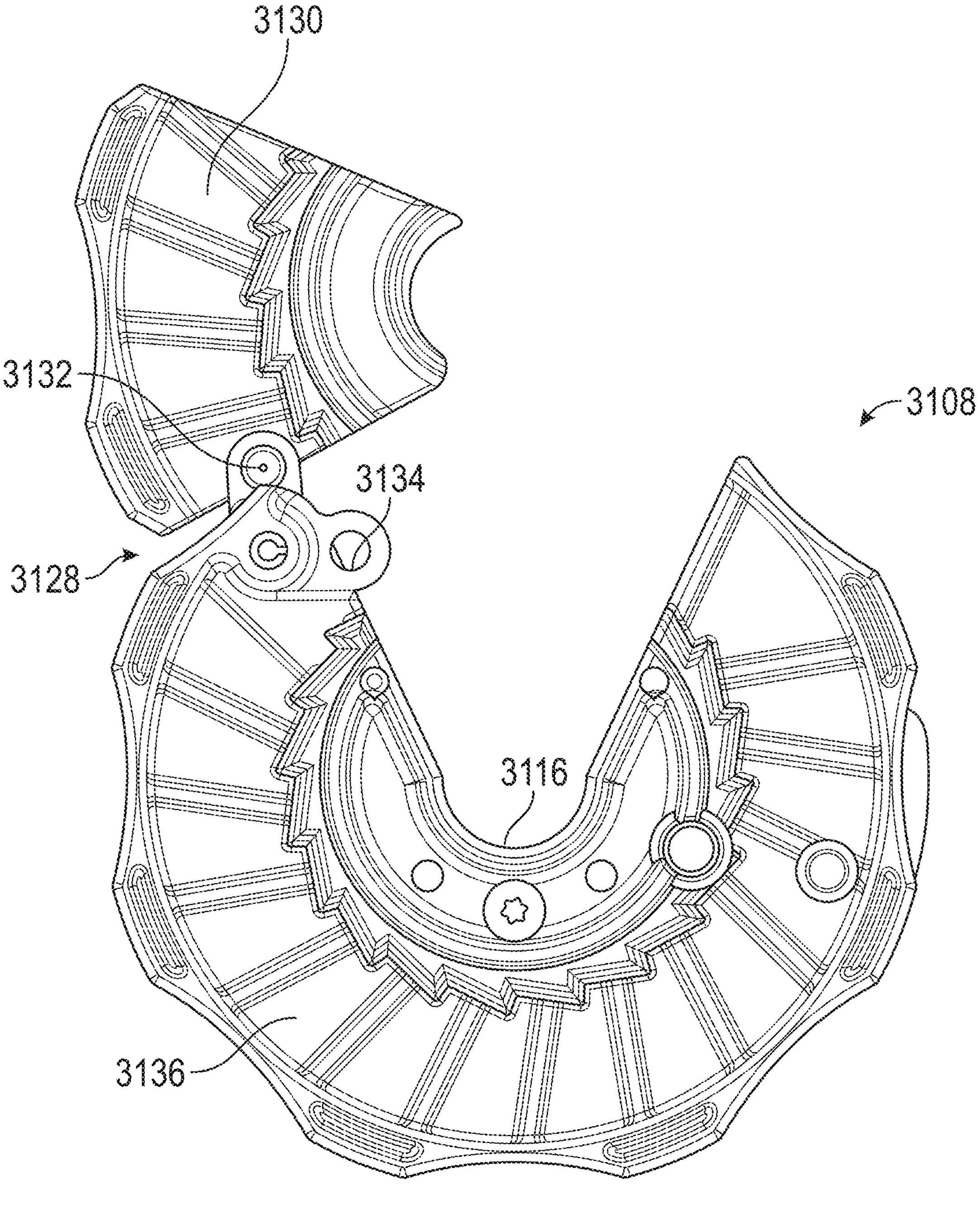
FIG. 90 is a front view of the rotatable member of the trimming device of FIG. 89, with the door member shown in the open position.

In some examples, trimming device 3100 can comprise a detent mechanism 3128 configured to retain the door member 3130 in the closed position during operation of the trimming device 3100. Referring to FIG. 90, the door member 3130 can comprise a projection/protrusion/detent 3132 configured to sit within an opening/aperture 3134 of a main body 3136 of the rotatable member 3108 when the door member 3130 is in the closed position (see FIG. 94). The engagement of the detent 3132 with the opening 3134 can selectively retain the door member 3130 in the closed position until sufficient force is placed upon the door member 3130 (e.g., manually by a user) to open the door member. In the illustrated example, the detent 3132 is a hemispherical protrusion and the opening 3134 has a corresponding circular shape, however, in other examples, the detent and opening can have any of various corresponding shapes.

Figure 89:
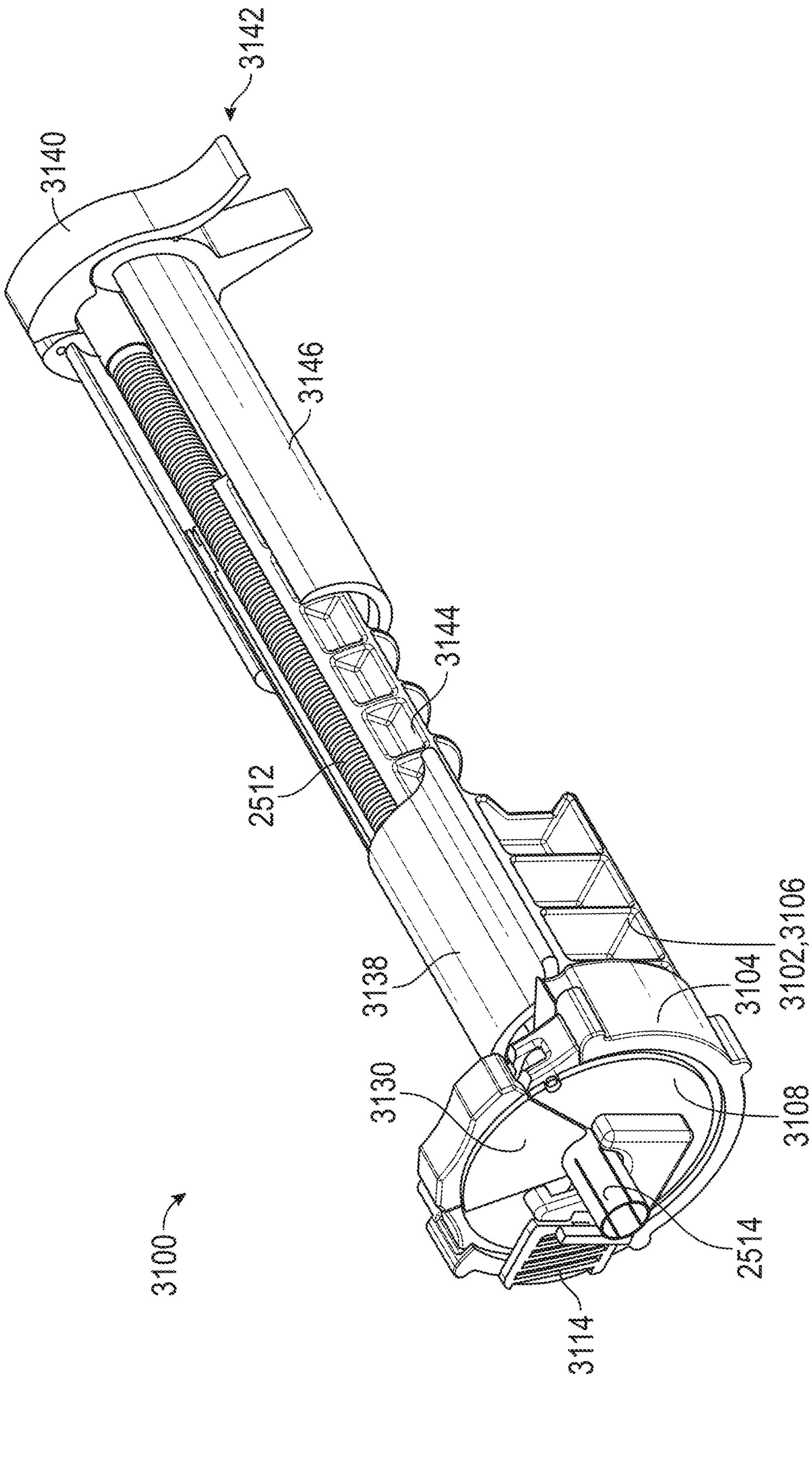
FIG. 89 is a perspective view of a trimming device, according to another example, showing a distal end portion of a delivery system disposed within the trimming device.
Figure 93:
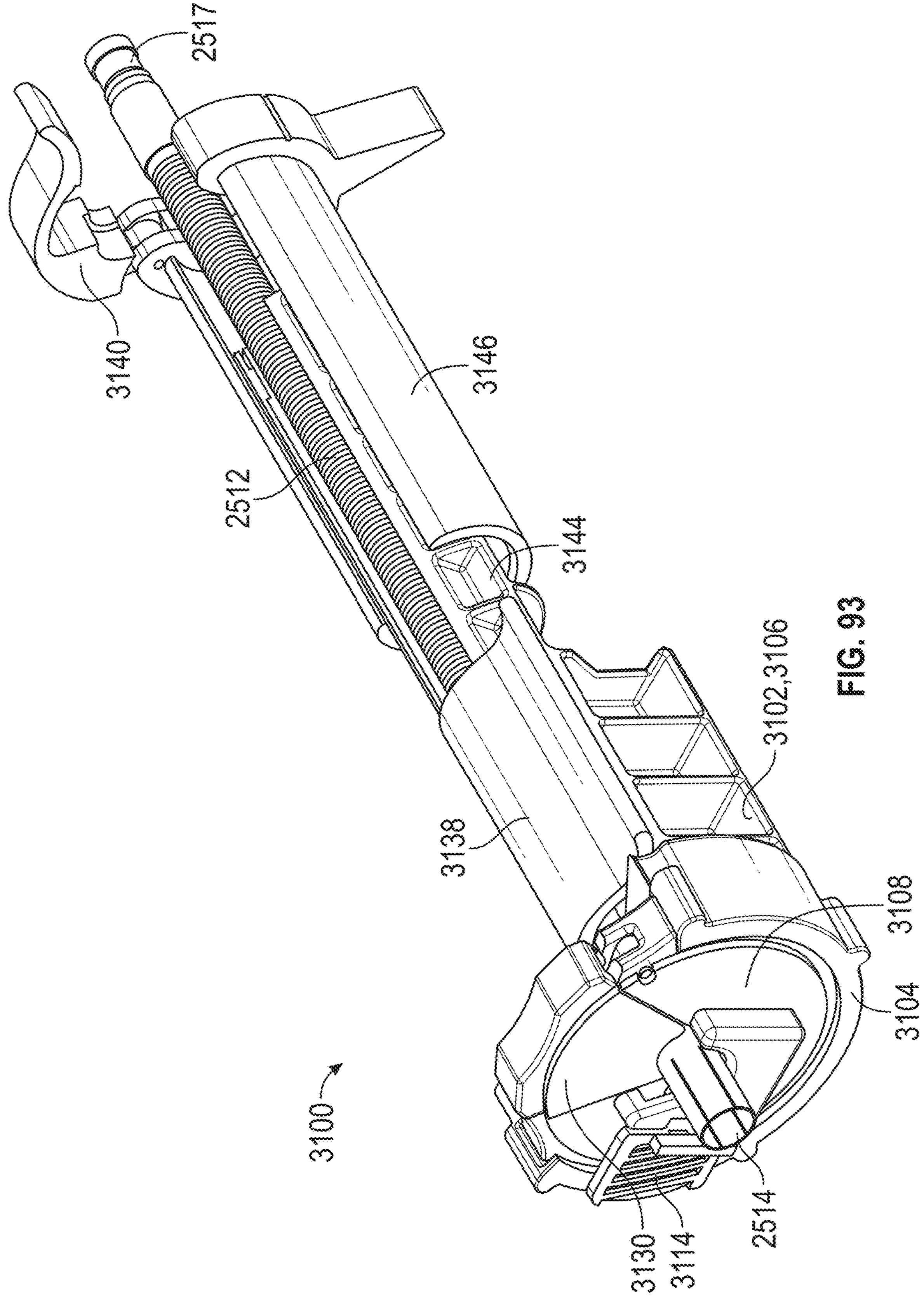
FIG. 93 is a perspective view of the trimming device of FIG. 89 showing a distal end portion of a delivery system disposed within the device and the second clamp member in the open position.

Referring to FIG. 93, the trimming device 3100 can comprise a first clamp member 3138 and first alignment feature (not shown) similar to clamp member 3030 and alignment feature 3036 described previously. Trimming device 3100 can further comprise a second clamp member 3140 positioned at the proximal end portion 3142 of the housing 3102. The second clamp member 3140 can be pivotably coupled to the support extension 3106 (such as via one or more hinges) and can be movable between an open position (FIG. 93) and a closed position (FIG. 89). The second clamp member 3140 can be configured to engage the connector 2517 to prevent movement of the capsule 2512 relative to the trimming device 3100. In some examples, the second clamp member 3140 can comprise a groove or recess sized to retain the connector 2517, in some examples, the second clamp member 3140 can comprise a gripper member configured to frictionally engage an outer surface of the connector 2517 and/or an outer surface of the capsule 2512.

Referring to FIG. 89, the support extension 3106 of the housing 3102 can comprise a first portion 3144 and a second portion 3146 that are movable relative to each other in a telescoping manner such that the overall length of the support extension 3106 is adjustable.

This advantageously allows the second clamp member 3140 to be positioned such that it aligns with the connector 2517 of the capsule 2512 (or with a selected location on the capsule 2512). Additionally, as the capsule 2512 can become longitudinally compressed during the loading process, it is advantageous to be able to adjust the length of the housing 3102 to ensure that the second clamp member 3140 engages the connector 2517 to prevent or mitigate unintended translation of the capsule 2512 within the trimming device 3100.

As shown in FIG. 91, trimming device 3100 can comprise a ratchet and pawl mechanism configured to allow the rotatable member 3108 to rotate only in a first direction (e.g., counterclockwise in the orientation shown in FIG. 91) while preventing rotation in a second direction (e.g., clockwise in the orientation shown in FIG. 91). The rotatable member 3108 can comprise a plurality of teeth 3148 disposed in a circular pattern on the rotatable member 3108, and the main body 3104 of the housing 3102 can comprise a pawl 3150 having an end portion configured to engage the teeth 3148. The teeth 3148 can be angled such that the pawl 3150 can slide along the teeth to allow rotation of the rotatable member 3108 in a first direction but prevent rotation of the rotatable member in a second direction via engagement of a respective tooth 3148 with the pawl 3150.

In use, the capsule 2512 can be disposed within the trimming device 3100 and the first clamp member 3138 can be actuated from the open position to the closed position (FIG. 89) to retain the capsule 2512 in position and position the capsule such that the cutting location is aligned with a cutting edge of the blade 3112. The second portion 3146 of the support extension 3106 can be actuated relative to the first portion 3144 (e.g., by sliding) to align the second clamp member 3140 with the connector 2517 of the capsule 2512. The second clamp member 3140 can be actuated to the closed position (see e.g., FIG. 89) to prevent translation of the capsule 2512 relative to the trimming device 3100. So aligned, the door member 3130 can be pivoted from the open position (FIG. 90) to the closed position (FIG. 89). The detent 3132 can engage the opening 3134 to retain the door member 3130 in the closed position.

The actuator member 3114 can then be actuated from the first/locked position to the second/unlocked position, thereby moving the blade holder 3110 (and thus the blade 3112) into the use position, inserting a point 3118 of the blade 3112 through the wall of the capsule 2512. The rotatable member 3108 can then be rotated 360 degrees to cut circumferentially through the capsule 2512 and remove the tabs 2514. The positioning of the blade 3112 as determined by the movement of the actuator member 3114 allows the user to cut through the capsule 2512 wall without damaging any interior components housed within the capsule. This configuration advantageously allows a single user to easily trim the tabs 2514 from the capsule, for example, by positioning the capsule 2512 within the trimming device 3100 and rotating the rotatable member 3108. Further, this configuration advantageously allows the tabs 2514 to be removed with a single 360-degree rotation of the rotatable member 3108, thus expediting the process and avoiding the need for further trimming.

Figure 96:
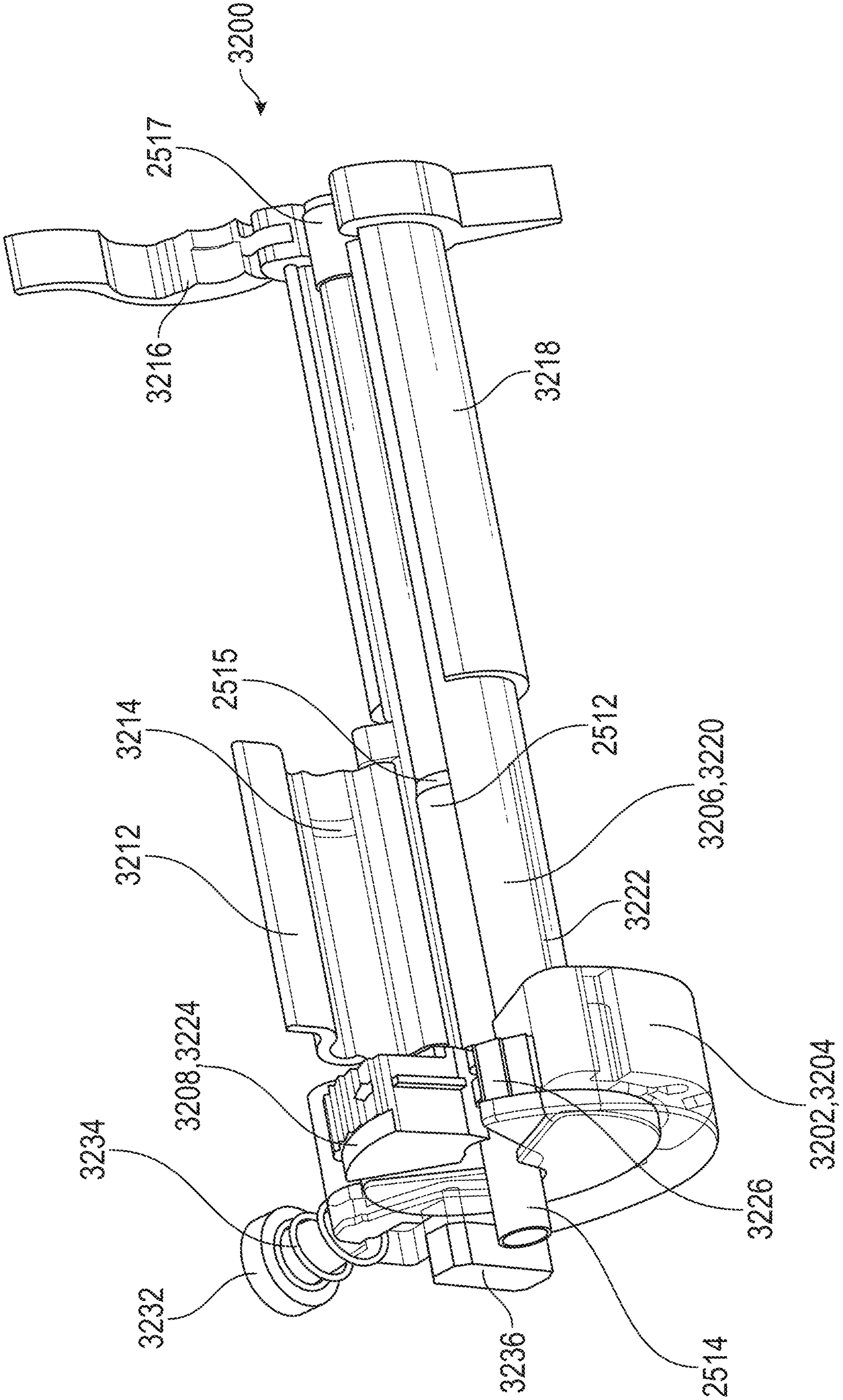
FIG. 96 is a perspective view of a trimming device, according to another example, showing a distal end portion of a delivery system disposed within the trimming device.
Figure 97:
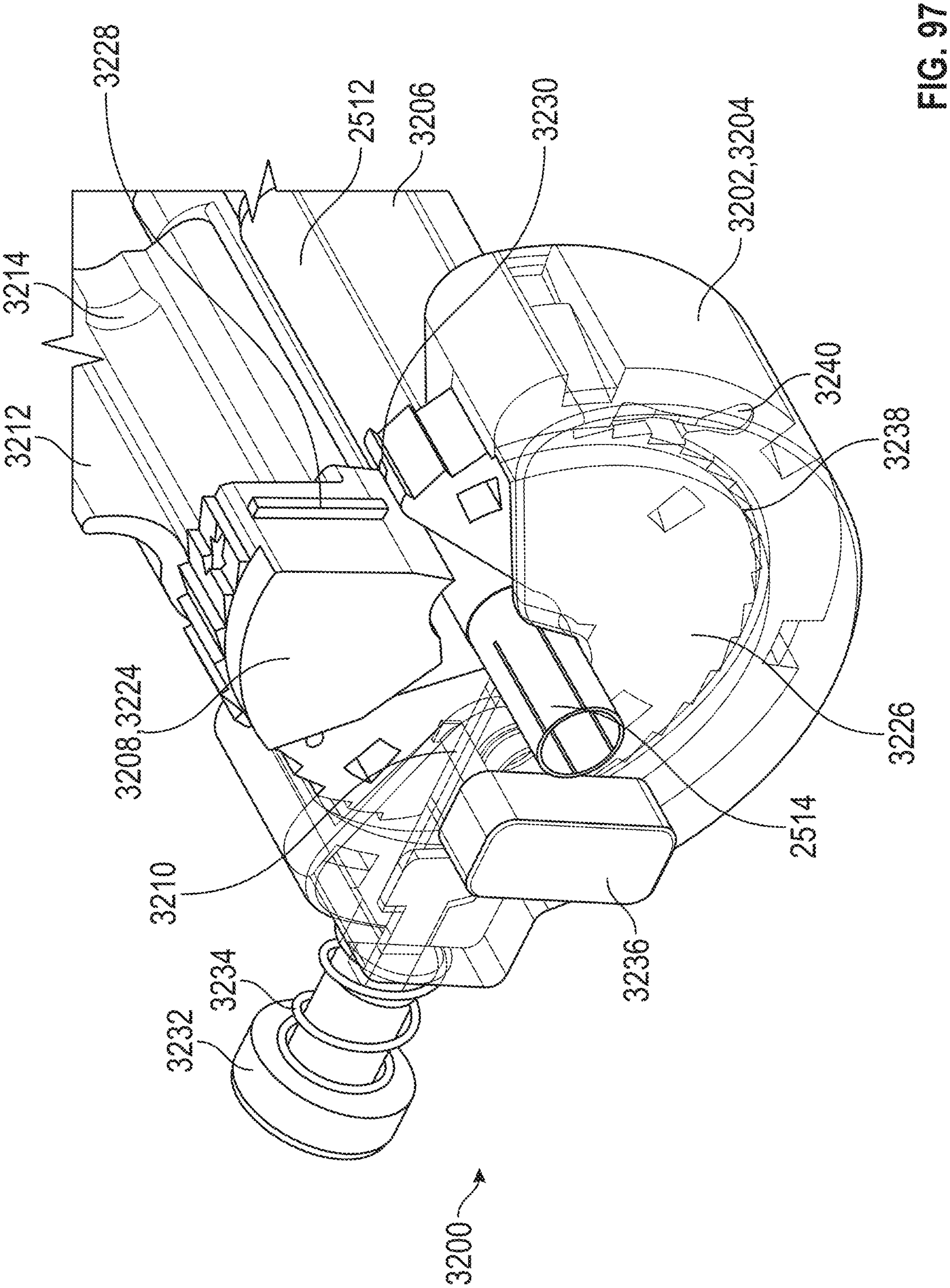
FIG. 97 is a perspective view of a distal end portion of the trimming device of FIG. 96 showing a distal end portion of a delivery system disposed within the trimming device and showing the door member in the open position.

FIGS. 96-97 illustrate another example of a trimming device 3200. Trimming device 3200 can be similar to trimming devices 3000 and 3100 described previously except where indicated otherwise. That is, trimming device 3200 can generally comprise a housing 3202 including a main body 3204 and a support extension 3206, a rotatable member 3208, and a blade holder 3210 (FIG. 97). It should be noted that any of the features described herein for trimming device 3200 can be adapted for use with trimming devices 3000 and/or 3100, and vice versa.

Trimming device 3200 can further comprise a first clamp member 3212 having a first alignment feature 3214 (similar to clamp member 3030 and alignment feature 3036 described previously) and a second clamp member 3216 coupled to a second end portion 3218 of the housing 3102, which is movable in a telescoping manner relative to a first portion 3220 such that the overall length of the support extension 3206 is adjustable.

Referring to FIG. 96, the first portion 3220 of the support extension 3206 can comprise a linearly extending recess 3222. The first clamp member 3212 can comprise a corresponding linear projection extending along an inner surface of the clamp member 3213. When the clamp member 3212 is in the closed position, the projection can be disposed within the recess 3222 to prevent inadvertent opening of the first clamp member 3212. The first clamp member 3212 can be opened by applying a radially-outwardly directed force (relative to a longitudinal axis of the trimming device 3200) to the clamp member 3212 to remove the projection from the recess 3222 prior to opening the clamp member 3212.

The rotatable member 3208 can comprise a door member 3224 that has a sliding fit/snap fit/press fit configuration with a main body 3226 of the rotatable member 3208. For example, as shown in FIG. 97, the door member 3224 can comprise a linear projection 3228 configured to be received in a slot 3230 of the main body 3226.

The trimming device 3200 includes an actuator member 3232, such as a button, that allows the position of the blade holder 3210 to be determined manually, such as by a user. Actuator member 3232 can be movable between a first position wherein the blade holder is in a safety/non-cutting/locked/retracted position (FIG. 97) to a second position wherein the blade holder 3210 (and therefore a blade disposed within the blade holder) is in a cutting/extended/use position. When in the use position, a cutting tip and cutting edge of the blade extend into a central bore of the rotatable member 3208 such that when a capsule 2512 is disposed in the central bore a cutting edge of the blade pierces the capsule. As shown in FIGS. 96-97, the actuator member 3232 can comprise a biasing member 3234 (such as a spring) configured to bias the actuator member 3232 into the first position.

In some examples, such as the illustrated example, the actuator member 3232 can be a first actuator member and the trimming device 3200 can further comprise a second actuator member 3236. Actuator member 3236 can be configured to retract the blade holder 3210 (and therefore the blade) from the use position to the retracted position. The second actuator member 3236 can be, for example, a button, knob, sliding member, etc. In some examples, the second actuator member 3236 can relieve a catch, allowing the blade holder 3210 to lift out of the use position.

As shown in FIG. 97, trimming device 3200 can comprise a ratchet and pawl mechanism configured to allow the rotatable member 3208 to rotate only in a first direction (e.g., counterclockwise in the orientation shown in FIG. 97) while preventing rotation in a second direction (e.g., clockwise in the orientation shown in FIG. 97). The rotatable member 3208 can comprise a plurality of teeth 3238 arranged around an outer circumference of the rotatable member 3208, and the main body 3204 of the housing 3202 can comprise a pawl 3240 having an end portion configured to engage the teeth. The teeth 3238 can be angled such that the pawl 3240 can slide along the teeth to allow rotation of the rotatable member in a first direction, but prevent rotation of the rotatable member 3208 in a second direction via engagement of a respective tooth 3238 with the pawl 3240.

In use, a user can position the capsule 2512 within the trimming device 3200 such that the locating feature 2515 of the capsule 2512 aligns with the first alignment feature 3214 and the connector 2517 aligns with the second clamp member 3216, as shown in FIG. 96. The first clamp member 3212 can then be actuated from the open position (FIG. 96) to the closed position to retain the capsule 2512 in position and position the capsule such that the cutting location is aligned with a cutting edge of the blade. The second clamp member 3216 can be actuated to the closed position to prevent translation of the capsule 2512 relative to the trimming device 3200. So aligned, the first actuator member 3232 can be actuated, thereby moving the blade holder 3210 (and thus the blade) into the use position, inserting a point of the blade through the wall of the capsule 2512. The rotatable member 3208 can be rotated 360 degrees to cut circumferentially through the capsule 2512 and remove the tabs 2514. The positioning of the blade as determined by the movement of the actuator member 3232 allows the user to cut through the capsule 2512 wall without damaging any interior components housed within the capsule. Once the tabs 2514 have been removed, the blade holder 3210 can be retracted using the second actuator member 3236. This configuration advantageously allows a single user to easily trim the tabs 2514 from the capsule, for example, by positioning the capsule 2512 within the trimming device 3200 and rotating the rotatable member 3208. Further, this configuration advantageously allows the tabs 2514 to be removed with a single 360-degree rotation of the rotatable member 3208, thus expediting the process and avoiding the need for further trimming.

Figure 98:
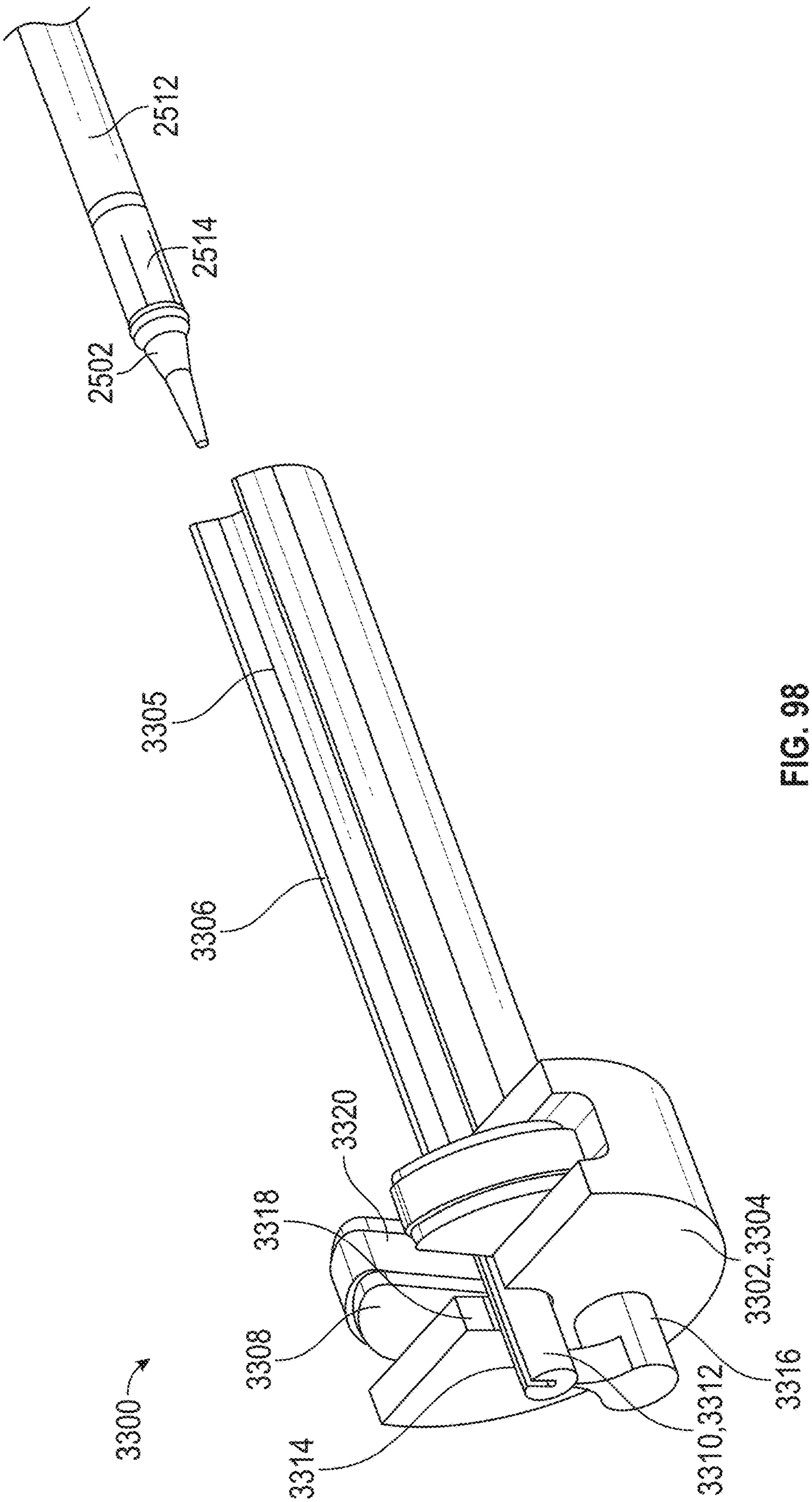
FIG. 98 is a perspective view of a trimming device, according to another example, with a distal end portion of a delivery system shown adjacent to the device.
Figure 99:
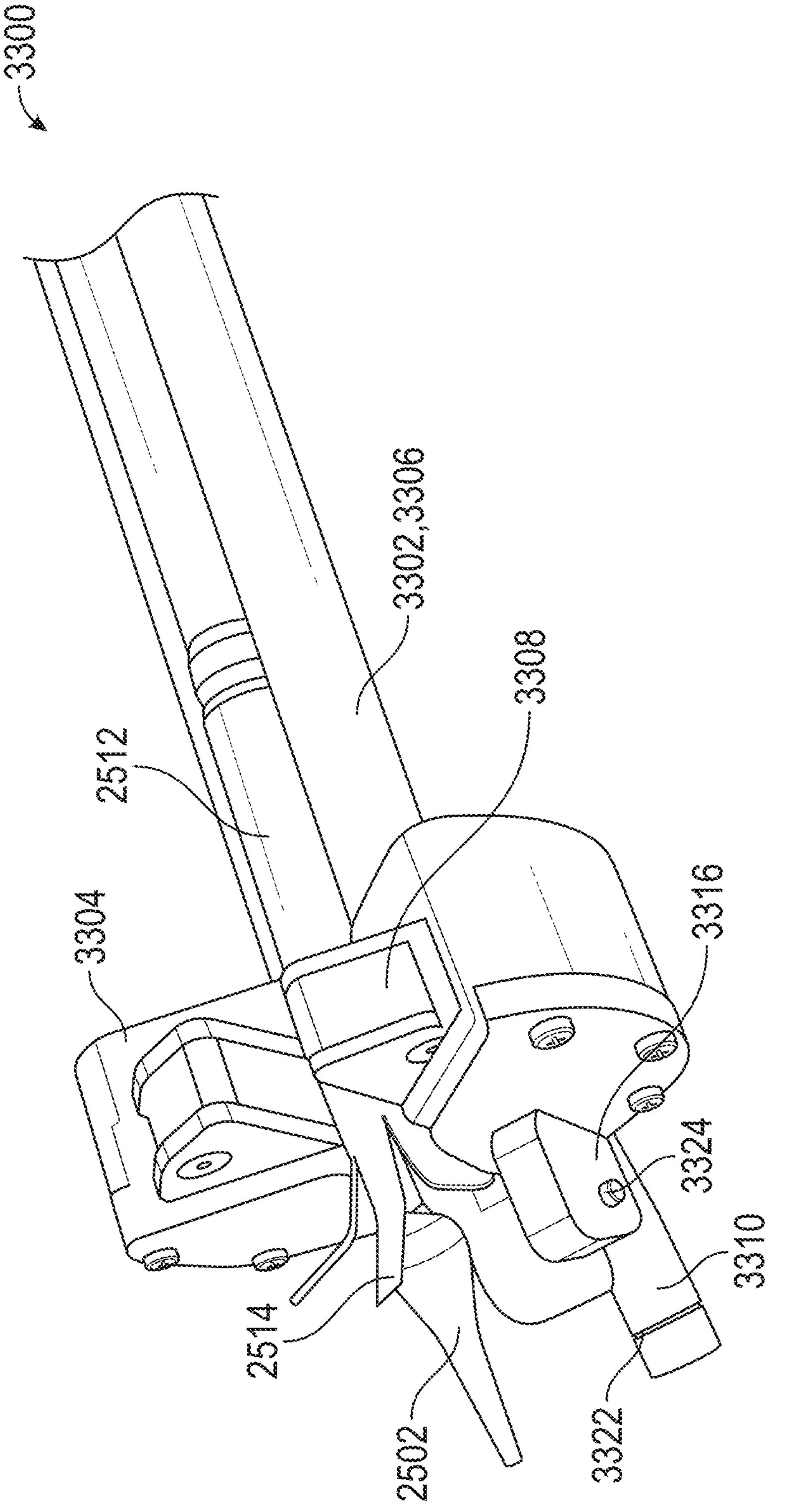
FIGS. 99-100 are various views of the trimming device of FIG. 98 with a distal end portion of a delivery system disposed within the device.
Figure 100:
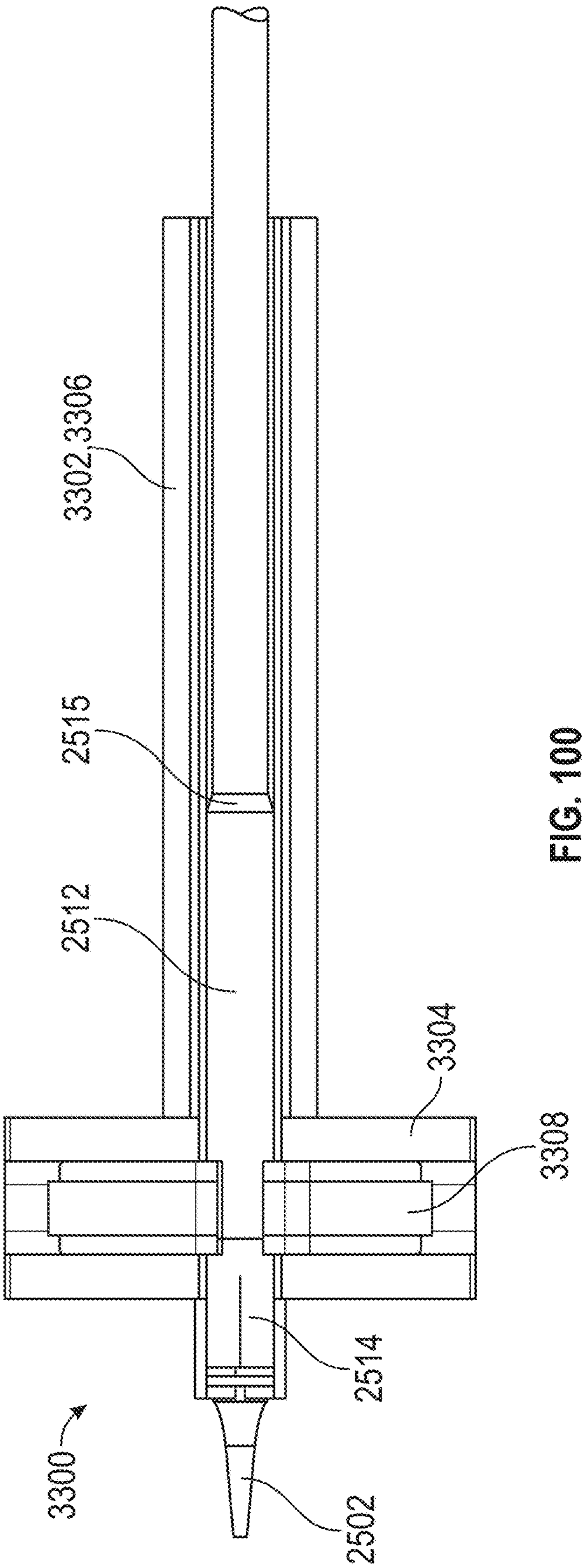

FIGS. 98-100 illustrate another example of a trimming device 3300. Trimming device 3300 can be similar to trimming devices 3000, 3100, and 3200 described previously except where indicated otherwise. That is, trimming device 3300 can generally comprise a housing 3302 including a main body 3304 and a support extension 3306 including a central recess 3305, a rotatable member 3308, and a blade holder (not shown) coupled to the rotatable member 3308, the blade holder configured to hold a blade. It should be noted that any of the features described herein for trimming device 3300 can be adapted for use with any of trimming devices 3000, 3100, and/or 3200, and vice versa.

Trimming device 3300 can further comprise a guide member 3310 coupled to the main body 3304 of the housing 3302. The guide member 3310 can comprise a cylindrical main body 3312 including a longitudinally extending central channel 3314. The channel 3314 can be sized to receive a first shaft of the delivery system, such as first shaft 2504 described previously.

The guide member 3310 can be coupled to the main body 3304 of the housing 3302 via a arm/holder member 3316 that positions the guide member 3310 within a central recess 3318 of the main body 3304 and a central recess 3320 of the rotatable member 3308. The holder member 3316 can position the guide member 3310 within the recesses 3318, 3320 such that the guide member 3310 is suspended within the recesses 3318, 3320 and does not contact the main body 3304 and/or rotatable member 3308. The distance between the guide member 3310 and the main body 3304 and/or rotatable member 3308 can be sized to allow the wall of the capsule 2512 to be inserted between the guide member 3310 and the main body 3304 and/or rotatable member 3308. The capsule 2512 can be advanced over the guide member 3310 such that a portion of the guide member 3310 is disposed within the capsule 2512, similar to the use of trimmer guide member 2478. The guide member 3310 can prevent or mitigate damage to interior components housed within the capsule 2512 during the cutting process.

In some examples, the guide member 3310 can comprise a circumferentially extending annular notch or groove 3322 (FIG. 99), similar to groove 2490 of trimmer guide member 2478 described previously. The groove 3322 can be aligned with the cutting edge of the blade (not shown) such that the cutting edge of the blade is disposed within the groove 3322. In some examples, such as shown in FIG. 99, the guide member 3310 can be pivotably coupled to the holder member 3316, such as using a pivot pin or fastener 3324. Such a configuration allows the guide member 3310 to be movable between a use position (wherein the guide member is disposed within the recesses 3318, 3320) and a non-use position (see e.g., FIG. 99).

In use, the guide member 3310 can be moved to the use position and a user can position the capsule 2512 within the trimming device 3300 such that the first shaft 2504 of the delivery apparatus is disposed within the channel 3314 of the guide member 3310. The user can position the selected cutting location of the capsule 2512 such that it is aligned with the groove 3322 of the guide member 3310 and therefore with the cutting edge of the blade. So aligned, the rotatable member 3308 can be rotated 360 degrees to cut circumferentially through the capsule 2512 and remove the tabs 2514. The positioning of the blade as restrained by the groove 3322 allows the user to cut through the capsule 2512 wall without damaging any interior components housed within the capsule. This configuration advantageously allows a single user to easily trim the tabs 2514 from the capsule, for example, by positioning the capsule 2512 within the trimming device 3300 and rotating the rotatable member 3308. Further, this configuration advantageously allows the tabs 2514 to be removed with a single 360-degree rotation of the rotatable member 3308, thus expediting the process and avoiding the need for further trimming.

Figure 101:
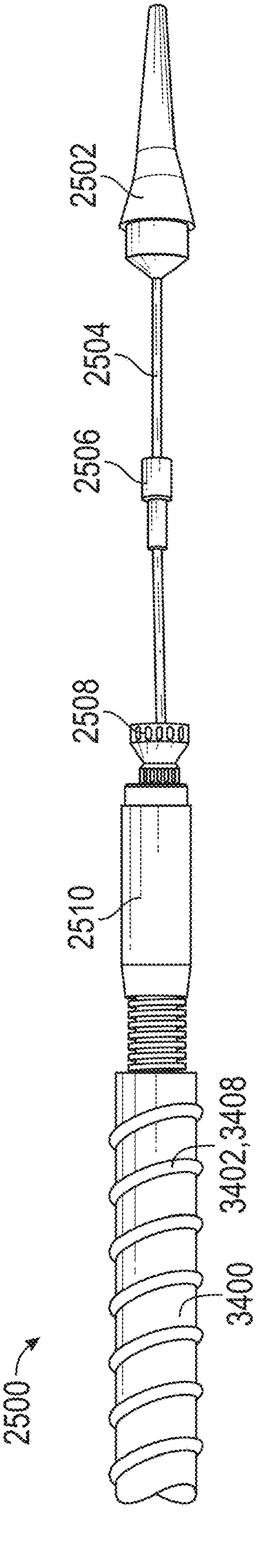
FIG. 101 is a side view of a distal end portion of a delivery system, according to one example.
Figure 102:
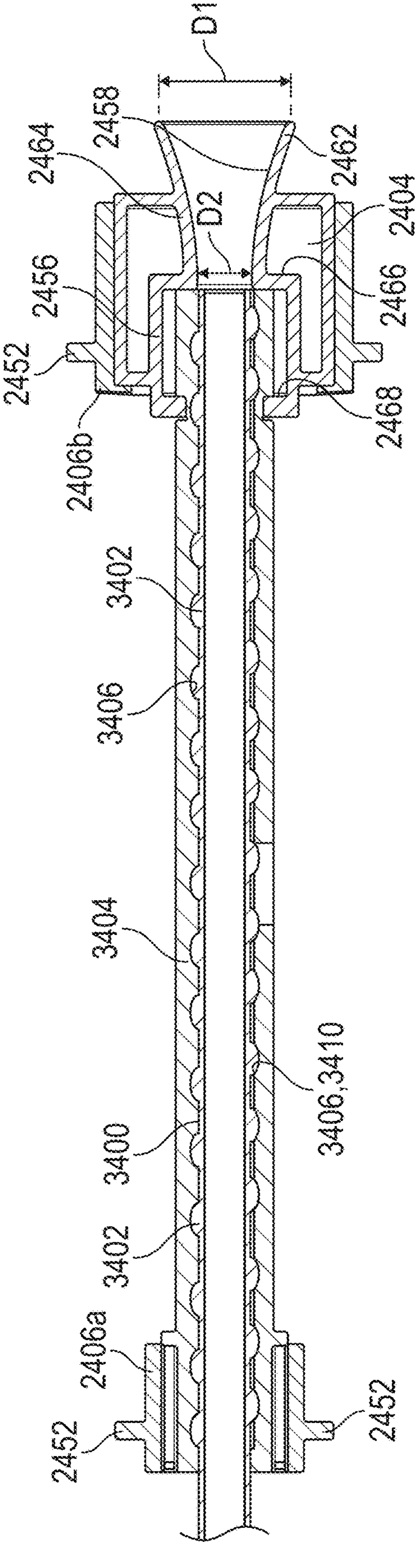
FIG. 102 is a cross-sectional side view of a distal end portion of a shaft of the delivery apparatus of FIG. 101 with an exemplary loading assembly disposed thereon.

Referring to FIGS. 101-102, in some examples, in lieu of capsule 2512 including tabs 2514 the delivery system 2500 can comprise a capsule 3400, which does not include tabs. In such examples, the capsule 3400 can include one or more engagement features 3402 (i.e., first engagement features) configured to engage one or more corresponding engagement features 3406 (i.e., second engagement features) of the support tube 3404. Support tube 3404 can be similar to support tube 2402 described previously except that support tube 3404 includes the second engagement features 3406.

When the capsule 3400 and support tube 3404 are assembled together, the engagement features 3402, 3406 interlock to form a rigid tube structure. Such a configuration supports the flexible capsule 3400 during the loading process, thereby eliminating the need for tabs (which hold the capsule in a rigid position as described previously with respect to FIGS. 53-58). This advantageously allows a single operator to load a prosthetic valve (e.g., valve 1000 described previously) into the loading assembly 2400, including support tube 3404 in lieu of support tube 2402.

Referring to FIG. 101, in some examples, the first engagement feature 3402 can comprise one or more protrusions 3408. In some examples, the protrusions 3408 can be formed by embedding one or more structural members within the wall of the capsule 3400. The capsule 3400 can comprise a plurality of layers (e.g., a liner, PTFE wrap, etc.), and the structural member(s) can be sandwiched between these layers and can have a thickness such that the shape of the structural member forms a protrusion on the outer surface of the capsule 3400. For example, the structural member can be a thick wire embedded within the wall of the capsule 3400. In the illustrated example, the protrusion 3400 has a helical/spiral shape extending around an outer circumference of the capsule, however, in other examples the protrusion(s) can have any of various shapes (e.g., a plurality of discrete rings). In other examples, the protrusion(s) 3408 can be disposed on an outer surface of the capsule 3400, for example, as an overmolded plastic shape.

As shown in FIG. 102, the second engagement feature 3406 can be, for example, one or more recesses 3410 in an inner surface of the support tube 3404. The recess(es) 3410 can have a shape corresponding to the shape of the protrusion, for example, a helix/spiral in the illustrated example. As described previously, the support tube 3404 can comprise a first lateral side portion 2403*a* and a second lateral side portion 2403*b*. To assemble the support tube 3404 over the capsule 3400 the first and second engagement features 3402, 3406 can be aligned with one another prior to securing the first and second side portions 2403 to one another (e.g., using clamps 2406). However, in other examples, the support tube 3404 can be a unitary construction that can be laterally advanced over the capsule, e.g., by threading the recess 3410 onto the protrusion 3408 and twisting the support tube 3404 to advance the support tube 3404 over the capsule 3400.

The engagement of the protrusion 3408 with the recess 3410 maximizes the contact between the capsule 3400 and the loading tube 3404 thereby advantageously distributing the loading force (e.g., the force applied to the capsule when loading a prosthetic valve) along the length of the capsule, avoiding damage to the capsule material.

Figure 103:
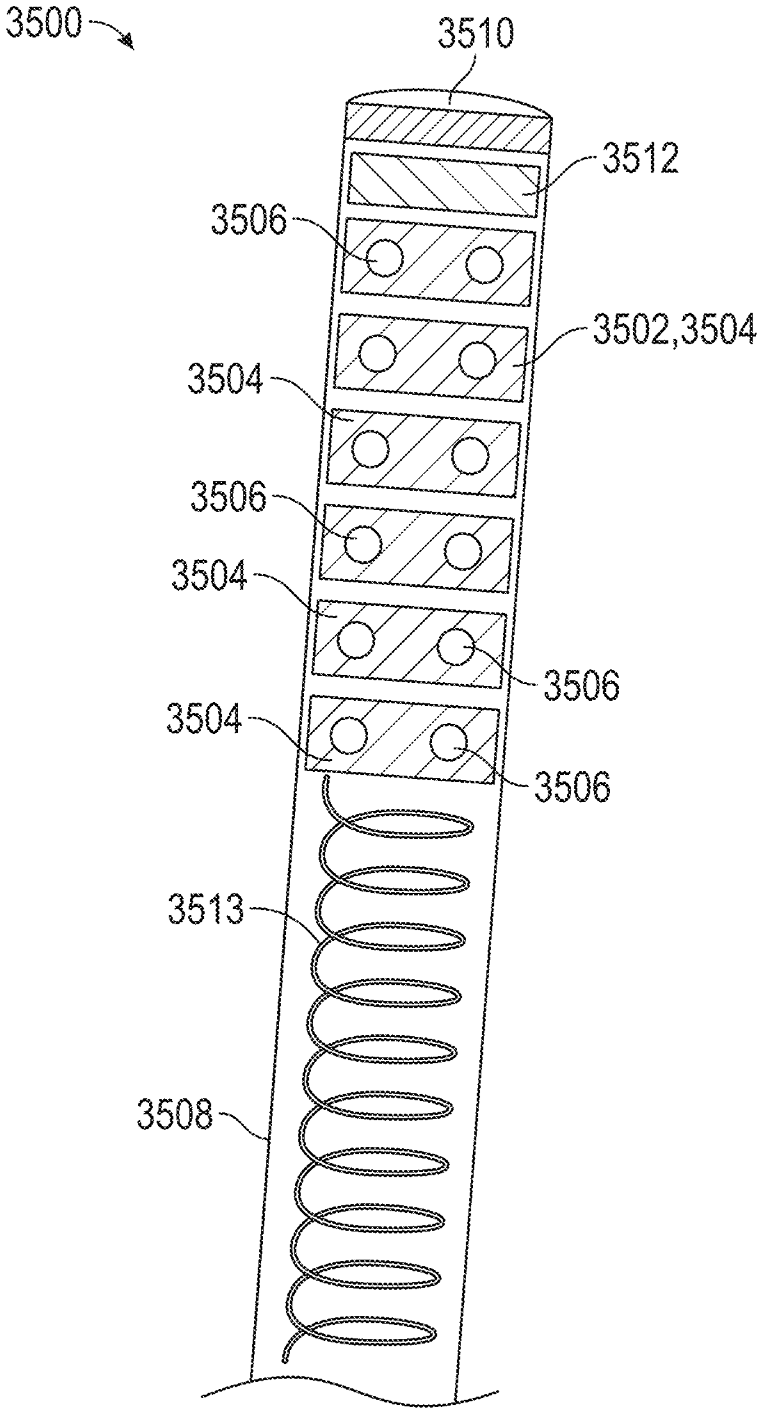
FIG. 103 is a perspective view of a shaft of an exemplary delivery system, with an outer wall of the shaft shown transparently.
Figure 104B:
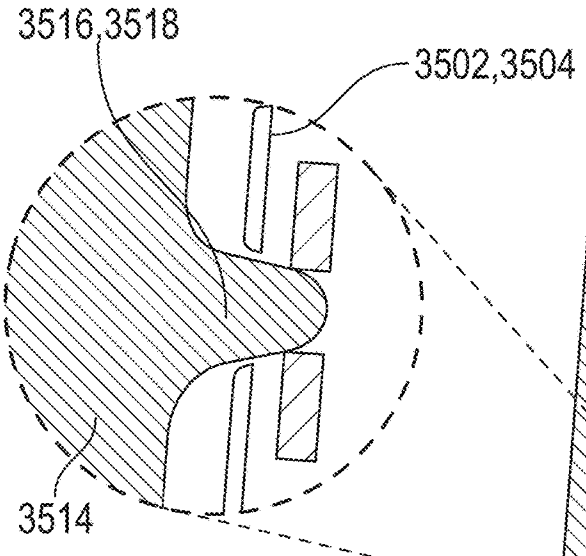
FIG. 104B is an enlarged view of a portion of FIG. 104A showing the structural feature in cross-section.

Referring now to FIGS. 103-104, in some examples, a capsule 3500 can comprise one or more first engagement features 3502, such as structural members 3504 comprising one or more openings/apertures/recesses 3506 that extend into a thickness of the structural member 3504. In some examples, the openings 3506 can extend entirely through the thickness of the structural member, such as shown in FIG. 103. In some examples, the openings 3506 can extend partially through the thickness, such as shown in FIG. 105.

In some examples, such as shown in FIG. 103, the capsule 3500 can comprise a plurality of structural members 3504 configured as loading bands. Each loading band 3504 can be an annular/ring member embedded within the wall 3508 of the capsule 3500 (e.g., sandwiched between the capsule layers). As mentioned, the loading bands 3504 can each comprise one or more openings 3506 extending into the thickness of the loading band. The loading bands 3504 can be configured (e.g., sized and shaped) to maintain the original outer diameter of the capsule 3500. This advantageously allows for the loading bands 3504 to be added without increasing the diameter of any components that will be advanced into the subject's vasculature. In some examples, the loading bands 3504 can comprise metal (e.g., Nitinol, titanium, stainless steel, etc.) and/or rigid plastic (e.g., PEEK, polycarbonate, etc.).

In illustrated example, the loading bands 3504 can be separate components embedded within the capsule wall 3508 such that they are spaced apart from one another in a longitudinal direction. This allows the capsule 3500 to maintain its flexibility, which advantageously allows the capsule 3500 to be advanced through the curvatures of the subject's vasculature. In some examples, the loading bands 3504 can have an interlocking configuration such that when a loading force is applied during the loading process the loading bands 3504 can contact/engage/overlap one another to advantageously distribute the loading force (e.g., the force applied to the capsule when loading a prosthetic valve) directly from one loading band to another along the length of the capsule 3500, avoiding damage to the capsule material. For example, the loading bands 3504 can have stepped/chamfered/mitered edge portions that allow a portion of a selected loading band to be received within a portion of an adjacent loading band, e.g., in a shiplap or tongue-in-groove configuration.

In some examples, the capsule can further comprise a polymer leading edge 3510, and/or a marker band 3512 disposed adjacent the leading edge 3510. The marker band 3512 can comprise, for example, a radiopaque marker secured to a commissure of the prosthetic heart valve to allow for visualization of the commissure under imaging (for example, fluoroscopy) during the implantation procedure. The capsule 3500 can further comprise a support structure 3513, such as an embedded coil. In some examples, the support structure can be a stainless steel coil.

Figure 104A:
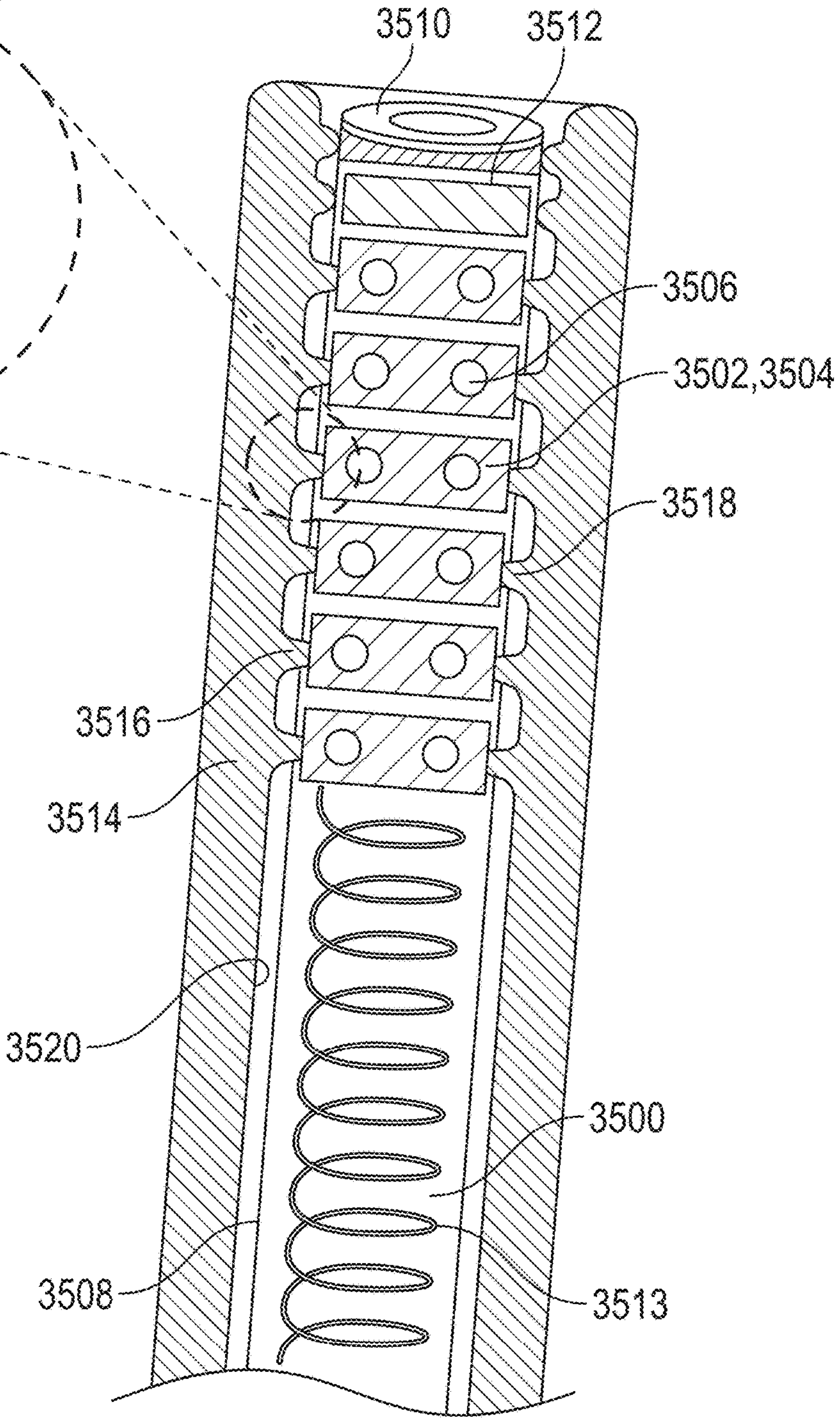
FIG. 104A is a perspective view of the shaft of FIG. 103 with an exemplary support tube disposed thereon, with the support tube shown in cross-section.
Figure 105:
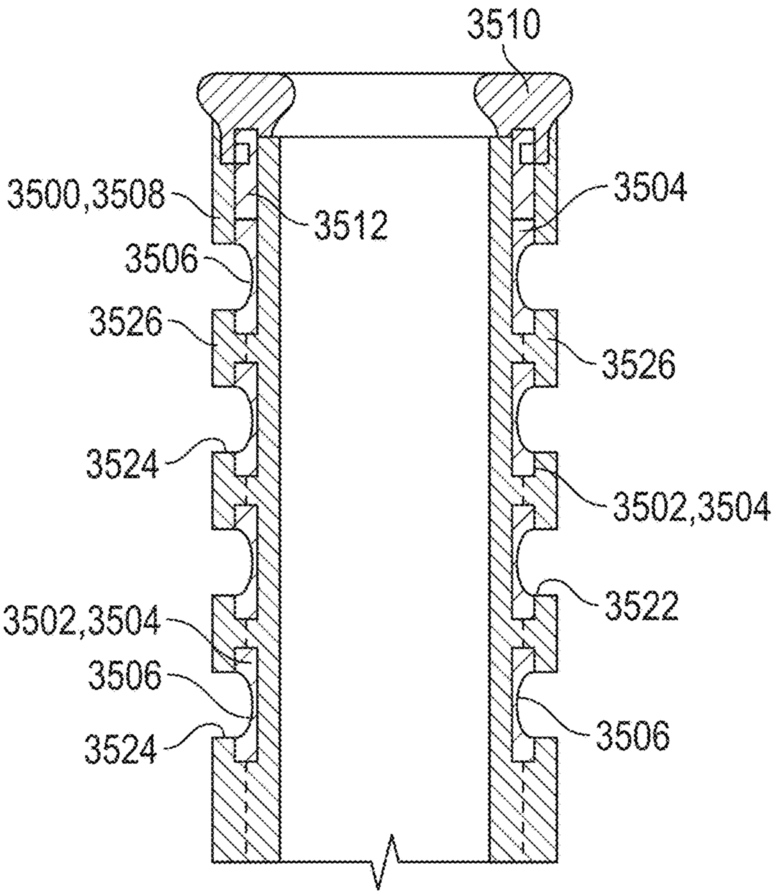
FIG. 105 is a cross-sectional side elevation view of a shaft of an exemplary delivery system.

Referring to FIG. 104A, the support tube 3514 can comprise one or more second engagement features 3516 (also referred to as corresponding engagement elements) configured to engage the first engagement features 3502. The support tube 3514 can be similar to support tube 2402 described previously. In some examples, the one or more second engagement features 3516 can comprise one or more projections/protrusions/nubs 3518 extending from an inner surface 3520 of the support tube 3514. As shown in FIGS. 104A-104B, the one or more projections 3518 of the support tube 3514 can be disposed within the openings 3506 of the structural members/loading bands 3504.

Figure 106A:
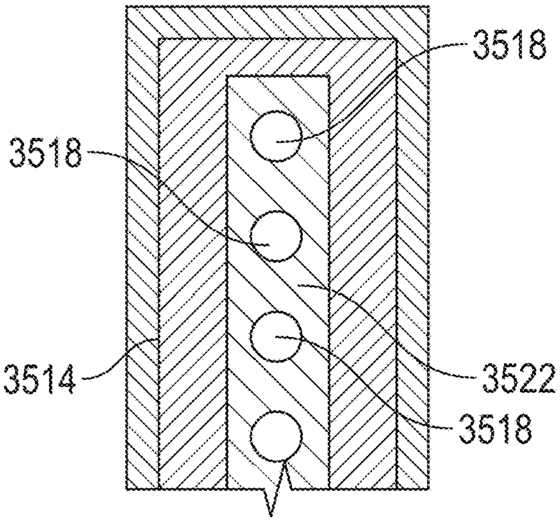
FIGS. 106A-108 are various views of exemplary projections disposed on a shaft of an exemplary delivery system.
Figure 106B:
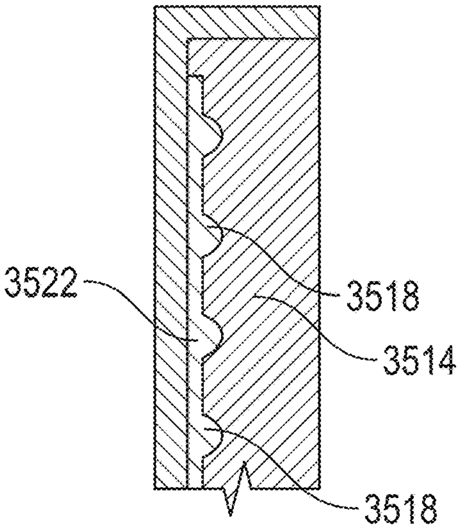

In some examples, the projections 3518 can be formed integrally with the halves of the support tube 3514, e.g., during molding of the support tube 3514. In other examples, the projections 3518 can be formed separately from the support tube 3514 and can be coupled thereto, e.g., using adhesives, welding, and/or mechanical means such as snap-fit, screws, etc. In some examples, such as shown in FIGS. 106A-106B the projections 3518 can be formed integrally as part of an elongated member 3522, which can be coupled to an internal surface 3520 of the support tube 3514. In some examples, the elongated member 3522 and the projections 3518 can comprise metal (e.g., Nitinol, titanium, stainless steel, etc.) and/or rigid plastic (e.g., PEEK, polycarbonate, etc.).

Figure 107A:
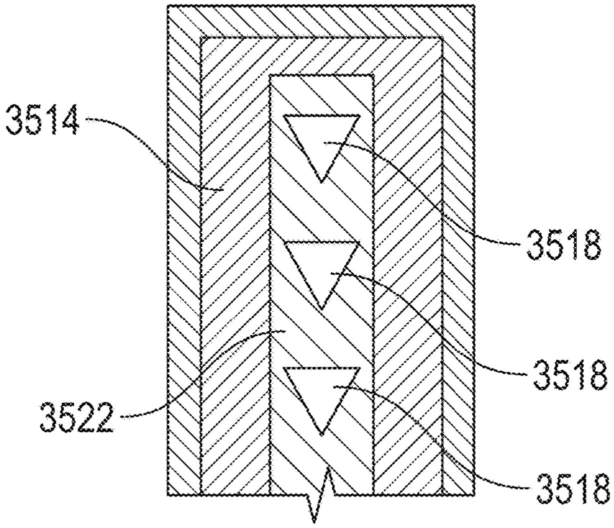
Figure 107B:
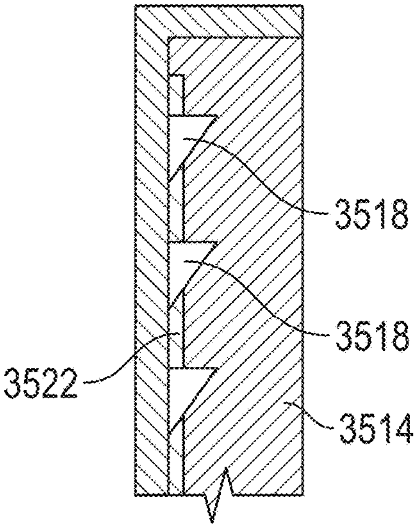
Figure 108:
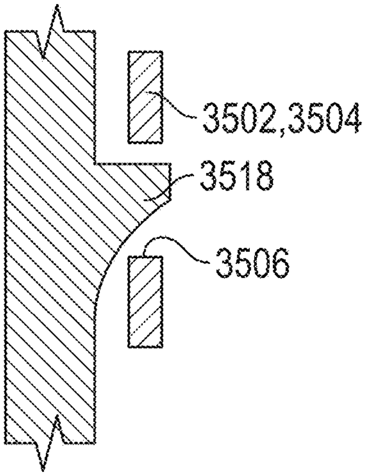
Figure 109:
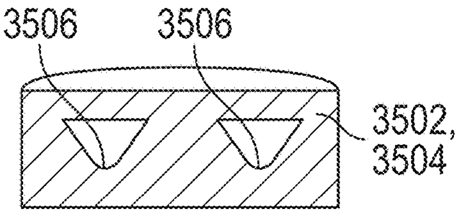
FIG. 109 is a perspective view of a structural member, according to one example.

In some examples, the projections 3518 can have a circular shape in cross-section, (e.g., as shown in FIGS. 106A-106B), and/or a triangular shape in cross-section (e.g., as shown in FIGS. 107A-107B), and/or a semi-circular shape in cross-section (e.g., as shown in FIG. 108). In other examples, the projections 3518 can have any of various shapes in cross-section, for example, square, rectangular, linear, oval, square oval, etc. The openings 3506 in the structural members/loading bands 3504 can be configured to receive the projections, e.g., by having a corresponding shape in cross-section. For example, the openings 3506 in FIG. 109 can receive the projections 3518 shown in FIG. 108.

In some examples, such as shown in FIG. 105, the openings 3506 in the structural members/loading bands 3504 can align with openings 3524 in the outer layer(s) 3526 of the capsule wall 3508. In other examples, a thin (e.g., 0.001 mm) outer layer of the capsule 3500 can extend over the openings 3506 in the structural members/loading bands 3504. In such examples, the corresponding engagement elements 3516 on the support tube 3514 can deform the outer layer into the opening 3506 when disposed in the opening 3506. The corresponding engagement elements 3516 can be configured (e.g., sized and shaped) such that when they are inserted into the openings 3506 and deform the outer layer without puncturing the outer layer.

FIGS. 110-117 illustrate another example of a crimping device 3600. Crimping device 3600 can be similar to crimping device 500 described previously, except that, in lieu of or in addition to retaining ring 544, crimping device 3600 can comprise one or more engagement elements 3608 configured to releasably retain the first and second side portions 3604, 3606 of the housing 3602 together. In some cases, crimping devices wherein the first and second side portions are held together with a retaining ring can split or come apart during the valve loading process, such as at a proximal/loading/inlet end of the device, potentially resulting in damage to the valve or delivery apparatus. The crimping devices disclosed herein, including crimping device 3600, include one or more engagement elements configured to retain the first and second side portions together, particularly at the inlet end portion of the device.

Crimping device 3600 can generally comprise a housing 3602 including a main body 3610 (also referred to as a valve crimping portion) and an extender portion 3612 (also referred to as a driver or actuator coupling portion), an actuator, and a pusher member removably coupled to the actuator. The pusher member can be the same as pusher member 508 described previously, and the actuator can be the same as actuator 506 described previously.

The main body 3610 of the housing 3602 can be similar to housing 108 described previously (e.g., comprising an inner funnel segment 3614 (FIGS. 112-113) and a plurality of ribs 3616), except that the main body 3610 comprises or is coupled to an extender portion 3612 extending from an inlet end of the main body 3610. The extender portion 3612 can be a substantially cylindrical member including an inner threaded surface 3618. An inner surface of the extender portion 3612 can comprise a threaded portion 3618 configured to interface with the threaded portion of the actuator (e.g., threaded portion 530 of actuator 506). The crimping device 3600 can be used to couple a prosthetic valve to a valve retaining member of the delivery apparatus in the manner described previously for crimping device 500.

Figure 110:
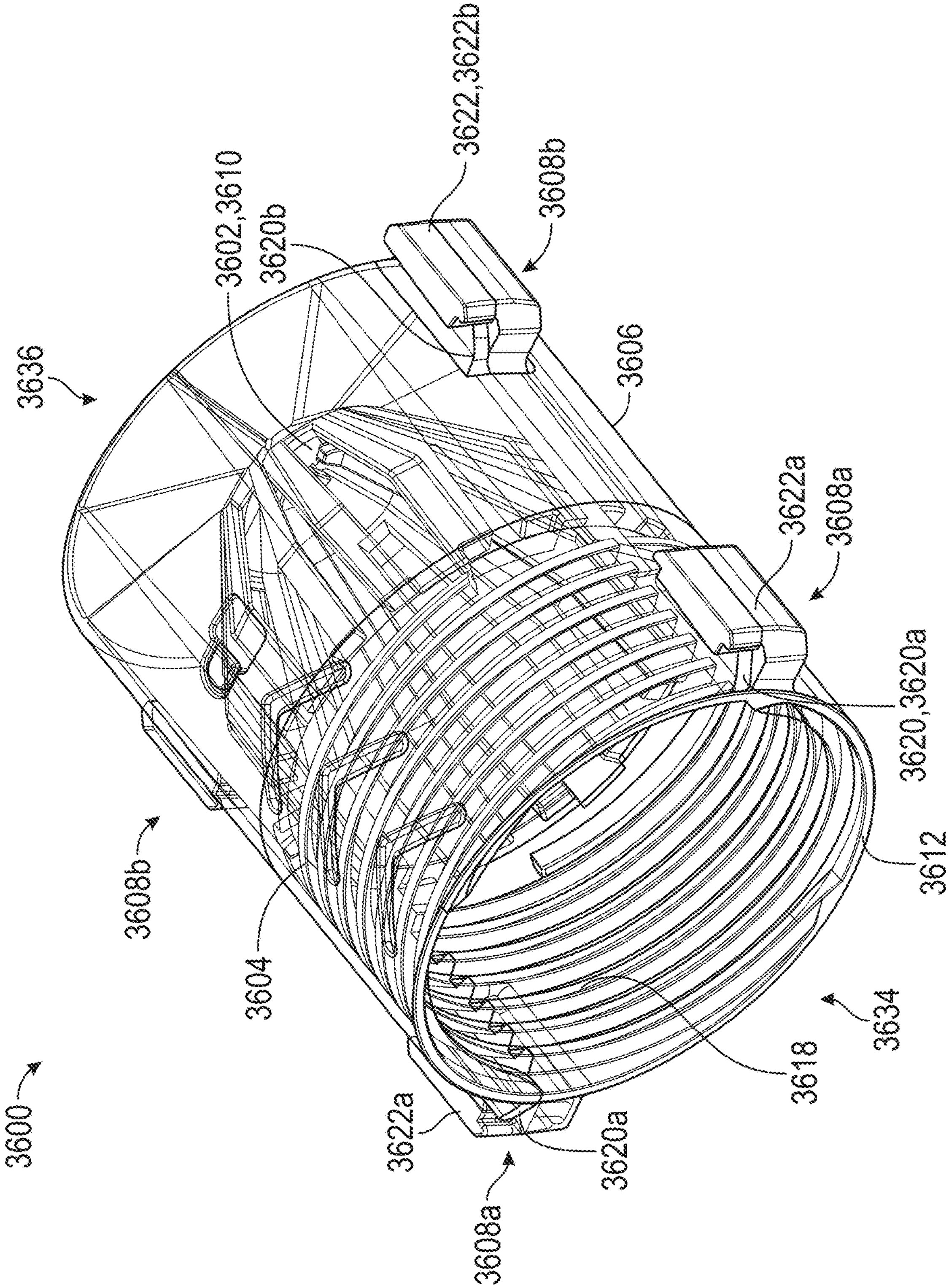
FIG. 110 is a perspective view of another example of a crimping device.

As mentioned, the housing 3602 comprises first and second side portions 3604, 3606 releasably held together via one or more engagement elements 3608. Each engagement element 3608 can comprise a first engagement member 3620 coupled to the first side portion 3604, and a second engagement member 3622 coupled to the second side portion 3606. The first and second engagement members 3620, 3622 can releasably engage one another to prevent separation of the first and second side portions 3604, 3606, as shown in FIG. 110.

Figure 111:
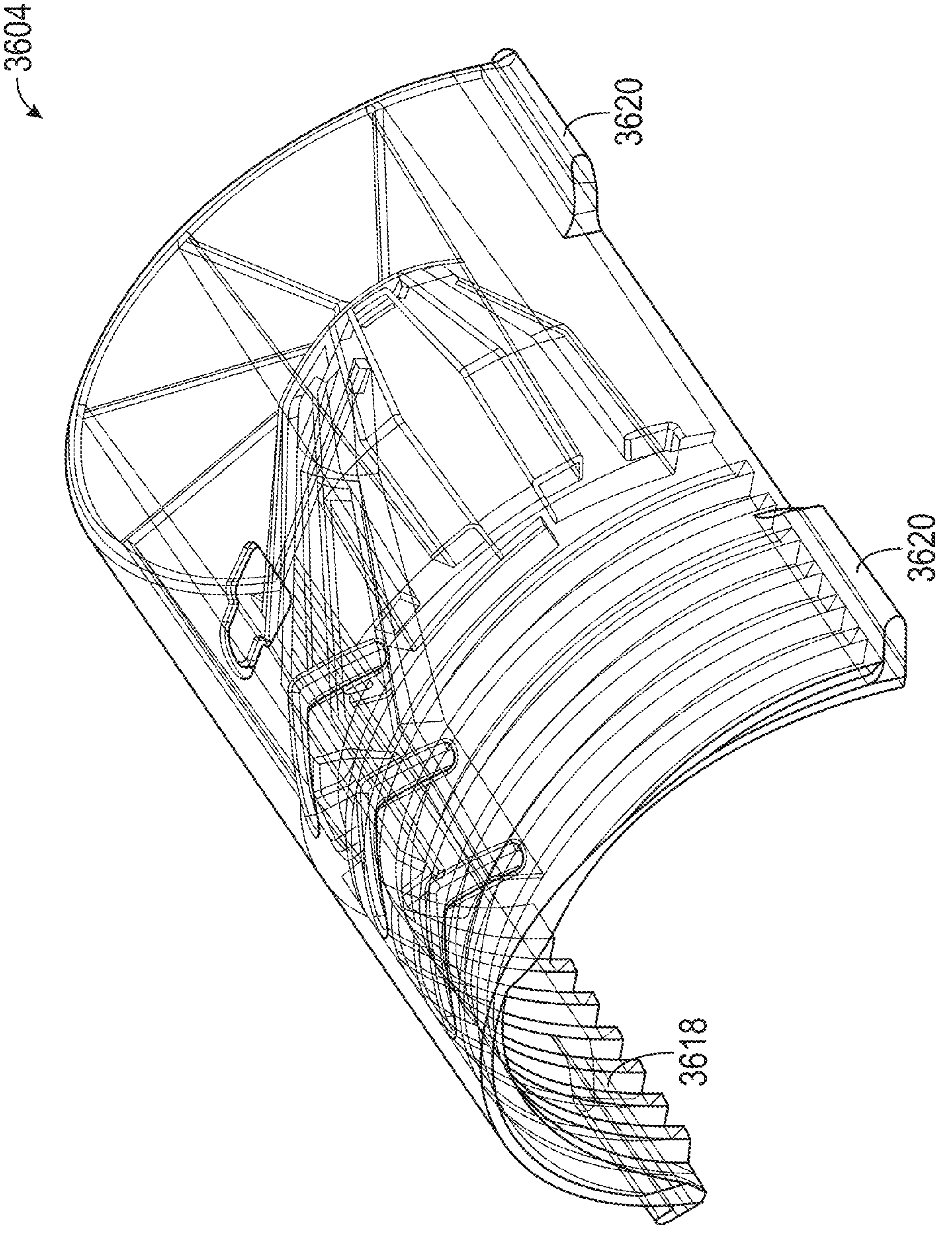
FIG. 111 is a perspective view of a side portion of the crimping device of FIG. 110.
Figure 112:
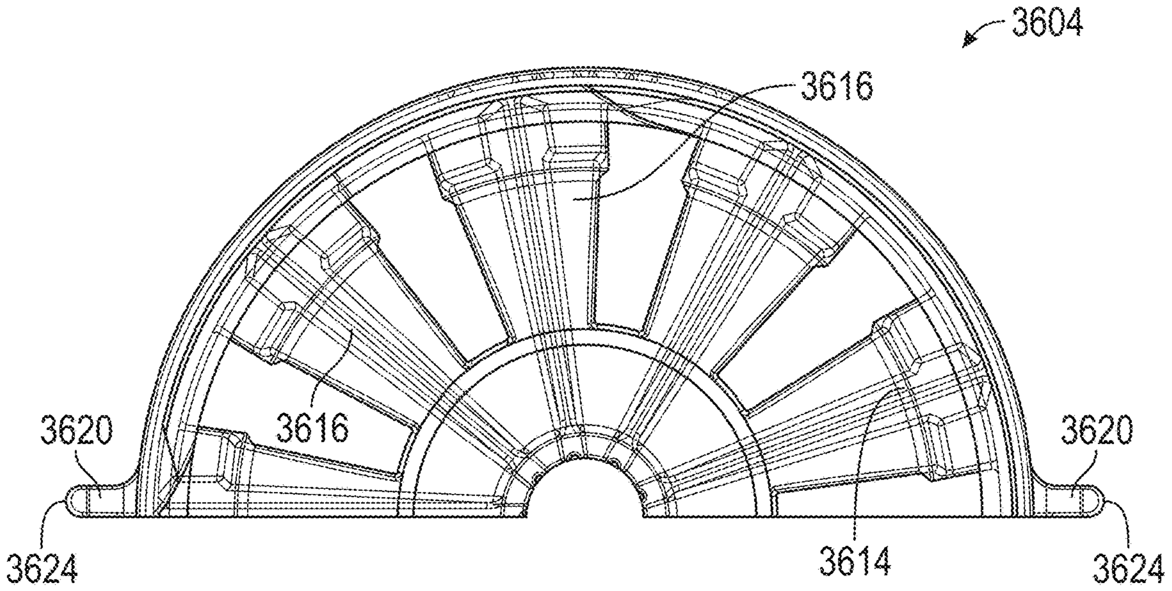
FIG. 112 is a front view of a side portion of the crimping device of FIG. 110.
Figure 113:
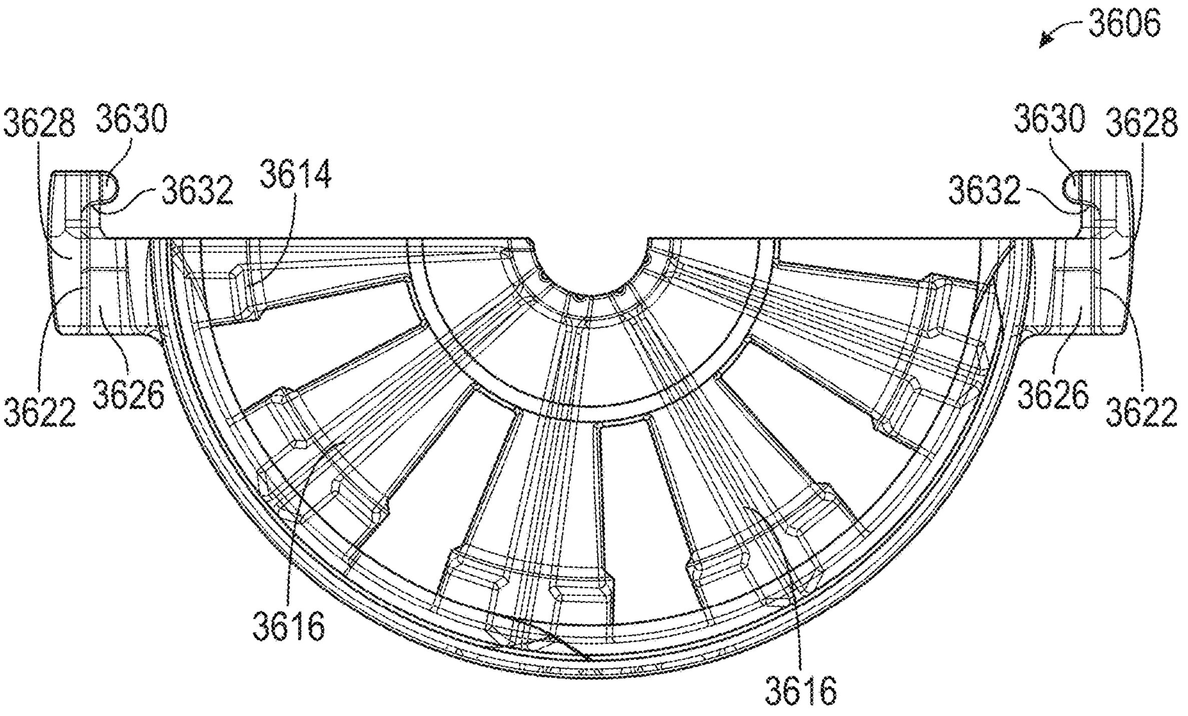
FIG. 113 is a front view of the other side portion of the crimping device of FIG. 110.

Referring to FIGS. 111-112, in some examples, the first engagement members 3620 can be projections/protrusions/flanges extending laterally from the outer surface of the first side portion 3604. In some examples, as shown in FIG. 112, the first engagement members 3620 (also referred to as flanges 3620) can have rounded side walls 3624. Referring to FIG. 113, the second engagement members 3622 can be members extending laterally from the outer surface of the second side member 3606. The second engagement members 3622 (also referred to as hooked members 3622) can be generally J-shaped or hooked, having a first laterally-extending portion 3626, a vertically-extending portion 3628, and a second laterally-extending portion 3630. The second engagement members 3622 can define a recess/bore/channel 3632 configured such that the first engagement members 3620 can be disposed within the channel 3632. For example, the first engagement members 3620 can be positioned such that they are aligned with the channel 3632 but axially offset from the channel along a longitudinal axis of the crimping device 3600, and the first side portion 3604 can be advanced axially such that the first engagement members 3620 slide within the channel 3632.

Referring again to FIG. 110, in some examples, such as the illustrated example, the crimping device 3600 can comprise four engagement elements 3608 arranged as two pairs of two engagement elements disposed diametrically opposite one another. The first pair of engagement elements 3608*a* can be disposed adjacent the inlet end portion 3634 of the crimping device 3600, and the second pair of engagement elements 3608*b* can be disposed adjacent the outlet end portion 3636 of the crimping device 3600.

Figure 114:
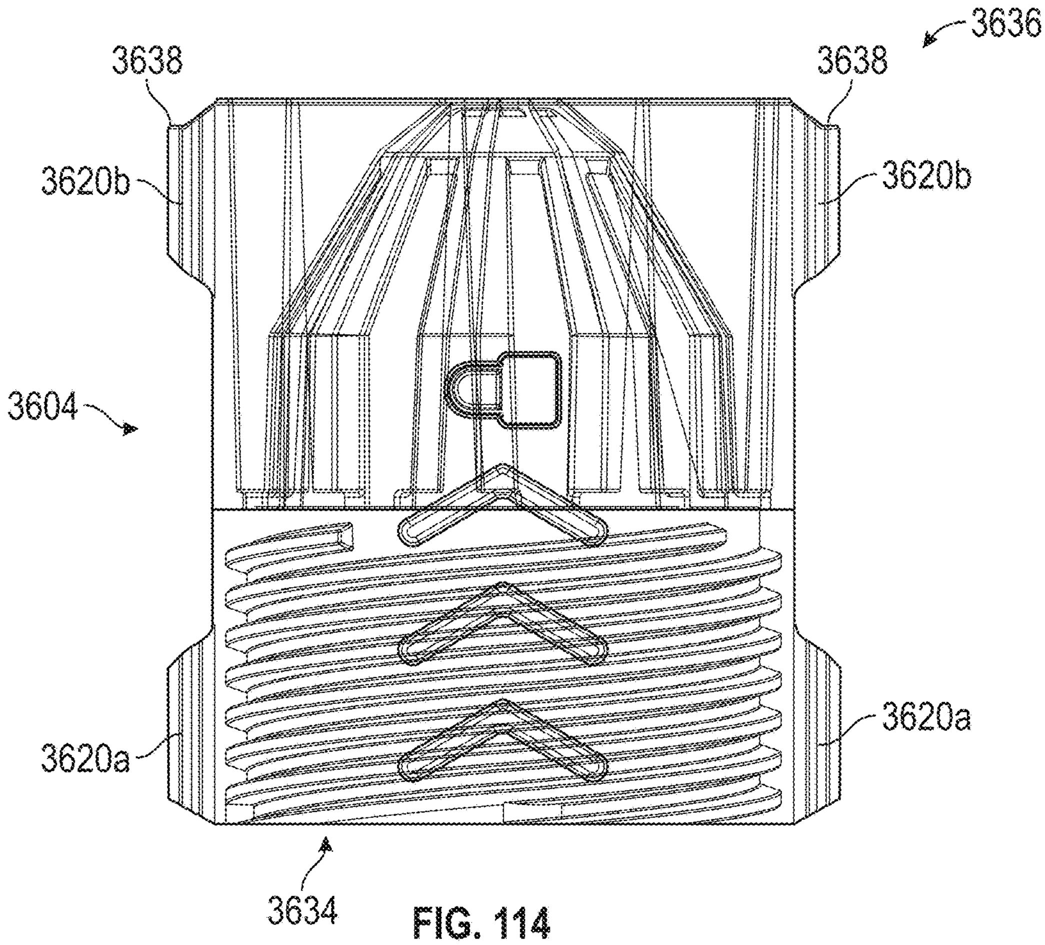
FIG. 114 is a top down view of the side portion of FIG. 111.
Figure 115:
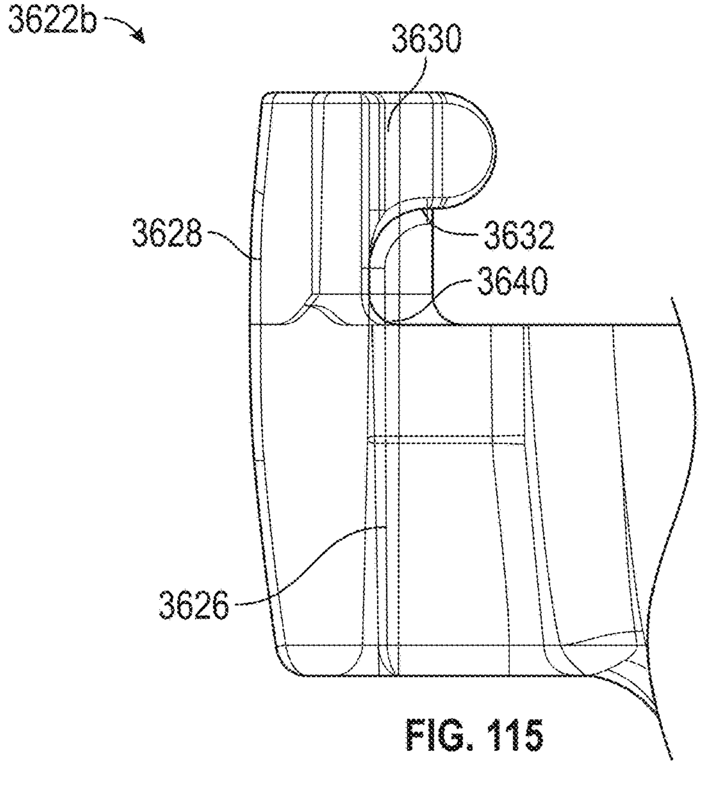
FIGS. 115-116 are front views of the engagement members of the side portion of FIG. 113.
Figure 116:
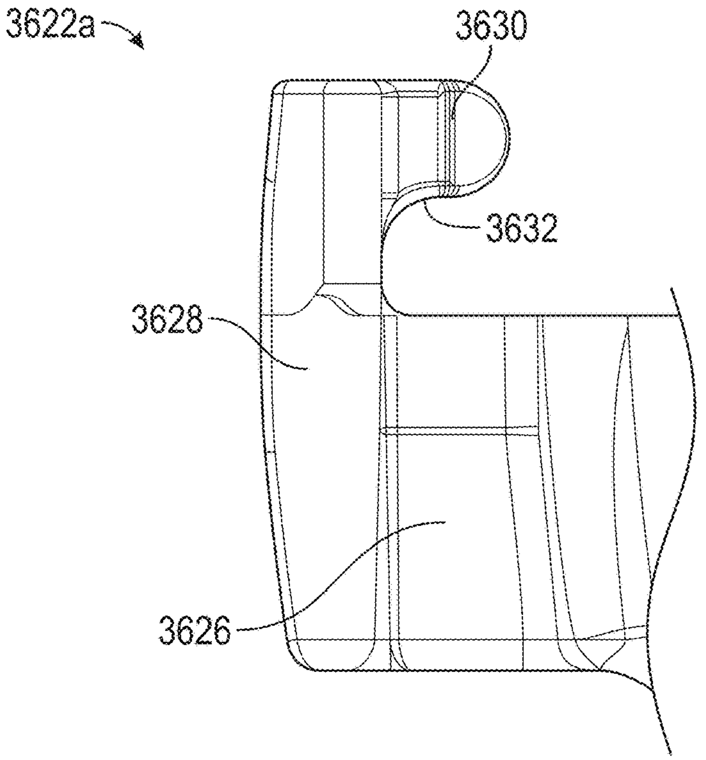

Referring to FIG. 114, the flanges 3620*b* of the second pair of engagement elements 3608*b* can each comprise a shoulder 3638 configured to engage a stopping surface 3640 (FIG. 115) of the hooked members 3622*b* of the second pair of engagement elements 3608*b*. As shown in FIGS. 115-116, the hooked members 3622*a*, 3622*b* of the first and second pairs of engagement elements 3608*a*, 3608*b* are generally the same, except that the hooked members 3622*b* include the stopping surface 3640. The engagement of the shoulder 3638 with the stopping surface 3640 serves as a hard stop to ensure that the first and second side portions 3604, 3606 are longitudinally aligned with one another. The shape of the hooked members 3622 retains the flange 3620 within the channel 3632, thereby preventing or mitigating the first and second side portions from moving laterally away from one another, and the engagement of the shoulder 3638 and the stopping surface 3640 prevents or mitigates the first and second side portions 3604, 3606 from moving axially relative to one another in a first direction. This advantageously prevents the inlet end portion 3634 of the crimping device 3600 from separating during the prosthetic valve crimping process.

Figure 117:
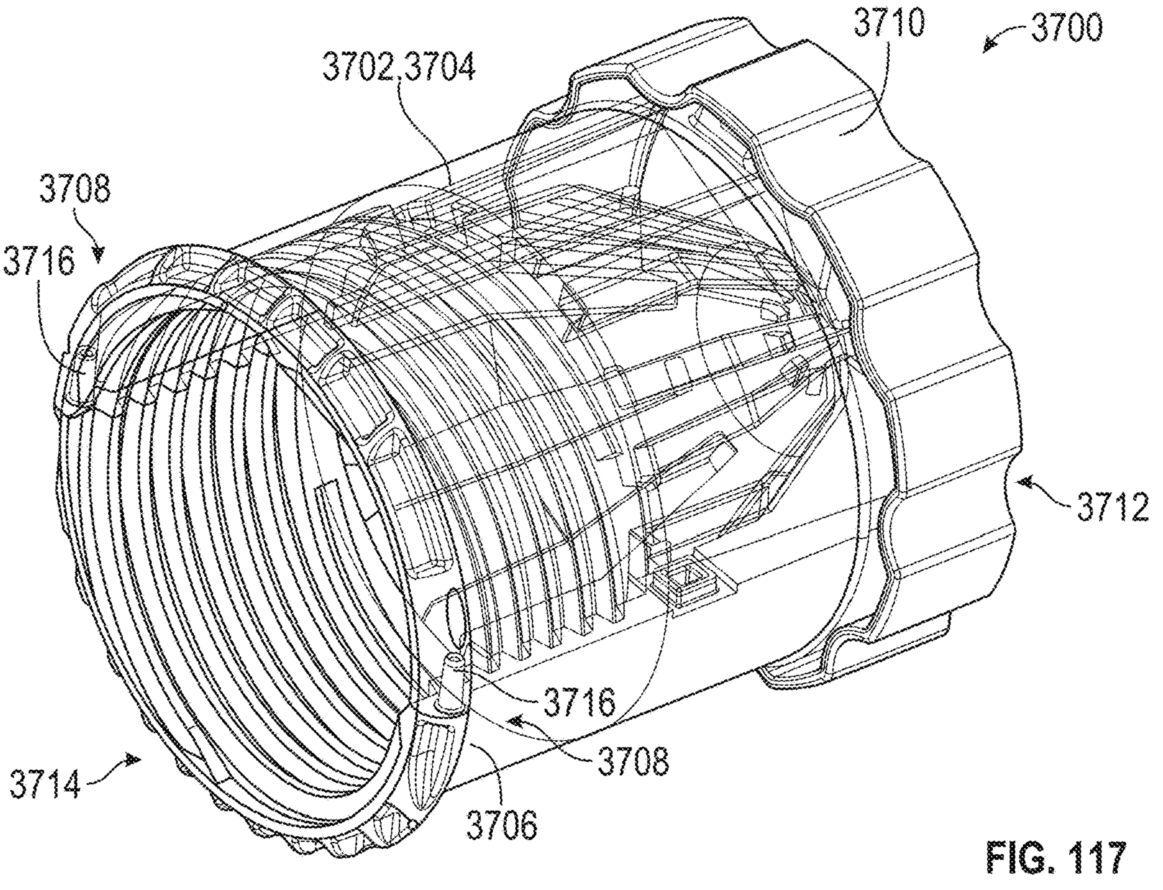
FIG. 117 is a perspective view of another example of a crimping device.

FIG. 117 illustrates another example of a crimping device 3700 including one or more engagement features 3708 that prevent or mitigate the first and second side portions 3704, 3706 of the housing 3702 from separating from one another during the prosthetic valve crimping process. The first side portion 3704 is shown translucently in FIG. 117 for purposes of illustration. Crimping device 3700 can be similar to crimping device 3600, except where noted otherwise. For example, crimping device 3700 can comprise a retaining ring 3710 configured to encircle the side portions 3704, 3706 at an outlet end portion 3712 of the device and releasably retain them together. Crimping device 3700 can further comprise one or more engagement features 3708 disposed adjacent the inlet end portion 3714 of the device 3700. In the illustrated example, the crimping device 3700 comprises two engagement features 3708 disposed diametrically opposite one another. However, in other examples, the device 3700 can comprise a greater or fewer number of engagement features 3708 and the features can be disposed offset from one another and/or at other locations axially along the length of the device.

The first side portion 3704 can comprise one or more recesses extending into one or more longitudinal side walls of the first side portion 3704, and the second side portion can comprise one or more projections 3716 extending from one or more longitudinal side walls of the second side portion 3706. The projections 3716 can be configured to extend into the recesses of the first side portion. In the illustrated example, the projections 3716 are cylindrical projections, however, in other examples, the projections can have any of various shapes and the recesses can have any of various corresponding shapes.

The engagement between the projections 3716 and the recesses can prevent or mitigates the first and second side portions 3704, 3706 from moving laterally away from one another. This advantageously prevents the inlet end portion 3714 of the crimping device 3700 from separating during the prosthetic valve crimping process.

Figure 118A:
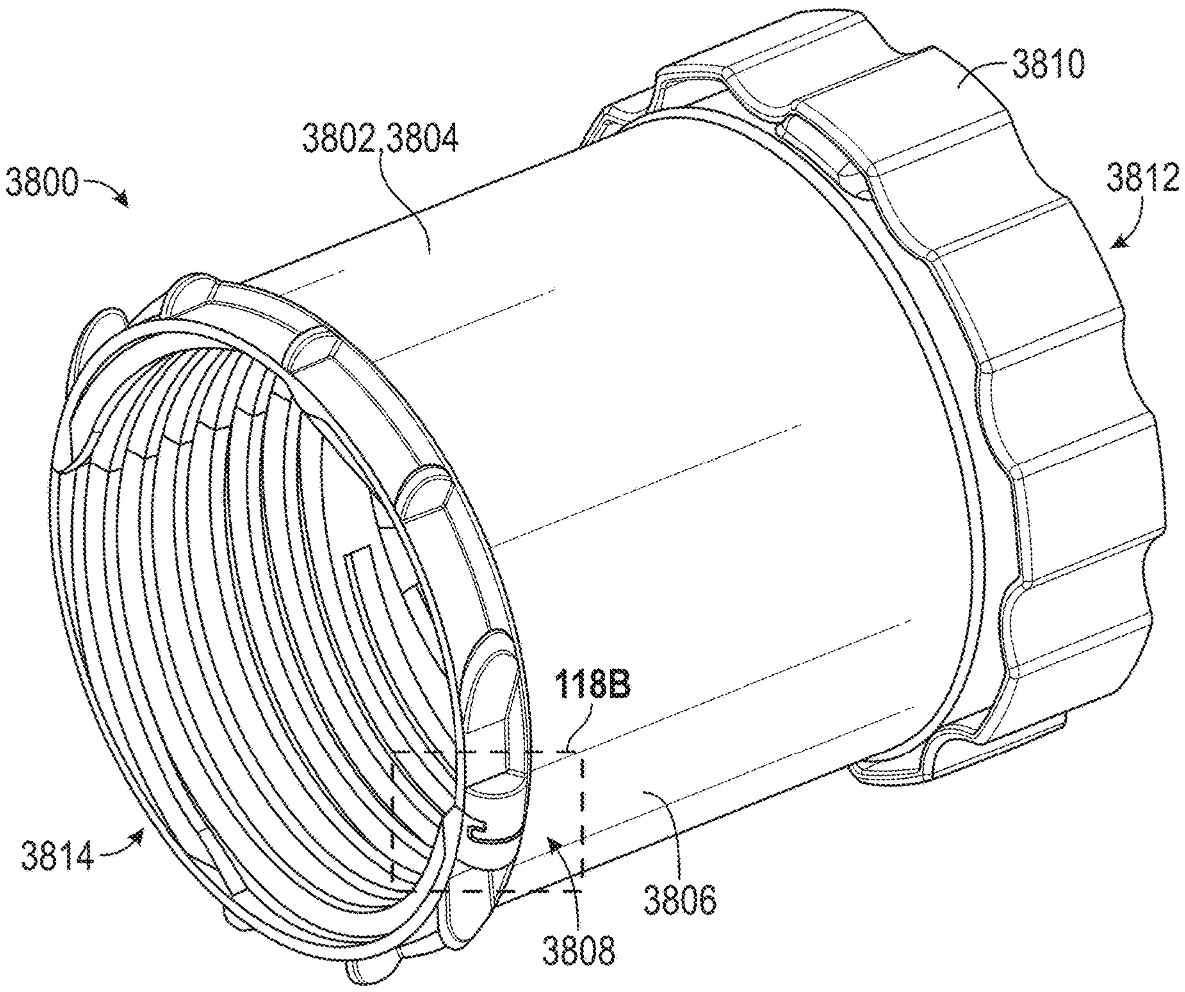
FIGS. 118A-118B show a perspective view of another example of a crimping device.
Figure 118B:
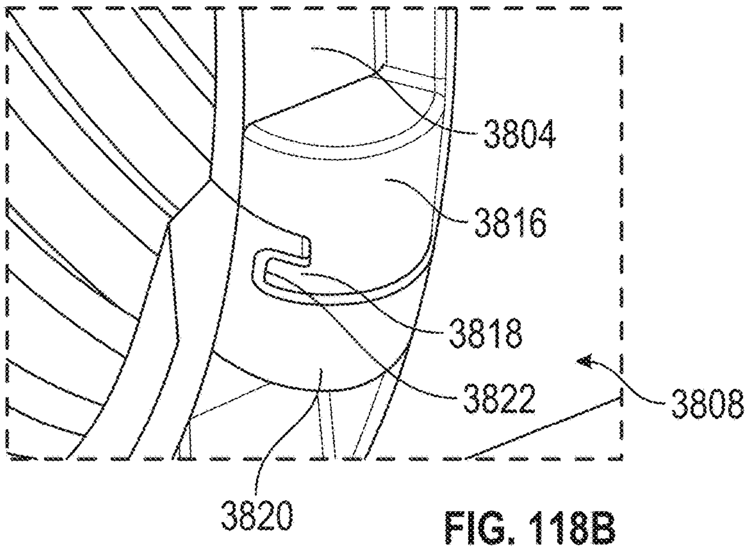

FIGS. 118A-118B illustrate another example of a crimping device 3800 including one or more engagement features 3808 that prevent or mitigate the first and second side portions 3804, 3806 of the housing 3802 from separating from one another during the prosthetic valve crimping process. Crimping device 3800 can be similar to crimping devices 3600 and 3700, except where noted otherwise. For example, crimping device 3800 can comprise a retaining ring 3810 configured to encircle the side portions 3804, 3806 at an outlet end portion 3812 of the device and releasably retain them together. Crimping device 3800 can further comprise one or more engagement features 3808 disposed adjacent the inlet end portion 3814 of the device 3800. In the illustrated example, the crimping device 3800 comprises two engagement features 3808 disposed diametrically opposite one another. However, in other examples, the device 3800 can comprise a greater or fewer number of engagement features 3808 and the features can be disposed offset from one another and/or at other locations axially along the length of the device.

Referring to FIG. 118B, the first side portion 3804 can comprise one or more first members 3816 having a hooked engagement portion 3818, and the second side portion 3806 can comprise one or more second members 3820 each having a corresponding recess 3822 configured (e.g., sized and shaped) to receive the hooked engagement portion 3818 to interlock the first and second members 3816, 3820. The engagement between the first and second members 3816, 3820 can prevent or mitigate the first and second side portions 3804, 3806 from moving laterally away from one another. This advantageously prevents the inlet end portion 3814 of the crimping device 3800 from separating during the prosthetic valve crimping process.

In the illustrated example, the interlocking features of the first and second members 3816, 3820 are the hooked engagement portion 3818 and the recess 3822, however, in other examples, the first and second members 3816, 3820 can have any of various interlocking shapes configured such that the first and second members 3816, 3820 can engage one another and retain the first and second side portions 3804, 3806 from lateral movement relative to one another.

Figure 119:
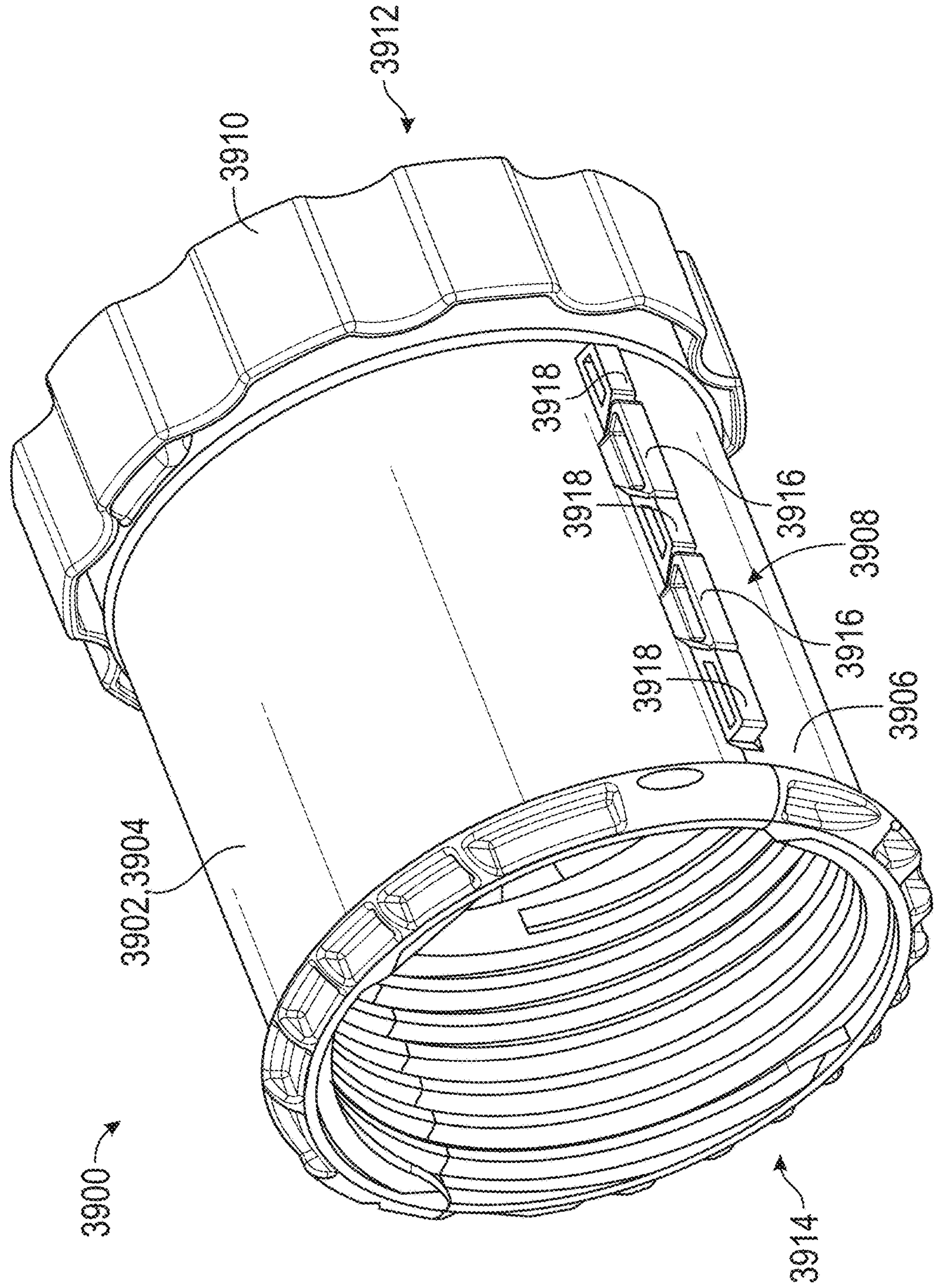
FIG. 119 is a perspective view of another example of a crimping device.

FIG. 119 illustrates another example of a crimping device 3900 including one or more engagement features 3908 that prevent or mitigate the first and second side portions 3904, 3906 of the housing 3902 from separating from one another during the prosthetic valve crimping process. Crimping device 3900 can be similar to crimping devices 3600, 3700, and 3800, except where noted otherwise. For example, crimping device 3900 can comprise a retaining ring 3910 configured to encircle the side portions 3904, 3906 at an outlet end portion 3912 of the device and releasably retain them together. Crimping device 3900 can further comprise one or more engagement features 3908 disposed longitudinally along the length of the device. In the illustrated example, the crimping device 3900 comprises two engagement features 3908 disposed diametrically opposite one another. However, in other examples, the device 3900 can comprise a greater or fewer number of engagement features 3908 and the features can be disposed circumferentially offset from one another and/or at other locations axially along the length of the device.

Referring still to FIG. 119, the first side portion 3904 can comprise one or more first members 3916 extending laterally from the one or more longitudinal edges of the first side portion. The second side portion 3906 can comprise one or more second members 3918 extending laterally from the one or more longitudinal edges of the second side portion 3906. The first and second members 3916, 3918 can be offset from one another along the length of the crimping device 3900 such that they are disposed in an alternating pattern. For example, as shown in FIG. 119, when the first and second side portions 3904, 3906 are coupled together, each first member 3916 can be disposed between two adjacent second members 3918. The first members 3916 can frictionally engage the second members 3918, to prevent or mitigate the first and second side portions 3904, 3906 from moving laterally away from one another. In some examples, the first and second members 3916, 3918 can comprise additional interlocking features. The disclosed configuration advantageously prevents the inlet end portion 3914 of the crimping device 3800 from separating during the prosthetic valve crimping process.

In the illustrated example, the first and second members 3916, 3918 are trapezoidal projections disposed in alternating orientations. That is, the first members 3916 are disposed with the shorter non-angled side adjacent the first side portion 3904 and the second members 3918 are disposed with the longer non-angled side adjacent the second side portion 3906. These alternating orientations allow the first and second members 3916, 3918 to interlock with one another as shown in FIG. 119. In other examples, the first and second members 3916, 3918 can have any of various shapes configured to interlock with one another along the length of the crimping device 3900 and retain the first and second side portions 3904, 3906 from lateral movement relative to one another.

Any of the described engagement features can be used in combination with one another. For example, the engagement features 3708 can be used in combination with the engagement features 3908 to additionally help retain the inlet end portion of a crimping device from separating.

Referring to FIGS. 120-123 as mentioned previously, a loading assembly such as assembly 2400 can generally comprise a support tube 2402, a loader member/funnel member 2404, and one or more fasteners/clamps 2406, see FIGS. 53-59. In some examples, in lieu of or in addition to clamps 2406, a loading assembly 2400 can comprise one or more clamps 4000. Clamp 4000 can be similar to clamp 2406 described previously except where noted otherwise. That is, clamp 4000 can comprise a C-shaped main body 4002, one or more ledges 4004 (FIG. 121) (e.g., two opposed ledges) extending radially inwardly from inner walls of the free edge portions of the clamp 4000 and extending along at least a portion of the length of the clamp, and one or more stopping surfaces 4006 (FIG. 121) extending radially inwardly toward a longitudinal axis of the clamp 4000. The clamp 4000 can also comprise an alignment feature 4008 (e.g., first and second ribs 4010 defining a channel 4012 between them), and one or more tabs 4014 extending radially outwardly from an outer surface of the clamp 4000.

Figure 120:
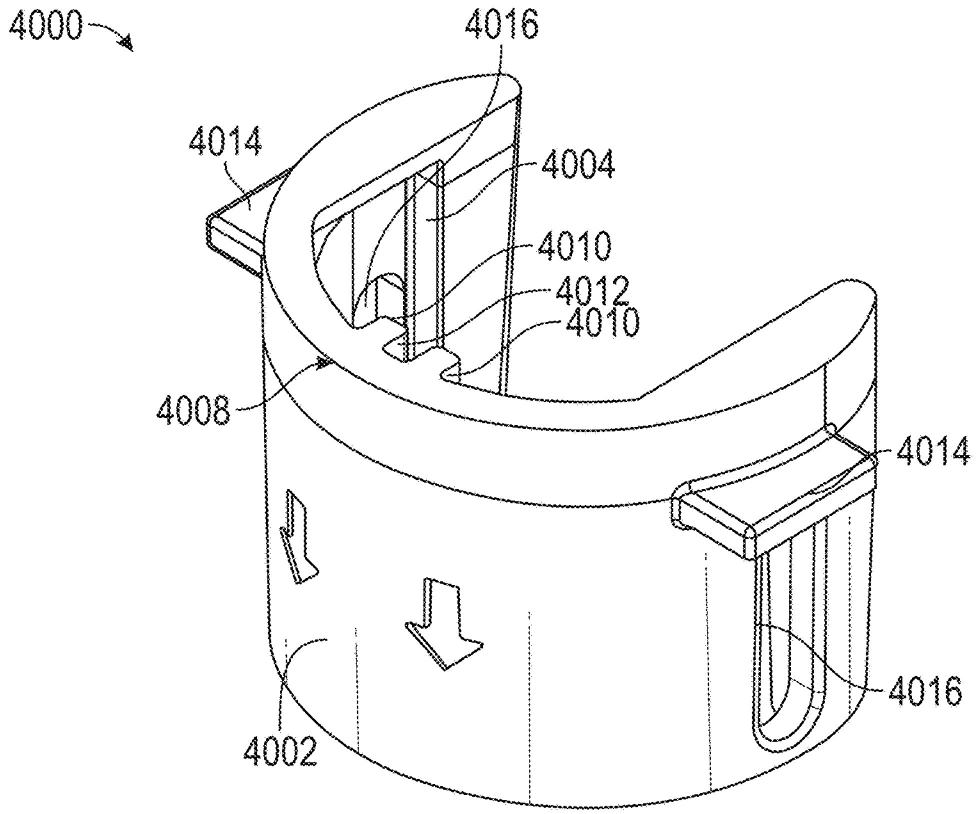
FIG. 120 is a perspective view of another example of a clamp member.

FIG. 120 illustrates an example wherein the clamp 4000 further comprises one or more slots 4016 extending through a wall of the main body 4002 and at least partially along the length of the clamp 4000. As shown, in some examples, the slots 4016 have an elongated, square-oval or pill shape. In other examples, the slots can be rectangular, square, triangular, non-linear (e.g., sinusoidal), etc. The slots 4016 reduce the surface area of the main body 4002 that contacts the support tube 2402 and provide additional flexibility to the clamp 4000, which reduces the amount of force required to insert/apply and remove the clamps 4000 from the support tube 2402. In some examples, the clamps 4000 can comprise a flexible material such as Nylon PA12.

Figure 121:
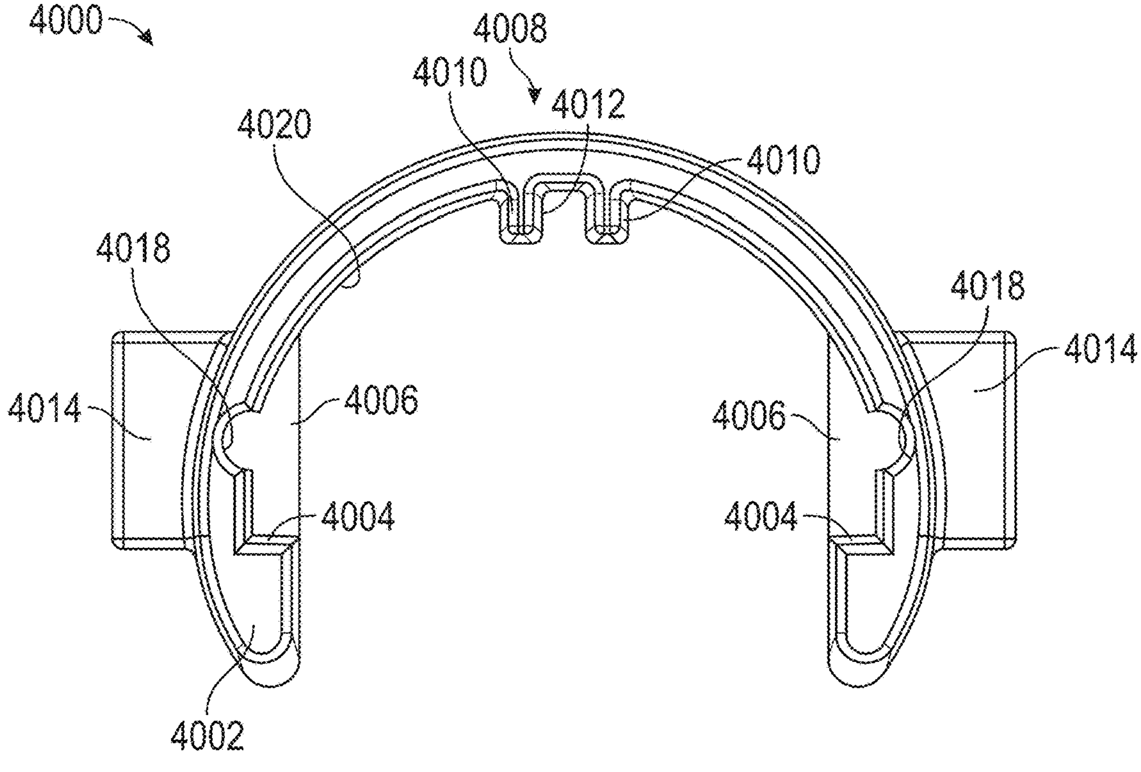
FIG. 121 is a front view of another example of a clamp member.

Referring to FIG. 121, in some examples, in lieu of or in addition to slots 4016, the clamp 4000 can comprise one or more relief cuts/slots/recesses 4018 on an internal surface 4020 of the clamp 4000. Each recess 4018 can extend into a thickness of the internal surface and at least partially along the length of the clamp. As shown, in some examples, the recesses 4018 can have a semi-circular shape in cross-section, however, in other examples, the relief cuts can have any of various shapes in cross-section including square, rectangular, triangular etc. The recesses 4018 can be disposed on the bending plane of the clamp 4000 such that they provide additional flexibility when pushing or pulling the clamp. This provides additional flexibility to the clamp 4000, which reduces the amount of force required to insert/apply and remove the clamp 4000 from the support tube 2402, particularly when the interaction between the clamp 4000 and the support tube 2402 is a tight interference fit.

Figure 122:
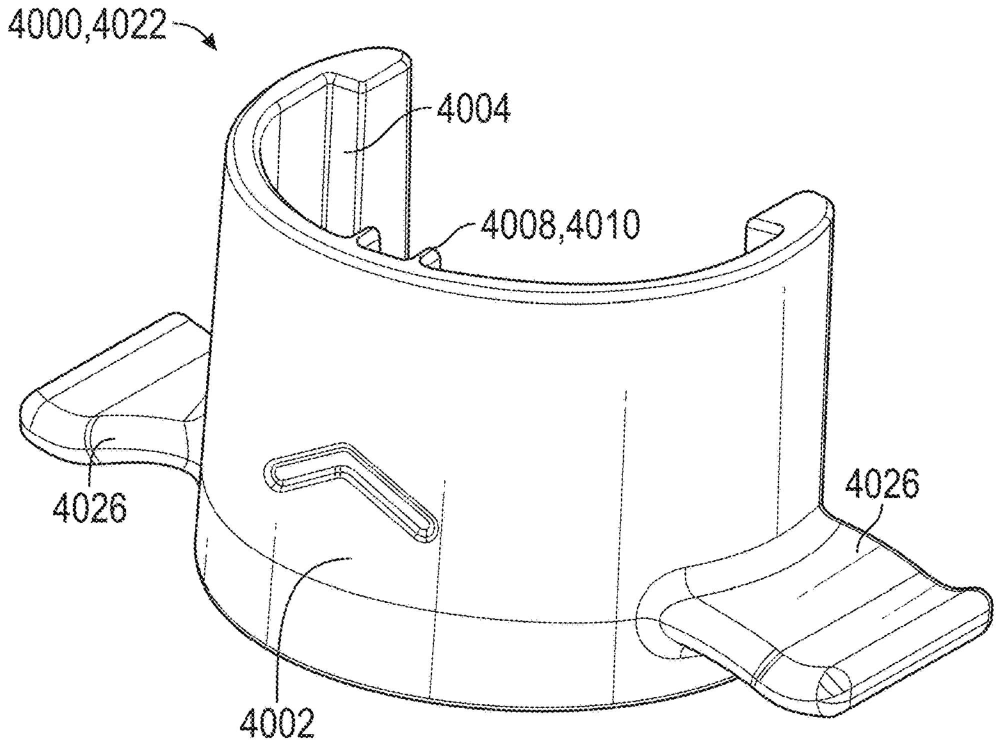
FIG. 122 is a perspective view of an exemplary clamp member configured as a loader lock.
Figure 123:
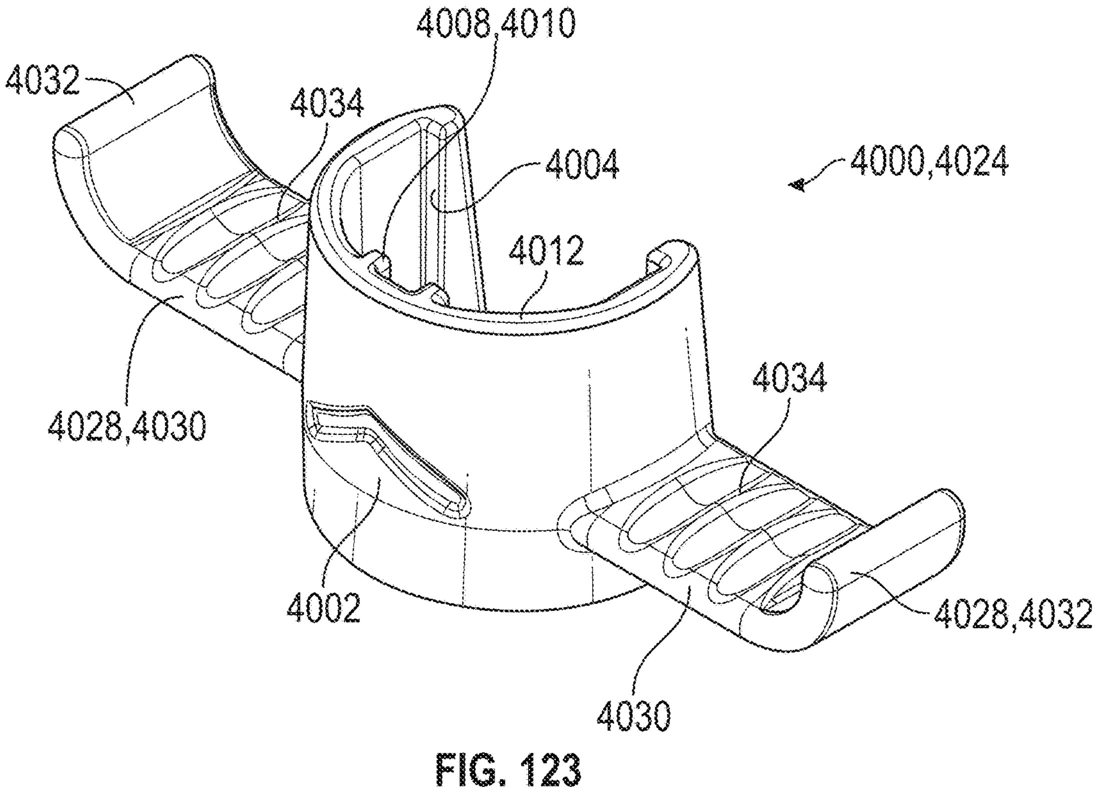
FIG. 123 is a perspective view of an exemplary clamp member configured as a support tube lock.

Referring to FIGS. 122-123, in some examples, in lieu of or in addition to the slots 4016 and/or recesses 4018, the one or more clamps 4000 can comprise elongated tab members configured to give the user a mechanical advantage during insertion or removal of the clamp 4000. FIG. 122 illustrates an example of a first clamp 4000 configured as a loader clamp 4022 (also called a loader lock 4022) incorporating this feature and configured to be disposed on a first or inlet end portion 2414 of the support tube 2402, and FIG. 123 illustrates an example of a second clamp 4000 configured as a support tube clamp 4024 (also called a support tube lock 4024) incorporating this feature and configured to be disposed on a second end portion 2416 of the support tube 2402.

The first clamp 4022 (e.g., the loader lock) can comprise first and second diametrically opposed tab members 4026 extending laterally from the main body 4002 of the clamp 4000. As shown in FIG. 122, the tab members 4026 can have an elongated shape, for example, when compared to the tab members 4014 shown in FIGS. 120-121. The tab members 4026 can each have a length between about 0.2 inches and about 0.9 inches, 0.3 inches and about 0.8 inches, 0.4 inches and about 0.7 inches, 0.4 inches and about 0.6 inches. In some examples, the tab members can each have a length of about 0.5 inches. The tab members 4026 can each comprise a curved and/or sinusoidal shape configured to create an ergonomic shape giving the user a mechanical advantage when applying force to the tab members 4026. The shape of the tab members 4026 can be configured to facilitate a user positioning their thumbs on the tabs to apply force to the loader lock 4022.

The second clamp 4024 can comprise first and second diametrically opposed tab members 4028 extending laterally from the main body 4002 of the clamp 4000. As shown in FIG. 123, the tab members 4028 can have an elongated shape, for example, when compared to tab members 4026 of FIG. 122. The tab members 4028 can each have a length of about 0.2 inches to about 1.5 inches, about 0.3 inches to about 1.4 inches, about 0.4 inches to about 1.3 inches, about 0.5 inches to about 1.2 inches, about 1.6 inches to about 1.1 inches, about 1.7 inches to about 1 inch. In some examples, the tab members 4028 can each have a length of about 1 inch. The tab members 4028 can comprise a laterally extending portion 4030 and a curved or hooked portion 4032 that extends in a direction away from the stopping surfaces 4006. The shape of the tab members 4028 can be configured to facilitate a user positioning their index and middle fingers on the tabs to apply force to the support tube lock 4024.

In some examples, one or more surfaces of the tab members 4028 can comprise a gripping interface 4034 for easy gripping and use by a user. The gripping interface 4034 can include, for example, a plurality of spaced ridges and troughs. The elongated shape of the tab members 4028 can give a user a mechanical advantage when applying force to the tab members 4028. In some examples, the tab members 4028 can comprise a curved and/or sinusoidal shape configured to create an ergonomic shape giving the user a further mechanical advantage when applying force to the tab members 4028.

In some examples, the tab members 4026 and/or 4028 can extend from the main body 4002 of the clamp member 4000 at a non-90 degree angle. For example, the tab members 4026/4028 can extend from the main body at any angle between about 1 degree and about 179 degrees, for example, between about 20 degrees and about 160 degrees, between about 45 degrees and about 135 degrees, between about 10 degrees and about 90 degrees, between about 90 degrees and about 160 degrees.

Figure 124:
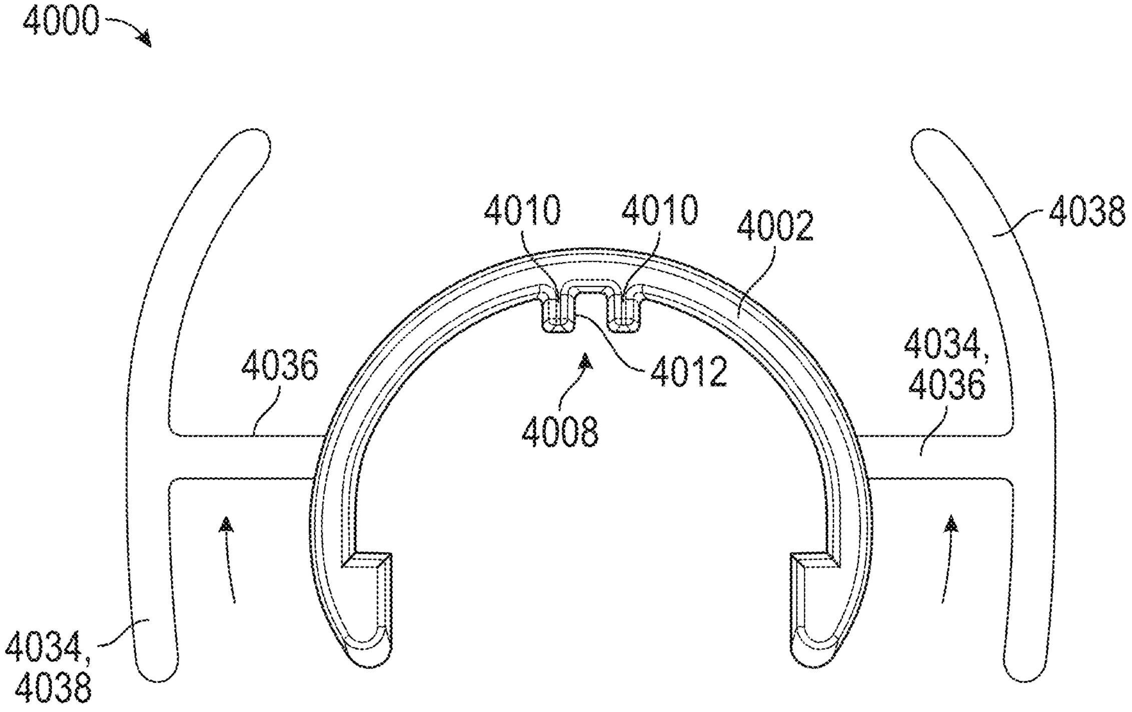
FIG. 124 is a front view of another example of a clamp member.

In some examples, the tab members 4026 and/or 4028 can have any of various shapes. For example, FIG. 124 illustrates an example of a clamp member 4000 having tab members 4035 that comprise a laterally extending portion 4036 and a vertically extending portion 4038. As shown in FIG. 124 the vertically extending portion can curve inwardly toward the main body 4002 of the clamp member.

Though the examples above may have been described with specific reference to a loader clamp (e.g., disposed on the inlet portion 2414) and/or a support tube clamp (e.g., disposed on a second end portion 2416 of the support tube 2402), it should be understood that any of the clamp members 4000 disclosed herein can be used as either a loader clamp, a support tube clamp, or both.

FIGS. 125-132 illustrate a method for using the crimping device 500 shown in FIGS. 74-76 in combination with the loading assembly 2400 shown in FIGS. 53-59 to crimp and load a prosthetic valve (such as prosthetic valve 1000 illustrated in FIG. 36) into a capsule or sheath of a delivery apparatus 2500 (FIG. 57), such as capsule 2512. In other examples, the crimping device 3600 shown in FIGS. 110-116 can be substituted for crimping device 500.

Figure 125:
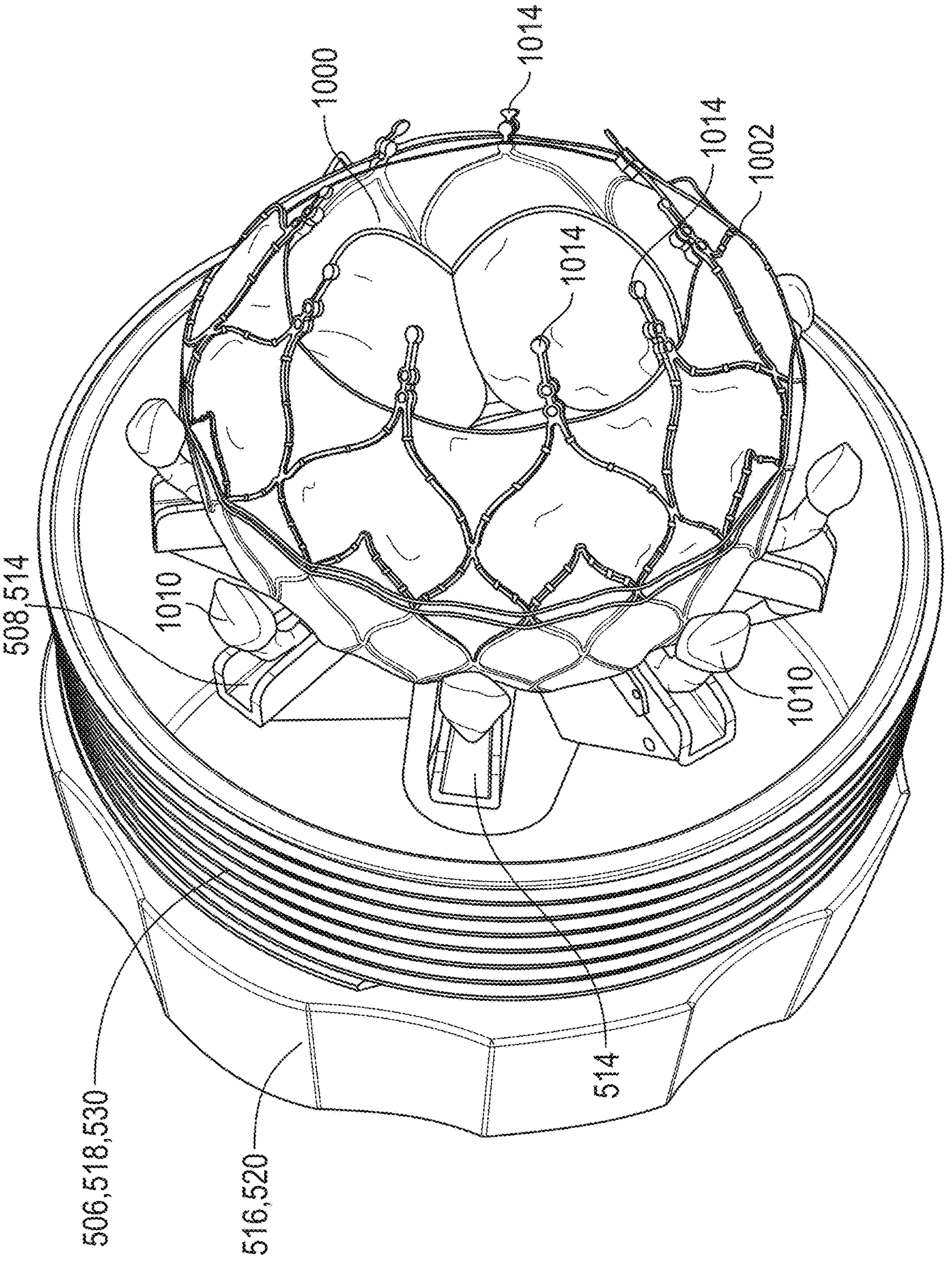
FIG. 125 is a perspective view of the prosthetic heart valve of FIG. 36 disposed within the actuator and pusher member of the crimping device of FIGS. 74-76.

Referring to FIG. 125, the prosthetic valve 1000 can be disposed on the pusher member 508 such that the second anchors 1010 are disposed within the seats 514 of the arms 512. The pusher member 508 can be removably coupled to the actuator 506.

Figure 126:
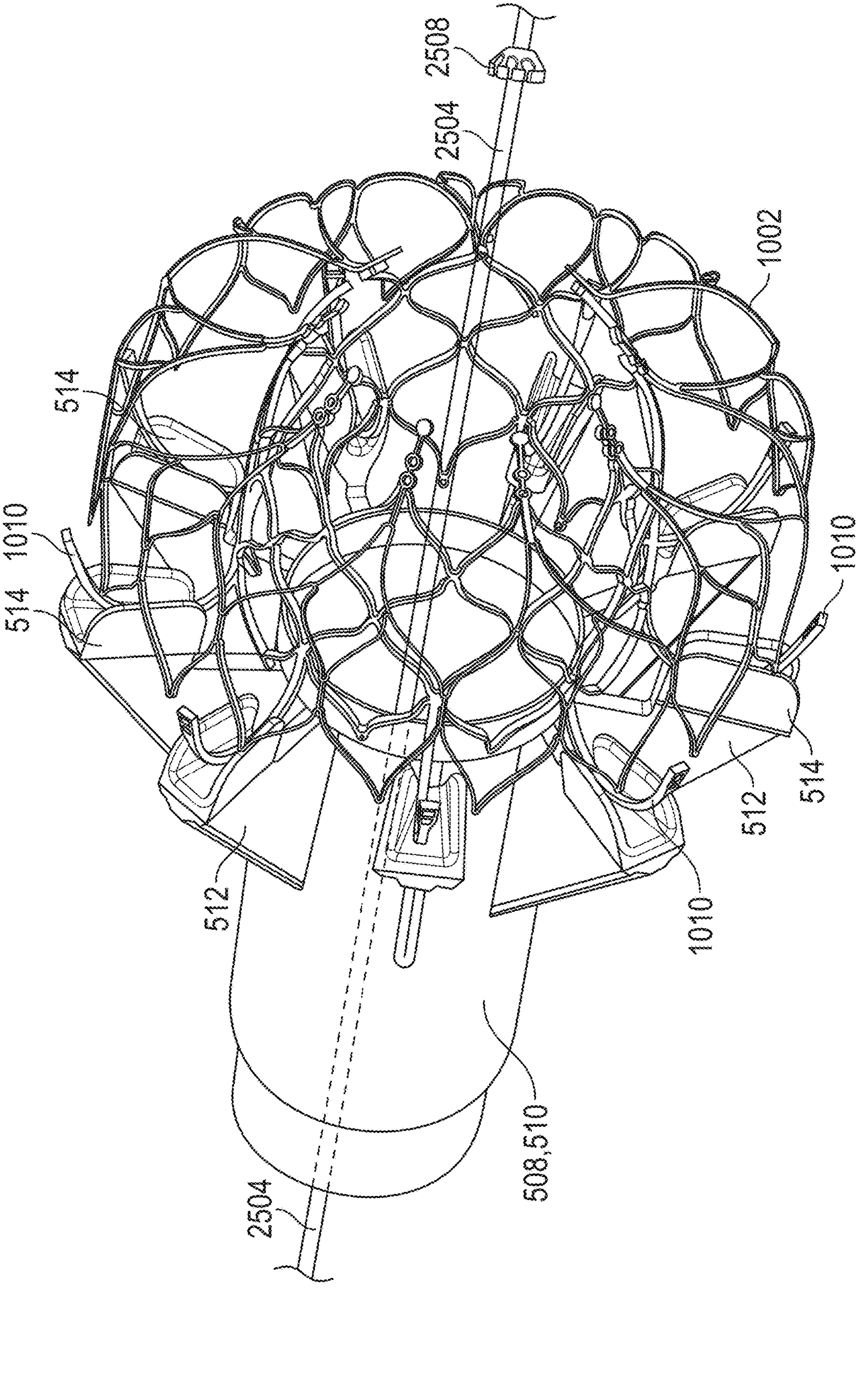
FIGS. 126-132 show an exemplary method of loading the prosthetic heart valve of FIG. 36 into the loading assembly of FIG. 53 using the crimping device of FIGS. 74-76.
Figure 127:
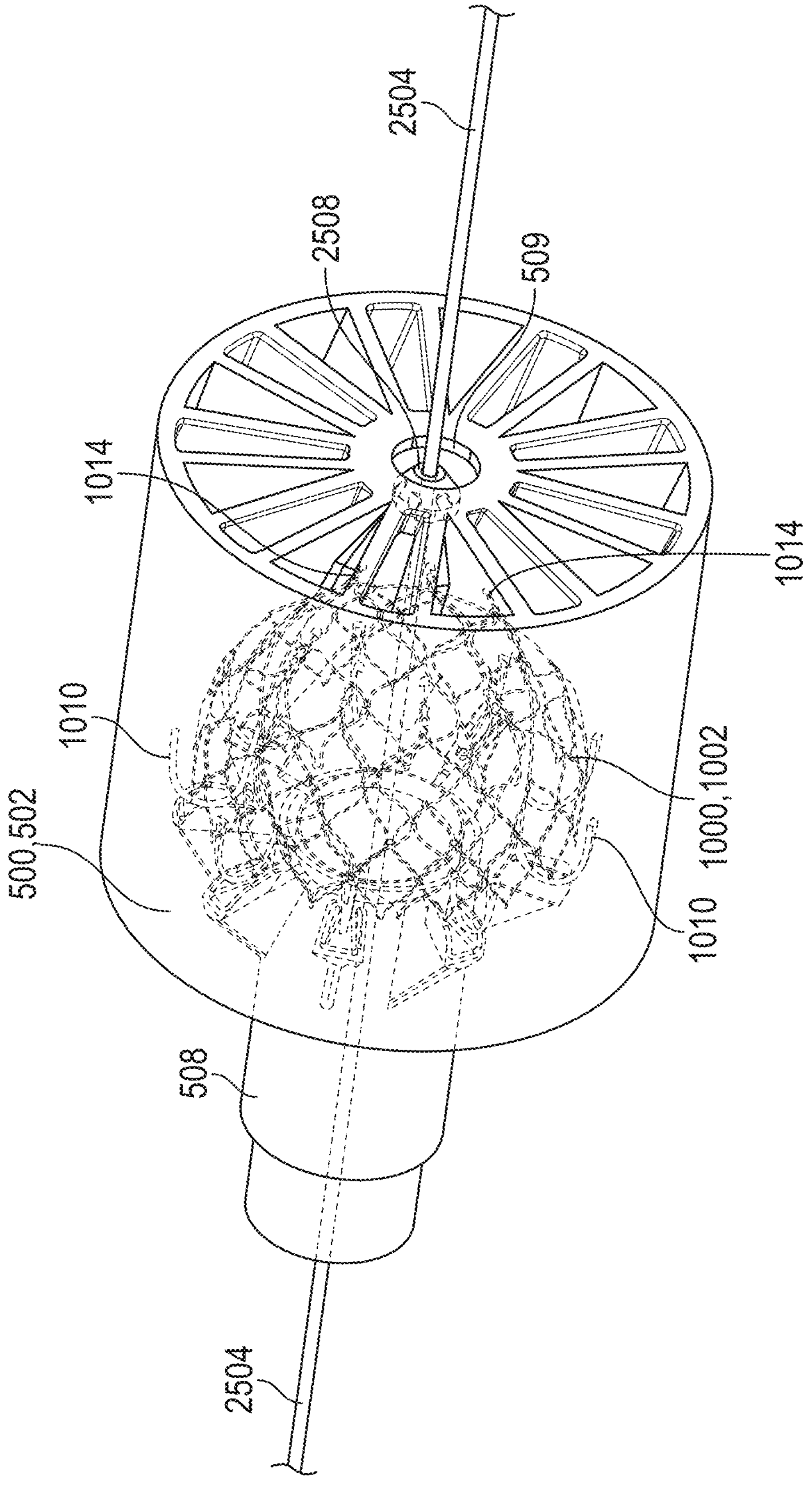

As shown in FIG. 126, the prosthetic valve 1000 and pusher member 508 (and the actuator 506 which is not shown in FIGS. 126-127 for purposes of illustration) can be disposed over the first shaft 2504 of the delivery apparatus 2500 (FIG. 57). The prosthetic valve 1000 can be oriented such that the enlarged end portions 1014 of the frame 1002 are positioned adjacent the valve retaining member 2508. Referring to FIG. 127, the housing 502 of the crimping device 500 can then be disposed over the first shaft 2504 such that it is disposed at least partially over the prosthetic valve 1000 and/or the valve retaining member 2508. The housing 502 can be disposed such that the arms 512 of the pusher member 508 (and thus the second anchors 1010 of the prosthetic valve 1000) are positioned between the ribs of the inner funnel segment 505 (FIG. 75).

Figure 128:
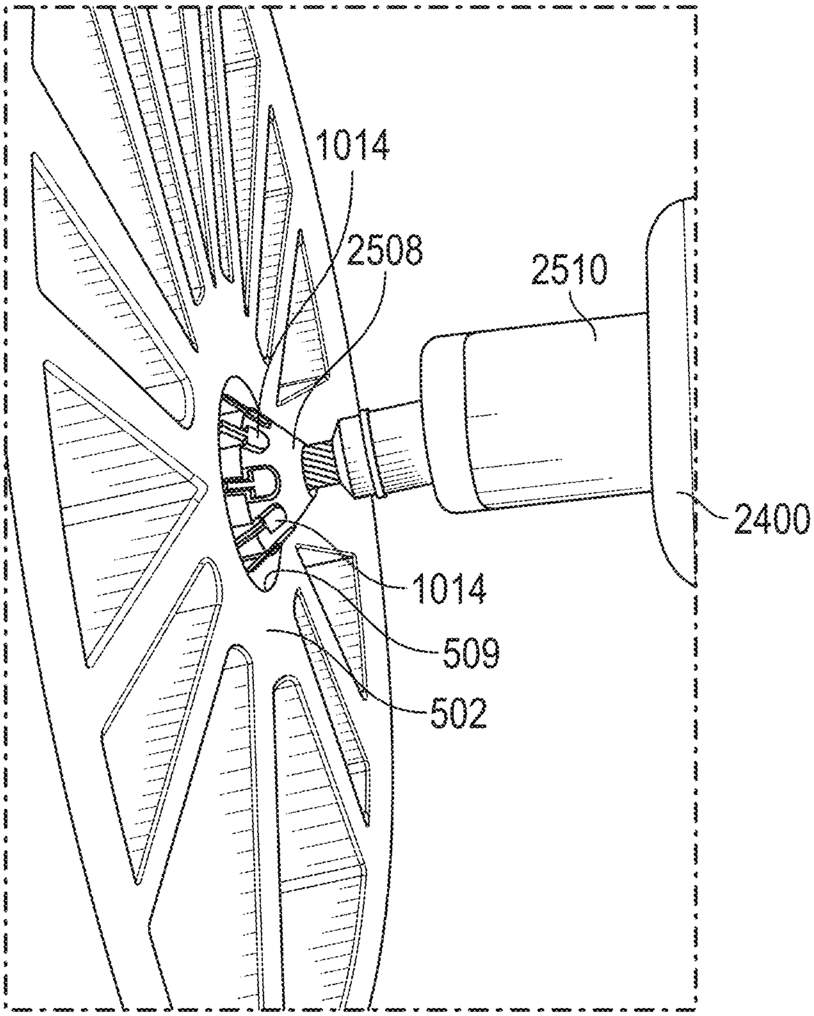

As described previously with respect to FIGS. 74-76, an inner surface of the housing 502 can comprise a threaded portion 532 (FIG. 75) configured to interface with the threaded portion 530 of the actuator 506 (FIG. 125). Once the housing 502 is disposed on the first shaft 2504, the pusher member 508 can be inserted into the housing 502 until the threads 530 of the actuator 506 engage the threads 532 (FIG. 75) of the housing. Thus engaged, the actuator 506 can be rotated and the threaded portions can translate the rotation into axial movement (e.g., pushing) of the pusher member 508, allowing the pusher member to advance axially forward into the housing thereby pushing prosthetic valve 1000 through the housing 502. As the prosthetic valve 1000 is pushed through the funnel segment 505 (FIG. 75), the prosthetic valve 1000 is radially compressed and pushed toward the outlet 509. As the prosthetic valve 1000 is advanced through the funnel segment 505, the ribs of the funnel segment 505 guide the enlarged end portion 1014 of the frame 1002 into the corresponding openings in the valve retaining member 2508, as shown in FIG. 128. The coupled valve retaining member 2508 and prosthetic valve 1000 can then be partially advanced through the outlet 509.

The loading assembly 2400 can be assembled (or in some cases partially assembled) on the delivery apparatus 2500 prior to the initial crimping using the crimping device 500, concurrently with the initial crimping, or after the initial crimping. The side portions 2403 of the support tube 2402 can be disposed over the capsule 2512 and the first clamp 2406*a* can be advanced over the second end portion 2416 of the support tube 2402 (e.g., in a direction toward the inlet end portion 2414 of the support tube) to retain the support tube 2402 in the assembled position. The holder member 2408 can be advanced (e.g., in a direction away from the inlet end portion 2414) over the extension portion 2424 (FIG. 53) of the support tube, folding the tab portions 2514 of the capsule 2512 back and retaining them between the holder member 2408 and the extension portion 2424.

Figure 129:
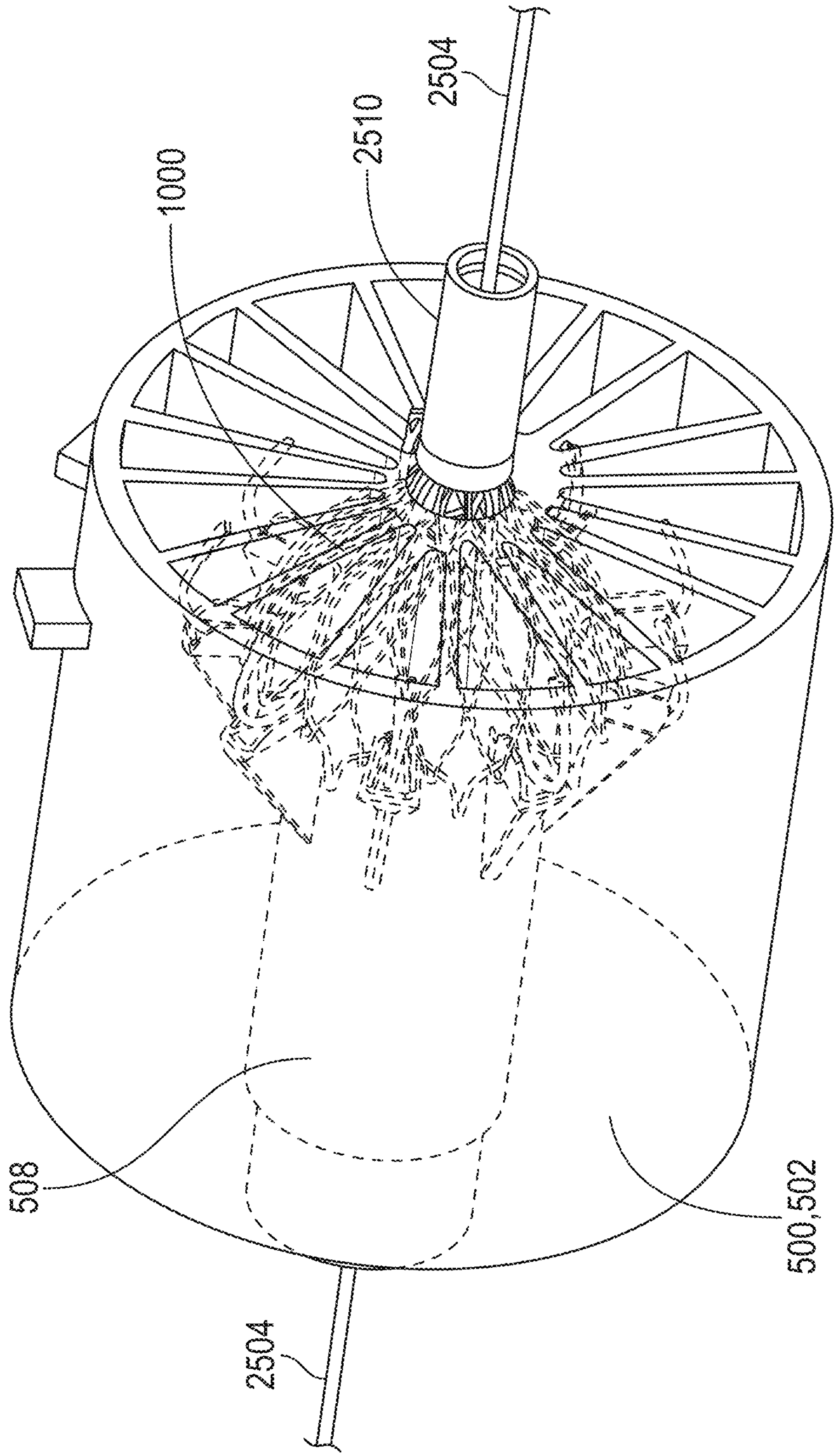

The capsule 2512 can be advanced (e.g., using the handle of the delivery apparatus 2500) until it contacts the crimping device 100 (see e.g., FIG. 61), and the prosthetic valve 1000 can be slowly drawn out from the crimping device 100. As shown in FIG. 128, the capsule 2512 can then be retracted (e.g., using the handle of the delivery apparatus) to ensure that the prosthetic valve 1000 is properly coupled with the valve retaining member 2508 while the actuator of the crimping device is held in place. As shown in FIG. 129, so coupled, the outer ring 2510 can be advanced (e.g., using the handle of the delivery apparatus) over the valve retaining member 2508 and a portion of the prosthetic valve 1000 within the valve retaining member 2508 (e.g., the arms 1012 with enlarged end portions 1014) to retain the enlarged end portions 1014 within the valve retaining member 2508 when the crimping device 500 is removed from the first shaft 2504.

Figure 130:
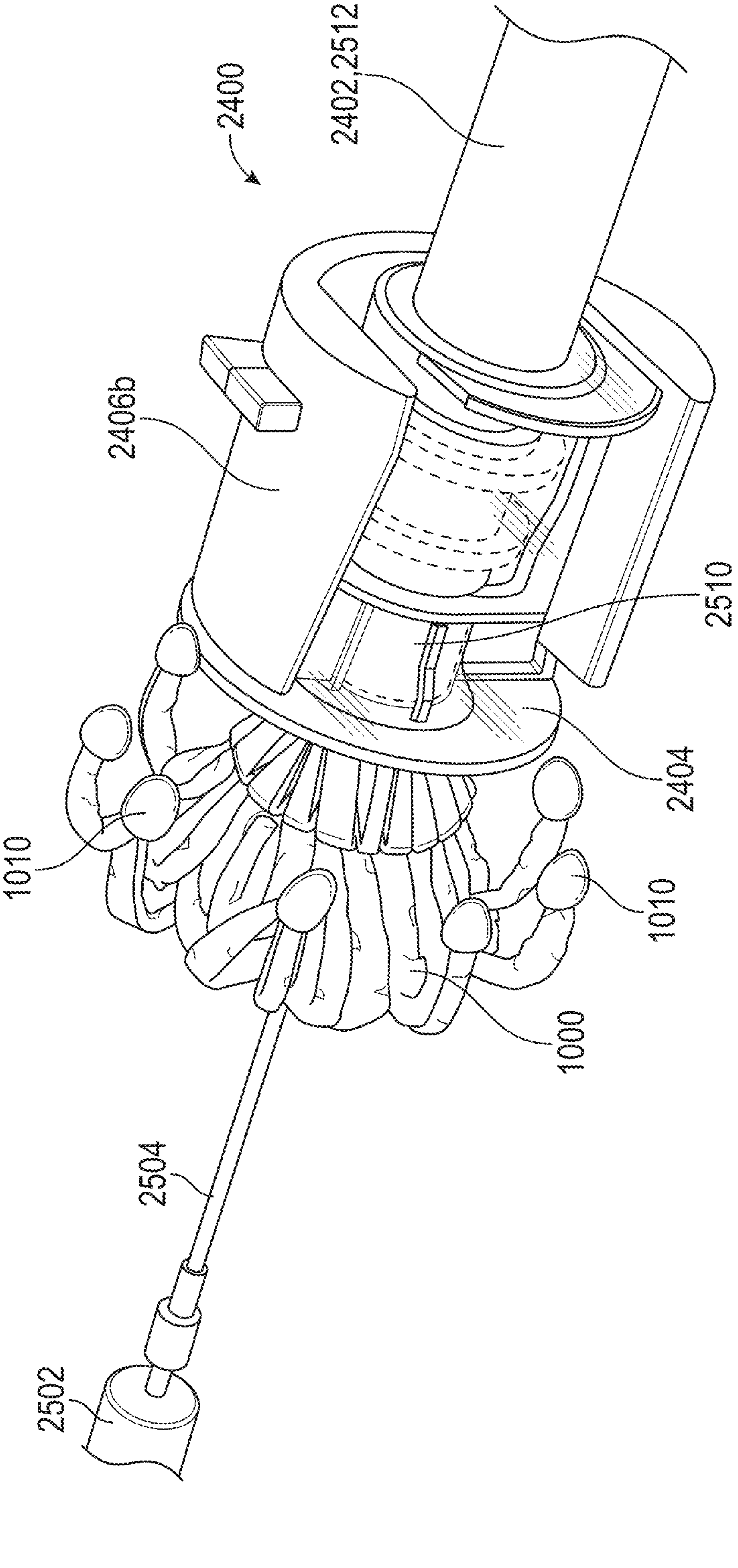
Figure 131:
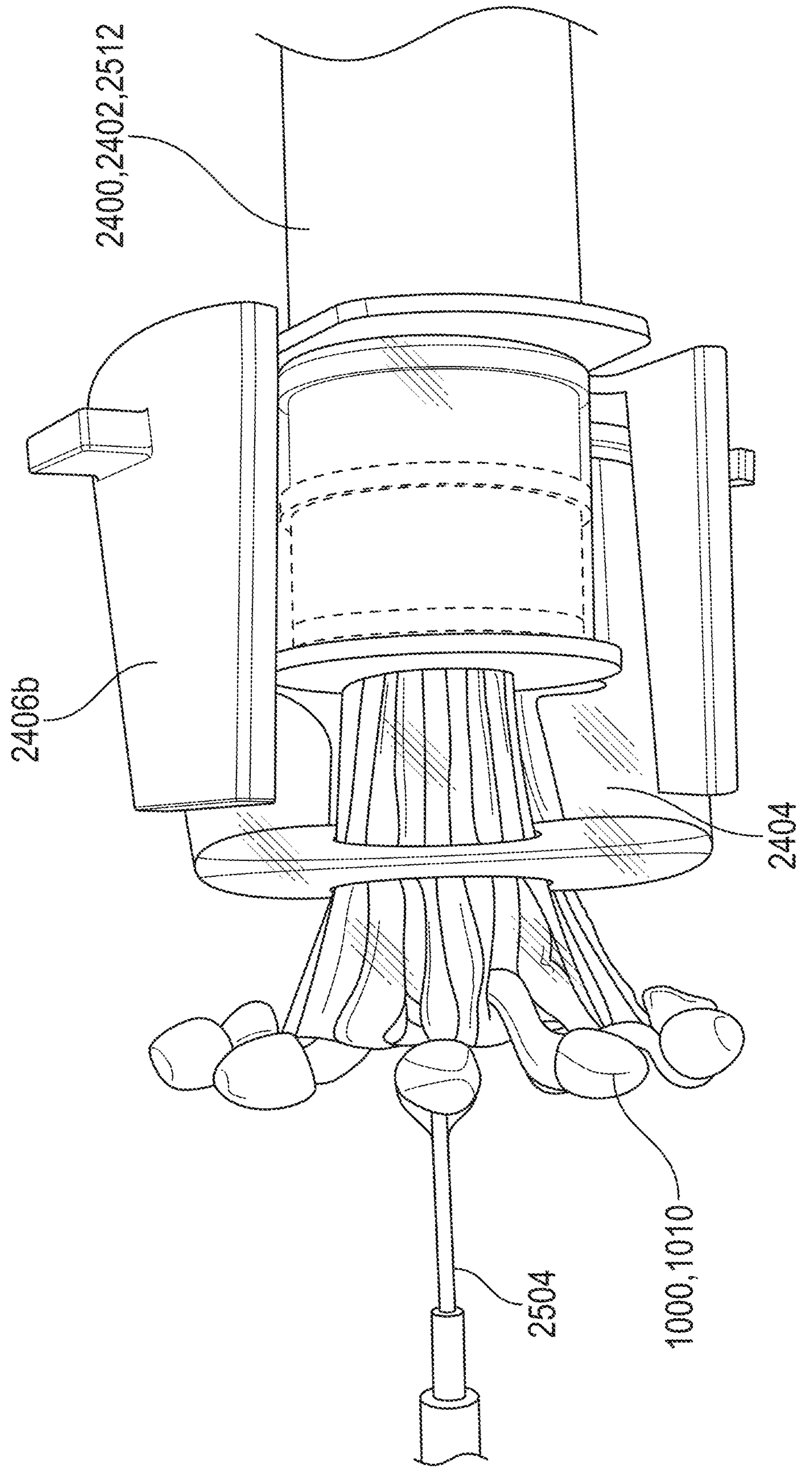

Referring to FIG. 130, the loading assembly 2400 can then be advanced over the outer ring 2510. In some examples, such as shown in FIG. 62, a guidewire shield 2506 can be advanced distally over the first shaft 2504 (e.g., using advancement tool 2516) to protect the first shaft 2504 during the remainder of the loading process. As shown in FIG. 131, the capsule 2512 (and therefore the attached loading assembly 2400) can be advanced over the prosthetic valve 1000 using the handle of the delivery apparatus 2500 (or the prosthetic valve 1000 can be retracted into the assembled capsule and loading assembly). As can be seen in FIG. 131, as the loading assembly 2400 is advanced over the prosthetic valve 1000, the funnel portion 2404 radially compresses the prosthetic valve 1000, allowing the prosthetic valve to be loaded into the capsule 2512 (within the support tube 2402). More particularly, as the capsule 2512 and loading assembly 2400 advance over the prosthetic valve 1000, the anchors 1010 of the prosthetic valve 1000 can contact and be inverted by the funnel member 2404 such that the prosthetic valve 1000 moves into a substantially straightened configuration wherein the anchors 1010 extend distally from the main body 1003 and are rotated approximately 180 degrees from their unrestrained configuration.

With the tab members 2514 (see e.g., FIG. 57) of the capsule 2512 folded back proximally over the capsule 2512 and held in place by the holder member 2408, the distal end portion of the capsule 2512 can remain taut as the prosthetic valve 1000 is inserted into the capsule. This prevents the capsule from bunching or buckling during the loading process. The support tube 2402 can also provide additional structural support to the capsule 2512. In certain examples, the funnel member 2404 of the loading assembly 2400 can be filled with saline solution (e.g., supplied from a port in the handle of the delivery apparatus) during loading of the prosthetic valve. In certain examples, free apices of the frame of the prosthetic valve can be guided inside the funnel portion 2458, for example using the tool 1516 (FIG. 62).

Figure 132:
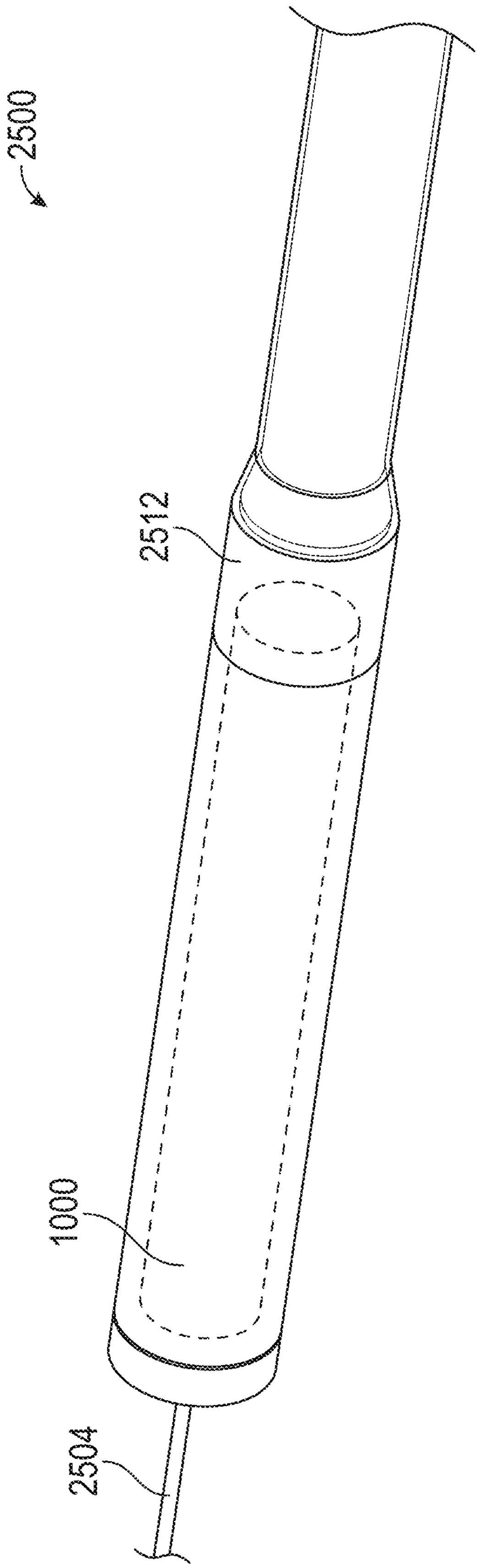

As shown in FIG. 132, once the prosthetic valve 1000 has been fully received within the capsule 2512, the loading assembly 2400 can be removed from the delivery apparatus 2500 (e.g., by removing the first and second clamps 2406, and removing the side portions 2460, 2403 of the funnel member 2404 and the support tube 2402). Once the prosthetic valve has been fully loaded in the capsule 2512, the tabs 2514 can be removed from the capsule 2512 using any of the tab cutting methods or devices described herein (e.g., using tab trimming device 3000). Tabs 2514 thus removed, the nosecone 2502 (FIG. 130) can be retracted proximally toward the capsule 2512 until a proximal edge of the nose cone 2502 abuts the distal edge of the capsule.

Any of the systems, devices, apparatuses, etc. herein can be sterilized (for example, with heat/thermal, pressure, steam, radiation, and/or chemicals, etc.) to ensure they are safe for use with patients, and any of the methods herein can include sterilization of the associated system, device, apparatus, etc. as one of the steps of the method. Examples of heat/thermal sterilization include steam sterilization and autoclaving. Examples of radiation for use in sterilization include, without limitation, gamma radiation, ultra-violet radiation, and electron beam. Examples of chemicals for use in sterilization include, without limitation, ethylene oxide, hydrogen peroxide, peracetic acid, formaldehyde, and glutaraldehyde. Sterilization with hydrogen peroxide may be accomplished using hydrogen peroxide plasma, for example.

ADDITIONAL EXAMPLES OF THE DISCLOSED TECHNOLOGY

In view of the above-described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A crimping device, comprising:

- a housing configured to receive a radially expandable and compressible prosthetic valve in a radially expanded state, the housing comprising a funnel segment extending at least partially along an axial length of the housing and an outlet in communication with the funnel segment;
- a pusher member having an outer diameter less than an inner diameter of the housing such that the pusher member can advance into the housing; and
- an actuator releasably coupled to the pusher member, wherein manual axial advancement of the actuator relative to the housing causes the prosthetic valve to move axially through the funnel segment such that at least a portion of the prosthetic valve compresses radially by engagement with the funnel segment and exits the crimping device via the outlet.

Example 2. The crimping device of any example herein, particularly example 1, wherein the funnel segment comprises a plurality of radially inwardly extending ribs spaced about an internal circumference of the housing.

Example 3. The crimping device of any example herein, particularly example 2, wherein the ribs extend radially inwardly toward a longitudinal axis of the housing.

Example 4. The crimping device of any example herein, particularly any one of examples 2-3, wherein the ribs increase in a radial direction from a first thickness adjacent an inlet end portion of the housing to a second thickness greater than the first thickness adjacent the outlet.

Example 5. The crimping device of any example herein, particularly any one of examples 2-4, wherein the ribs comprise a first tapered portion disposed at a first angle and a second tapered portion disposed at a second angle.

Example 6. The crimping device of any example herein, particularly example 5, wherein the first angle is lesser than the second angle.

Example 7. The crimping device of any example herein, particularly any one of examples 5-6, wherein the first and second tapered portions are configured to crimp a prosthetic valve at different rates.

Example 8. The crimping device of any example herein, particularly any one of examples 1-7, wherein the housing comprises two or more separable portions, and wherein each separable portion comprises a portion of the funnel segment.

Example 9. The crimping device of any example herein, particularly example 8, further comprising a retaining member configured to releasably retain the two or more separable portions together.

Example 10. The crimping device of any example herein, particularly any one of examples 1-9, wherein the pusher member comprises a plurality of circumferentially spaced, radially extending arms.

Example 11. The crimping device of any example herein, particularly example 10, wherein the arms are configured to be movably disposed between the ribs of the funnel segment.

Example 12. The crimping device of any example herein, particularly any one of examples 10-11, each arm comprising a holding portion having first and second walls defining a channel between them.

Example 13. The crimping device of any example herein, particularly any one of examples 1-12, wherein the pusher member comprises a first end portion having a first diameter and a second end portion having a second diameter smaller than the first diameter.

Example 14. The crimping device of any example herein, particularly example 13, the second end portion comprising one or more releasable locking features configured to engage one or more corresponding locking features on the actuator.

Example 15. The crimping device of any example herein, particularly example 14, wherein the one or more locking features comprise resilient latches.

Example 16. The crimping device of any example herein, particularly any one of examples 14-15, wherein the locking features of the actuator comprise openings.

Example 17. The crimping device of any example herein, particularly any one of examples 1-16, wherein the actuator comprises a base and one or more extension members extending from the base.

Example 18. The crimping device of any example herein, particularly example 17, wherein the one or more extension members are configured to maintain an angular alignment between the actuator and the housing during crimping of a prosthetic valve.

Example 19. The crimping device of any example herein, particularly any one of examples 17-18, wherein the one or more extension members comprise a central extension member having an inner bore and one or more linear guide members.

Example 20. The crimping device of any example herein, particularly example 19, wherein the one or more linear guide members comprise elongated members tapering from a first thickness adjacent a radially outer edge of the actuator to a second thickness adjacent the central extension member.

Example 21. The crimping device of any example herein, particularly any one of examples 19-20, wherein the one or more linear guide members are configured to be movably disposed between one or more ribs of the funnel segment.

Example 22. The crimping device of any example herein, particularly any one of examples 1-17, wherein the one or more extension members comprise a first cylindrical extension member defining an inner bore and a second cylindrical extension member disposed about a radially outer circumference of the base.

Example 23. The crimping device of any example herein, particularly example 22, wherein the first cylindrical extension member has a first height and the second cylindrical extension member has a second height, and wherein the first height is less than the second height.

Example 24. The crimping device of any example herein, particularly any one of examples 1-23, wherein the actuator further comprises an engagement mechanism configured to releasably engage a corresponding engagement mechanism on the housing such that the actuator and the housing can be locked together once the prosthetic valve has at least partially advanced through the outlet.

Example 25. The crimping device of any example herein, particularly any one of examples 1-24, wherein the pusher member and the actuator each comprise an inner bore configured to receive a shaft of a delivery apparatus.

Example 26. The crimping device of any example herein, particularly any one of examples 1-25, wherein the actuator and the housing are configured to be pressed together in an axial direction.

Example 27. A crimping device, comprising:

- a housing configured to receive a radially expandable and compressible prosthetic valve in a radially expanded state, the housing comprising:
- a funnel segment extending at least partially along an axial length of the housing and comprising a plurality of ribs spaced about the circumference of the housing, the ribs extending inwardly toward a longitudinal axis of the housing, and
- an outlet in communication with the funnel segment;
- a pusher member configured to abut a prosthetic valve within the housing when a prosthetic valve is received in the housing, the pusher member comprising:
  - a stem having a first end portion, and a second end portion comprising one or more resilient latches, and
  - a plurality of arms extending from the first end portion, each arm comprising a seat configured to engage an adjacent end portion of a prosthetic valve;
- an actuator releasably coupled to the pusher member via one or more openings engaged with the one or more resilient latches; and
- wherein manual axial advancement of the actuator relative to the housing causes the prosthetic valve to move axially through the funnel segment such that at least a portion of the prosthetic valve compresses radially by engagement with the funnel segment and exits the crimping device via the outlet.

Example 28. The crimping device of any example herein, particularly example 27, wherein the ribs increase along their length from a first thickness adjacent an inlet end portion of the housing to a second thickness greater than the first thickness adjacent the outlet.

Example 29. The crimping device of any example herein, particularly any one of examples 27-28, wherein the housing comprises two or more side portions, and wherein each side portion comprises a portion of the funnel segment.

Example 30. The crimping device of any example herein, particularly example 29, further comprising a retaining member configured to releasably retain the two or more side portions together.

Example 31. The crimping device of any example herein, particularly any one of examples 27-30, wherein the plurality of arms extend radially from the pusher member.

Example 32. The crimping device of any example herein, particularly example 31, wherein the arms are configured to be movably disposed between the ribs of the funnel segment.

Example 33. The crimping device of any example herein, particularly any one of examples 31-32, wherein the seat of each arm comprises first and second walls defining a channel between them.

Example 34. The crimping device of any example herein, particularly any one of examples 27-33, wherein the pusher member comprises a first end portion having a first diameter and a second end portion having a second diameter smaller than the first diameter.

Example 35. The crimping device of any example herein, particularly example 34, the second end portion comprising one or more releasable locking features configured to engage one or more corresponding locking features on the actuator.

Example 36. The crimping device of any example herein, particularly any one of examples 27-35, wherein the actuator comprises a base, a central extension member having an inner bore, and one or more linear guide members.

Example 37. The crimping device of any example herein, particularly example 36, wherein the one or more linear guide members comprise elongated members tapering from a first thickness adjacent a radially outer edge of the actuator to a second thickness adjacent the central extension member.

Example 38. The crimping device of any example herein, particularly example 37, wherein the one or more linear guide members are configured to be movably disposed between one or more ribs of the funnel segment.

Example 39. The crimping device of any example herein, particularly any one of examples 27-38, wherein the actuator further comprises an engagement mechanism configured to releasably engage a corresponding engagement mechanism on the housing such that the actuator and the housing can be locked together once the prosthetic valve has at least partially advanced through the outlet.

Example 40. The crimping device of any example herein, particularly any one of examples 27-39, wherein the pusher member and the actuator each comprise an inner bore configured to receive a shaft of a delivery apparatus.

41. An assembly, comprising:
- a crimping device, comprising:
  - a housing comprising an inner bore having a funnel segment extending at least partially along an axial length of the housing and an outlet in communication with the funnel segment, the funnel segment comprising a plurality of radially inwardly extending ribs spaced about an internal circumference of the funnel segment,
  - a pusher member comprising a plurality of circumferentially spaced radially extending arms configured to be movably disposed between the ribs of the funnel segment, and
  - an actuator releasably coupled to the pusher member, the actuator and pusher member configured to be axially movable relative to the housing; and
- a radially expandable and compressible prosthetic valve disposed within the funnel segment, the prosthetic valve comprising a frame, a valvular structure disposed within the frame, and a plurality of connecting arms extending from the frame and comprising enlarged end portions;
- wherein manual axial advancement of the actuator and pusher member relative to the housing causes the prosthetic valve to move axially through the funnel segment such that at least a portion of the prosthetic valve compresses radially by engagement with the funnel segment and exits the crimping device via the outlet.

Example 42. The assembly of any example herein, particularly example 41, wherein the pusher member has an outer diameter less than an inner diameter of the housing such that the pusher member is advanceable into and out of the housing.

Example 43. The assembly of any example herein, particularly any one of examples 41-42, wherein each arm of the pusher member comprises a holding portion having first and second walls defining a channel between them, and wherein the prosthetic valve comprises a plurality of anchors configured to be disposed within respective channels.

Example 44. The assembly of any example herein, particularly any one of examples 41-43, wherein the frame of the prosthetic valve is a self-expandable frame.

Example 45. An assembly, comprising:
- a delivery apparatus comprising a shaft and a valve retaining member coupled to a distal end portion of the shaft, the valve retaining member comprising a plurality of circumferentially spaced slots;
- a crimping device disposed on the shaft, the crimping device comprising:
  - a housing defining an inner bore having a funnel segment extending at least partially along an axial length of the housing and an outlet in communication with the funnel segment, the funnel segment comprising a plurality of radially inwardly extending ribs spaced about an internal circumference of the funnel segment,
  - a pusher member comprising a plurality of circumferentially spaced radially extending arms configured to be movably disposed between the ribs of the funnel segment, and
  - an actuator releasably coupled to the pusher member, the actuator and pusher member configured to be axially movable relative to the housing;
- a radially expandable and compressible prosthetic valve disposed within the funnel segment, the prosthetic valve comprising a frame, a valvular structure disposed within the frame, and a plurality of connecting arms extending from the frame and comprising enlarged end portions;
- wherein manual axial advancement of the actuator and pusher member relative to the housing causes the prosthetic valve to move axially through the funnel segment such that at least a portion of the prosthetic valve compresses radially by engagement with the funnel segment and exits the crimping device via the outlet; and
- wherein the enlarged end portions of the connecting arms are configured to extend into the circumferentially spaced slots of the valve retaining member to restrain the prosthetic valve from movement relative to the valve retaining member.

Example 46. A method of crimping a prosthetic valve, comprising:
- inserting a prosthetic valve in a radially expanded state into an inlet end portion of a crimping device, the crimping device comprising a housing defining a funnel segment extending at least partially along an axial length of the housing and an outlet in communication with the funnel segment;
- aligning a pusher member with a first end portion of the prosthetic valve adjacent the inlet end portion, the pusher member releasably coupled to an actuator; and
- applying an axial force to the actuator to advance the actuator and pusher member into the housing such that the prosthetic valve is advanced through the funnel segment thereby radially compressing the prosthetic valve.

Example 47. The method of any example herein, particularly example 46, further comprising advancing the prosthetic valve through an outlet in an outlet end portion of the housing.

Example 48. The method of any example herein, particularly example 47, wherein the crimping device is disposed on a first shaft of a delivery apparatus, the delivery apparatus further comprising a valve retaining member coupled to a distal end portion of the shaft, and wherein advancing the prosthetic valve through the outlet comprises advancing a plurality of connecting arms extending from the prosthetic valve into a plurality of circumferentially spaced slots in the valve retaining member.

Example 49. The method of any example herein, particularly any one of examples 46-48, wherein aligning the pusher member with a first end portion of the prosthetic valve comprises disposing a plurality of anchors extending from the prosthetic valve into a plurality of channels defined in the pusher member.

Example 50. A crimping device, comprising:

a housing configured to receive a radially expandable and compressible prosthetic valve in a radially expanded state, the housing comprising a funnel segment extending at least partially along an axial length of the housing and an outlet in communication with the funnel segment;

a pusher member configured to abut the prosthetic valve within the housing, the pusher member having an outer diameter less than an inner diameter of the housing such that the pusher member can advance into the housing;

an actuator releasably coupled to the pusher member, the actuator comprising a base member and one or more elongated guide members extending from the base member, each elongated guide member comprising a slot extending at least partially along the length of the guide member and a slidable member slidably disposed within the slot and releasably coupled to the housing; and wherein axial advancement of the housing relative to the base member causes the slidable members to slide within their respective slots such that the pusher member is inserted into the housing causing the prosthetic valve to move axially through the funnel segment such that at least a portion of the prosthetic valve compresses radially by engagement with the funnel segment and exits the crimping device via the outlet.

Example 51. The crimping device of any example herein, particularly example 50, wherein the elongated guides are spaced about a perimeter of the base member.

Example 52. The crimping device of any example herein, particularly any one of examples 50-51, wherein the elongated guides comprise a first end portion and a second end portion, and wherein the second end portion comprises a bracket configured to releasably couple the base member.

Example 53. The crimping device of any example herein, particularly any one of examples 50-52, wherein each slidable member comprises a main portion and a protrusion, the protrusion disposed within a respective slot to slidably couple the slidable member to the elongated guide.

Example 54. The crimping device of any example herein, particularly example 53, wherein the slidable member comprises an aperture configured to receive a fastener to releasably couple the slidable member to the housing.

Example 55. An assembly, comprising:

a crimping device, comprising:

a housing configured to receive a radially expandable and compressible prosthetic valve in a radially expanded state, the housing comprising a funnel segment extending at least partially along an axial length of the housing and an outlet in communication with the funnel segment;

a pusher member configured to abut the prosthetic valve within the housing, the pusher member having an outer diameter less than an inner diameter of the housing such that the pusher member can advance into the housing;

an actuator releasably coupled to the pusher member, the actuator comprising a base member and one or more elongated guides extending from the base member, each elongated guide comprising a slot extending at least partially along the length of the guide and a slidable member slidably disposed within the slot and releasably coupled to the housing; and a radially expandable and compressible prosthetic valve disposed within the funnel segment, the prosthetic valve comprising a frame, a valvular structure disposed within the frame, and a plurality of connecting arms extending from the frame and comprising enlarged end portions;

wherein axial advancement of the housing relative to the base member causes the slidable members to slide within their respective slots such that the pusher member is inserted into the housing causing the prosthetic valve to move axially through the funnel segment such that at least a portion of the prosthetic valve compresses radially by engagement with the funnel segment and exits the crimping device via the outlet.

Example 56. The assembly of any example herein, particularly example 55, wherein each arm of the pusher member comprises a seat having first and second walls defining a channel between them, and wherein the prosthetic valve comprises a plurality of anchors configured to be disposed within respective channels.

Example 57. An assembly, comprising:

a delivery apparatus comprising a shaft and a valve retaining member coupled to a distal end portion of the shaft, the valve retaining member comprising a plurality of circumferentially spaced slots;

a crimping device disposed on the shaft, the crimping device comprising:

a housing configured to receive a radially expandable and compressible prosthetic valve in a radially expanded state, the housing comprising a funnel segment extending at least partially along an axial length of the housing and an outlet in communication with the funnel segment;

a pusher member configured to abut the prosthetic valve within the housing, the pusher member having an outer diameter less than an inner diameter of the housing such that the pusher member can advance into the housing;

an actuator releasably coupled to the pusher member, the actuator comprising a base member and one or more elongated guides extending from the base member, each elongated guide comprising a slot extending at least partially along the length of the guide and a slidable member slidably disposed within the slot and releasably coupled to the housing; and a radially expandable and compressible prosthetic valve disposed within the funnel segment, the prosthetic valve comprising a frame, a valvular structure disposed within the frame, and a plurality of connecting arms extending from the frame and comprising enlarged end portions;

wherein axial advancement of the housing relative to the base member causes the slidable members to slide within their respective slots such that the pusher member is inserted into the housing causing the prosthetic valve to move axially through the funnel segment such that at least a portion of the prosthetic valve compresses radially by engagement with the funnel segment and exits the crimping device via the outlet; and wherein the enlarged end portions of the connecting arms are configured to extend into the circumferentially spaced slots of the valve retaining member to restrain the prosthetic valve from movement relative to the valve retaining member.

58. A method of crimping a prosthetic valve, comprising:

inserting a prosthetic valve in a radially expanded state into an inlet end portion of a housing of a crimping device, the housing defining a funnel segment extending at least partially along an axial length of the housing and an outlet in communication with the funnel segment;

coupling one or more slidable members of an actuator to the housing, the actuator comprising a plurality of slidable members disposed within slots in elongated guides extending from a base member of the actuator; and advancing the actuator and the housing together such that a pusher member coupled to the base member of the actuator advances the prosthetic valve into the housing and through the funnel segment thereby radially compressing the prosthetic valve.

Example 59. The method of any example herein, particularly example 58, wherein advancing the pusher member into the housing comprises applying an axial force to the housing such that the housing slides along the elongated guides relative to the base member.

Example 60. The method of any example herein, particularly any one of examples 58-59, further comprising aligning the pusher member with a first end portion of the prosthetic valve such that a plurality of anchors extending from the prosthetic valve are disposed in a plurality of seats defined in the pusher member.

Example 61. The method of any example herein, particularly example 60, further comprising advancing the prosthetic valve through an outlet in an outlet end portion of the housing.

Example 62. The method of any example herein, particularly example 61, wherein the crimping device is disposed on a first shaft of a delivery apparatus, the delivery apparatus comprising a valve retaining member coupled to a distal end portion of the first shaft, and wherein advancing the prosthetic valve through the outlet comprises advancing a plurality of connecting arms extending from the prosthetic valve into a plurality of circumferentially spaced slots in the valve retaining member.

Example 63. A crimping device, comprising:

a housing configured to receive a radially expandable and compressible prosthetic valve in a radially expanded state, the housing comprising a funnel segment extending at least partially along an axial length of the housing and an outlet in communication with the funnel segment;

an outer shell in which the housing is disposed, the shell having a cylindrical shape and comprising a threaded inner surface;

an actuator comprising a base and a cylindrical extension member having a correspondingly threaded outer surface configured to engage with the threaded inner surface of the outer shell;

a pusher member coupled to the base of the actuator, the pusher member having a plurality of radially extending arms configured to engage the prosthetic valve within the housing; and wherein the threaded portions are configured to convert rotation of the actuator into axial advancement of the pusher member into the funnel segment of the housing causing the prosthetic valve to move axially through the funnel segment such that at least a portion of the prosthetic valve compresses radially by engagement with the funnel segment and exits the crimping device via the outlet.

Example 64. The crimping device of any example herein, particularly example 63, wherein the outer shell comprises one or more alignment features disposed on an inner surface of the shell, and wherein the alignment features engage the housing to restrain the housing against rotation relative to the outer shell.

Example 65. The crimping device of any example herein, particularly any one of examples 63-64, wherein the pusher member comprises one or more latches configured to couple the actuator such that the pusher member can rotate relative to the actuator but is advanced by axial movement of the actuator.

Example 66. The crimping device of any example herein, particularly any one of examples 63-65, wherein the outer shell comprises two or more side portions, and wherein each side portion comprises a portion of the threaded inner surface.

Example 67. The crimping device of any example herein, particularly example 66, further comprising a retaining member configured to releasably retain the two or more side portions together.

Example 68. A method of crimping a prosthetic valve, comprising:

inserting a prosthetic valve in a radially expanded state into a housing of a crimping device, the crimping device comprising an outer shell having a threaded inner surface, the housing disposed within the outer shell and defining a funnel segment extending at least partially along a length of the housing and an outlet in communication with the funnel segment;

aligning a pusher member with a first end portion of the prosthetic valve adjacent the inlet end portion, the pusher member releasably coupled to an actuator having an extension member comprising a threaded outer surface;

inserting the extension member of the actuator between an outer surface of the housing and an inner surface of the outer shell such that the threaded inner surface of the outer shell engages the threaded outer surface of the extension member;

rotating the actuator such that the threaded portions convert the rotational motion into axial motion of the actuator relative to the outer shell, thereby advancing the pusher member and the prosthetic valve into the housing and advancing the prosthetic valve through the funnel segment to radially compress the prosthetic valve.

Example 69. The method of any example herein, particularly example 68, further comprising advancing the prosthetic valve through the outlet.

Example 70. The method of any example herein, particularly example 69, wherein the crimping device is disposed on a first shaft of a delivery apparatus, the delivery apparatus comprising a valve retaining member coupled to a distal end portion of the first shaft, and wherein advancing the prosthetic valve through the outlet comprises advancing a plurality of connecting arms extending from the prosthetic valve into a plurality of circumferentially spaced slots in the valve retaining member.

Example 71. A crimping device, comprising:

a housing configured to receive a radially expandable and compressible prosthetic valve in a radially expanded state, the housing comprising a funnel segment extending at least partially along an axial length of the housing, an outlet in communication with the funnel segment, and an extender coupled to an inlet portion of the housing and comprising a threaded inner surface;

an actuator comprising a base and a cylindrical extension member having a correspondingly threaded outer surface configured to engage with the threaded inner surface of the extender;

a pusher member coupled to the base of the actuator via one or more coupling members and configured to abut the prosthetic valve within the housing, the pusher member having an outer diameter less than an inner diameter of the housing such that the pusher member can advance into the housing; and wherein the threaded inner surface of the housing and the threaded outer surface of the extender are configured to convert rotation of the actuator into axial advancement of the pusher member into the funnel segment of the housing causing the prosthetic valve to move axially through the funnel segment such that at least a portion of the prosthetic valve compresses radially by engagement with the funnel segment and exits the crimping device via the outlet.

Example 72. The crimping device of any example herein, particularly example 71, wherein the extender has an outer diameter greater than an outer diameter of the housing, and wherein the extender and housing are coupled via a tapered portion that tapers from the outer diameter of the extender to the outer diameter of the housing.

Example 73. A method of crimping a prosthetic valve, comprising:

inserting a prosthetic valve in a radially expanded state into a housing of a crimping device, the housing comprising a funnel segment extending at least partially along a length of the housing an outlet in communication with the funnel segment, and an extender coupled to an inlet end portion of the housing, the extender comprising a threaded inner surface;

aligning a pusher member with a first end portion of the prosthetic valve adjacent the inlet end portion, the pusher member releasably coupled to an actuator having an extension member comprising a threaded outer surface;

inserting the extension member of the actuator between an outer surface of the housing an inner surface of the outer shell such that the threaded inner surface of the outer shell engages the threaded outer surface of the extension member;

rotating the actuator such that the threaded portions convert the rotational motion into axial motion of the actuator relative to the outer shell and such that the pusher member advances into the housing thereby advancing the prosthetic through the funnel segment to radially compress the prosthetic valve.

Example 74. The method of any example herein, particularly example 73, further comprising advancing the prosthetic valve through the outlet.

Example 75. A crimping device, comprising:

a housing configured to receive a radially expandable and compressible prosthetic valve in a radially expanded state, the housing comprising a funnel segment extending at least partially along an axial length of the housing and an outlet in communication with the funnel segment;

an actuator comprising:

a base having an aperture extending through a thickness of the base, the aperture comprising a threaded inner surface, a threaded member having a threaded outer surface engaged with the threaded inner surface of the aperture, one or more extension members coupling the actuator to the housing; and a pusher member coupled to the threaded member such that the threaded member can rotate relative to the pusher member and axially advance the pusher member, the pusher member configured to abut the prosthetic valve within the housing; and wherein rotation of the threaded member axially advances the pusher member into the funnel segment of the housing causing the prosthetic valve to move axially through the funnel segment such that at least a portion of the prosthetic valve compresses radially by engagement with the funnel segment.

Example 76. The crimping device of any example herein, particularly example 75, wherein the funnel segment comprises a plurality of radially inwardly extending ribs spaced about an internal circumference of the housing.

Example 77. The crimping device of any example herein, particularly any one of examples 75-76, wherein the ribs comprise a first tapered portion disposed at a first angle and a second tapered portion disposed at a second angle.

Example 78. The crimping device of any example herein, particularly any one of examples 75-77, wherein the pusher member comprises a plurality of circumferentially spaced radially extending arms.

Examples 79. The crimping device of any example herein, particularly example 78, wherein the arms are configured to be movably disposed between the ribs of the funnel segment.

Example 80. The crimping device of any example herein, particularly any one of examples 75-79, wherein the pusher member comprises a first end portion having a first diameter and a second end portion having a second diameter smaller than the first diameter.

Example 81. The crimping device of any example herein, particularly example 80, the second end portion comprising one or more releasable locking features configured to engage an annular shoulder of the threaded member.

Example 82. The crimping device of any example herein, particularly example 81, wherein the annular shoulder is a first annular shoulder and wherein the threaded member further comprises a second annular shoulder configured to abut a distal edge of the pusher member.

Example 83. The crimping device of any example herein, particularly any one of examples 81-82, wherein the one or more locking features comprise resilient latches.

Example 84. The crimping device of any example herein, particularly any one of examples 75-83, wherein the one or more extension members are configured to be disposed adjacent an outer surface of the housing and wherein each extension member is coupled to the housing via a respective fastener that extends through an aperture in the extension member.

Example 85. The crimping device of any example herein, particularly example 84, wherein each fastener extends into a corresponding aperture in the outer surface of the housing.

Example 86. The crimping device of any example herein, particularly any one of examples 84-85, wherein each fastener and each aperture are correspondingly threaded, and wherein an end portion of each fastener frictionally engages an outer surface of the housing.

Example 87. The crimping device of any example herein, particularly any one of examples 75-86, wherein the pusher member and the threaded member each comprise an inner bore configured to receive a shaft of a delivery apparatus.

Example 88. The crimping device of any example herein, particularly any one of examples 75-87, wherein the one or more extension members extend into an interior of the housing and are coupled to an inner surface of the housing.

Example 89. A method of crimping a prosthetic valve, comprising:

- inserting a prosthetic valve in a radially expanded state into a housing of a crimping device, the housing comprising a funnel segment extending at least partially along a length of the housing and an outlet in communication with the funnel segment;
- coupling an actuator to the housing via one or more extension members extending from a base of the actuator, the actuator comprising a threaded aperture extending through a thickness of the base and a threaded member having a correspondingly threaded outer surface engaged with the threaded aperture;
- aligning a pusher member coupled to the threaded member with a first end portion of the prosthetic valve adjacent the inlet end portion; and
- rotating the threaded member such that the threaded member and pusher member advance axially relative to the housing and such that the pusher member advances into the housing thereby advancing the prosthetic through the funnel segment to radially compress the prosthetic valve.

Example 90. The method of any example herein, particularly example 89, further comprising advancing the prosthetic valve through the outlet.

Example 91. The method of any example herein, particularly any one of examples 89-90, wherein coupling the actuator to the housing via one or more extension members comprises inserting a respective fastener through a corresponding aperture in each extension member such that the fastener engages the housing.

Example 92. A crimping device, comprising:

- a housing configured to receive a radially expandable and compressible prosthetic valve in a radially expanded state, the housing comprising a funnel segment extending at least partially along an axial length of the housing and an outlet in communication with the funnel segment;
- an actuator comprising:
  - a handle including a lever member configured to advance an actuator member when actuated,
  - a holder portion extending from the handle and configured to receive the housing, the holder portion having a first end portion including a retaining member configured to releasably couple the housing, and
  - a pusher member coupled to the actuator member and configured to abut a prosthetic valve when a prosthetic valve is placed within the housing; and
- wherein actuation of the lever member axially advances the actuator member, and thereby the pusher member, such that the pusher member advances into the funnel segment of the housing causing the prosthetic valve to move axially through the funnel segment such that at least a portion of the prosthetic valve compresses radially by engagement with the funnel segment.

Example 93. The crimping device of any example herein, particularly example 92, wherein the pusher member comprises a first end portion having a first diameter and a second end portion having a second diameter smaller than the first diameter.

Example 94. The crimping device of any example herein, particularly example 93, wherein the pusher member is coupled to the actuator member via an extender, the extender comprising a base portion, a central extension member, and a pusher member holder having an inner recess, and wherein the second end portion of the extender can be inserted into the inner recess to couple the pusher member to the extender.

Example 95. The crimping device of any example herein, particularly example 94, the second end portion of the pusher member comprising one or more releasable locking features configured to engage an annular shoulder of the extender to retain the second end portion within the recess.

Example 96. The crimping device of any example herein, particularly example 95, wherein the annular shoulder is a first annular shoulder and wherein the inner recess further comprises a second annular shoulder configured to abut a distal edge of the pusher member.

Example 97. The crimping device of any example herein, particularly any one of examples 95-96, wherein the one or more locking features comprise resilient latches.

Example 98. The crimping device of any example herein, particularly any one of examples 92-97, wherein the funnel segment comprises a plurality of radially inwardly extending ribs spaced about an internal circumference of the housing.

Example 99. The crimping device of any example herein, particularly example 98, wherein the ribs comprise a first tapered portion disposed at a first angle and a second tapered portion disposed at a second angle.

Example 100. The crimping device of any example herein, particularly any one of examples 92-99, wherein the pusher member comprises a plurality of circumferentially spaced radially extending arms.

Example 101. The crimping device of any example herein, particularly example 100, wherein the arms are configured to be movably disposed between the ribs of the funnel segment.

Example 102. The crimping device of any example herein, particularly any one of examples 92-101, wherein the retaining member comprises an outlet configured to align with the outlet of the housing when the housing is coupled to the retaining member.

Example 103. A method of crimping a prosthetic valve, comprising:

- inserting a prosthetic valve in a radially expanded state into a housing of a crimping device, the housing disposed within a retaining member of an actuator and comprising a funnel segment extending at least partially along a length of the housing an outlet in communication with the funnel segment;

actuating a trigger of the actuator to advance an actuator member axially toward the housing such that a pusher member coupled to the actuator member abuts a first end portion of the prosthetic valve within the housing;

continuing to actuate the trigger such that the pusher member advances into the housing thereby advancing the prosthetic through the funnel segment of the housing to radially compress the prosthetic valve.

Example 104. The method of any example herein, particularly example 103, further comprising advancing at least a portion of the prosthetic valve through the outlet.

Example 105. The method of any example herein, particularly any one of examples 103-104, wherein the pusher member is coupled to the actuator member via an extender, the extender comprising a base portion, a central extension member, and a pusher member holder having an inner recess, and wherein a second end portion of the extender can be inserted into the inner recess to couple the pusher member to the extender.

Example 106. A crimping device, comprising:

a housing configured to receive a radially expandable and compressible prosthetic valve in a radially expanded state, the housing comprising a funnel segment extending at least partially along an axial length of the housing and an outlet in communication with the funnel segment;

an actuator comprising:

a fluid chamber having a first end portion and a second end portion, the first end portion comprising an aperture and the second end portion comprising an inlet, and a piston having a shaft member extending through the aperture and a piston head member disposed within the fluid chamber and forming a seal with the fluid chamber; and a pusher member coupled to the shaft member of the piston and configured to abut the prosthetic valve within the housing;

wherein flowing fluid into the fluid chamber via the inlet axially advances the piston and thereby the pusher member such that the pusher member advances into the funnel segment of the housing causing the prosthetic valve to move axially through the funnel segment such that at least a portion of the prosthetic valve compresses radially by engagement with the funnel segment.

Example 107. The crimping device of any example herein, particularly example 106, wherein the inlet is coupled to a fluid reservoir.

Example 108. The crimping device of any example herein, particularly any one of examples 106-107, further comprising one or more extension members extending from the first end portion of the fluid chamber and coupling the actuator to the housing Example 109. The crimping device of any example herein, particularly example 108, wherein the one or more extension members are configured to disposed adjacent an outer surface of the housing and wherein each extension member is coupled to the housing via a respective fastener that extends through an aperture in the extension member.

Example 110. The crimping device of any example herein, particularly example 109, wherein each fastener extends into a corresponding aperture in the outer surface of the housing.

Example 111. The crimping device of any example herein, particularly any one of examples 109-110, wherein each fastener and each aperture are correspondingly threaded, and wherein an end portion of each fastener frictionally engages an outer surface of the housing.

Example 112. The crimping device of any example herein, particularly any one of examples 106-111, wherein the pusher member comprises a first end portion having a first diameter and a second end portion having a second diameter smaller than the first diameter, the second end portion comprising one or more releasable locking features.

Example 113. The crimping device of any example herein, particularly example 112, wherein the releasable locking features couple one or more openings in the first end portion of the piston to couple the piston and the pusher member to one another.

Example 114. The crimping device of any example herein, particularly any one of examples 112-113, wherein the one or more locking features comprise resilient latches.

Example 115. The crimping device of any example herein, particularly any one of examples 106-114, wherein the funnel segment comprises a plurality of radially inwardly extending ribs spaced about an internal circumference of the housing.

Example 116. The crimping device of any example herein, particularly example 115, wherein the ribs comprise a first tapered portion disposed at a first angle and a second tapered portion disposed at a second angle.

Example 117. The crimping device of any example herein, particularly any one of examples 106-116, wherein the pusher member comprises a plurality of circumferentially spaced radially extending arms.

Example 118. The crimping device of any example herein, particularly example 117, wherein the arms are configured to be movably disposed between the ribs of the funnel segment.

Example 119. A crimping device, comprising:

a housing configured to receive a radially expandable and compressible prosthetic valve in a radially expanded state, the housing comprising a funnel segment extending at least partially along an axial length of the housing and an outlet in communication with the funnel segment;

an actuator comprising:

a base member comprising one or more extension members configured to couple the actuator to the housing, a movable portion including a linear rack member comprising a plurality of teeth, and a pinion member comprising a corresponding plurality of teeth configured to engage the plurality of teeth of the linear rack member such that rotational movement of the pinion member causes axial movement linear rack member and thereby of the movable portion; and a pusher member coupled to the movable portion and configured to abut the prosthetic valve within the housing; and wherein rotation of the pinion member axially advances the movable portion and thereby the pusher member such that the pusher member advances into the funnel segment of the housing causing the prosthetic valve to move axially through the funnel segment such that at least a portion of the prosthetic valve compresses radially by engagement with the funnel segment.

Example 120. The crimping device of any example herein, particularly example 119, further comprising an actuator member configured to rotate the pinion when actuated by a user.

Example 121. A method of crimping a prosthetic valve, comprising:

inserting a prosthetic valve in a radially expanded state into a housing of a crimping device, the housing comprising a funnel segment extending at least partially along a length of the housing an outlet in communication with the funnel segment;

coupling an actuator to the housing, the actuator comprising a base member comprising one or more extension members configured to couple the actuator to the housing, a movable portion including a linear rack comprising a plurality of teeth, and a pinion comprising a corresponding plurality of teeth configured to engage the plurality of teeth of the linear rack;

rotating the pinion to cause axial movement of the movable portion toward the housing such that a pusher member coupled to the movable portion abuts a first end portion of the prosthetic valve within the housing;

continuing to rotate the pinion such that the pusher member advances into the housing thereby advancing the prosthetic through the funnel segment of the housing to radially compress the prosthetic valve.

Example 122. The method of any example herein, particularly example 121, further comprising advancing the prosthetic valve through the outlet.

Example 123. The method of any example herein, particularly any one of examples 121-122, wherein the rotating the pinion comprises rotating an actuator member coupled to the pinion.

Example 124. A crimping device, comprising:

a housing configured to receive a radially expandable and compressible prosthetic valve in a radially expanded state, the housing comprising a funnel segment extending at least partially along an axial length of the housing and an outlet in communication with the funnel segment;

an actuator comprising:

a base member comprising one or more extension members configured to couple the actuator to the housing, a cam member comprising a lobe shape and pivotably coupled to the base member;

a lever member coupled to the cam member such that rotation of the lever member causes corresponding rotation of the cam member;

a pusher member positioned between the cam member and the housing, and configured to abut the prosthetic valve within the housing; and wherein rotation of the lever member causes corresponding rotation of the cam member, which contacts the pusher member thereby axially advancing the pusher member into the funnel segment of the housing causing the prosthetic valve to move axially through the funnel segment such that at least a portion of the prosthetic valve compresses radially by engagement with the funnel segment.

Example 125. A crimping device, comprising:

a housing configured to receive a radially expandable and compressible prosthetic valve in a radially expanded state, the housing comprising a funnel segment extending at least partially along an axial length of the housing and an outlet in communication with the funnel segment;

an actuator comprising:

a base member comprising one or more extension members configured to couple the actuator to the housing, a linear rack member comprising a plurality of teeth, and a pawl member configured to engage the plurality of teeth of the linear rack member to allow movement of the linear rack member in a first direction and restrain the linear rack member against movement in a second, opposing direction; and a pusher member coupled to the linear rack member and configured to abut the prosthetic valve within the housing; and wherein actuation of the pawl axially advances the linear rack member and thereby the pusher member such that the pusher member advances into the funnel segment of the housing causing the prosthetic valve to move axially through the funnel segment such that at least a portion of the prosthetic valve compresses radially by engagement with the funnel segment.

Example 126. The crimping device of any example herein, particularly example 125, wherein the pawl is coupled to an actuator member configured to actuate the pawl to cause movement of the linear rack member in the first direction.

Example 127. The crimping device of any example herein, particularly any one of examples 125-126, further comprising a locking member configured to help restrain the linear rack member against movement in the second direction.

Example 128. The crimping device of any example herein, particularly example 127, wherein the locking member is a pawl.

Example 129. A crimping device, comprising:

a housing configured to receive a radially expandable and compressible prosthetic valve in a radially expanded state, the housing comprising a funnel segment extending at least partially along an axial length of the housing, an outlet in communication with the funnel segment, and a handle extending from the housing and configured such that a user can grip the handle;

a lever pivotably coupled to the housing, the lever comprising a protrusion configured to abut a pusher member disposed within an inlet portion of the housing; and wherein rotation of the lever causes engagement of the protrusion with the pusher member, and thereby axially advances the pusher member into the funnel segment of the housing causing the prosthetic valve to move axially through the funnel segment such that at least a portion of the prosthetic valve compresses radially by engagement with the funnel segment.

Example 130. The crimping device of any example herein, particularly example 129, wherein the pusher member is coupled to the protrusion.

Example 131. The crimping device of any example herein, particularly any one of examples 129-130, wherein the handle comprises a locking feature and the lever comprises a corresponding locking feature such that the handle and lever can be releasably locked together.

Example 132. A crimping device, comprising:

a housing configured to receive a radially expandable and compressible prosthetic valve in a radially expanded state, the housing comprising a funnel segment extending at least partially along an axial length of the housing and an outlet in communication with the funnel segment;

an actuator comprising:

a lever having a first end portion pivotably coupled to the housing and a second end portion, the lever comprising a protrusion configured to abut a pusher member disposed within an inlet portion of the housing, a mounting member at a second location on the housing circumferentially opposite the first location, the mounting member comprising an aperture extending through a thickness of the mounting member, an actuator member extending through the aperture in the mounting member and through an aperture in the second end portion of the lever, and a driver member disposed on the actuator member adjacent a first surface of the lever such that actuation of the driver member advances the driver member axially along the actuator member thereby advancing the second end portion of the lever toward the mounting member; and wherein advancement of the lever causes engagement of the protrusion with the pusher member and thereby axially advances the pusher member into the funnel segment of the housing causing the prosthetic valve to move axially through the funnel segment such that at least a portion of the prosthetic valve compresses radially by engagement with the funnel segment.

Example 133. The crimping device of any example herein, particularly example 132, wherein the actuator member comprises a threaded outer surface and wherein the driver member comprises a correspondingly threaded surface.

Example 134. The crimping device of any example herein, particularly any one of examples 132-133, wherein the driver member comprises a wingnut.

Example 135. An assembly, comprising:

a delivery apparatus comprising a first shaft and a second shaft disposed over the first shaft;

a crimping device, comprising:

a housing disposed over the first shaft and configured to receive a radially expandable and compressible prosthetic valve in a radially expanded state, the housing comprising a funnel segment extending at least partially along an axial length of the housing and an outlet in communication with the funnel segment, a pusher member having an outer diameter less than an inner diameter of the housing such that the pusher member can advance into the housing, and an actuator releasably coupled to the pusher member, wherein axial advancement of the actuator relative to the housing causes the prosthetic valve to move axially through the funnel segment such that at least a portion of the prosthetic valve compresses radially by engagement with the funnel segment and exits the crimping device via the outlet; and a loading assembly, comprising:

a support tube disposed over the second shaft and comprising first and second side portions; and a funnel member disposed over a first end portion of the support tube, the funnel member comprising first and second side portions.

Example 136. The assembly of any example herein, particularly example 135, wherein the loading assembly further comprises a clamp member coupling the first and second side portions of the support tube to one another.

Example 137. The assembly of any example herein, particularly example 136, wherein the clamp member is a first clamp member and the loading assembly further comprises a second clamp member coupling the first and second side portions of the funnel member to one another.

Example 138. A method of loading a prosthetic valve into a delivery apparatus, comprising:

disposing a support tube of a loading assembly over a capsule of the delivery apparatus, the support tube comprising first and second side portions;

disposing a housing of a crimping device over a shaft of the delivery apparatus such that an outlet end portion of the crimping device is adjacent an inlet end portion of the loading assembly, the housing defining a funnel segment extending at least partially along an axial length of the housing and an outlet in communication with the funnel segment;

inserting a prosthetic valve in a radially expanded state into an inlet end portion of the housing;

advancing the prosthetic valve axially through the funnel segment of the housing and at least partially through the outlet;

disposing a funnel member of the loading assembly over at least a portion of the prosthetic valve, the funnel member comprising first and second side portions; and advancing the loading assembly axially over the prosthetic valve, thereby radially crimping the prosthetic valve and advancing the prosthetic valve into the capsule of the delivery apparatus.

Example 139. The method of any example herein, particularly example 138, further comprising advancing a clamp member over a first end portion of the support tube to retain the first and second side portions together.

Example 140. The method of any example herein, particularly example 139, wherein the clamp member is a first clamp member, and wherein the method further comprises advancing a second clamp member over at least a portion of the funnel member to retain the first and second side portions together.

Example 141. The method of any example herein, particularly any one of examples 138-140, wherein advancing the prosthetic valve through the funnel segment of the housing comprises:

aligning a pusher member of the crimping device with a first end portion of the prosthetic valve adjacent the inlet end portion of the housing, the pusher member releasably coupled to an actuator; and applying an axial force to the actuator to advance the actuator and pusher member into the housing such that the prosthetic valve is advanced through the funnel segment.

Example 142. A crimping device, comprising:

a housing configured to receive a radially expandable and compressible prosthetic valve in a radially expanded state, the housing comprising:

a funnel segment extending at least partially along an axial length of the housing and comprising a plurality of ribs spaced about a circumference of the housing, the ribs extending inwardly toward a longitudinal axis of the housing, and an outlet in communication with the funnel segment;

a pusher member configured to abut a prosthetic valve within the housing when a prosthetic valve is received in the housing, the pusher member comprising a plurality of arms extending from a first end portion, each arm comprising a seat configured to engage an adjacent end portion of a prosthetic valve;

an actuator coupled to the pusher member; and wherein the housing is configured to receive the actuator in a selected angular orientation, and the actuator is configured to be slidably advanced into the housing at the selected angular orientation to move a prosthetic valve axially through the funnel segment such that at least a portion of the prosthetic valve compresses radially by engagement with the funnel segment and exits the crimping device via the outlet.

Example 143. The crimping device of any example herein, particularly example 142, the pusher member further comprising a stem having a first end portion, and a second end portion comprising one or more resilient latches.

Example 144. The crimping device of any example herein, particularly example 143, wherein the actuator is releasably coupled to the pusher member via one or more openings engaged with the one or more resilient latches.

Example 145. The crimping device of any example herein, particularly any one of examples 142-144, wherein the ribs increase along their length from a first thickness adjacent an inlet end portion of the housing to a second thickness greater than the first thickness adjacent the outlet.

Example 146. The crimping device of any example herein, particularly any one of examples 142-145, wherein the housing comprises two or more side portions, and wherein each side portion comprises a portion of the funnel segment.

Example 147. The crimping device of any example herein, particularly example 146, further comprising a retaining member configured to releasably retain the two or more side portions together.

Example 148. The crimping device of any example herein, particularly any one of examples 142-147, wherein the plurality of arms extend radially from the pusher member.

Example 149. The crimping device of any example herein, particularly example 148, wherein the arms are configured to be movably disposed between the ribs of the funnel segment.

Example 150. The crimping device of any example herein, particularly any one of examples 142-149, wherein the seat of each arm comprises first and second walls defining a channel between them.

Example 151. The crimping device of any example herein, particularly any one of examples 142-150, wherein the pusher member comprises a first end portion having a first diameter and a second end portion having a second diameter smaller than the first diameter.

Example 152. The crimping device of any example herein, particularly example 151, the second end portion comprising one or more releasable locking features configured to engage one or more corresponding locking features on the actuator.

Example 153. The crimping device of any example herein, particularly any one of examples 142-152, wherein the actuator comprises a base, a central extension member having an inner bore, and one or more linear guide members.

Example 154. The crimping device of any example herein, particularly example 153, wherein the one or more linear guide members comprise elongated members tapering from a first thickness adjacent a radially outer edge of the actuator to a second thickness adjacent the central extension member.

Example 155. The crimping device of any example herein, particularly any one of examples 153-154, wherein the one or more linear guide members are configured to be movably disposed between one or more ribs of the funnel segment to retain the actuator at the selected angular orientation relative to the housing.

Example 156. The crimping device of any example herein, particularly any one of examples 142-155, wherein the actuator further comprises an engagement mechanism configured to releasably engage a corresponding engagement mechanism on the housing such that the actuator and the housing can be locked together once the prosthetic valve has at least partially advanced through the outlet.

Example 157. The crimping device of any example herein, particularly any one of examples 142-156, wherein the pusher member and the actuator each comprise an inner bore configured to receive a shaft of a delivery apparatus.

Example 158. A loading assembly, comprising:

a support tube configured to be disposed over a shaft of a delivery apparatus, the support tube comprising first and second side portions;

a first clamp member removably coupled to a first end portion of the support tube to retain the first and second side portions together;

a funnel member disposed over a second end portion of the support tube and configured to be disposed over at least a portion of a prosthetic valve, the funnel member comprising first and second side portions;

a second clamp member removably coupled to a first end portion of the funnel member to retain the first and second side portions together; and wherein the loading assembly is configured such that axial advancement of the funnel member over a prosthetic valve or retraction of the prosthetic valve inside the funnel member radially compresses the prosthetic valve by engagement with the funnel member.

Example 159. The loading assembly of any example herein, particularly example 158, wherein the first and second clamps are C-shaped members.

Example 160. The loading assembly of any example herein, particularly any one of examples 158-159, wherein the first and second side portions of the support tube each comprise first and second diametrically opposed flanges.

Example 161. The loading assembly of any example herein, particularly any one of examples 158-160, wherein the first and second clamp members each comprise a ledge extending radially inwardly and axially along at least a portion of the length of the clamp.

Example 162. The loading assembly of any example herein, particularly any one of examples 158-161, further comprising a holder member configured to retain a portion of the shaft between an inner surface of the holder member and an outer surface of the support tube.

Example 163. The loading assembly of any example herein, particularly any one of examples 158-162, wherein the funnel member comprises a funnel portion tapering from a first diameter at an inlet end portion to a second, smaller diameter at an outlet end portion.

Example 164. The loading assembly of any example herein, particularly any one of examples 158-163, further comprising a trimmer guide member having a main body having a circumferentially extending groove and a guide arm, the main body configured to abut an end portion of the prosthetic valve within the capsule.

Example 165. The loading assembly of any example herein, particularly example 164, wherein the guide arm has an axially-extending portion with an end surface that aligns with the circumferentially extending groove.

Example 166. The loading assembly of any example herein, particularly any one of examples 158-165, wherein the first end portion of the support tube comprises a rib extending axially along at least a portion of the length of the support tube, and wherein the first clamp member comprises a channel configured to receive the rib.

Example 167. The loading assembly of any example herein, particularly any one of examples 158-166, wherein the funnel member comprises an edge portion configured to sit within a corresponding recess on a second end portion of the support tube.

Example 168. A crimping device, comprising:

a housing configured to receive a radially expandable and compressible prosthetic valve in a radially expanded state, the housing comprising a funnel segment extending at least partially along an axial length of the housing and an outlet in communication with the funnel segment;

a pusher member configured to abut the prosthetic valve within the housing, the pusher member having an outer diameter less than an inner diameter of the housing such that the pusher member can advance into the housing;

an actuator releasably coupled to the pusher member, the actuator comprising a base member and one or more elongated guide members extending from the base member, each elongated guide member comprising a slot extending at least partially along the length of the guide member and a slidable member slidably disposed within the slot and releasably coupled to the housing; and wherein axial advancement of the housing relative to the base member causes the slidable members to slide within their respective slots such that the pusher member is inserted into the housing causing the prosthetic valve to move axially through the funnel segment such that at least a portion of the prosthetic valve compresses radially by engagement with the funnel segment and exits the crimping device via the outlet.

Example 169. A crimping device, comprising:

a housing configured to receive a radially expandable and compressible prosthetic valve in a radially expanded state, the housing comprising a funnel segment extending at least partially along an axial length of the housing and an outlet in communication with the funnel segment;

an outer shell in which the housing is disposed, the shell having a cylindrical shape and comprising a threaded inner surface;

an actuator comprising a base and a cylindrical extension member having a correspondingly threaded outer surface configured to engage with the threaded inner surface of the outer shell;

a pusher member coupled to the base of the actuator, the pusher member having a plurality of radially extending arms configured to engage the prosthetic valve within the housing; and wherein the threaded surfaces are configured to convert rotation of the actuator into axial advancement of the pusher member into the funnel segment of the housing causing the prosthetic valve to move axially through the funnel segment such that at least a portion of the prosthetic valve compresses radially by engagement with the funnel segment and exits the crimping device via the outlet.

Example 170. A crimping device, comprising:

a housing configured to receive a radially expandable and compressible prosthetic valve in a radially expanded state, the housing comprising a funnel segment extending at least partially along an axial length of the housing and an outlet in communication with the funnel segment;

an actuator comprising:

a base having an aperture extending through a thickness of the base, the aperture comprising a threaded inner surface, a threaded member having a threaded outer surface engaged with the threaded inner surface of the aperture, one or more extension members coupling the actuator to the housing; and a pusher member coupled to the threaded member such that the threaded member can rotate relative to the pusher member and axially advance the pusher member, the pusher member configured to abut the prosthetic valve within the housing; and wherein rotation of the threaded member axially advances the pusher member into the funnel segment of the housing causing the prosthetic valve to move axially through the funnel segment such that at least a portion of the prosthetic valve compresses radially by engagement with the funnel segment.

Example 171. A crimping device, comprising:

a housing configured to receive a radially expandable and compressible prosthetic valve in a radially expanded state, the housing comprising a funnel segment extending at least partially along an axial length of the housing and an outlet in communication with the funnel segment;

an actuator comprising:

a handle including a lever member configured to advance an actuator member when actuated, a holder portion extending from the handle and configured to receive the housing, the holder portion having a first end portion including a retaining member configured to releasably couple the housing, and a pusher member coupled to the actuator member and configured to abut a prosthetic valve when a prosthetic valve is placed within the housing; and wherein actuation of the lever member axially advances the actuator member, and thereby the pusher member, such that the pusher member advances into the funnel segment of the housing causing the prosthetic valve to move axially through the funnel segment such that at least a portion of the prosthetic valve compresses radially by engagement with the funnel segment.

Example 172. A loading assembly for a prosthetic valve, comprising:

a support tube positionable around a delivery capsule of a delivery apparatus, the support tube comprising a proximal end portion and a distal end portion; and a funnel member releasably couplable to the distal end portion of the support tube and configured to radially compress and guide a prosthetic valve into the delivery capsule as the loading assembly is advanced over the prosthetic valve or as the prosthetic valve is retracted inside the loading assembly.

Example 173. The loading assembly of any example herein, particularly example 172, further comprising an annular holder member configured to be disposed between the support tube and the funnel member to retain tab members of a delivery capsule folded proximally against an outer surface of the distal end portion of the support tube.

Example 174. The loading assembly of any example herein, particularly any one of examples 172-173, wherein the support tube comprises separable members held together by a clamp member.

Example 175. A crimping device, comprising:

a housing configured to receive a radially expandable and compressible prosthetic valve in a radially expanded state, the housing comprising a funnel segment extending at least partially along an axial length of the housing, an outlet in communication with the funnel segment, and an extender extending from an inlet portion of the housing and comprising a threaded inner surface;

an actuator comprising a base and a cylindrical extension member having a correspondingly threaded outer surface shaped to engage with the threaded inner surface of the extender portion;

a pusher member coupled to the base of the actuator and sized to abut the prosthetic valve within the housing; and wherein the threaded inner surface of the housing and the threaded outer surface of the actuator are adapted to convert rotation of the actuator into axial advancement of the pusher member into the funnel segment of the housing causing the prosthetic valve to move axially through the funnel segment.

Example 176. A loading assembly, comprising:

a support tube configured to be disposed over a shaft of a delivery apparatus, the support tube comprising first and second side portions;

a holder member disposed over a first end portion of the support tube, the holder member configured to retain one or more tabs of a delivery apparatus to retain a delivery capsule in a taut position;

a first clamp member removably coupled to a first end portion of the support tube to retain the first and second side portions together;

a funnel member disposed over a second end portion of the support tube and configured to be disposed over at least a portion of a prosthetic valve, the funnel member comprising first and second side portions;

a second clamp member removably coupled to a first end portion of the funnel member to retain the first and second side portions together; and wherein the loading assembly is configured such that axial advancement of the funnel member over a prosthetic valve or retraction of the prosthetic valve inside the funnel member radially compresses the prosthetic valve by engagement with the funnel member.

Example 177. The loading assembly of any example herein, particularly example 176, wherein the holder member comprises a flexible material and has a sinusoidal shape in cross section comprising a plurality of peaks and valleys.

Example 178. A tab trimming device, comprising:

an annular main body defining a central bore, the main body including a recess extending from a circumferentially outer edge of the main body into the central bore;

a blade removably coupled to the main body, the blade comprising a cutting edge positioned to extend into the central bore;

wherein the central bore is configured to receive a shaft of a delivery system, and wherein rotation of the tab trimming device around the shaft severs a selected portion of the shaft using the cutting edge of the blade.

Example 179. The tab trimming device of any example herein, particularly example 178, in combination with a trimmer guide member having a main body having a circumferentially extending groove and a guide arm, the trimmer guide member configured to be positioned such that an end surface of the guide arm contacts a first surface of the blade.

Example 180. A tab trimming device, comprising:

a housing comprising a main body and a support extension, the support extension configured to receive a shaft of a delivery system;

a rotatable member comprising an inner bore configured to receive a portion of the shaft of the delivery system, the rotatable member disposed at least partially within the main body and rotatable relative to the main body;

a blade holder coupled to the rotatable member, the blade holder configured to removably couple a blade having a cutting edge;

wherein rotation of the rotatable member around the shaft of the delivery system causes the cutting edge of the blade to sever a selected portion of the shaft.

Example 181. The tab trimming device of any example herein, particularly example 180, wherein the housing further comprises a clamp member pivotably coupled to the support extension, the clamp member and the support extension each comprising a portion of an alignment feature, the alignment feature being configured such that when a corresponding alignment feature of the shaft is disposed within the alignment feature of the housing, the selected portion of the shaft is aligned with the cutting edge of the blade.

Example 182. The tab trimming device of any example herein, particularly any one of examples 180-181, wherein the alignment feature is a first alignment feature and the housing further comprises a second alignment feature disposed at a proximal end portion of the housing and configured to restrain a shaft disposed within the housing against movement relative to the housing.

Example 183. A tab trimming device, comprising:

a housing comprising a main body and a support extension, the support extension configured to receive a shaft of a delivery system;

a rotatable member comprising an inner bore configured to receive a portion of the shaft of the delivery system, the rotatable member disposed at least partially within the main body and rotatable relative to the main body;

a blade holder removably coupled to a blade, the blade holder coupled to the rotatable member and being movable relative to the rotatable member between a first position wherein a cutting edge of the blade does not extend into the inner bore and a second position wherein a cutting edge of the blade extends into the inner bore;

wherein rotation of the rotatable member when the blade holder is in the second position is configured to sever a selected portion of the shaft of the delivery system using the cutting edge of the blade; and wherein the rotatable member comprises a door member coupled to the blade holder via a cam member, the door member being movable between an open position and a closed position, and wherein movement of the door member between the open position and the closed position causes corresponding movement of the blade holder between the first position and the second position.

Example 184. A tab trimming device, comprising:

a housing comprising a main body and a support extension, the support extension configured to receive a shaft of a delivery system;

a rotatable member comprising an inner bore configured to receive a portion of the shaft of the delivery system, the rotatable member disposed at least partially within the main body and rotatable relative to the main body, the rotatable member comprising an inner bore in which a portion of the shaft is disposed;

a blade holder removably coupled to a blade, the blade holder being coupled to an actuator and being movable relative to the rotatable member via the actuator between a first position wherein a cutting edge of the blade does not extend into the inner bore and a second position wherein a cutting edge of the blade extends into the inner bore;

wherein rotation of the rotatable member when the blade holder is in the second position is configured to sever a selected portion of the shaft of the delivery system using the cutting edge of the blade.

Example 185. The tab trimming device of any example herein, particularly example 184, wherein the actuator is a first actuator and the tab trimming device further comprises a second actuator configured to move the blade holder from the second position to the first position.

Example 186. A tab trimming device, comprising:

a housing comprising a main body and a support extension extending from the main body, the support extension configured to receive a shaft of a delivery system;

a rotatable member disposed at least partially within the main body and rotatable relative to the main body, the rotatable member comprising an inner bore in which a portion of the shaft is disposed, the rotatable member being coupled to a blade having a cutting edge, a portion of the cutting edge extending into the inner bore;

a guide member pivotably coupled to the main body and comprising a body member including a circumferentially extending groove, the guide member being movable between a first position and a second position wherein the guide member is disposed within the inner bore such that there is a space between the guide member and an inner surface of the rotatable member sized to receive a wall of the shaft;

wherein rotation of the rotatable member allows the cutting edge of the blade to sever a selected portion of the shaft of the delivery system.

Example 187. An assembly, comprising:

a loading assembly, comprising:

a support tube configured to be disposed over a shaft of a delivery apparatus, the support tube comprising first and second side portions, an inner surface of the support tube comprising one or more engagement elements, a first clamp member removably coupled to a first end portion of the support tube to retain the first and second side portions together, a funnel member disposed over a second end portion of the support tube and configured to be disposed over at least a portion of a prosthetic valve, the funnel member comprising first and second side portions, and a second clamp member removably coupled to a first end portion of the funnel member to retain the first and second side portions together; and a delivery apparatus, comprising:

a shaft configured to receive a prosthetic valve in a radially compressed configuration, an outer surface of the shaft comprising one or more corresponding engagement elements configured to interlock with the one or more engagement elements of the support tube to form a rigid structure.

Example 188. The assembly of any example herein, particularly example 187, wherein the one or more engagement elements comprise a helical recess and the one or more corresponding engagement elements comprise a helical protrusion.

Example 189. An assembly, comprising:

a loading assembly, comprising:

a support tube configured to be disposed over a shaft of a delivery apparatus, the support tube comprising first and second side portions, an inner surface of the support tube comprising one or more engagement elements, the one or more engagement elements comprising a plurality of protrusions extending from an inner surface of the support tube;

a first clamp member removably coupled to a first end portion of the support tube to retain the first and second side portions together, a funnel member disposed over a second end portion of the support tube and configured to be disposed over at least a portion of a prosthetic valve, the funnel member comprising first and second side portions, and a second clamp member removably coupled to a first end portion of the funnel member to retain the first and second side portions together; and a delivery apparatus, comprising:

a shaft configured to receive a prosthetic valve in a radially compressed configuration, the shaft comprising one or more corresponding engagement elements disposed within a wall of the shaft, the one or more corresponding engagement elements comprising a plurality of openings configured to interlock with the plurality of protrusions of the support tube to form a rigid structure.

Example 190. A crimping device, comprising:

a housing sized to receive a radially expandable and compressible prosthetic heart valve in a radially expanded state, the housing comprising:

a funnel segment extending at least partially along an axial length of the housing, an outlet in communication with the funnel segment, an extender portion extending from an inlet portion of the housing and comprising a threaded inner surface, and first and second side portions each comprising a portion of the funnel segment, the first side portion comprising a first portion of an engagement feature and the second side portion comprising a second portion of the engagement feature;

an actuator comprising a base and a cylindrical extension member having a correspondingly threaded outer surface configured to engage with the threaded inner surface of the extender portion;

a pusher member coupled to the base of the actuator and configured to abut the prosthetic valve within the housing; and wherein the inner surface of the housing and the threaded outer surface of the actuator are configured to convert rotation of the actuator into axial advancement of the pusher member into the funnel segment of the housing causing the prosthetic valve to move axially through the funnel segment;

wherein engagement between the first and second portions of the engagement feature retains the first and second side portions of the housing against lateral movement relative to one another at an inlet end portion of the housing.

Example 191. The crimping device of any example herein, particularly example 190, wherein the first portion of the engagement feature is a recess extending into a longitudinal side wall of the first side portion of the housing and wherein the second portion of the engagement feature is a projection extending from a longitudinal side wall of the second portion of the housing.

Example 192. The crimping device of any example herein, particularly example 190, wherein the first portion of the engagement feature is a first hooked member, and the second portion of the engagement feature is a second hooked member, and wherein the first and second hooked members are configured to interlock with one another.

Example 193. The crimping device of any example herein, particularly example 190, wherein the first portion of the engagement feature comprises a plurality of first members and the second portion of the engagement feature comprises a plurality of second members, and wherein each first member can be disposed between adjacent second members such that the first and second members frictionally engage one another.

Example 194. A loading assembly, comprising:

a support tube configured to be disposed over a shaft of a delivery apparatus, the support tube comprising first and second side portions;

a first clamp member removably coupled to a first end portion of the support tube to retain the first and second side portions together;

a funnel member disposed over a second end portion of the support tube and configured to be disposed over at least a portion of a prosthetic valve, the funnel member comprising first and second side portions;

a second clamp member removably coupled to a first end portion of the funnel member to retain the first and second side portions together; and wherein the loading assembly is configured such that axial advancement of the funnel member over a prosthetic valve or retraction of the prosthetic valve inside the funnel member radially compresses the prosthetic valve by engagement with the funnel member;

wherein the first and second clamp members each comprise a c-shaped main body, comprising one or more elongated slots extending through a thickness of the main body, the elongated slots reducing the amount of force required to insert or remove the first and second clamp members onto the support tube.

Example 195. A loading assembly, comprising:

a support tube configured to be disposed over a shaft of a delivery apparatus, the support tube comprising first and second side portions;

a first clamp member removably coupled to a first end portion of the support tube to retain the first and second side portions together;

a funnel member disposed over a second end portion of the support tube and configured to be disposed over at least a portion of a prosthetic valve, the funnel member comprising first and second side portions;

a second clamp member removably coupled to a first end portion of the funnel member to retain the first and second side portions together; and wherein the loading assembly is configured such that axial advancement of the funnel member over a prosthetic valve or retraction of the prosthetic valve inside the funnel member radially compresses the prosthetic valve by engagement with the funnel member;

wherein the first and second clamp members each comprise a c-shaped main body, comprising one or more recesses disposed longitudinally along an inner wall of the main body, the recesses reducing the amount of force required to insert or remove the first and second clamp members onto the support tube.

Example 196. A loading assembly, comprising:

a support tube configured to be disposed over a shaft of a delivery apparatus, the support tube comprising first and second side portions;

a first clamp member removably coupled to a first end portion of the support tube to retain the first and second side portions together;

a funnel member disposed over a second end portion of the support tube and configured to be disposed over at least a portion of a prosthetic valve, the funnel member comprising first and second side portions;

a second clamp member removably coupled to a first end portion of the funnel member to retain the first and second side portions together; and wherein the loading assembly is configured such that axial advancement of the funnel member over a prosthetic valve or retraction of the prosthetic valve inside the funnel member radially compresses the prosthetic valve by engagement with the funnel member;

wherein the first and second clamp members each comprise a c-shaped main body and one or more tab members extending laterally from the main body, the tab members providing a mechanical advantage and thus reducing the amount of force required to insert or remove the first and second clamp members onto the support tube.

Example 197. The loading assembly of any example herein, particularly example 196, wherein the one or more tab members of the first clamp member comprise a laterally extending portion and a curved or hooked portion extending toward a first end portion of the first clamp member.

Example 198. The loading assembly of any example herein, particularly any one of examples 196-197, wherein the one or more tab members of the second clamp member comprise a sinusoidal shape.

Example 199. A system for loading a prosthetic valve into a delivery apparatus for advancement into a patient's body, comprising:

a radially expandable and compressible prosthetic valve comprising a plurality of connecting arms extending from a first end portion;

the delivery apparatus comprising a shaft including a valve retaining member disposed on the shaft, the valve retaining member comprising a plurality of slots shaped to receive the plurality of connecting arms of the prosthetic valve, the delivery apparatus further comprising a capsule extending over the shaft and sized to receive and retain the prosthetic valve in a radially compressed configuration;

a crimping device comprising a housing sized to receive the prosthetic valve in a radially expanded state, the housing comprising a funnel segment extending at least partially along an axial length of the housing, and an outlet in communication with the funnel segment, wherein axial advancement of the prosthetic valve through the funnel segment causes radial compression of the prosthetic valve thereby allowing the plurality of connecting arms to be received within the plurality of slots of the valve retaining member;

a loading assembly comprising a support tube shaped to be coupled to or disposed over the capsule, and a funnel member disposed on a first end portion of the support tube; and wherein the loading assembly is adapted to receive the valve retaining member with the plurality of connecting arms of the prosthetic valve coupled thereto such that axial advancement of the support tube and funnel member over the prosthetic valve radially compresses the prosthetic valve and loads the prosthetic valve into the capsule.

Example 200. The system of any example herein, particularly example 199, the crimping device further comprising a pusher member sized to abut the prosthetic valve within the housing and to axially advance the prosthetic valve through the funnel segment.

Example 201. The system of any example herein, particularly example 200, the crimping device further comprising an actuator coupled to the pusher member, the actuator comprising a base and a cylindrical extension member having a threaded outer surface shaped to engage corresponding threads on an inner surface of the housing.

Example 202. The system of any example herein, particularly any one of examples 199 through 201, wherein the housing of the crimping device comprises two or more side portions, and wherein each side portion comprises a portion of the funnel segment.

Example 203. The system of any example herein, particularly example 202, wherein the two or more side portions comprise first and second side portions releasably coupled to one another using one or more engagement elements, wherein each engagement element of the one or more engagement elements comprises a first engagement member coupled to the first side portion and a second engagement member coupled to the second side member.

Example 204. The system of any example herein, particularly example 203, wherein the first engagement members are flanges extending laterally from an outer surface of the first side portion, and the second engagement members are hooked members shaped to receive the flanges.

Example 205. The system of any example herein, particularly example 204, wherein coupling the first and second side portions to one another comprises positioning the flanges adjacent the hooked members and axially advancing the flanges into channels of the hooked members.

Example 206. The system of any example herein, particularly any one of examples 199 through 205, wherein the delivery apparatus further comprises an outer ring disposed over the shaft, the outer ring sized to advance over the valve retaining member and a portion of the prosthetic valve to retain the plurality of connecting arms within the slots of the valve retaining member.

Example 207. The system of any example herein, particularly any one of examples 199 through 206, wherein the prosthetic valve further comprises a plurality of anchors extending from a second end portion, the anchors sized to fit within a plurality of seats each disposed on a respective arm extending from a pusher member sized to abut the prosthetic valve within the housing of the crimping device.

Example 208. The system of any example herein, particularly any one of examples 199 through 207, wherein the prosthetic valve comprises an inner frame portion and an outer frame portion.

Example 209. The system of any example herein, particularly any one of examples 199 through 208, wherein the prosthetic valve is sized to be implanted in a patient's native mitral or tricuspid valve.

Example 210. The system of any example herein, particularly any one of examples 199 through 209, wherein the prosthetic valve includes a valvular structure coupled within a frame, the valvular structure comprising a plurality of leaflets each comprising pericardium.

Example 211. The system of any example herein, particularly any one of examples 199 through 210, wherein the prosthetic valve is self-expandable.

In view of the many possible examples to which the principles of the disclosure may be applied, it should be recognized that the illustrated examples are only examples and should not be taken as limiting the scope of the disclosure. Rather, the scope is at least as broad as the following claims and equivalents of the recited features. We therefore claim all that comes within the scope and spirit of these claims.

We claim:

1. A system for loading a delivery apparatus, the system comprising:

a housing sized to receive a radially expanded prosthetic heart valve, the housing comprising a funnel segment extending at least partially along an axial length of the housing, an outlet in communication with the funnel segment, an actuator configured to help move the prosthetic heart valve at least partially through the funnel segment and at least partially out of the outlet; and a loading assembly, comprising:

a support tube disposable over a capsule of a delivery apparatus, a funnel member disposable over a portion of the support tube and disposable over at least a portion of the prosthetic valve, wherein the loading assembly is configured such that axial advancement of the funnel member over the prosthetic valve or retraction of the prosthetic valve through the funnel member radially compresses the prosthetic valve by engagement with the funnel member.

2. The system of claim 1, wherein the housing comprises an extender portion having a first threaded surface, and wherein the actuator comprises a second threaded surface configured to engage the first threaded surface of the extender portion.

3. The system of claim 1, further comprising a pusher member coupled to the actuator, wherein the actuator is configured to cause axial advancement of the pusher member such that the pusher member advances the prosthetic heart valve at least partially through the funnel segment and at least partially out of the outlet.

4. The system of claim 1, further comprising a first clamp member disposable over a portion of the funnel member, and a second clamp member disposable over a second end portion of the support tube.

5. The system of claim 4, wherein the support tube comprises first and second portions and wherein the first and second portions are retained together by the first clamp member and the second clamp member.

6. The system of claim 4, wherein the first and second clamp members each comprise a first and second ribs extending from an inner surface, the first and second ribs defining a channel between them.

7. The system of claim 6, wherein a portion of the support tube comprises a third rib extending axially along at least a portion of a length of the support tube, and wherein when the loading assembly is assembled, the third rib is configured to be disposed within the channel of the second clamp member.

8. The system of claim 7, wherein the funnel member comprises a fourth rib extending axially along an outer surface of the funnel member, and wherein when the loading assembly is assembled, the fourth rib is configured to be disposed within the channel of the funnel member.

9. The system of claim 1, wherein the first and second clamp members each comprise a main body, wherein the first clamp member comprises one or more first tab members extending laterally away from the main body, and wherein the first tab members have a sinusoidal shape, and wherein the second clamp member comprises one or more second tab members extending laterally away from the main body, and wherein the second tab member have a length greater than a length of the first tab members.

10. The system of claim 1, wherein the loading assembly further comprises a ring configured to retain a portion of the capsule of the delivery apparatus between an inner surface of the ring and an outer surface of the support tube.

11. A system usable for coupling a medical device and a delivery apparatus, wherein the medical device is radially expandable and compressible, the system comprising:
- a crimping device, comprising
  - a housing having an inlet sized to receive the medical device in a radially expanded state, the housing comprising a funnel segment extending at least partially along an axial length of the housing, and an outlet in communication with the funnel segment, and
  - an actuator configured to engage a pusher member such that rotation of the actuator axially advances the pusher member to move the medical device along the funnel segment of the housing to at least partially crimp the medical device and to advance at least a portion of the medical device out of the outlet, such that the medical device can be coupled to the delivery apparatus;
- a support tube having first and second portions positionable around a capsule of the delivery apparatus, the support tube comprising a proximal end portion and a distal end portion; and
- a funnel member releasably couplable to the distal end portion of the support tube and configured to radially compress and guide the medical device into the capsule as the funnel member is advanced over the medical device or as the medical device is retracted through the funnel member.

12. The system of claim 11, wherein the crimping device is configured such that after the medical device is moved along the funnel segment of the housing to at least partially crimp the medical device and to advance at least a portion of the medical device out of the outlet, and the medical device is coupled to the delivery apparatus, the crimping device can be removed from around the medical device before the funnel member is separately used to radially compress and guide the medical device into the capsule.

13. The system of claim 11, further comprising a first clamp member and a second clamp member, wherein the first clamp member includes a first alignment feature configured to engage a corresponding alignment feature on a proximal end portion of the support tube, and wherein the first clamp member further includes two opposed first tabs extending from an outer surface of the first clamp member, the first tabs each comprising a laterally extending portion.

14. The system of claim 13, wherein the second clamp member includes a second alignment feature configured to engage a corresponding alignment feature of the funnel member, the second clamp member further including two opposed second tab members, each comprising a sinusoidal shape.

15. The system of claim 14, wherein the funnel member further comprises first and second flanges extending from an outer surface of the funnel member, wherein the second clamp member comprises a stopping surface configured to engage the first and second flanges of the funnel member to prevent the second clamp member from advancing past a selected location.

16. A system usable for loading a medical device into a capsule of a delivery apparatus, comprising:
- a loading assembly, comprising:
  - a support tube configured to be disposed over the capsule of the delivery apparatus;
  - a funnel member disposable over a portion of the support tube and disposable over at least a portion of the medical device;
  - wherein the loading assembly is configured such that axial advancement of the funnel member over the medical device or retraction of the medical device through the funnel member radially compresses the medical device as the medical device is moved into the capsule.

17. The system of claim 16, further comprising a first clamp member disposable over a portion of the funnel member, and a second clamp member disposable over a second end portion of the support tube.

18. The system of claim 16, wherein an outer surface of a first end portion of the support tube comprises one or more recesses extending inwardly toward a central axis of the support tube, and wherein the funnel member comprises an annular shoulder disposed within the one or more recesses when the loading assembly is in an assembled configuration.

19. The system of claim 16, further comprising a crimping device, comprising
- a housing having an inlet sized to receive the medical device in a radially expanded state, the housing comprising a funnel segment extending at least partially along an axial length of the housing, and an outlet in communication with the funnel segment, and
- an actuator configured to help move the medical device along the funnel segment of the housing to at least partially crimp the medical device and to advance at least a portion of the medical device out of the outlet, such that the medical device can be coupled to the delivery apparatus.

20. The system of claim 19, wherein the actuator is configured to engage a pusher member of the crimping device such that rotation of the actuator axially advances the pusher member to move the medical device along the funnel segment of the housing to at least partially crimp the medical device and advance at least the portion of the medical device out of the outlet to facilitate coupling the medical device to the delivery apparatus.

21. The system of claim 19, wherein the crimping device is configured such that after facilitating coupling of the medical device to the delivery apparatus, the crimping device can be removed from around the medical device, and wherein after the crimping device removed from around the medical device, the loading assembly is then used to radially compress and move the medical device into the capsule.

22. A system comprising:
- a delivery apparatus including a shaft comprising a capsule;
- a crimping device including
  - a housing, and an actuator configured to help advance a radially expanded medical device in a funnel segment of the housing to at least partially crimp the medical device;

a loading assembly, comprising a support tube comprising a first portion and a second portion configured to be assembled over the capsule of the delivery apparatus;

a funnel member comprising a first funnel member portion and a second funnel member portion configured to be assembled over a portion of the support tube and configured such that it can be disposed over at least a portion of the medical device, the assembled funnel member comprising an inlet end having a first diameter and an outlet end having a second, smaller diameter;

wherein the loading assembly is configured such that axial advancement of the inlet end of the funnel member over the medical device or retraction of the medical device in the funnel member from the inlet end toward the outlet end radially compresses the medical device as the medical device enters the capsule.

23. The system of claim 22, wherein the outlet end of the funnel member is configured to be positioned adjacent to a distal end portion of the capsule of the delivery apparatus when assembled over the portion of the support tube.

24. The system of claim 22, further comprising a holder member disposed over a distal end portion of the support tube and configured to retain a distal end portion of the capsule relative to the distal end portion of the support tube.

25. A system usable for coupling a medical device and a delivery apparatus, wherein the medical device is radially expandable and compressible, the system comprising:

a crimping device, comprising a housing having an inlet sized to receive the medical device in a radially expanded state, the housing comprising a funnel segment extending at least partially along an axial length of the housing, and an outlet in communication with the funnel segment, and an actuator configured to engage a pusher member such that rotation of the actuator axially advances the pusher member to move the medical device along the funnel segment of the housing to at least partially crimp the medical device and to advance at least a portion of the medical device out of the outlet, such that the medical device can be coupled to the delivery apparatus;

a support tube having first and second portions positionable around a capsule of the delivery apparatus, the support tube comprising a proximal end portion and a distal end portion; and a first clamp member and a second clamp member, wherein the first clamp member includes a first alignment feature configured to engage a corresponding alignment feature on a proximal end portion of the support tube, and wherein the first clamp member further includes two opposed first tabs extending from an outer surface of the first clamp member, the first tabs each comprising a laterally extending portion.

* * * * *